US012337113B2

(12) United States Patent
Rose et al.

(10) Patent No.: US 12,337,113 B2
(45) Date of Patent: Jun. 24, 2025

(54) HEADGEAR FOR USE WITH A PATIENT INTERFACE

(71) Applicant: Fisher & Paykel Healthcare Limited, Auckland (NZ)

(72) Inventors: Hamish Joshua Rose, Auckland (NZ); Matthew James Pedersen, Auckland (NZ); Craig Robert Prentice, Auckland (NZ); Tony William Spear, Auckland (NZ); Bruce Michael Walls, Auckland (NZ); Dana Willfroth, Auckland (NZ); Simon Mittermeier, Auckland (NZ); Melissa Catherine Bornholdt, Auckland (NZ); Gregory James Olsen, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 15/748,612

(22) PCT Filed: Jul. 29, 2016

(86) PCT No.: PCT/IB2016/054539
§ 371 (c)(1),
(2) Date: Jan. 29, 2018

(87) PCT Pub. No.: WO2017/021836
PCT Pub. Date: Feb. 9, 2017

(65) Prior Publication Data
US 2019/0001095 A1  Jan. 3, 2019

Related U.S. Application Data

(60) Provisional application No. 62/360,052, filed on Jul. 8, 2016, provisional application No. 62/358,790, filed on (Continued)

(51) Int. Cl.
*A61M 16/06* (2006.01)
*A61M 16/00* (2006.01)
(Continued)

(52) U.S. Cl.
CPC .... *A61M 16/0683* (2013.01); *A61M 16/0069* (2014.02); *A61M 16/0605* (2014.02);
(Continued)

(58) Field of Classification Search
CPC .......... A61M 16/0825; A61M 16/0069; A61M 16/0605; A61M 16/0633; A61M 16/0683;
(Continued)

(56) References Cited

U.S. PATENT DOCUMENTS 1,395,761 A * 11/1921 Monro ................. A62B 18/084
128/207.11
RE20,211 E    12/1936 Motsinger
(Continued)

FOREIGN PATENT DOCUMENTS

AU    2014 201 197 A1    3/2014
AU    2021 225 241       9/2021
(Continued)

OTHER PUBLICATIONS

A. Benatar, "Ultrasonic Welding of Plastics and Polymeric Composites," Power Ultrasonics: Applications of High-Intensity Ultrasound, 2015, Woodhead Publishing, pp. 295-312 (Year: 2015).*
(Continued)

*Primary Examiner* — Colin W Stuart
(74) *Attorney, Agent, or Firm* — VIA LLP

(57) ABSTRACT

An interface for positive pressure therapy includes a mask assembly, a headgear assembly and a connection port assembly. The headgear assembly includes a component formed from two layers of 3D fabric folded. The mask assembly includes a seal member that has an upper portion movably connected to an integrated lower portion, wherein the upper portion rolls during hinging movement of the upper portion relative to the lower portion. The headgear assembly allows connection to the mask assembly in a direction substantially
(Continued)

normal to a direction of strap tension. The connection port assembly includes a swivel elbow with a valve member that controls flow through a port that opens toward the user. The valve member is provided with a tapered bead that helps prevent the valve member from sticking in a given position. Also, a connector for connecting a respiratory tube to an elbow connector.

27 Claims, 88 Drawing Sheets

Related U.S. Application Data on Jul. 6, 2016, provisional application No. 62/305,284, filed on Mar. 8, 2016, provisional application No. 62/232,293, filed on Sep. 24, 2015, provisional application No. 62/209,822, filed on Aug. 25, 2015, provisional application No. 62/199,513, filed on Jul. 31, 2015, provisional application No. 62/199,547, filed on Jul. 31, 2015.

(51) Int. Cl.
*A61M 16/08* (2006.01)
*A61M 16/20* (2006.01)

(52) U.S. Cl.
CPC .... *A61M 16/0633* (2014.02); *A61M 16/0825* (2014.02); *A61M 16/208* (2013.01); *A61M 2205/42* (2013.01); *A61M 2207/00* (2013.01); *A61M 2209/06* (2013.01)

(58) Field of Classification Search
CPC ............ A61M 16/208; A61M 2205/42; A61M 2207/00; A61M 2209/06; A61M 16/00; A61M 16/06; A61M 16/0694; A61M 2205/02; F16F 1/362; A47H 23/02; A47H 23/14; A62C 2/10; A62B 18/08; A62B 18/084
USPC ............ 128/205.25; 267/142, 145, 146; 156/196, 217, 218, 221, 222, 226, 227; 428/57–62, 121–130, 192, 193, 196; 160/330, 113
See application file for complete search history.

(56) References Cited

U.S. PATENT DOCUMENTS

| | | | |
|---|---|---|---|
| 3,295,529 A | 1/1967 | Corrigall et al. | |
| 3,424,633 A | 1/1969 | Corrigall et al. | |
| 3,624,663 A * | 11/1971 | Jones | B63C 11/12 2/424 |
| 4,051,556 A * | 10/1977 | Davenport | A42B 3/08 2/421 |
| 4,494,538 A * | 1/1985 | Ansite | A62B 18/00 128/201.25 |
| 4,534,344 A * | 8/1985 | Constance-Hughes | A62B 18/02 128/201.15 |
| 4,593,688 A | 6/1986 | Payton | |
| 4,595,003 A * | 6/1986 | Shoemaker | A62B 18/02 128/201.19 |
| 4,782,605 A | 11/1988 | Chapnick | |
| 4,910,806 A * | 3/1990 | Baker | B63C 11/12 128/201.11 |
| 5,038,776 A * | 8/1991 | Harrison | A62B 18/084 128/207.11 |
| 5,069,205 A * | 12/1991 | Urso | A62B 18/084 128/201.24 |
| 5,394,568 A | 3/1995 | Brostrom et al. | |
| 5,481,763 A | 1/1996 | Brostrom et al. | |
| 5,490,567 A * | 2/1996 | Speer | A62C 8/06 169/50 |
| 6,338,342 B1 | 1/2002 | Fecteau et al. | |
| 6,338,367 B1 * | 1/2002 | Khokar | D03D 41/004 139/11 |
| 6,422,238 B1 | 7/2002 | Lithgow | |
| 6,470,886 B1 | 10/2002 | Jestrabek-Hart | |
| 6,805,117 B1 * | 10/2004 | Ho | A61M 16/0683 128/207.17 |
| 6,861,379 B1 | 3/2005 | Blaszczykiewicz | |
| 7,219,669 B1 | 5/2007 | Lovell et al. | |
| 7,225,811 B2 | 6/2007 | Ruiz et al. | |
| 7,497,097 B2 | 3/2009 | Herr | |
| 7,509,958 B2 | 3/2009 | Amarasinghe et al. | |
| 7,779,832 B1 | 8/2010 | Ho | |
| 7,904,971 B2 | 3/2011 | Doria et al. | |
| 8,136,525 B2 * | 3/2012 | Lubke | A61M 16/0875 128/206.28 |
| 8,505,538 B2 | 8/2013 | Amarasinghe | |
| 8,522,784 B2 * | 9/2013 | Ng | A61M 16/0816 128/206.28 |
| 9,168,349 B2 * | 10/2015 | Amarasinghe | A61M 16/0666 |
| D797,277 S * | 9/2017 | Blanch | D24/110 |
| D810,277 S * | 2/2018 | Amarasinghe | D24/110.1 |
| 2002/0195108 A1 | 12/2002 | Mittelstadt et al. | |
| 2003/0051732 A1 | 3/2003 | Smith et al. | |
| 2008/0092906 A1 | 4/2008 | Gunaratnam et al. | |
| 2010/0258132 A1 * | 10/2010 | Moore | A61M 16/0683 128/207.11 |
| 2011/0197341 A1 * | 8/2011 | Formica | A61M 16/0683 2/209.3 |
| 2011/0220113 A1 * | 9/2011 | Newman | A61M 16/0605 128/206.24 |
| 2012/0152255 A1 | 6/2012 | Barlow et al. | |
| 2013/0008446 A1 | 1/2013 | Carroll et al. | |
| 2013/0139822 A1 | 6/2013 | Gibson et al. | |
| 2013/0213400 A1 | 8/2013 | Barlow et al. | |
| 2013/0220327 A1 | 8/2013 | Barlow et al. | |
| 2013/0291870 A1 | 11/2013 | Ging et al. | |
| 2014/0190486 A1 * | 7/2014 | Dunn | A61M 16/0683 128/205.25 |
| 2014/0209098 A1 * | 7/2014 | Dunn | A61M 16/06 128/206.21 |
| 2014/0251338 A1 * | 9/2014 | Asvadi | A61M 16/06 128/206.22 |
| 2016/0045700 A1 * | 2/2016 | Amarasinghe | A61M 16/06 128/205.25 |
| 2019/0001095 A1 | 1/2019 | Rose et al. | |

FOREIGN PATENT DOCUMENTS

| | | |
|---|---|---|
| CN | 102245250 A | 11/2011 |
| CN | 103068431 A | 4/2013 |
| CN | 103906545 A | 7/2014 |
| CN | 103930168 A | 7/2014 |
| CN | 106604756 A | 4/2017 |
| EP | 3328475 | 6/2018 |
| EP | 2373368 | 5/2020 |
| JP | 2012-511341 | 5/2012 |
| JP | 2014-529432 | 11/2014 |
| JP | 2018-528042 | 9/2018 |
| NZ | 585295 | 12/2011 |
| NZ | 592064 | 5/2014 |
| NZ | 616559 | 5/2015 |
| WO | WO 2000/074758 | 12/2000 |
| WO | WO 2002/047749 | 6/2002 |
| WO | WO 2004/041341 | 5/2004 |
| WO | WO 2005/063326 | 7/2005 |
| WO | WO 2006/130903 | 12/2006 |
| WO | WO 2007/006089 | 1/2007 |
| WO | WO 2008/030831 | 3/2008 |
| WO | WO 2009/109005 | 9/2009 |
| WO | WO 2010/066004 | 6/2010 |
| WO | WO 2012/027792 | 3/2012 |
| WO | WO 2012/040791 | 4/2012 |
| WO | WO 2012/045127 | 4/2012 |
| WO | WO 2013/026091 | 2/2013 |
| WO | WO 2013/026092 | 2/2013 |

(56) References Cited

FOREIGN PATENT DOCUMENTS

| WO | WO 2014/015382 | 1/2014 |
| WO | WO 2014/165906 | 10/2014 |
| WO | WO 2015/022629 | 2/2015 |
| WO | WO 2016/032343 | 3/2016 |
| WO | WO 2016/075658 | 5/2016 |
| WO | WO 2017/021836 | 2/2017 |

OTHER PUBLICATIONS

International Search Report, Application No. PCT/IB2016/054539; 6 pages; Dec. 6, 2016.
Extended European Search Report in Application No. 16832392.1; dated Jan. 7, 2019; 7 pages.
International Search Report, re PCT Application No. PCT/IB2016/054539, mailed Dec. 6, 2016.
Lov, "D3 spacer knit fabrics for medical devices", Taschenbuch Für Die Textil Industrie 2003, Schiele & Schön, pp. 26-29.
"Stretch spacer knits provide alternative to neoprene. (Orthopaedics)." Medica Textiles, Dec. 2002: 3. Business Insights: Global. Web. Dec. 1, 2015.
Office Action for Japanese Application No. 2018-524572, dated Aug. 17, 2020.
Australian Examination Report for Australian Patent Application No. 2016303454, dated Sep. 3, 2020 in 4 pages.
Chinese Office Action for Chinese Patent Application No. 201680057234.7, dated Sep. 25, 2020 in 12 pages.

\* cited by examiner

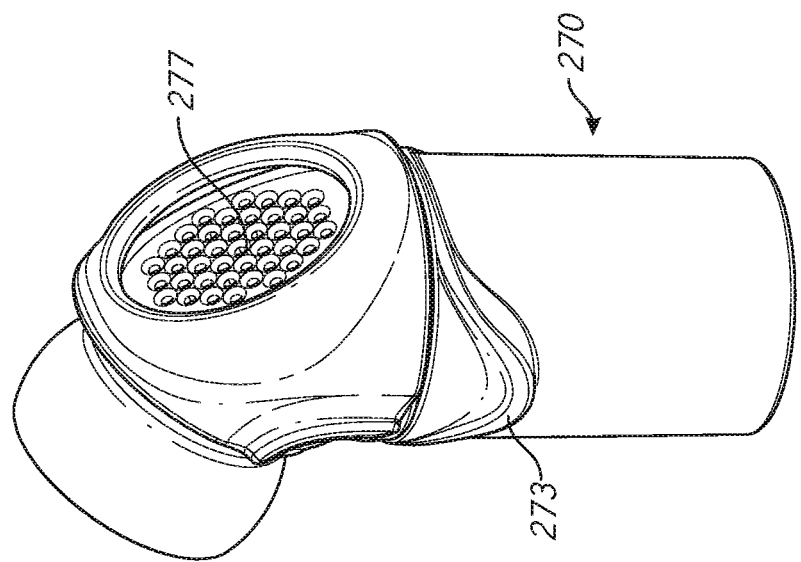
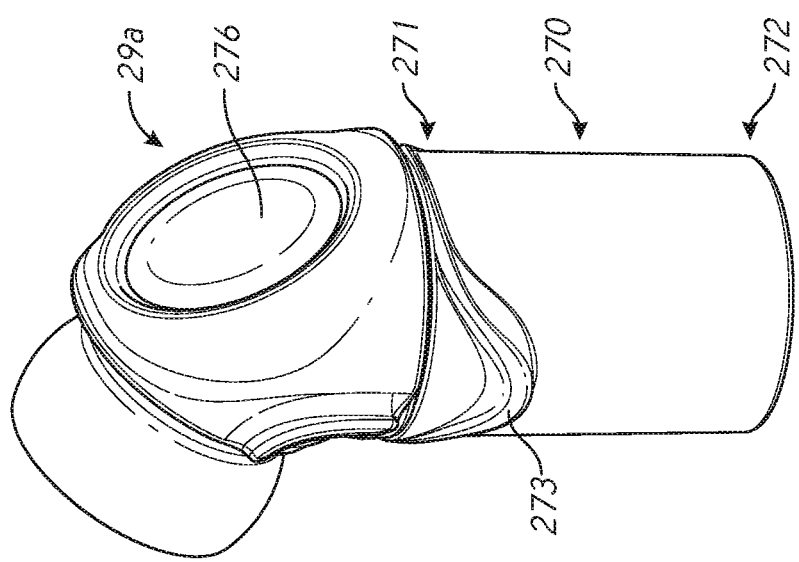
FIG. 23B
FIG. 23A

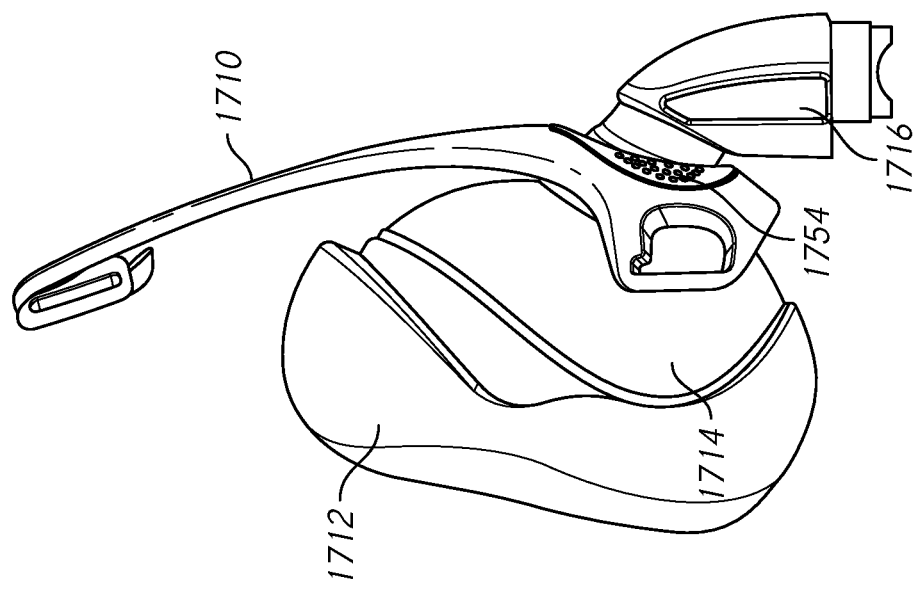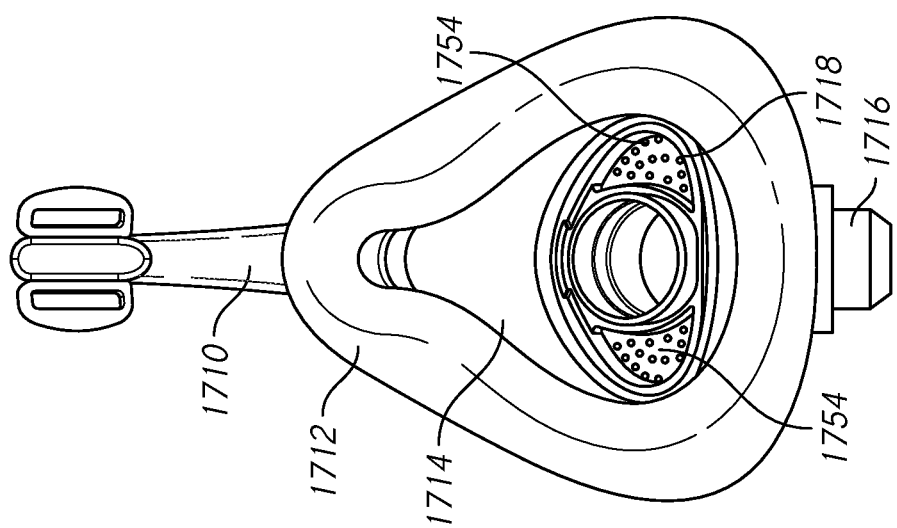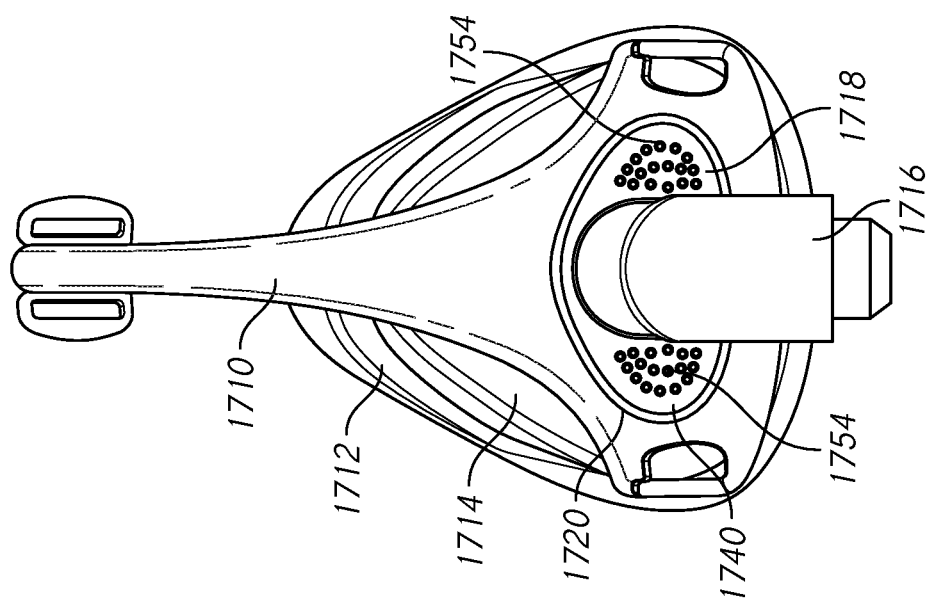

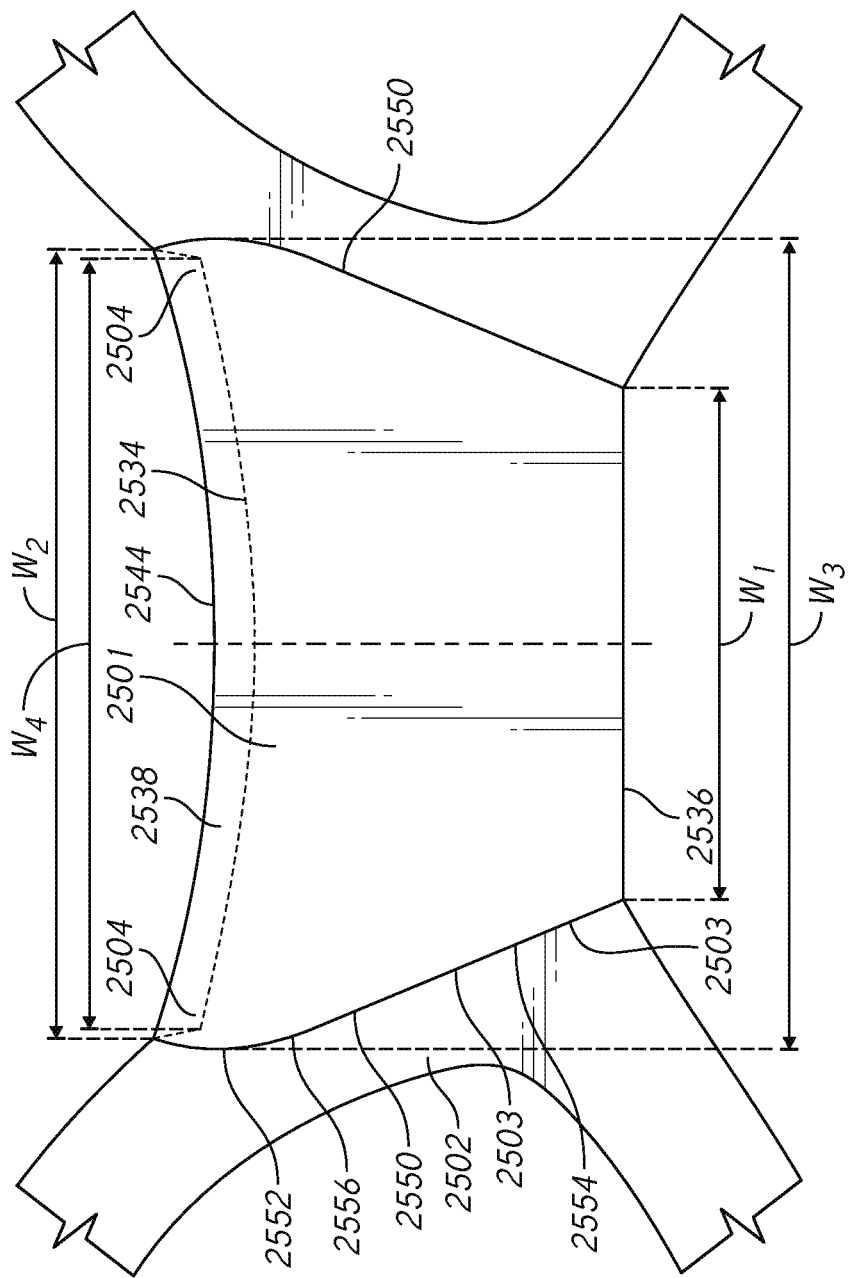

HEADGEAR FOR USE WITH A PATIENT INTERFACE

REFERENCED DISCLOSURES

The present disclosure references various features of U.S. Patent Application No. 62/199,513, filed 31 Jul. 2015, U.S. Patent Application No. 62/199,547, filed 31 Jul. 2015, U.S. Patent Application No. 62/209,822, filed 25 Aug. 2015, U.S. Patent Application No. 62/232,293, filed 24 Sep. 2015, U.S. Patent Application No. 62/305,284, filed Mar. 8, 2016, U.S. Patent Application No. 62/358,790, filed Jul. 6, 2016, and U.S. Patent Application No. 62/360,052, filed Jul. 8, 2016. The entire disclosures of those applications are hereby made part of this specification as if set forth fully herein and incorporated by reference for all purposes, for all that they contain.

FIELD OF THE DISCLOSURE

The present invention generally relates to patient interfaces for respiratory therapy. The present invention generally relates to an elbow assembly of a patient interface such as a face mask that covers at least one of a nose and a mouth of a user to supply respiratory gas under positive pressure. More particularly, the present invention relates to such elbow assemblies that have an anti-asphyxia valve (an AA valve) arranged to enable the user to continue to breathe, if the respiratory gas supply is switched off or stops for any reason. The invention also relates to a connector for connecting a conduit to a patient interface, such as via an elbow assembly, preferably the elbow assemblies disclosed herein. The present invention also relates to headgear used to secure respiratory masks to a user's head.

BACKGROUND

Many types of headgear exist for use with patient interfaces for respiratory therapy. However, because in some applications (e.g., treatment of obstructive sleep apnoea (OSA)) the patient interface is worn often and/or for extended periods of time, a need exists for continued improvement to improve the convenience and comfort for the user, whilst maintaining or improving the sealing function of the interface.

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user.

Such full face masks commonly are secured to a head of the user with headgear. In order to sufficiently reduce leakage, the headgear typically is tightened, which results in an elevated pressure being exerted on a bridge of a user's nose. In other words, as the headgear is tightened, the seal typically applies a progressively increasing load on the bridge of the nose. Such masks are typically provided with an elbow assembly comprising a tubular conduit which extends through 90 degrees, one end of the conduit being in fluid communication with the mask, the other end of the conduit being connected to a breathing gas delivery tube. It can be a problem that AA valves in such elbow assemblies do not open or close fully or reliably.

A large variety of respiratory masks have been devised. Many of these masks are configured to provide sealed communication with a user's airway, by sealing around parts of the user's nose and/or mouth. These masks are commonly used to provide therapies, such as, but not limited to, non-invasive ventilation (NIV) and constant positive airway pressure (CPAP). CPAP therapy is commonly used to treat obstructive sleep apnea (OSA) and involves providing a constant supply of pressurized air to a user's airway. This splints the airway open, thus minimizing airway collapse and reducing apneas. As part of this therapy, a bias-flow venting system is used to flush exhaled carbon dioxide ($CO_2$) from within the mask, which reduces or eliminates the likelihood of rebreathing.

Bias-flow venting systems can become a source of discernable noise. Drafts can be annoying to both the user and/or their bed partner and may result in reduced compliance with the therapy. Bias-flow venting systems can also be difficult to clean, which may result in contamination or reduced compliance with the therapy. Such bias-flow venting systems can also add bulk to the respiratory mask, further reducing the user's comfort while wearing the respiratory mask and, thus, the user's likelihood of complying.

Other common problems experienced in relation to current headgear include the headgear being too heavy, bulky and hot, which can be uncomfortable for the user. Headgear made from traditional materials can be slow to dry after being washed. This can impact patients because often the headgear will not dry within a day and patients will be forced to either not wear their mask or wear it with wet headgear. This inconvenience associated with cleaning of the headgear can lead to some patients choosing not to wash the headgear at all, which can become unhygienic.

SUMMARY OF THE INVENTION

It is an object of the present disclosure to provide one or more constructions and/or methods that will at least go some way towards improving on the above or that will at least provide the public or the medical profession with a useful choice. The present disclosure also relates to bias-flow venting systems for respiratory masks. Such bias-flow venting systems are configured to diffuse exhausted air, while improving ease of cleaning, reducing noise, and/or improving compactness of the respiratory mask. An object of the present disclosure is to provide a respiratory mask with a bias-flow venting system, which will at least provide the public with a useful choice According to an aspect of the invention there is provided an elbow assembly configured to connect a mask assembly to an air and/or other gases conduit, the elbow assembly comprising an elbow and a sleeve, the elbow comprising inner and outer walls and defining an air flow channel therebetween, the inner wall comprising a port on a side of the elbow, the sleeve being coupled with the elbow; the sleeve comprising a flap, wherein when the flap is at a first position, the flap at least partially blocks the port and allows gas from the air conduit to pass to a user via the elbow, and when the flap is at a second position, the flap at least partially blocks the air conduit thereby allowing gas to flow from the user to a location outside of the elbow assembly via the port and the air flow channel, wherein the air flow channel directs air away from the side of the elbow, the flap comprising an elongate bead which projects from the flap and is configured to contact the inner wall of the elbow when the flap is in the first position so as to space the flap from the inner wall of the elbow, the bead comprising at least one tapered portion configured such that part of the bead projects further from the flap than another part of the bead, when the flap is viewed from the side.

In some embodiments, the bead extends around at least part of the periphery of the valve flap.

In some embodiments, wherein the bead extends around the entire periphery of the valve flap.

In some embodiments, the flap may comprise a hinge which pivotally mounts the flap on the elbow, the bead extending around the periphery of the flap to the hinge.

In some embodiments, the bead comprises an arcuate bead portion distal from the hinge, the bead portion being arcuate when the flap is viewed in plan.

In some embodiments, the bead comprises at least one linear bead portion adjacent the hinge, the bead portion being straight when the flap is viewed in plan.

In some embodiments, the at least one linear bead portion comprises a sealing surface which is wider than the width of the remainder of the bead.

In some embodiments, the width of the at least one linear bead portion is substantially identical to a height of a surface of another part of the elbow assembly against which the at least one linear bead portion seals, when the flap is in the first position.

In some embodiments, a transitional wall is defined between the at least one linear bead portion and the remainder of the flap, the transitional wall extending from the margin of the linear bead portion to the body of the flap, the transitional wall being configured to provide structural stiffness to the flap.

In some embodiments, the transitional wall is inclined relative to the plane of the valve flap.

In some embodiments, the bead is substantially 'n' shaped when the flap is viewed in plan.

In some embodiments, the bead is substantially 'D' shaped when the flap is viewed in plan.

In some embodiments, the bead tapers inwardly towards the valve flap from a position distal from the hinge to a position adjacent the hinge, that is, the bead projects further from the flap at a position distal from the hinge.

In some embodiments, the bead tapers such that the bead blends into the valve flap, at a position adjacent the hinge.

In some embodiments, the bead comprises a top surface which contacts the inner wall of the elbow when the flap is in the first position, and opposed side walls extending between the valve flap and the top surface, the top surface forming a sealing surface.

In some embodiments, at least one side wall is curved.

In some embodiments, the shape of one side wall is different from the shape of another side wall.

In some embodiments, the profile of one side wall is such that the side wall curves from the top surface into a plane of the valve flap.

In some embodiments, at least one side wall is substantially straight in profile so that that side wall extends in a straight line between the top surface and the valve flap.

In some embodiments, the straight side wall is inclined relative to the plane of the valve flap.

In some embodiments, the bead is formed integrally with the valve flap.

In some embodiments, a plurality of beads are provided.

In some embodiments, the elbow assembly further comprises an orientation feature arranged to facilitate mounting the support and the valve flap in the desired orientation relative to the elbow and sleeve.

In some embodiments, the orientation feature comprises a slot on one of the support and the elbow or sleeve and a protrusion on the other of the support and the elbow or sleeve, the protrusion being received in the slot when the support and the valve flap are mounted in the desired orientation.

In some embodiments, the air flow channel comprises two air flow channels.

In some embodiments, the sleeve further comprises a bump extending around an outer surface of the sleeve and a recess adjacent to the bump.

In some embodiments, the bump and the recess are adapted to receive a swiveling component incorporating a ridge to engage with the bump.

In some embodiments, the sealing surface is substantially straight when viewed from the side.

In some embodiments, the sealing surface comprises a curved or inclined portion when viewed from the side.

In some embodiments, the flap is configured such that the flap is biased away from the elbow towards the sleeve, at least when the flap is in the second position.

In some embodiments, the flap is configured such that the flap is biased away from the first position, at least when the flap is in the second position.

In some embodiments, the flap is biased away from the second position in a direction also away from the first position.

In some embodiments, the flap comprises a recess on an opposite face of the flap to the bead.

In some embodiments, the recess is oblong.

In some embodiments, the recess is adjacent a hinge of the flap.

In some embodiments, the bead may comprise an arcuate bead portion distal from the hinge, the bead portion being arcuate when the flap is viewed in plan. The bead may additionally or alternatively comprise at least one linear bead portion adjacent the hinge, the bead portion being straight when the flap is viewed in plan. In one example, the bead is substantially 'n' shaped when the flap is viewed in plan.

The bead may taper inwardly towards the valve flap from a position distal from the hinge to a position adjacent the hinge, that is, the bead projects further from the flap at a position distal from the hinge. The bead may taper such that the bead blends into the valve flap, at a position adjacent the hinge.

In some embodiments, the bead preferably comprises a top surface which contacts the inner wall of the elbow when the flap is in the first position, and opposed side walls extending between the valve flap and the top surface. At least one side wall may be curved. At least one side wall may be straight. The profile shape of one side wall may be different from the shape of another side wall. In one example, the profile of one side wall is such that the side wall curves from the top surface into a plane of the valve flap. In one example, at least one side wall is substantially straight in profile so that that side wall extends in a straight line between the top surface and the valve flap. The straight side wall may be inclined relative to the plane of the valve flap.

In some embodiments, the bead may be formed integrally with the valve flap. A plurality of beads may be provided.

In some embodiments, the flap may comprise a flap support, the flap support being mounted on at least one of the elbow and the sleeve. An orientation feature may be provided and arranged to facilitate mounting the support and the valve flap in the desired orientation relative to the elbow and sleeve. The orientation feature may comprise a slot on one of the support and the elbow or sleeve and a protrusion on the other of the support and the elbow or sleeve, the protrusion being received in the slot when the support and the valve flap are mounted in the desired orientation.

In some embodiments, the flow channel may comprise two flow channels.

In some embodiments, the sleeve may further comprise a bump extending around an outer surface of the sleeve and a recess adjacent to the bump. The bump and the recess may be adapted to receive a swiveling component incorporating a ridge to engage with the bump.

According to another aspect of the invention there is provided an anti-asphyxiation valve for mounting in an elbow assembly configured to connect a mask assembly to an air and/or other gases conduit, the elbow assembly comprising an elbow and a sleeve, the elbow comprising inner and outer walls and defining an air and/or other gases flow channel therebetween, the inner wall comprising a port on a side of the elbow, the sleeve being coupled with the elbow; the valve comprising a support and a flap pivotally mounted on the support, wherein when the valve flap assembly is mounted in an elbow and assembly and when the flap is at a first position, the flap at least partially blocks the port and allows gas from the conduit to pass to a user via the elbow, and when the flap is at a second position, the flap at least partially blocks the conduit thereby allowing gas to flow from the user to a location outside of the elbow assembly via the port and the flow channel, wherein the flow channel directs air and/or other gases away from the side of the elbow, the flap comprising an elongate bead which projects from the flap and is configured to contact the inner wall of the elbow when the flap is in the first position so as to space the flap from the inner wall of the elbow, the bead comprising at least one tapered portion configured such that part of the bead projects further from the flap than another part of the bead, when viewed from the side.

In some embodiments, the elongate bead extends around at least part of the periphery of the valve flap.

In some embodiments, the elongate bead extends around the entire periphery of the valve flap.

In some embodiments, the valve flap comprises a hinge which pivotally couples the valve flap to the conduit, the elongate bead extending around the periphery of the flap to the hinge.

In some embodiments, the elongate bead comprises an arcuate bead portion distal from the hinge, the arcuate bead portion being arcuate when the flap is viewed in plan.

In some embodiments, the elongate bead comprises at least one linear bead portion adjacent the hinge, the at least one linear bead portion being straight when the flap is viewed in plan.

In some embodiments, the at least one linear bead portion comprises a sealing surface which is wider than the width of the remainder of the elongate bead.

In some embodiments, the width of the at least one linear bead portion is substantially identical to a height of a surface of another part of the conduit against which the at least one linear bead portion seals, when the flap is in the first position.

In some embodiments, a transitional wall is defined between the at least one linear bead portion and the remainder of the valve flap, the transitional wall extending from a margin of the linear bead portion to the body of the flap, the transitional wall being configured to provide structural stiffness to the flap.

In some embodiments, the transitional wall is inclined relative to the plane of the valve flap.

In some embodiments, the elongate bead is substantially 'n' shaped when the flap is viewed in plan.

In some embodiments, the elongate bead is substantially 'D' shaped when the flap is viewed in plan.

According to another aspect, there is provided a connector for connecting an air and/or other gases conduit, directly or indirectly, to a patient interface, the connector comprising a first end and a second end; and a wall defining a gases pathway between the first end and the second end. The first end is configured to couple to an elbow connector and the second end is configured to couple to a respiratory gases tube, including via a tube connector, such as a collar, that terminates the respiratory tube, and further wherein the second end of the connector is configured to prevent fixed attachment of the second end of the connector to the elbow connector.

Preferably, the second end of the connector is dimensioned relative to the elbow connector so as to provide said prevention. More particularly, according to a preferred embodiment, an engaging portion of the elbow connector is configured to be received inside the connector and the inner dimension of the second end is greater than the external dimension of the engaging portion of the elbow connector.

Preferably, the connector is configured to releasably and sealably be secured to the elbow connector via a click or snap fit. To this end, a projection or recess may be provided on a surface (preferably an interior surface) of the connector and the engaging portion of the elbow connector may include a corresponding recess or projection. Thus the invention may further provide an elbow connector configured to engage the novel and inventive connector.

According to preferred embodiments, the connector comprises a projection on an outer surface thereof that is configured to act as a mechanical stop to limit the extent to which a respiratory tube may be pushed onto the connector. The external projection is preferably also configured to provide a grip for a user's fingers for facilitating removal of the connector from the elbow connector. It should be noted that this external projection may be used with or without the connector being configured to prevent engagement of the second end thereof with the engaging portion of the elbow connector (e.g. elbow 29 or 29a).

According to another aspect, there is provided a connector for connecting an air and/or other gases conduit, directly or indirectly, to a patient interface, the connector comprising a first end and a second end; and a wall defining a gases pathway between the first end and the second end. The first end is configured to couple to an elbow connector and the second end is configured to couple to a respiratory gases tube, and further wherein the connector comprises a projection on an outer surface thereof that is configured to act as a mechanical stop to limit the extent to which a respiratory tube may be pushed onto the connector and/or to provide a grip for a user's fingers for facilitating removal of the connector from the elbow connector.

In some configurations, an elbow connector is configured to couple to the connector of any of the above statements.

According to another aspect, there is provided an anti-asphyxiation valve for a respiratory mask, comprising: a conduit comprising a first end, a second end, and a port on a side of the conduit between the first end and the second end, the first end being configured to receive a flow of gas from a gas source and the second end being coupled to the respiratory mask; and a valve flap assembly comprising a support and a valve flap pivotally coupled to the support, wherein when the support of the valve flap assembly is coupled to the conduit and when the valve flap is at a first position, the valve flap at least partially blocks the port and allows gas entering the first end of the conduit to flow to the second end of the conduit, and when the flap is at a second position, the valve flap at least partially blocks the first end of the conduit such that expiratory gas entering the second end of the conduit to flow from the second end to a location outside of the conduit via the port, the valve flap comprising an elongate bead which projects from the valve flap and is configured to contact a portion of an inner wall of the conduits surrounding the port when the flap is in the first position so as to space the valve flap from the inner wall of the conduit, the bead comprising at least one tapered portion configured such that part of the bead projects further from the flap than another part of the bead, when viewed from the side.

In some embodiments, the elongate bead extends around at least part of the periphery of the valve flap.

In some embodiments, the elongate bead extends around the entire periphery of the valve flap.

In some embodiments, the flap comprises a hinge which pivotally couples the valve flap to the conduit, the elongate bead extending around the periphery of the flap to the hinge.

In some embodiments, the elongate bead comprises an arcuate bead portion distal from the hinge, the arcuate bead portion being arcuate when the flap is viewed in plan.

In some embodiments, the elongate bead comprises at least one linear bead portion adjacent the hinge, the at least one linear bead portion being straight when the flap is viewed in plan.

In some embodiments, the at least one linear bead portion comprises a sealing surface which is wider than the width of the remainder of the elongate bead.

In some embodiments, the width of the at least one linear bead portion is substantially identical to a height of a surface of another part of the conduit against which the at least one linear bead portion seals, when the flap is in the first position.

In some embodiments, a transitional wall is defined between the at least one linear bead portion and the remainder of the valve flap, the transitional wall extending from a margin of the linear bead portion to the body of the flap, the transitional wall being configured to provide structural stiffness to the flap.

In some embodiments, the transitional wall is inclined relative to the plane of the valve flap.

In some embodiments, the elongate bead is substantially 'n' shaped when the flap is viewed in plan.

In some embodiments, the elongate bead is substantially 'D' shaped when the flap is viewed in plan.

In some embodiments, the elongate bead tapers inwardly towards the valve flap from a position distal from the hinge to a position adjacent the hinge, that is, the elongate bead projects further from the flap at a position distal from the hinge.

In some embodiments, the elongate bead tapers such that the elongate bead blends into the valve flap, at a position adjacent the hinge.

In some embodiments, the elongate bead comprises a top surface which contacts the inner wall of the elbow conduit when the flap is in the first position, and opposed side walls extending between the valve flap and the top surface, the top surface forming a sealing surface.

In some embodiments, at least one side wall is curved.

In some embodiments, the shape of one side wall is different from the shape of another side wall.

In some embodiments, the profile of one side wall is such that the side wall curves from the top surface into a plane of the valve flap.

In some embodiments, at least one side wall is substantially straight in profile so that that side wall extends in a straight line between the top surface and the valve flap.

In some embodiments, the straight side wall is inclined relative to the plane of the valve flap.

In some embodiments, the elongate bead is formed integrally with the valve flap.

In some embodiments, a plurality of beads are provided.

In some embodiments, the flap further comprises a flap support, the flap support being mounted on at least one of the elbow and the sleeve.

In some embodiments, the anti-asphyxiation valve further comprises an orientation feature arranged to facilitate mounting the support and the valve flap in the desired orientation relative to the elbow and sleeve.

In some embodiments, the orientation feature comprises a slot on one of the support and the elbow or sleeve and a protrusion on the other of the support and the elbow or sleeve, the protrusion being received in the slot when the support and the valve flap are mounted in the desired orientation.

In some embodiments, the air flow channel comprises two air flow channels.

In some embodiments, the sleeve further comprises a bump extending around an outer surface of the sleeve and a recess adjacent to the bump.

In some embodiments, the bump and the recess are adapted to receive a swiveling component incorporating a ridge to engage with the bump.

In some embodiments, the sealing surface is substantially straight when viewed from the side.

In some embodiments, the sealing surface comprises a curved or inclined portion when viewed from the side.

In some embodiments, the flap is configured such that the flap is biased away from the elbow towards the sleeve, at least when the flap is in the second position.

In some embodiments, the flap is configured such that the flap is biased away from the first position, at least when the flap is in the second position.

In some embodiments, the flap is biased away from the second position in a direction also away from the first position.

In some embodiments, the flap comprises a recess on an opposite face of the flap to the elongate bead.

In some embodiments, the recess is oblong.

In some embodiments, the recess is adjacent a hinge of the flap.

It will be appreciated that while air may be provided as respiratory assistance, this may be supplemented or replaced with other gases. Additionally or alternatively, medications may be provided to patients, such as via a nebulizer that is coupled to the patient interface or more typically, part of the breathing circuit feeding gases to the patient. As such references to "air" and even "gases" are not to be interpreted narrowly and the invention.

According to another aspect, there is provided a kit for a respiratory mask that comprises a connection housing emplaced over the patient's face when in use. The connection housing comprising a cushion end portion configured to engage a cushion housing for contacting the user's face, and a connection ring opposite the cushion end portion. The connection ring comprising a first connection-housing raised portion and a second connection-housing raised portion, each generally arcuate and extending away from the cushion end portion and each comprising at least one array of holes, extending along at least a part of the respective arc, configured to pass expiratory gas expired by the user to the ambient atmosphere when in use, and the first connection-housing raised portion and the second connection-housing raised portion defining therebetween a generally arcuate first connection-housing recessed portion and a generally arcuate second connection-housing recessed portion, wherein the first connection-housing recessed portion arc length is less than the second connection-housing recessed portion arc length. The kit also comprises an annular socket configured to pass inspiratory gas from a gas supply to the connection housing. The socket comprising a generally arcuate first socket raised portion and a generally arcuate second socket raised portion, wherein the first socket raised portion arc length is less than the second socket raised portion arc length, and the first socket raised portion and the second socket raised portion defining therebetween a generally arcuate first socket slot and a generally arcuate second socket slot. The socket is configured to removably engage with the connection housing as a unitary structure, such that, when engaged, the first socket raised portion unites with the first connection-housing recessed portion, the second socket raised portion unites with the second connection-housing recessed portion, the first connection-housing raised portion passes through the frame opening and unites with the first socket slot, and the second connection-housing raised portion passes through the frame opening and unites with the second socket slot, and such that, when in use, the inspiratory gas is passed to and the expiratory gas is passed from the respiratory mask via the unitary structure.

In some configurations, a swivel connector is configured to deliver inspiratory gas to a user. The swivel connector comprising a generally tubular first end and a truncated ball joint at a second end opposite the first end, the truncation defining a ball joint opening configured to pass the inspiratory gas therethrough, wherein the socket is configured to receive the truncated ball joint, when in use.

In some configurations, the first socket slot is opposite the second socket slot.

In some configurations, the first connection-housing raised portion is opposite the second connection-housing raised portion.

In some configurations, a frame is emplaced over the connection housing when in use. The frame comprising a frame housing comprising a frame opening and the socket, emplaced within the frame opening.

In some configurations, the frame housing is molded to the socket.

In some configurations, the first connection-housing raised portion and the second connection-housing raised portion each comprises generally L-shaped end portions at regions most distal from the cushion end portion, and the first socket raised portion and the second socket raised portion each comprises generally L-shaped side portions at regions adjacent the first socket slot and the second socket slot, the generally L-shaped end portions of the first connection-housing raised portion and the second connection-housing raised portion configured to seal with the generally L-shaped side portions of the first socket raised portion and the second socket raised portion.

In some configurations, the first connection-housing raised portion and the second connection-housing raised portion each comprises generally straight end portions at regions most distal from the cushion end portion, and the first socket raised portion and the second socket raised portion each comprises generally straight side portions at regions adjacent the first socket slot and the second socket slot, the generally straight end portions of the first connection-housing raised portion and the second connection-housing raised portion configured to seal with the generally straight side portions of the first socket raised portion and the second socket raised portion.

According to another aspect, there is provided a kit for a respiratory mask that comprises a connection housing emplaced over the patient's face when in use. The connection housing comprises a cushion end portion configured to engage a connection housing for contacting the user's face, and a connection ring opposite the cushion end portion. The connection ring comprises a first connection-housing raised portion and a second connection-housing raised portion, each generally arcuate and extending away from the cushion end portion and each comprising at least one array of holes, extending along at least a part of the respective arc, configured to pass expiratory gas expired by the user to the ambient atmosphere when in use, and the first connection-housing raised portion and the second connection-housing raised portion defining therebetween a generally arcuate first connection-housing recessed portion and a generally arcuate second connection-housing recessed portion, wherein the first connection-housing recessed portion arc length is less than the second connection-housing recessed portion arc length. The kit further comprises: a frame emplaced over the connection housing when in use. The frame comprises a frame housing comprising a frame opening defining a generally annular frame opening periphery, an annular socket configured to pass inspiratory gas from a gas supply to the connection housing, the socket within the frame housing in a concentric arrangement with the frame opening and spaced from the frame opening periphery by a generally arcuate first frame raised portion and by a generally arcuate second frame raised portion, wherein the first frame raised portion arc length is less than the second frame raised portion arc length, the spaces between the socket and the frame opening periphery comprising a first frame gap and a second frame gap. The frame is configured to removably engage with the connection housing as a unitary structure, such that, when engaged, the first frame raised portion unites with the first connection-housing recessed portion, the second frame raised portion unites with the second connection-housing recessed portion, the first connection-housing raised portion passes through the frame opening and unites with the first frame gap, and the second connection-housing raised portion passes through the frame opening and unites with the second frame gap, and such that, when in use, the inspiratory gas is passed to and the expiratory gas is passed from the respiratory mask via the unitary structure.

In some configurations, a swivel connector is configured to deliver inspiratory gas to a user, the swivel connector comprising a generally tubular first end and a truncated ball joint at a second end opposite the first end, the truncation defining a ball joint opening us configured to pass the inspiratory gas therethrough, wherein the socket is configured to receive the truncated ball joint, when in use.

In some configurations, the first socket slot is opposite the second socket slot.

In some configurations, the first connection-housing raised portion is opposite the second connection-housing raised portion.

In some configurations, the frame housing molded to the socket.

In some configurations, the first connection-housing raised portion and the second connection-housing raised portion each comprises generally L-shaped end portions at regions most distal from the cushion end portion, and the first socket raised portion and the second socket raised portion each comprises generally L-shaped side portions at regions adjacent the first socket slot and the second socket slot, the generally L-shaped end portions of the first connection-housing raised portion and the second connection-housing raised portion configured to seal with the generally L-shaped side portions of the first socket raised portion and the second socket raised portion.

In some configurations, the first connection-housing raised portion and the second connection-housing raised portion each comprises generally straight end portions at regions most distal from the cushion end portion, and the first socket raised portion and the second socket raised portion each comprises generally straight side portions at regions adjacent the first socket slot and the second socket slot, the generally straight end portions of the first connection-housing raised portion and the second connection-housing raised portion configured to seal with the generally straight side portions of the first socket raised portion and the second socket raised portion.

According to another aspect, there is provided a kit for a respiratory mask that comprises a swivel connector configured to deliver inspiratory gas to a user, the swivel connector comprising a generally tubular first end and a truncated ball joint at a second end opposite the first end, the truncation defining a ball joint opening configured to pass the inspiratory gas therethrough; a connection housing emplaced over the user's face when in use. The connection housing comprises a connection-housing opening configured, in use, to receive the inspiratory gas from the swivel connector and to receive an expiratory gas expired by the user, a cushion end portion, opposite the connection-housing opening, configured to engage a cushion housing for contacting the user's face. The kit also comprises a hollow socket including an enclosed interior region. The enclosed interior region comprises a connection-housing engagement region generally circumferential around a first end of the socket, the connection-housing engagement region engaging the connection-housing opening when in use and configured to receive therefrom the expiratory gas. The connection-housing engagement region comprises a first diameter, a ball-joint engagement region generally circumferential around a second end of the socket opposite the first end, the ball-joint engagement region engaging the truncated ball joint of the swivel connector when in use and configured to receive therefrom the inspiratory gas, the ball-joint engagement region comprising a second diameter less than the first diameter, a generally arcuate first bearing region and a generally arcuate second bearing region, each extending from the ball-joint engagement region toward the connection-housing engagement region, and each engaging the truncated ball joint of the swivel connector when in use, the first bearing region and the second bearing region defining therebetween a generally arcuate first expiratory region and a generally arcuate second expiratory region, a third diameter between the first expiratory region and the second expiratory region being greater than the second diameter and less than or equal to the first diameter, and each of the first expiratory region and the second expiratory region comprising at least one array of holes configured to pass therethrough the expiratory gas to the ambient atmosphere outside the socket. The first expiratory region arc length and the second expiratory region arc length are greater than the first bearing region arc length and the second bearing region arc length, and the frame is configured such that, when in use, the inspiratory gas is passed to the respiratory mask and the expiratory gas is passed from the respiratory mask to the ambient atmosphere via the socket.

In some configurations, a frame is emplaced over the connection housing when in use, the frame comprising a frame housing comprising a frame opening defining a generally annular frame opening periphery and the socket emplaced within the frame opening.

In some configurations, the frame housing is molded to the socket.

In some configurations, an interior of a length of the swivel connector including the second end, the entire truncated ball joint, and a region directly adjacent the truncated ball joint extending toward the first end has a continuous cylindrical or continuous tapered cylindrical profile.

In some configurations, an interior profile of the truncated ball joint generally tracks a corresponding exterior profile of the truncated ball joint.

In some configurations, the swivel connector and the socket are configured such that, when the truncated ball joint of the swivel connector is maximally rotated within the ball-joint engagement region of the socket in any direction, the second end of the swivel connector fully overhangs the ball-joint engagement region within the socket.

In some configurations, the swivel connector and the socket are configured such that, when the truncated ball joint of the swivel connector is at a neutral position within the ball-joint engagement region of the socket, the second end of the swivel connector fully overhangs the first bearing region and the second bearing region within the socket.

In some configurations, the exterior profile of the ball-joint engagement region, facing the ambient atmosphere, has a continuous slope.

In some configurations, the exterior profile of the ball-joint engagement region, facing the ambient atmosphere, has a first slope for a distance from the second end to a point and a second slope, different from the first slope, for the remaining length of the ball-joint engagement region from the point extending toward the first end.

According to another aspect, there is provided a respiratory mask assembly that comprises a cushion housing; a frame having an opening and an inner wall that defines the opening; a swivel elbow configured to provide inspiratory gas from a gas supply, the swivel elbow having a ball-joint; and an annular insert positioned within the opening of the frame. The annular insert comprises a cover portion; a collar portion extending away from a periphery of the cover portion in a direction towards a user when in use; an interior region defined by the cover portion and the collar portion, the interior region configured to pass inspiratory gas from the gas supply to the connection housing and receive expiratory gas expired by the user; a swivel elbow socket extending through the cover portion and configured to engage the ball-joint; and vent regions positioned on the cover portion and located on lateral sides of the swivel elbow socket, the vent regions having vent holes extending through the cover portion to pass expiratory gas received by the interior region to the ambient atmosphere when in use. The collar portion engages the inner wall of the opening such that the vent insert is positioned within the opening and connected to the frame, and the collar portion engages the cushion housing such that the cushion housing is attached to the frame via the vent insert.

In some configurations, the swivel elbow socket further comprises lateral socket sidewalls configured to engage the ball-joint, the lateral socket sidewalls extending away from the inner surface of the cover portion into the interior region of the annular insert. Central portions of the lateral socket sidewalls extend a greater distance into the interior region of the annular insert than end portions of the lateral socket sidewalls.

In some configurations, the swivel elbow socket further comprises lower socket sidewall configured to engage a lower portion of the ball-joint, the lower socket sidewall extending away from the inner surface of the cover portion into the interior region of the annular insert. End portions of the lower socket sidewall and end portions of the lateral sidewalls extend an equal distance into the interior region of the annular insert.

In some configurations, the swivel elbow socket further comprises upper socket sidewall configured to engage an upper portion of the ball-joint, the upper socket sidewall extending away from an inner surface of the cover portion into the interior region of the annular insert. Wherein end portions of the upper socket sidewall and end portions of the lateral sidewalls extend an equal distance into the interior region of the annular insert.

In some configurations, the end portions of the lateral sidewalls are integrally molded with an interior surface of the collar portion.

In some configurations, the collar portion is welded to the inner wall of the opening of the frame along a weld region.

In some configurations, each vent region expirates expired gas in a different draft direction.

In some configurations, the vent holes have a planar shape.

In some configurations, the annular insert further comprises a recessed portion positioned between a bottom portion of the ball-joint and the collar portion, wherein the recessed portion is configured to provide a shallow user accessible cavity to remove dirt accumulation within the interior region.

In some configurations, the ball-joint has a cut-away region on the bottom portion of the ball-joint that engages the recessed portion.

According to another aspect, there is provided a respiratory mask assembly that comprises a frame; a cushion housing; a swivel elbow configured to provide inspiratory gas from a gas supply, the swivel elbow having a ball-joint; and an annular socket attached to the frame. The annular socket comprises a cover portion; a collar portion extending away from an inner surface of the cover portion in a direction towards a user when in use, the collar portion connected to the cushion housing such that the cushion housing is attached to the frame; an interior region defined by the cover portion and the collar portion, the interior region configured to pass inspiratory gas from the gas supply to the connection housing and receive expiratory gas expired by the user; and a swivel elbow socket extending through the cover portion and configured to engage the ball-joint, the swivel elbow socket comprising lateral socket sidewalls configured to engage the ball-joint, the lateral socket sidewalls extending away from the inner surface of the cover portion into the interior region of the annular socket, wherein central portions of the lateral socket sidewalls extend a greater distance into the interior region of the annular socket than end portions of the lateral socket sidewalls.

In some configurations, the swivel elbow socket further comprises lower socket sidewall configured to engage a lower portion of the ball-joint, the lower socket sidewall extending away from the inner surface of the cover portion into the interior region of the annular socket. End portions of the lower socket sidewall and end portions of the lateral sidewalls extend an equal distance into the interior region of the annular socket.

In some configurations, the swivel elbow socket further comprises upper socket sidewall configured to engage an upper portion of the ball-joint, the upper socket sidewall extending away from an inner surface of the cover portion into the interior region of the annular socket. End portions of the upper socket sidewall and end portions of the lateral sidewalls extend an equal distance into the interior region of the annular socket.

In some configurations, the end portions of the lateral sidewalls are integrally molded with an interior surface of the collar portion.

In some configurations, a recessed portion positioned between a bottom portion of the ball-joint and the collar portion. The recessed portion is configured to provide a shallow user accessible cavity to remove dirt accumulation within the interior region.

In some configurations, the ball-joint has a cut-away region on the bottom portion of the ball-joint that engages the recessed portion.

In some configurations, the annular socket is configured to be inserted into and removably fastened to the frame.

In some configurations, the annular socket further comprises at least one vent region having vent holes extending through the cover portion to pass expiratory gas received by the interior region to the ambient atmosphere when in use.

In some configurations, each vent region expirates expired gas in a different draft direction.

In some configurations, the vent holes have a planar shape.

According to another aspect, there is provided a respiratory mask assembly that comprises a frame; a cushion; a connection housing having the cushion attached to a first end; and a connection ring attached to a second end of the connection housing that is opposite the first end. The connection ring comprises a central opening extending through the connection ring; and at least one raised portion extending in a direction away from the connection housing and defining a portion of the central opening, the at least one raised portion comprising at least one least one array of holes. The respiratory mask assembly further comprises an annular socket attached to the frame. The annular socket comprises a tubular center portion extending through the frame and a gases supply; and at least one slot extending through the annular socket and positioned adjacent to the tubular center portion such that a portion of the at least one slot is defined by an outer surface of the tubular center portion. The connection ring is configured to be removably positioned over the outer surface of the tubular center portion such that the tubular center portion extends through the central opening of the connection ring, and the at least one raised portion is configured to be inserted into the at least one slot such that the at least one raised portion extends through the annular socket, and wherein an inner surface of the tubular socket defines a flow path to the cushion for inspiratory gas from a gas supply, and the outer surface of the tubular socket defines a flow path from the cushion to the at least one array of holes for expiratory gases to be vented to atmosphere.

In some configurations, a swivel connector is configured to deliver inspiratory gas to a user, the swivel connector comprises a generally tubular first end and a truncated ball joint at a second end opposite the first end, the truncation defining a ball joint opening configured to pass the inspiratory gas therethrough, wherein the tubular center portion is configured to receive the truncated ball joint, when in use.

In some configurations, the at least one slot further comprises a first socket slot and a second socket slot that is opposite a first socket slot, and the at least raised portion further comprises a first raised portion and a second raised portion that is opposite a first raised portion.

In some configurations, the annular socket and the frame are integrally formed.

In some configurations, the annular socket is configured to be inserted into and removably fastened to the frame.

In some configurations, the annular socket further comprises L-shaped end portions positioned on an end of the tubular center portion opposite the cushion; and the connection ring further comprises L-shaped side portions positioned on an end of the at least one raised portion opposite the cushion, wherein the L-shaped end portions engage the L-shaped side portions to form a seal between the annular socket and the connection ring.

In some configurations, the annular socket further comprises straight end portions positioned on an end of the tubular center portion opposite the cushion; and the connection ring further comprises straight side portions positioned on an end of the at least one raised portion opposite the cushion, wherein the straight end portions engage straight side portions to form a seal between the annular socket and the connection ring.

In some configurations, a respiratory mask assembly comprises a frame; a cushion; a connection housing attached to the cushion on a first end that is opposite to a second end; a swivel connector configured to provide inspiratory gas from a gas supply, the swivel connector having a truncated ball joint; and an annular socket attached to the frame and to the second end of the connection housing. The annular socket comprises a connection-housing engagement region configured to engage the connection housing; a ball-joint engagement region configured to engage the truncated ball joint of the swivel connector; and at least one venting region positioned between the connection-housing engagement region and the ball-joint engagement region, the at least one venting region having at least one array of holes extending through the at least one venting region and configured to pass therethrough expiratory gas to the ambient atmosphere outside the annular socket. An inner surface of the truncated ball joint defines a flow path to the cushion for inspiratory gas from a gas supply, and an outer surface of the truncated ball joint defines a flow path from the cushion to the at least one array of holes for expiratory gases to be vented to atmosphere.

In some configurations, the annular socket and the frame are integrally formed.

In some configurations, the annular socket is configured to be inserted into and removably fastened to the frame.

In some configurations, the swivel connector and the annular socket are configured such that, when the truncated ball joint is maximally rotated within the ball-joint engagement region in any direction, an open end of the truncated ball joint fully overhangs the ball-joint engagement region within the annular socket.

In some configurations, the swivel connector and the annular socket are configured such that, when the truncated ball joint is at a neutral position within the ball-joint engagement region of the annular socket, an open end of the truncated ball fully overhangs the ball-joint engagement region within the annular socket.

In some configurations, the annular socket further comprises a first bearing region and a second bearing region engaging opposite sides of the truncated ball joint, wherein the first and second bearing regions extend from the ball-joint engagement region in a direction toward the cushion such that recessed regions are formed between the first and second bearing regions.

In some configurations, venting regions are positioned within the recessed regions.

In some configurations, flow paths to the venting regions are defined by the first and second bearing regions, an inner surface of the annular socket, and an outer surface of the truncated ball joint.

According to another aspect, there is provided a respiratory mask assembly that comprises a cushion including a connection ring and a frame. The connection ring comprises an opening; and at least one raised portion extending in a direction away from the cushion and defining a portion of the opening, the at least one raised portion comprising at least one exhaust hole. The frame comprises a central conduit extending through the frame and configured to receive inspiratory gas from a gases supply; at least one slot extending through the frame; and an annular collar extending from a patient-facing side of the frame and surrounding the central conduit and the at least one slot. The connection ring is configured to be removably attachable to the annular collar, and the at least one raised portion is configured to extend into the at least one slot. When attached, the at least one raised portion and the central conduit at least in part define a flow path from the cushion to the at least one exhaust hole for expiratory gases to be vented to atmosphere.

In some configurations, the at least one slot is position adjacent the central conduit.

In some configurations, the cushion further comprises a connection housing positioned between the cushion and the connection ring such that the cushion is attached to a first end and the connection ring is attached to a second end.

In some configurations, a portion of the at least one slot is defined by an outer surface of the central conduit.

In some configurations, when attached, the central conduit at least in part defines a flow path to the cushion for inspiratory gas from a gas supply.

In some configurations, further comprises a swivel connector configured to deliver inspiratory gas to a user, the swivel connector comprising a generally tubular first end and a truncated ball joint at a second end opposite the first end, the truncation defining a ball joint opening configured to pass the inspiratory gas therethrough, wherein the central conduit is configured to receive the truncated ball joint, when in use.

In some configurations, the at least one slot further comprises a first socket slot and a second socket slot that is opposite a first socket slot, and the at least raised portion further comprises a first raised portion and a second raised portion that is opposite a first raised portion.

In some configurations, the annular collar and the frame are integrally formed.

In some configurations, the annular collar is configured to be inserted into and removably fastened to the frame.

In some configurations, the central conduit further comprises L-shaped end portions positioned on an end of the tubular center portion opposite the cushion. The connection ring further comprises L-shaped side portions positioned on an end of the at least one raised portion opposite the cushion. The L-shaped end portions engage the L-shaped side portions to form a seal between the central conduit and the connection ring.

In some configurations, the central conduit further comprises straight end portions positioned on an end opposite the cushion; and the connection ring further comprises straight side portions positioned on an end of the at least one raised portion opposite the cushion, wherein the straight end portions engage straight side portions to form a seal between the central conduit and the connection ring.

According to another aspect, there is provided a respiratory mask assembly that comprises a frame; a cushion; a connection housing attached to the cushion on a first end that is opposite to a second end; a swivel connector configured to provide inspiratory gas from a gas supply, the swivel connector having a truncated ball joint; and an annular socket attached to the frame and to the second end of the connection housing. The annular socket comprises a connection-housing engagement region configured to engage the connection housing; a ball-joint engagement region configured to engage the truncated ball joint of the swivel connector; and at least one venting region positioned between the connection-housing engagement region and the ball-joint engagement region, the at least one venting region having at least one array of holes extending through the at least one venting region and configured to pass therethrough expiratory gas to the ambient atmosphere outside the annular socket. An inner surface of the truncated ball joint defines a flow path to the cushion for inspiratory gas from a gas supply. An outer surface of the truncated ball joint defines a flow path from the cushion to the at least one array of holes for expiratory gases to be vented to atmosphere.

In some configurations, the annular socket and the frame are integrally formed.

In some configurations, the annular socket is configured to be inserted into and removably fastened to the frame.

In some configurations, the swivel connector and the annular socket are configured such that, when the truncated ball joint is maximally rotated within the ball-joint engagement region in any direction, an open end of the truncated ball joint fully overhangs the ball-joint engagement region within the annular socket.

In some configurations, the swivel connector and the annular socket are configured such that, when the truncated ball joint is at a neutral position within the ball-joint engagement region of the annular socket, an open end of the truncated ball fully overhangs the ball-joint engagement region within the annular socket.

In some configurations, the annular socket further comprises a first bearing region and a second bearing region engaging opposite sides of the truncated ball joint, wherein the first and second bearing regions extend from the ball-joint engagement region in a direction toward the cushion such that recessed regions are formed between the first and second bearing regions.

In some configurations, venting regions are positioned within the recessed regions.

In some configurations, flow paths to the venting regions are defined by the first and second bearing regions, an inner surface of the annular socket, and an outer surface of the truncated ball joint.

According to another aspect, there is provided a respiratory mask assembly that comprises a frame; a cushion; a swivel connector having a first end configured to receive inspiratory gas from a gas supply and a second end; and an annular socket attached to the frame. The annular socket comprises a cushion engagement region configured to engage the cushion; a swivel connector engagement region configured to engage the second end of the swivel connector, and comprising a first bearing region, a second bearing region, and recessed regions formed between the first and second bearing regions; and at least one venting region positioned between the cushion engagement region and the swivel connector engagement region, wherein the at least one venting region is adjacent recessed regions.

According to another aspect, there is provided a respiratory mask assembly that comprises a frame; a cushion; a swivel connector having a first end configured to receive inspiratory gas from a gas supply and a second end; and an annular socket attached to the frame. The annular socket comprises a cushion engagement region configured to engage the cushion; a swivel connector engagement region configured to engage the second end of the swivel connector, and comprising a first bearing region, a second bearing region, and recessed regions formed between the first and second bearing regions; and at least one venting region positioned between the cushion engagement region and the swivel connector engagement region, wherein the at least one venting region is adjacent recessed regions.

In some configurations, an inner surface of the swivel connector defines an inspiratory flow path to the cushion for inspiratory gas from a gas supply.

In some configurations, the swivel connection is a truncated ball joint.

In some configurations, an outer surface of the swivel connector defines at least in part an expiratory flow path from the cushion to the at least one array of holes for expiratory gases to be vented to atmosphere.

In some configurations, the at least one venting region further comprises at least one array of holes extending through the at least one venting region and configured to pass therethrough expiratory gas to the ambient atmosphere outside the annular socket.

In some configurations, the annular socket and the frame are integrally formed.

In some configurations, the annular socket is configured to be inserted into and removably fastened to the frame.

In some configurations, the swivel connector and the annular socket are configured such that, when the truncated ball joint is maximally rotated within the ball-joint engagement region in any direction, an open end of the truncated ball joint fully overhangs the ball-joint engagement region within the annular socket.

In some configurations, the swivel connector and the annular socket are configured such that, when the truncated ball joint is at a neutral position within the ball-joint engagement region of the annular socket, an open end of the truncated ball fully overhangs the ball-joint engagement region within the annular socket.

In some configurations, the annular socket further comprises a first bearing region and a second bearing region engaging opposite sides of the truncated ball joint, wherein the first and second bearing regions extend from the ball-joint engagement region in a direction toward the cushion such that recessed regions are formed between the first and second bearing regions.

In some configurations, venting regions are positioned within the recessed regions.

In some configurations, flow paths to the venting regions are defined by the first and second bearing regions, an inner surface of the annular socket, and an outer surface of the truncated ball joint.

One or more embodiments involve a headgear structure having at least portions made from a three-dimensional (3D) spacer fabric.

In a first aspect, the present disclosure relates to a headgear for use with a respiratory mask, comprising a component formed from two layers of 3D fabric folded from a sheet or tube of 3D fabric to have a folded edge, the folded edge forming an edge of the headgear.

In some embodiments, the component is a back panel, the headgear comprising a lower strap and an upper strap extending from the back panel to connect to the mask, the folded edge forming an edge of the back panel.

In some embodiments, the folded edge forms a bottom edge of the back panel.

In some embodiments, the bottom edge of the back panel extends across the back of a user's neck in use.

In some embodiments, the two layers of 3D fabric are joined together by bonding, stitching or welding at other edges of the component.

In some embodiments, the two layers of 3D fabric are stitched together at an edge to have a seamed edge, the seamed edge forming an edge of the headgear.

In some embodiments, the seamed edge is at an edge of the component opposite to the folded edge of the component.

In some embodiments, the folded edge is a first folded edge and the 3D fabric comprises a second folded edge at an edge of the component opposite to the first folded edge.

In some embodiments, the folded edge is a first folded edge and the 3D fabric comprises a second folded edge at an edge of the component opposite to the first folded edge, and a join in one of the two layers of 3D fabric.

In some embodiments, the join is in an outer layer of the 3D fabric.

In some embodiments, the join is a welded joint.

In some embodiments, the two layers of 3D fabric are joined together by bonding, stitching or welding at all other edges of the component.

In some embodiments, the 3D fabric has a right side and a wrong side, and is folded so that the wrong side of the fabric is on the inside of the component and the right side of the fabric on the outside of the component.

In some embodiments, the back panel comprises a perimeter portion formed from a material suitable for use in headgear such as a foam material or a fabric material, one or more edges of the two layers of 3D fabric attached to the perimeter portion.

In some embodiments, the perimeter portion extends around the two layers of 3D fabric from one end of the folded edge to the other end of the folded edge.

In some embodiments, the back panel comprises a said perimeter portion along each lateral edge of the back panel.

In some embodiments, the material of the perimeter portion extends into and forms at least part of a strap of the headgear.

In some embodiments, one or more edges of the two layers of 3D fabric other than the folded edge are attached to the perimeter portion by bonding, stitching or welding.

In some embodiments, the two layers of 3D fabric are welded or bonded together to the perimeter portion along each lateral edge of the two layers of 3D fabric.

In some embodiments, the folded edge is curved.

In some embodiments, the 3D fabric is wrapped around or covers another component of the headgear.

In some embodiments, the headgear comprises a back panel formed from a material suitable for use in headgear such as a foam material or a fabric material, and the 3D fabric is wrapped around or covers the material.

In some embodiments, the 3D fabric has a folded edge at an upper and at a lower edge of the back panel, and a join in one layer of the two layers of 3D fabric.

In some embodiments, the join is in an outer layer of the two layers of 3D fabric.

In some embodiments, the join is a welded joint.

In some embodiments, the join in the layer of 3D fabric joins the 3D fabric to the material underlying the layer of 3D fabric.

In some embodiments, the headgear comprises a non-bonding or non-welding material or film between the material underlying the 3D fabric and either one or both layers of 3D fabric, the non-bonding or non-welding film or material preventing one or both layers of the 3D fabric from attaching to the underlying material of the headgear.

In some embodiments, the headgear comprises a non-bonding or non-welding material or film between the underlying material an inner layer of the 3D fabric which prevents the join in the outer layer of 3D fabric from joining the underlying material and the inner layer of 3D fabric In some embodiments, the component is a strap of the headgear, for example a lower strap, or upper strap, or top strap.

In some embodiments, a join between layers of the 3D fabric or within a layer of the 3D fabric is made with the fabric turned wrong side out, the fabric then turned right side out so that the join is located inside the two layers of 3D fabric.

In some embodiments, one or more edges of the two layers of 3D fabric other than the folded edge are welded to a portion of the headgear, wherein one of the two layers of 3D fabric overlaps an edge of the other one of the two layers of 3D fabric so that the weld includes a first region formed from both of the two layers of 3D fabric and the portion of the headgear, and a second region formed from one of the two layers of 3D fabric and the portion of the headgear.

In some embodiments, the component is a back panel, the headgear comprising a lower strap and an upper strap extending from the back panel to connect to the mask, the folded edge forming an edge of the back panel, and wherein the portion of the headgear is a perimeter portion of the back panel formed from a material suitable for use in headgear such as a foam material or a fabric material.

In some embodiments, in the weld an internal layer of the two layers of 3D fabric is located between the portion of the headgear and an external layer of the two layers of 3D fabric, and wherein the external layer of 3D fabric overlaps the edge of the internal layer of 3D fabric.

In some embodiments, in use the external layer of the two layers of 3D fabric is an outer layer of the two layers of 3D fabric that faces away from the user's head in use.

In another aspect, the present disclosure relates to a headgear for use with a respiratory mask, comprising a component formed from two layers of 3D fabric, wherein one or more edges of the two layers of 3D fabric are welded to a portion of the headgear, one of the two layers of 3D fabric overlapping an edge of the other one of the two layers of 3D fabric so that the weld includes a first region formed from both of the two layers of 3D fabric and the portion of the headgear, and a second region formed from one of the two layers of 3D fabric and the portion of the headgear.

In some embodiments, a headgear according to the second aspect comprises the features of any one or more of the above statements in relation to the first aspect.

In another aspect, the present disclosure relates to a headgear for use in combination with a respiratory mask where the headgear is at least partially constructed from a 3D fabric, and wherein welding is used to seal edges and/or provide structure and/or define cushioned regions of the headgear.

In some embodiments, an over-moulding is used to finish and seal the edges.

In some embodiments, a reinforcement member is applied to at least one region of the headgear.

In some embodiments of the above aspects of the present disclosure, the 3D fabric is a 3D spacer fabric.

In another aspect, the present disclosure relates to a headgear for use with a respiratory mask. The headgear includes a back panel formed from 3D fabric and having a top edge, a bottom edge and lateral edges, the top edge having a length greater than the bottom edge, the lateral edges connecting the top edge to the bottom edge. The headgear also includes perimeter portions formed from a foam laminate material and comprising straps to connect to the mask; and stitching fastening the lateral edges of the back panel to the perimeter portions along a join. The lateral edges and the top edge form an angle $\theta$, and the angle $\theta$ is between 70 and 120 degrees.

In some embodiments, the angle $\theta$ is between 85 and 105 degrees.

In some embodiments, the angle $\theta$ is approximately 90 degrees.

In some embodiments, the top edge is curved.

In some embodiments, the back panel is formed from a folded and sewn sheet of 3D fabric, the back panel further comprising a folded edge opposite a seam allowance.

In some embodiments, lateral edges of the seam allowance are positioned laterally inward of the lateral edges of the back panel.

In some embodiments, the lateral edges of the seam allowance are positioned laterally inward of the stitching.

In some embodiments, a distance between the lateral edges of the seam allowance is less than a widest distance between the lateral edges of the back panel.

In some embodiments, a distance between the lateral edges of the seam allowance is less than a width of the top edge.

In some embodiments, a width and length of the stitching is consistent along the length of the join.

In some embodiments, the stitching is formed by utilizing back and forth stitching.

In some embodiments, the stitching is formed by utilizing zigzag stitching.

In some embodiments, the perimeter portions further includes an upper strap edge connected to an upper strap of the perimeter portion; and a receiving edge that engages with the lateral edge of the back panel. The upper strap edge and the receiving edge form a corner having an angle $\beta$, and the angle $\beta$ is greater than 70 degrees.

In some embodiments, the angle $\beta$ is approximately 90 degrees.

In some embodiments, a convex region of the lateral edges is connected to the top edge.

In some embodiments, a concave region of the lateral edges is connected to the bottom edge, wherein the convex region and the concave region are connected at an inflection point.

In some embodiments, the inflection point is located below the seam allowance.

In some embodiments, a linear region of the lateral edges is connected to the bottom edge. The convex region and the linear region are connected at a tangent point.

In some embodiments, the tangent point is located below the seam allowance.

In some embodiments, the tangent point is located below the seam allowance.

In another aspect, the present disclosure relates to a headgear for use with a respiratory mask. The headgear includes a back panel formed from 3D fabric and having a top edge, a bottom edge and lateral edges, the top edge having a length greater than the bottom edge, the lateral edges connecting the top edge to the bottom edge; perimeter portions formed from a foam laminate material and comprising straps to connect to the mask; and stitching fastening the lateral edges of the back panel to the perimeter portions along a join. The lateral edges extend laterally outward from the top edge.

In some embodiments, the stitching is formed by utilizing back and forth stitching.

In some embodiments, the stitching is formed by utilizing zigzag stitching.

In some embodiments, the lateral edges extend laterally outward from the bottom edge.

In some embodiments, the top edge is curved.

In some embodiments, the back panel is formed from a folded and sewn sheet of 3D fabric, the back panel further comprising a folded edge opposite a seam allowance.

In some embodiments, lateral edges of the seam allowance are positioned laterally inward of the lateral edges of the back panel.

In some embodiments, the lateral edges of the seam allowance are positioned laterally inward of the stitching.

In some embodiments, a distance between the lateral edges of the seam allowance is less than a widest distance between the lateral edges of the back panel.

In some embodiments, a distance between the lateral edges of the seam allowance is less than a width of the top edge.

In some embodiments, a width and length of the stitching is consistent along the length of the join.

In some embodiments, the perimeter portions further includes an upper strap edge connected to an upper strap of the perimeter portion; and a receiving edge that engages with the lateral edge of the back panel. The upper strap edge and the receiving edge form a corner having an angle $\beta$, and the angle $\beta$ is greater than 70 degrees.

In some embodiments, the angle $\beta$ is approximately 90 degrees.

In some embodiments, a convex region of the lateral edges is connected to the top edge.

In some embodiments, a concave region of the lateral edges is connected to the bottom edge, wherein the convex region and the concave region are connected at an inflection point.

In some embodiments, the inflection point is located below the seam allowance.

In some embodiments, a linear region of the lateral edges is connected to the bottom edge, wherein the convex region and the linear region are connected at a tangent point.

In some embodiments, the tangent point is located below the seam allowance.

In another aspect, the present disclosure relates to a headgear for use with a respiratory mask. The headgear includes a panel formed from a first material having a first set of mechanical properties, the panel comprising a top edge, a bottom edge and lateral edges, the top edge having a length greater than the bottom edge, the lateral edges connecting the top edge to the bottom edge; perimeter portions formed from a second material having a second set of mechanical properties and comprising straps to connect to the mask, wherein the second material and the second set of mechanical properties are more rigid than the first material and the first set of mechanical properties; and stitching fastening the lateral edges of the back panel to the perimeter portions along a join. The lateral edges and the top edge form an angle θ, and the angle θ is between 70 and 120 degrees.

In some embodiments, the angle θ is between 85 and 105 degrees.

In some embodiments, the angle θ is approximately 90 degrees.

In some embodiments, the top edge is curved.

In some embodiments, the back panel is formed from a folded and sewn sheet of 3D fabric, the back panel further comprising a folded edge opposite a seam allowance.

In some embodiments, lateral edges of the seam allowance are positioned laterally inward of the lateral edges of the back panel.

In some embodiments, the lateral edges of the seam allowance are positioned laterally inward of the stitching.

In some embodiments, a distance between the lateral edges of the seam allowance is less than a widest distance between the lateral edges of the back panel.

In some embodiments, a distance between the lateral edges of the seam allowance is less than a width of the top edge.

In some embodiments, a width and length of the stitching is consistent along the length of the join.

In some embodiments, the stitching is formed by utilizing back and forth stitching.

In some embodiments, the stitching is formed by utilizing zigzag stitching.

In some embodiments, the perimeter portions further includes an upper strap edge connected to an upper strap of the perimeter portion; and a receiving edge that engages with the lateral edge of the back panel. The upper strap edge and the receiving edge form a corner having an angle β, and the angle β is greater than 70 degrees.

In some embodiments, the angle β is approximately 90 degrees.

In some embodiments, a convex region of the lateral edges is connected to the top edge.

In some embodiments, a concave region of the lateral edges is connected to the bottom edge, wherein the convex region and the concave region are connected at an inflection point.

In some embodiments, the inflection point is located below the seam allowance.

In some embodiments, a linear region of the lateral edges is connected to the bottom edge, wherein the convex region and the linear region are connected at a tangent point.

In some embodiments, the tangent point is located below the seam allowance.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 23A is a perspective view of a configuration of a connector and elbow assembly.

FIG. 23B is a perspective view of the connector and elbow assembly of FIG. 23A with a portion removed.

FIG. 41A shows a front view of a respiratory mask assembly with a vented insert having an integrated elbow socket.

FIG. 41B shows a rear view of the respiratory mask assembly with a vented insert having an integrated elbow socket of FIG. 41A.

FIG. 41C shows a side view of the respiratory mask assembly with a vented insert having an integrated elbow socket of FIG. 41A.

FIG. 72 shows an alternative headgear arrangement having an alternative lateral edge arrangement.

FIG. 73 shows another alternative headgear arrangement having an alternative lateral edge arrangement.

FIG. 74 shows the alternative headgear arrangement of FIG. 73 with dimensions of the seam allowance relative to the lateral edges of the back panel.

Figure 1:
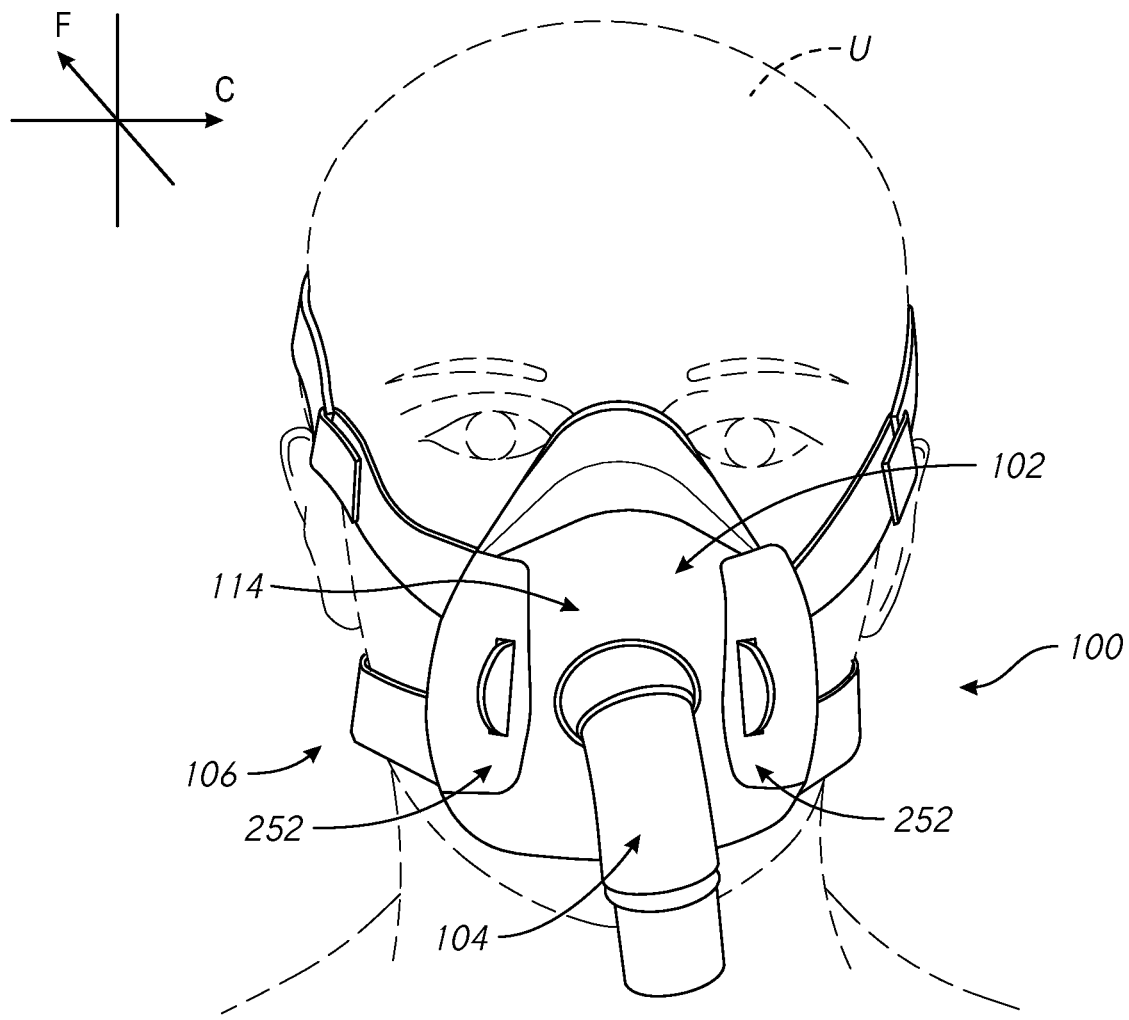
FIG. 1 is front view of a user wearing an interface that is arranged and configured in accordance with certain features, aspects and advantages of the present invention.

In the drawings, the first digit of each reference number typically indicates the figure in which the element first appears. Throughout the drawings, reference numbers may be reused to indicate correspondence between referenced elements. Nevertheless, use of different numbers does not necessarily indicate a lack of correspondence between elements. And, conversely, reuse of a number does not necessarily indicate that the elements are the same.

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Details regarding several illustrative embodiments for implementing the apparatuses and methods described herein are now described with reference to the figures. In the following description, numerous specific details are set forth to provide a more thorough understanding of various embodiments of the present disclosure. It will be apparent to one of skill in the art, however, that the systems and methods of the present disclosure may be practiced without one or more of these specific details.

In order to facilitate an understanding of the systems and methods discussed herein, a number of terms are defined below. The terms defined below, as well as other terms used herein, should be construed broadly to include, without limitation, the provided definitions, the ordinary and customary meanings of the terms, and/or any other implied meanings for the respective terms. Thus, the definitions below do not limit the meaning of these terms, but only provide example definitions.

In connection with dimensions, the term approximately should be understood to mean within standard manufacturing tolerances or deviations that result and/or can be expected during manufacturing. In addition, the term approximately can extend up to and including dimensions that would round to the stated value.

The term generally should be understood to mean "for the most part." For example, a component that is generally cylindrical need not necessarily conform to a perfect cylinder (a surface or solid bounded by two parallel planes and generated by a straight line moving parallel to the given planes and tracing a curve bounded by the planes and lying in a plane perpendicular or oblique to the given planes). Rather, a generally cylindrical component should be understood to be cylinder-like in that it has a circular profile along a cross-section and an elongate longitudinal profile.

The term respiratory mask is a broad term and is to be given its ordinary and customary meaning to a person of ordinary skill in the art (that is, it is not to be limited to a special or customized meaning) and includes, without limitation, various user interfaces for NIV and CPAP.

The term seal refers to a substantially, but not necessarily perfectly, air-tight closure. For example, a cushion can seal against a user's face in a way that allows the bulk flow of gas to be directed to and from the user via the cushion, while potentially allowing a small amount of gas to escape from between the cushion and the user's face in a way that does not interrupt the bulk flow.

The term top refers to a direction proximal the nose of a user when in use.

The term bottom refers to a direction proximal the lower lip of a user when in use.

The term static noise refers to ambient noise from the respiratory system when in use.

The term dynamic noise refers to additional noise from the respiratory system when in use, beyond the ambient noise, from breathing caused by increases and decreases in air flow and velocity.

The term periphery refers to the limits or edge of an area or object. For an annular (ring-shaped) object, such as a hollow cylinder, the outer periphery refers to the outermost limits or edge of the hollow cylinder, facing the ambient environment. The inner periphery refers to the inner limits or edge of the hollow cylinder, facing the central bore. For a solid object with an internal hole, the periphery of the hole refers to the limits or edge of the hole along the solid object, facing toward the center of the hole.

Figure 2:
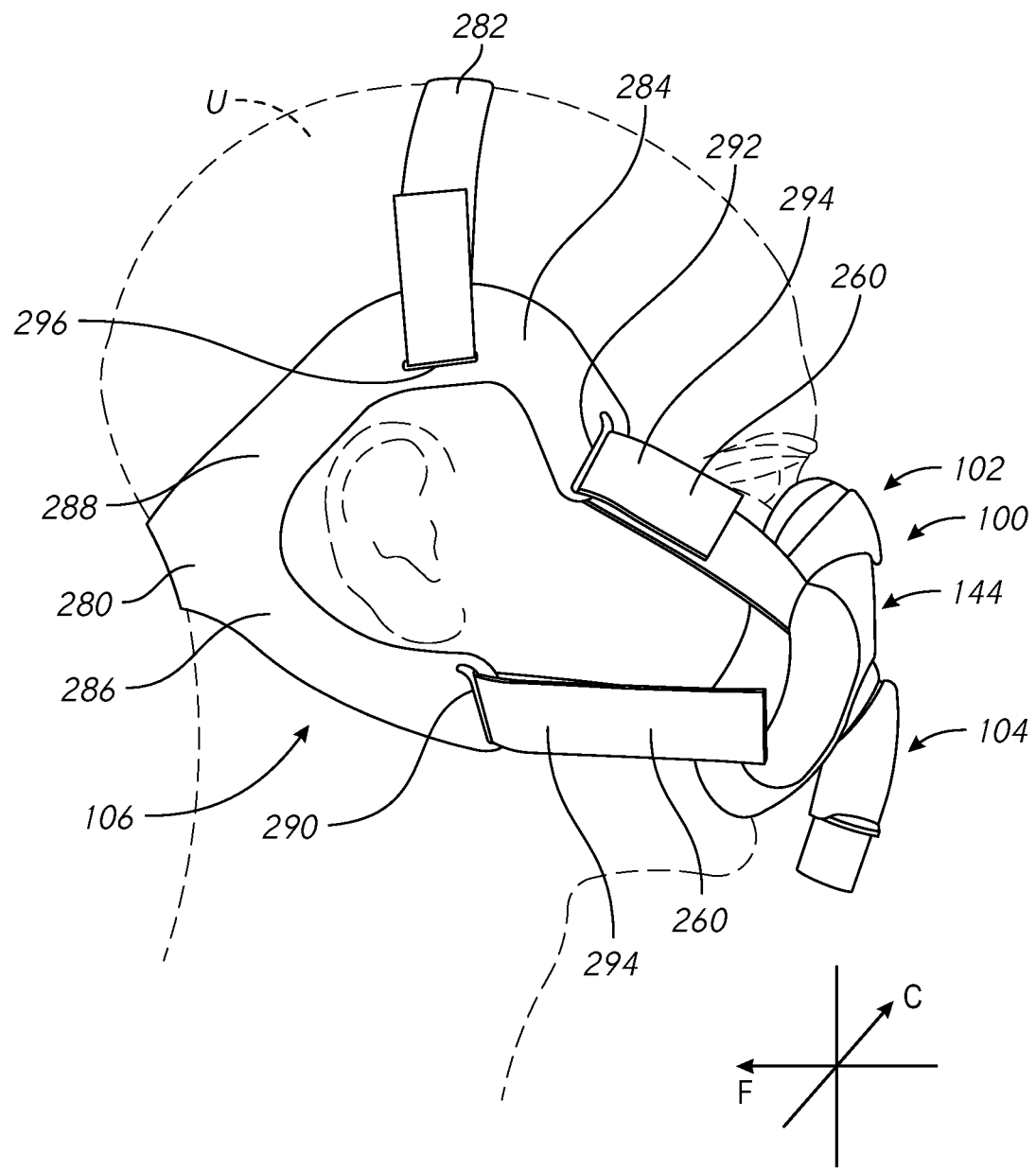
FIG. 2 is a side view of a user wearing the interface of FIG. 1.

With reference initially to FIGS. 1 and 2, an interface 100 is shown in position on a user U. The interface 100 comprises an interface that can be used in the field of respiratory therapy. The interface 100 has particular utility with forms of positive pressure respiratory therapy. For example, the interface 100 can be used for administering continuous positive airway pressure ("CPAP") treatments. In addition, the interface 100 can be used with variable positive airway pressure ("VPAP") treatments and bi-level positive airway pressure ("BiPAP") treatments. The interface can be used with any suitable CPAP system.

The interface 100 can comprise any suitable mask configuration. For example, certain features, aspects and advantages of the present invention can find utility with nasal masks, full face masks, oronasal masks or any other positive pressure mask. The illustrated mask is a full face mask. The illustrated interface 100 generally comprises a mask assembly 102, a connection port assembly 104 and a headgear assembly 106.

Figure 3:
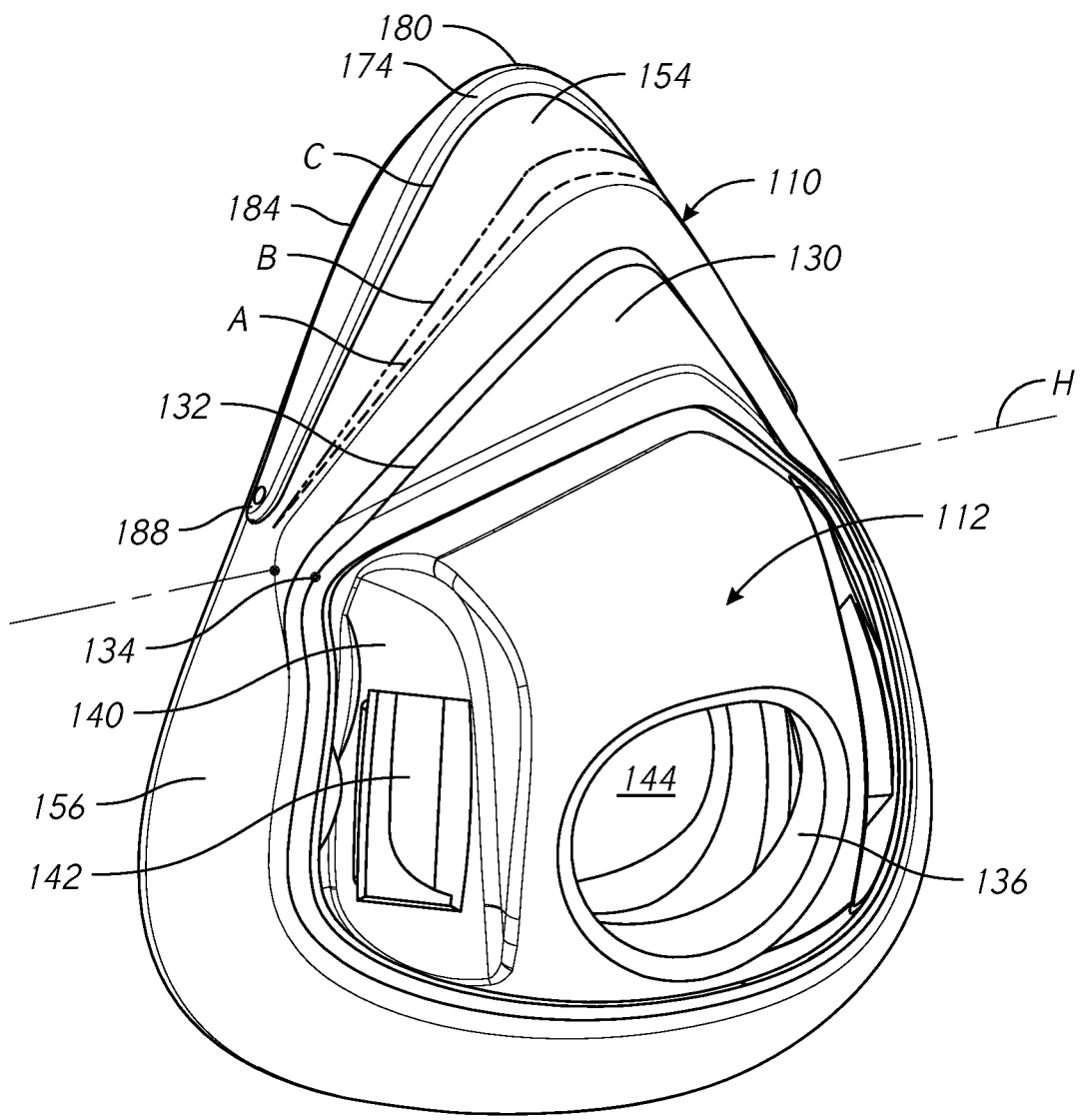
FIG. 3 is a perspective view of a mask seal and mask seal clip of the interface of FIG. 1.
Figure 4:
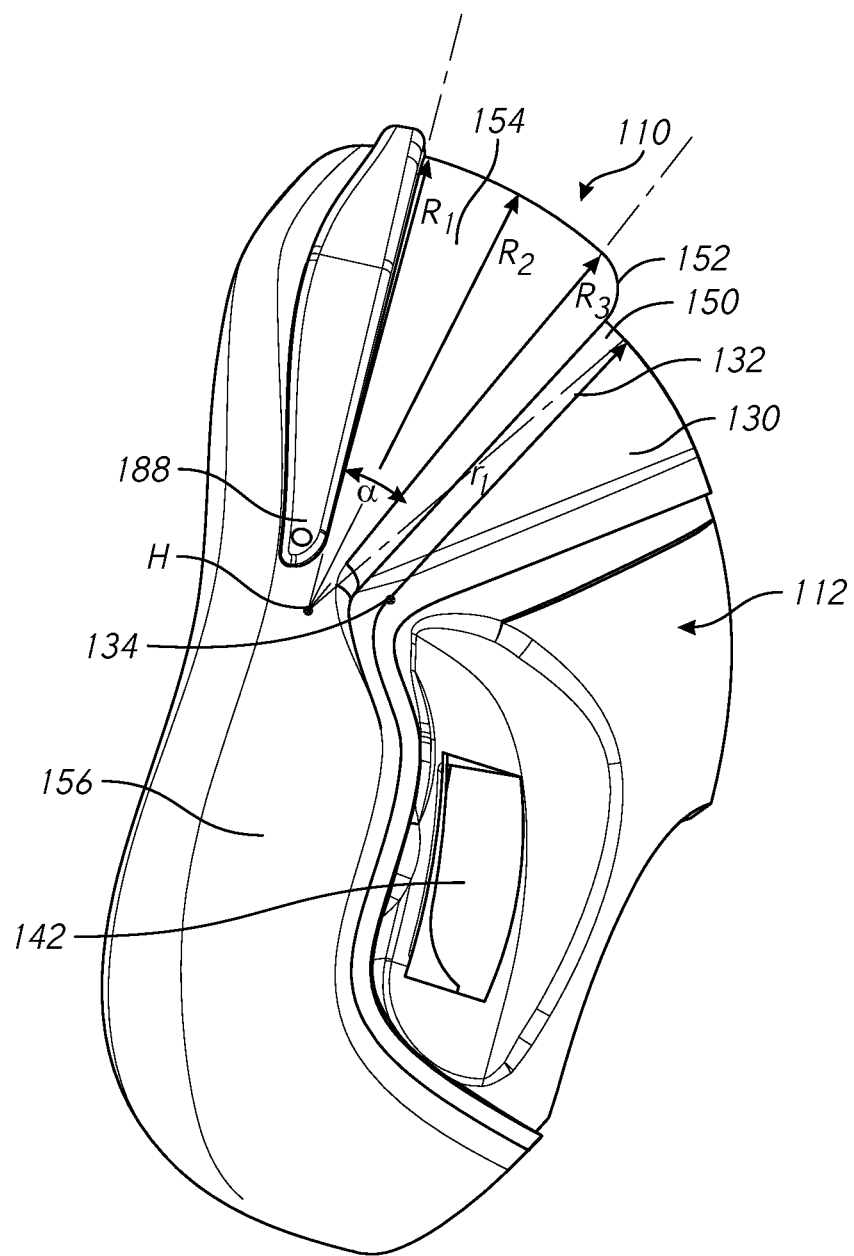
FIG. 4 is a side view of the mask seal and mask seal clip of FIG. 3.

With reference to FIGS. 3 and 4, the mask assembly 102 generally comprises a mask seal 110, which can include a mask seal clip 112, and a mask base 114. The mask seal clip 112 preferably connects the mask seal 110 to the mask base 114. While the illustrated mask seal 110 and mask seal clip 112 are formed separately and secured together, in some configurations, the mask seal 110 and the mask seal clip 112 can be integrated into a single component. In some configurations, the mask seal 110 is overmolded onto the mask seal clip 112.

With reference to FIG. 3, the mask seal clip 112 is relatively more rigid, stiffer or more inflexible than the mask seal 110. In some configurations, the mask seal clip 112 is formed of a polycarbonate material. In some configurations, at least a portion of the mask seal clip 112 is formed of a polycarbonate or other rigid or semi-rigid material. In some configurations, the mask seal clip 112 is formed at least partially of silicone or another suitable material. In such configurations, at least the silicone portion of the mask seal clip 112 may be formed to be relatively thicker compared to the more flexible portions of the mask seal 110. The mask seal clip 112 provides structural support to the mask seal 110 in the illustrated configuration.

The illustrated mask seal also comprises a generally central passage 144 that is defined by a wall 146. In the illustrated configuration, the wall 146 generally encloses the passage 144. Preferably, the wall 146 is generally cylindrical in configuration and extends through the wall 126. Other configurations are possible.

With reference to FIG. 4, the mask seal clip 112 preferably is arranged such that it is generally flush with an inner rim 150 of the mask seal 110. In the illustrated configuration, the mask seal 110 comprises a relatively small radius portion 152 that joins an upper portion 154. The upper portion 154 of the mask seal 110 is configured to extend over a nasal region of the user. In some configurations, the upper portion 154 is configured to extend over a nasal bridge region of the user U.

Figure 10:
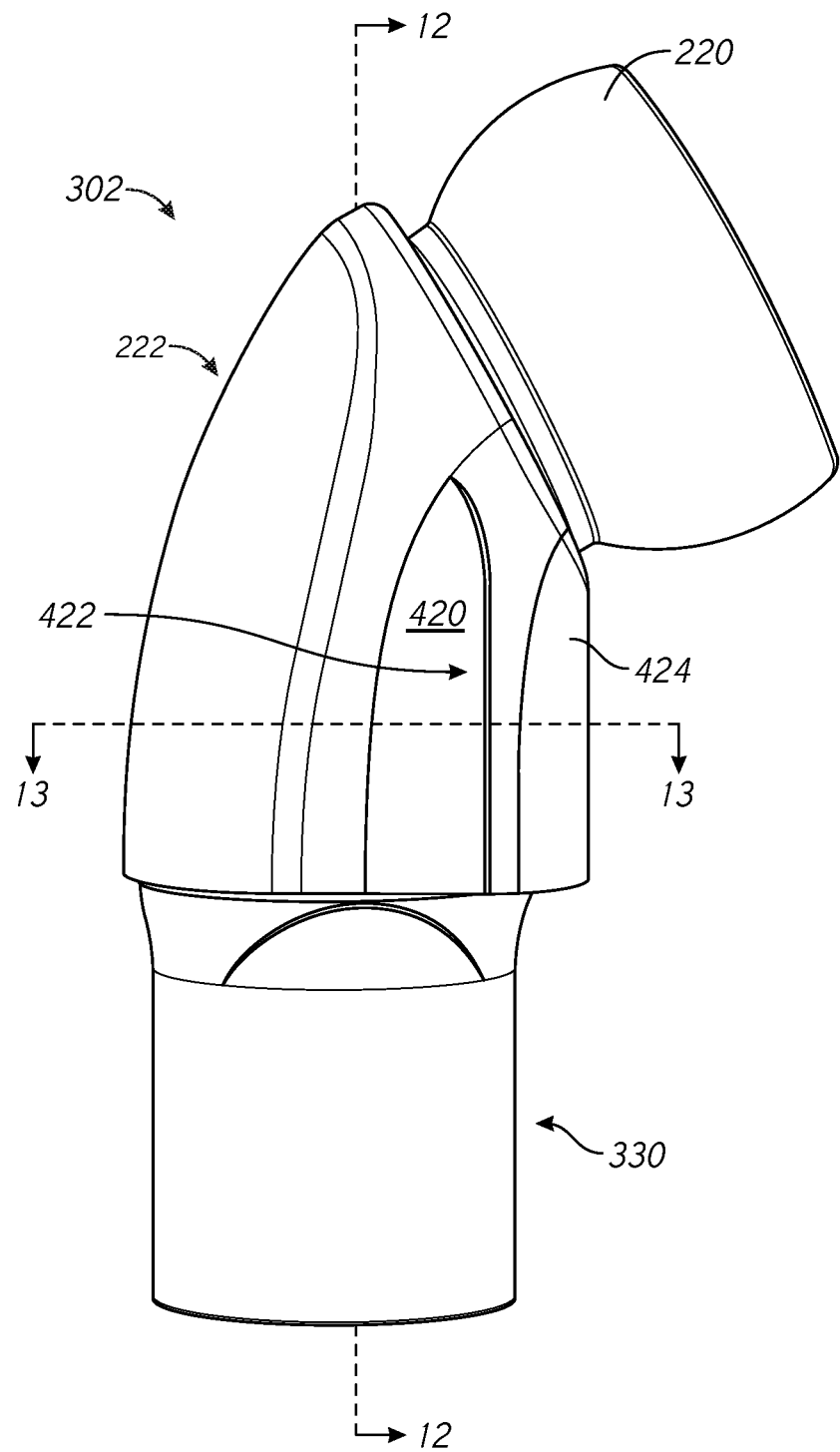
FIG. 10 is a side view of another configuration of an elbow assembly.

The upper portion 154 is connected with a lower portion 156 of the seal member 110. The lower portion 156 extends laterally outward from the mask seal clip 112. In addition, the lower portion 156 wraps rearward and inward, as shown in FIG. 4. Together, on a proximal side of the full face mask assembly 102, the upper portion 154 and the lower portion 156 combine to define a face contacting flange 160, which is shown in FIG. 10. The face contacting flange 160 is configured to underlie a lower lip of the user, extend along the outside of the mouth, extend upward along the cheekbones and extend across the bridge of the nose of the user. Thus, the illustrated face contacting flange 160 defines a generally tear-drop shaped opening 162. When the mask assembly 102 is seated on the face of the user, the flange 160 will lie flat over the bridge of the nose, the cheekbones, the outside of the mouth and below the lower lip of the user. With a supply of positive pressure air, the mask seal 110 will balloon and seal against the face of the user to reduce or eliminate the likelihood of leakage between the flange 160 and the face of the user.

The upper portion 154 of the mask seal 110 is designed to roll over onto an outer surface 170 of the mask assembly 102. In the illustrated configuration, the outer surface of the mask seal 110 smoothly rolls into abutment with the outer surface of the mask seal clip 112 such that the outer surface of the mask seal clip 112 forms a support surface. In some configurations, the outer surface 170 onto which the upper portion 154 rolls comprises at least a portion of the outer surface of the mask seal clip 112. In some configurations, the outer surface 170 onto which the upper portion 154 rolls comprises almost exclusively the outer surface of the mask seal clip 112. In some configurations, the upper portion 154 rolls onto another portion of the mask seal 110. In some configurations, the upper portion 154 rolls onto the mask seal base 114.

With reference now to FIGS. 1 and 2, the mask assembly 102 includes the mask base 114, which is more rigid than the mask seal 110. The mask base 114 can be formed of any suitable material. In some configurations, the mask base 114 is formed of a polycarbonate material such that it is capable of flexing for connection with the mask seal 110 and/or the mask seal clip 112.

Figure 5:
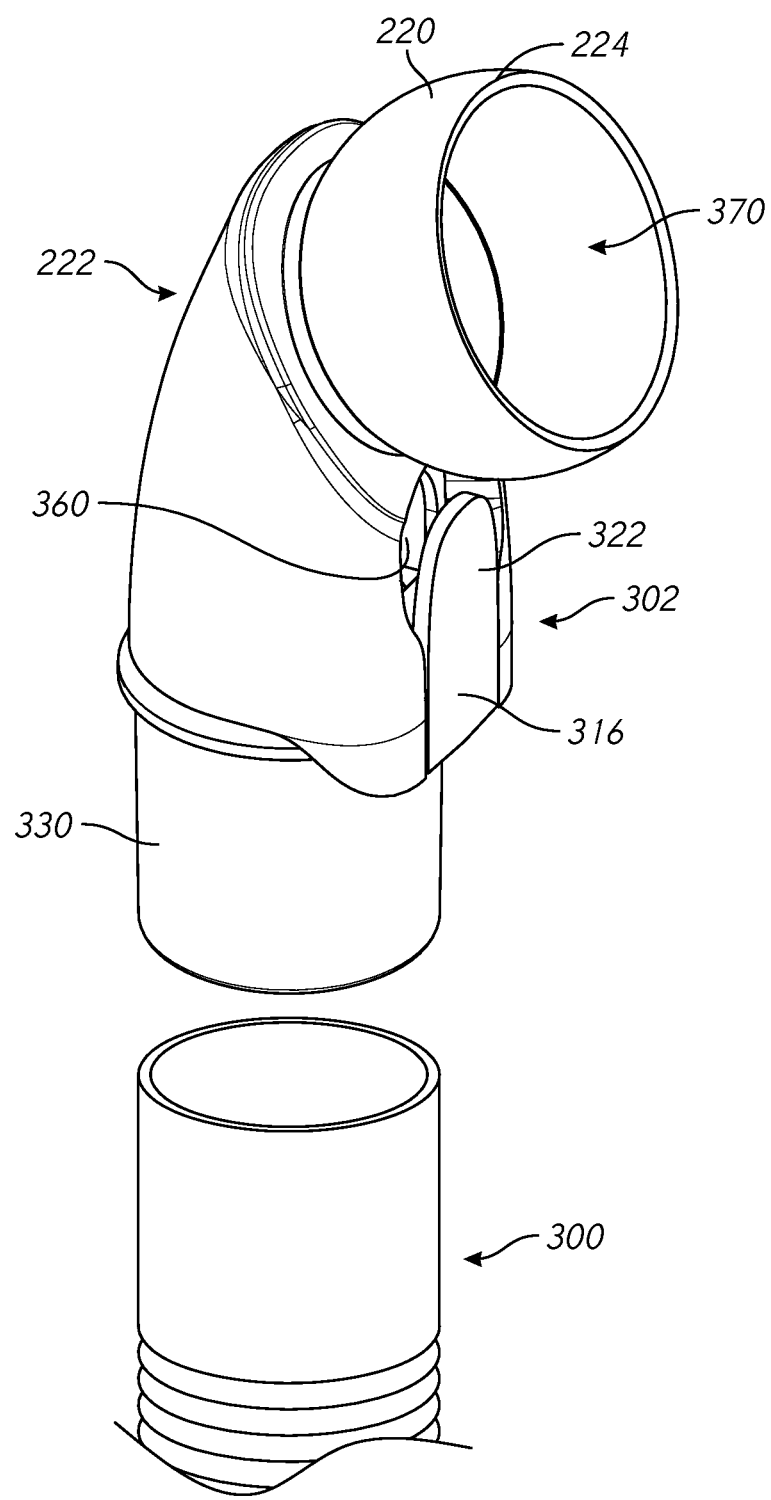
FIG. 5 is a perspective view of an elbow assembly arranged to be connected to the interface of FIG. 1.
Figure 6:
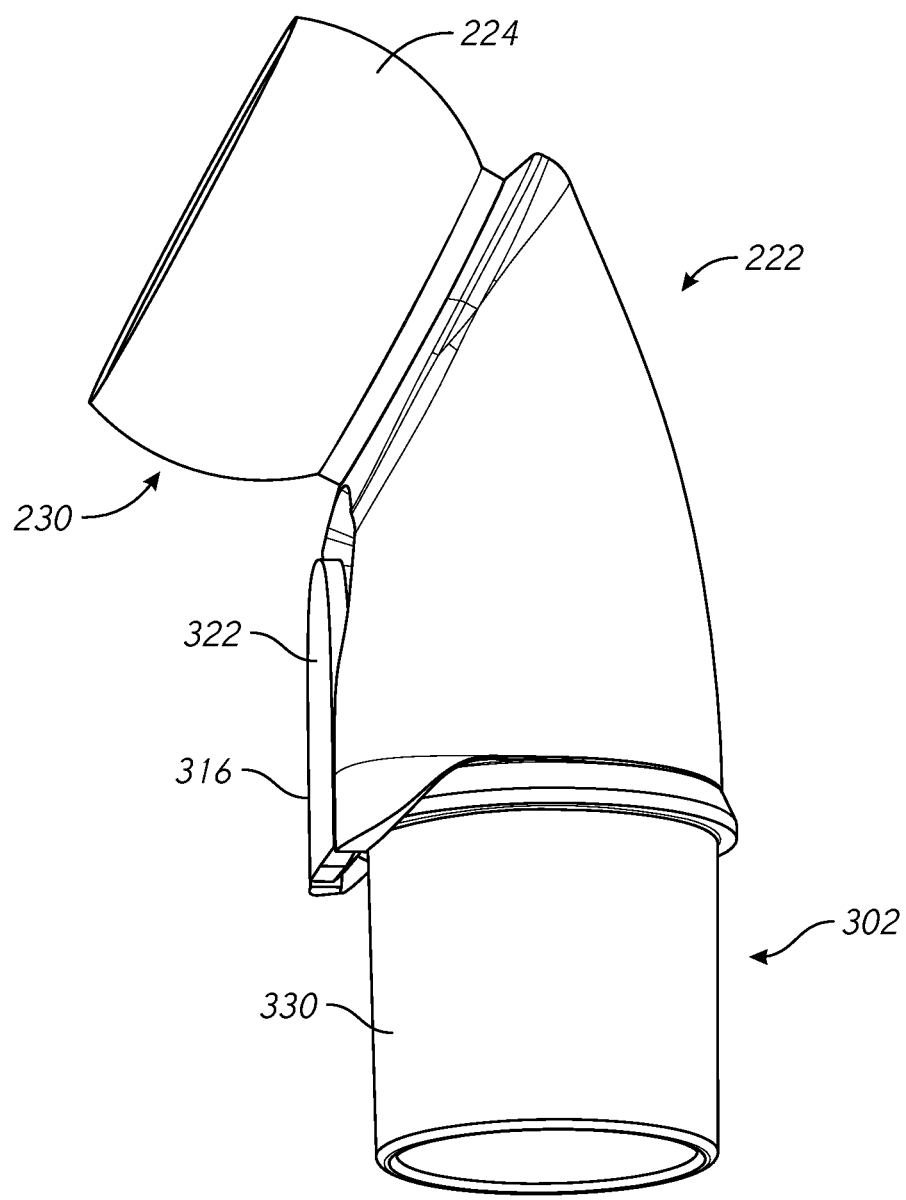
FIG. 6 is a side elevation view of the elbow assembly of FIG. 5.

Central passage 144 may be radiused to receive a ball end 220 of a swiveling elbow 222, such as that shown in FIG. 5. As better shown in FIG. 6, the ball end 220 has a contoured surface 224 that can be snap fit into the contoured surface 214 formed in the mask base 114. The connection between the two contoured surfaces 214, 224 allows the surfaces to slide relatively freely with each other such that the position of the swiveling elbow 222 can be easily changed. In some configurations, the elbow 222 could be configured for rotation or swiveling without having a ball-joint configuration.

With reference to FIG. 2, in addition to the straps 260, the headgear assembly 106 also comprises a back strap 280 and a top strap 282. Other head gear assemblies also can be used. The back strap 280 extends around the back of the head of the user U at a location generally above a nape of the neck but generally below the occipital protuberance. At a location rearward of the ear of the user, the back strap 280 forks into an upper arm 284 and a lower arm 286. The upper arm 284 arcs upward to a location above the ear of the user and then arcs downward to a location generally forward of the ear of the user. The lower arm 286 arcs downward to a location generally below the ear of the user and extends slightly forward of the ear.

The straps 260 can be connected to the back strap 280 in any suitable manner. In the illustrated configuration, the straps 260 connect to the upper arm 284 and the lower arm 286 respectively. Preferably, the upper arm 284 and the lower arm 286 are more rigid than the straps 260 such that the arms 284, 286 generally maintain shape as the headgear assembly 106 is being donned. In some configurations, each of the upper arm 284 and the lower arm 286 supports its own weight. In some configurations, each of the upper arm 284 and the lower arm 286 is structured to be tangle-free during donning. For example, the arms 284, 286 have sufficient torsion stiffness to reduce the likelihood of twisting when being put on.

Preferably, the straps 260 connect to at least one of the upper arm 284 and the lower arm 286 at a location forward of the ear. Such a configuration helps the user to locate the straps 260 without much difficulty. In addition, because the straps 260 in the illustrated configuration are embedded into the clips 252, the ends of the upper arms 284 and the lower arms 286 can comprise slots 290, 292 such that the straps 260 can be threaded through the slots 290, 292. In addition, the straps 260 can comprise an adjustment mechanism 294, such as a Velcro or buckle configuration. The adjustment mechanism 294 allows a force between the mask seal 110 and the face of the user U to be adjusted. Any suitable adjustment mechanism 294 can be used.

As shown in FIG. 2, the top strap 282 preferably is flexible and has an adjustable length. The top strap 282 connects to the upper arms 284 through a slot 296 and reduces the likelihood of the upper arms 284 sliding down the head of the user and contacting the ears of the user. Preferably, the top strap 282 connects to the upper arms 284 at a location generally above the ears of the user.

Advantageously, as shown in FIGS. 1 and 2, the straps 260 exert a force in the direction of the arrow F while they connect to the mask base 114 by movement in the direction C, which direction is generally normal to the direction of the force F. In other words, the straps 360 are tensioned by pulling forward and the clips 252 are connected to the mask base 114 by movement in a direction normal to the forward pull. Such a configuration eases securement of the interface 100 on the face of the user.

With reference again to FIG. 5, the elbow 222 connects to a conduit 300 through a disconnectable swivel assembly 302. As shown in the section view of FIG. 8, the elbow 222 comprises a stem 304 that comprises an inner wall 306 at the base. The inner wall 306 comprises a recess 308.

Figure 9:
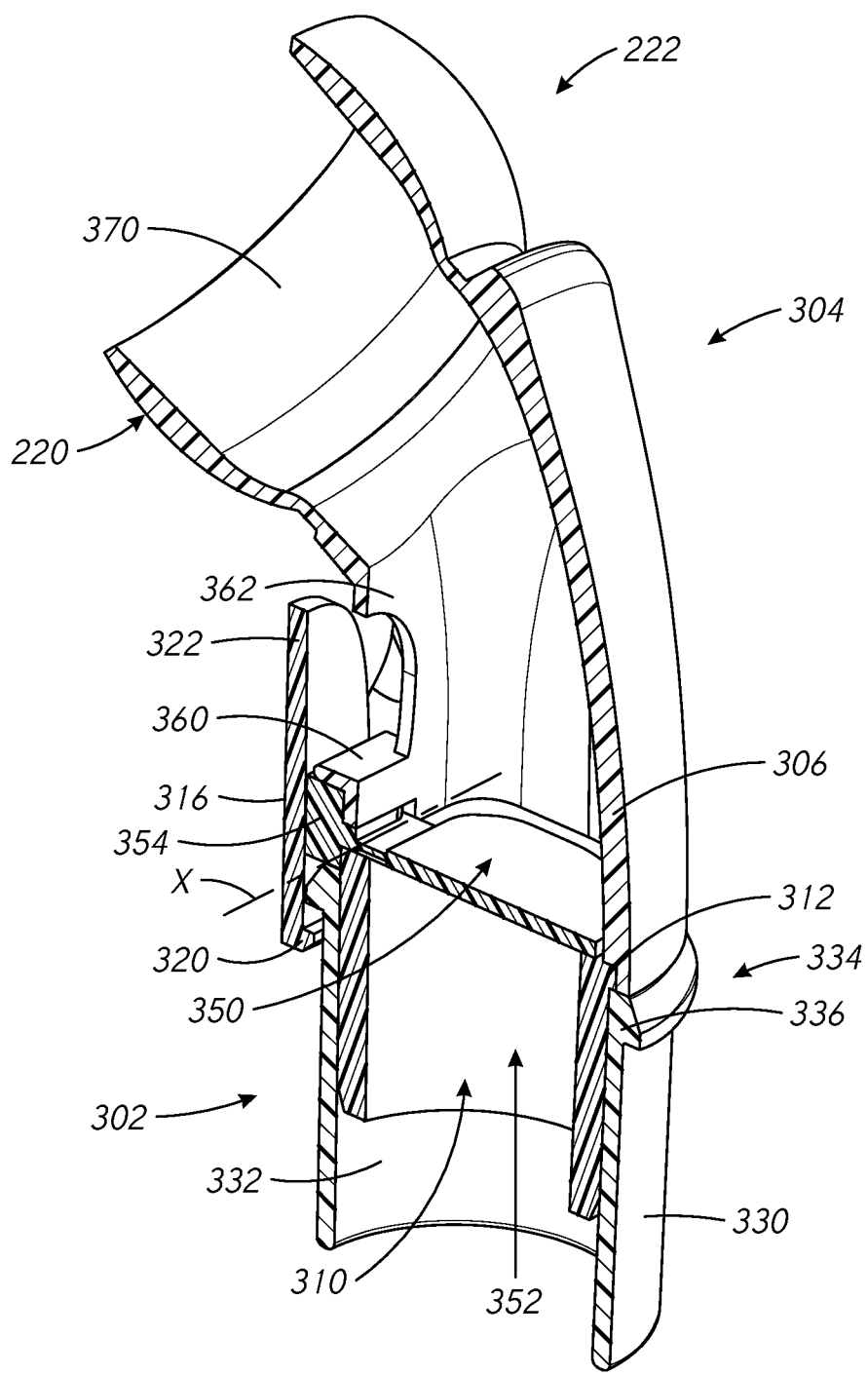
FIG. 9 is a sectioned perspective view of the elbow assembly of FIG. 5.

A sleeve 310 comprises a flange 312 that is received within the recess 308. The sleeve 310 can be secured into position within the elbow 222 using any suitable technique. The sleeve 310 comprises a generally cylindrical outer wall 314. The flange 312 comprises a section that extends outward to connect to a lever 316. Preferably, the flange 312 and the lever 316 are integrally formed. With reference to FIG. 9, the lever 316 includes a lower inwardly extending catch 320 and is capable of pivoting about the section that connects the lever 316 to the flange 312. Thus, pressing inward on an upper portion 322 of the lever 316 results in the catch 320 moving away from the generally cylindrical outer wall 314 of the sleeve 310.

A swivel 330 comprises a generally cylindrical inner wall 332. The inner wall 332 slides over the outer wall 314 of the sleeve 310 such that a sliding fit results between the swivel 330 and the sleeve 310. An upper portion 334 comprises a shoulder 336. The catch 320 of the lever 316 can secure the swivel 330 in axial position on the sleeve 310 by engaging with the shoulder 336. When the upper portion 322 of the lever 316 is depressed, the catch 320 moves away from the shoulder 336, which allows the swivel 330 to be removed from the sleeve 310.

Figure 8:
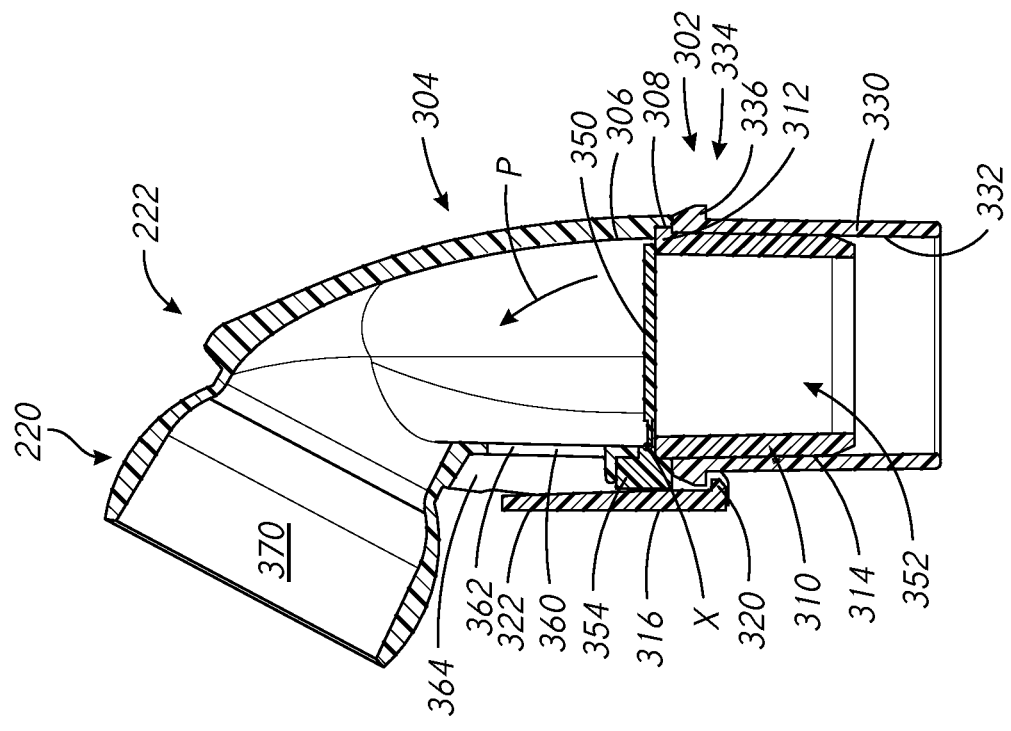
FIG. 8 is a sectioned side elevation view of the elbow assembly of FIG. 5.
Figure 7:
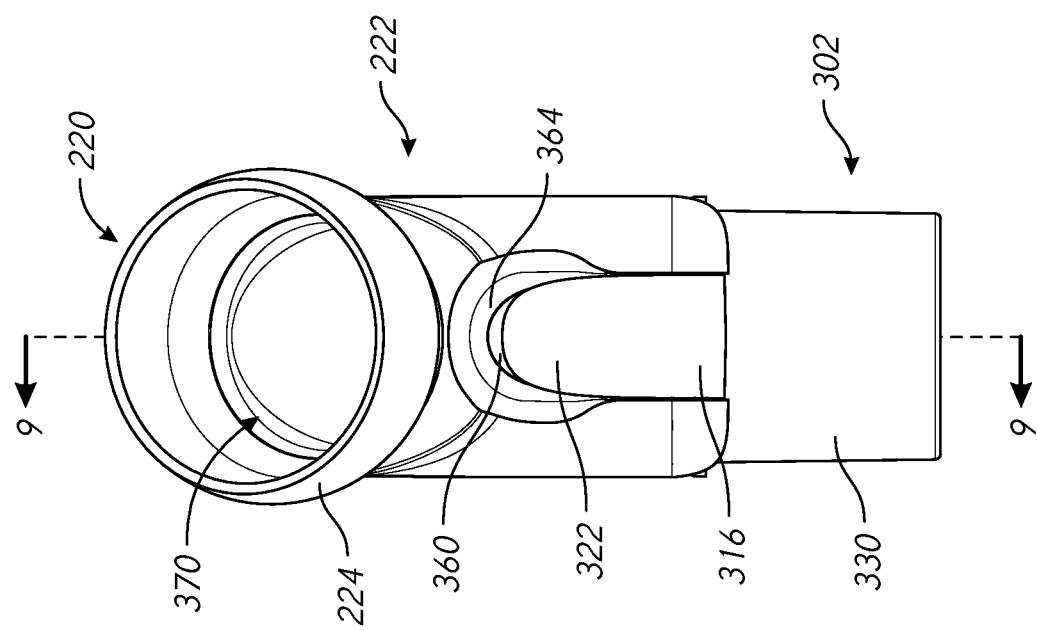
FIG. 7 is a rear elevation view of the elbow assembly of FIG. 5.

A flap 350 can be mounted between the stem 304 and the sleeve 310. In the illustrated configuration, the flap 350 extends into a flow channel 352 from a base 354 that is sandwiched between the stem 304 and the sleeve 310. The flap 350 can pivot upward (as shown in FIG. 8, see arrow P) about an axis X (see FIG. 9) away from the sleeve 310 such that flow from a positive pressure generator can continue generally unobstructed to the user through the interface 100. The flap 350 pivots downward into contact with the sleeve 310 to seal the flow channel 352 in the event that the positive pressure source stops providing a pressurized flow of air. In some configurations, the flap 350 will not fully contact the sleeve 310. In some configurations, the flap 350 will not seal the channel 352 when in the down position.

With reference to FIG. 9, a port 360 is defined through the elbow 222 at a location above the flap 350. The port 360 preferably is positioned along a portion of the elbow 222 that is in the vicinity of the axis X. In some configurations, the port 360 is positioned to be substantially shielded by the flap 350 from an inspiratory flow of air. In other words, as the air pivots the flap 350 away from the sleeve 310, the flap 350 is moved into a position that at least partially or completely covers the port 360.

In some configurations, the port 360 extends through a wall of the elbow 222 that comprises a generally planar inner wall 362. The generally planar inner wall 362 helps the flap 350 to generally seal the port 360 when the flap is moved upward away from the flange 312 of the sleeve 310.

In some configurations, the lever 316 overlies a majority of the port 360 such that the port 360 is generally obscured from view. As shown in FIG. 8, however, a gap 364 preferably surrounds at least a portion of the lever 316 such that a relatively free flow of air can pass through the port 360 when the flap 350 does not overly the port 360. In addition, in some configurations, the port 360 and the lever 316 are positioned on a same side of the elbow 222 as an opening 370 defined within the ball end 220, which opening is positioned within the mask assembly 102 when the connection port assembly 104 is assembled to the mask assembly 102. Advantageously, such a positioning places the port 360 in a position on the elbow 222 that faces the user. Such a location further obscures the port 360 from view during use, which results in a more aesthetically pleasing configuration. Moreover, because flow through the port 360 will be very infrequent, having the port 360 disposed toward the user will not cause any significant discomfort for the user.

While not shown, the elbow 222 also can comprise one or more bias flow vent holes. The bias flow vent holes preferably are positioned in a forwardly directed orientation such that any bias flow does not directly impinge upon the user.

Figure 11:
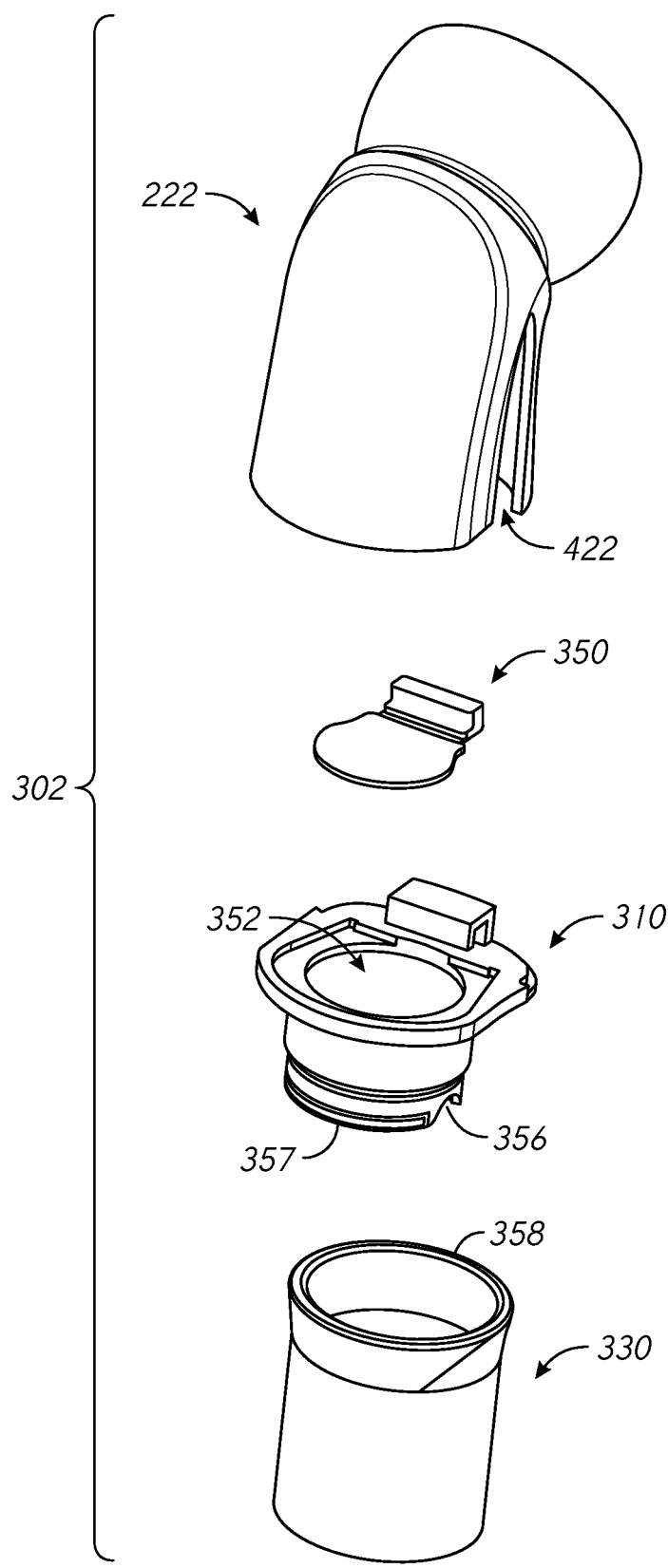
FIG. 11 is an exploded view of the elbow assembly of FIG. 10.
Figure 12:
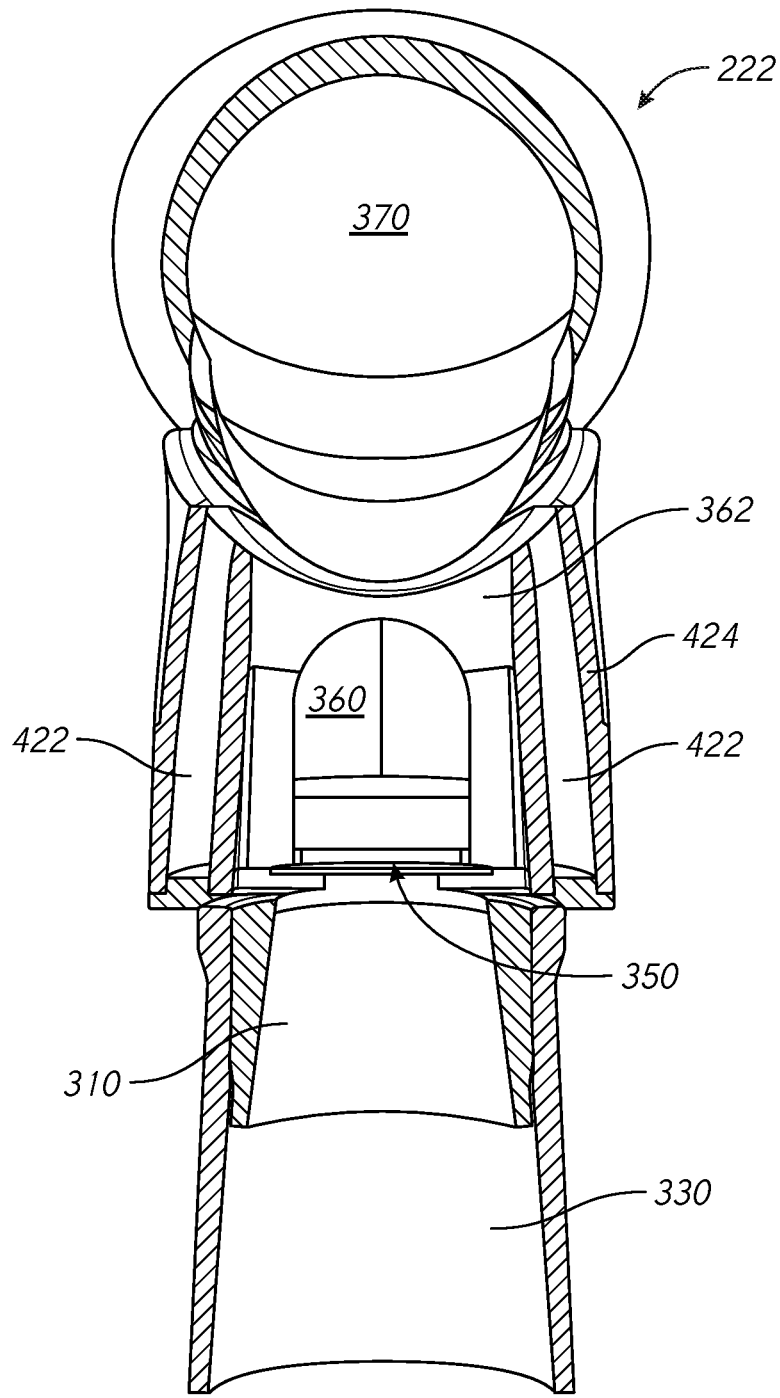
FIG. 12 is a cross-sectional view taken along line 12-12 of FIG. 10.
Figure 13:
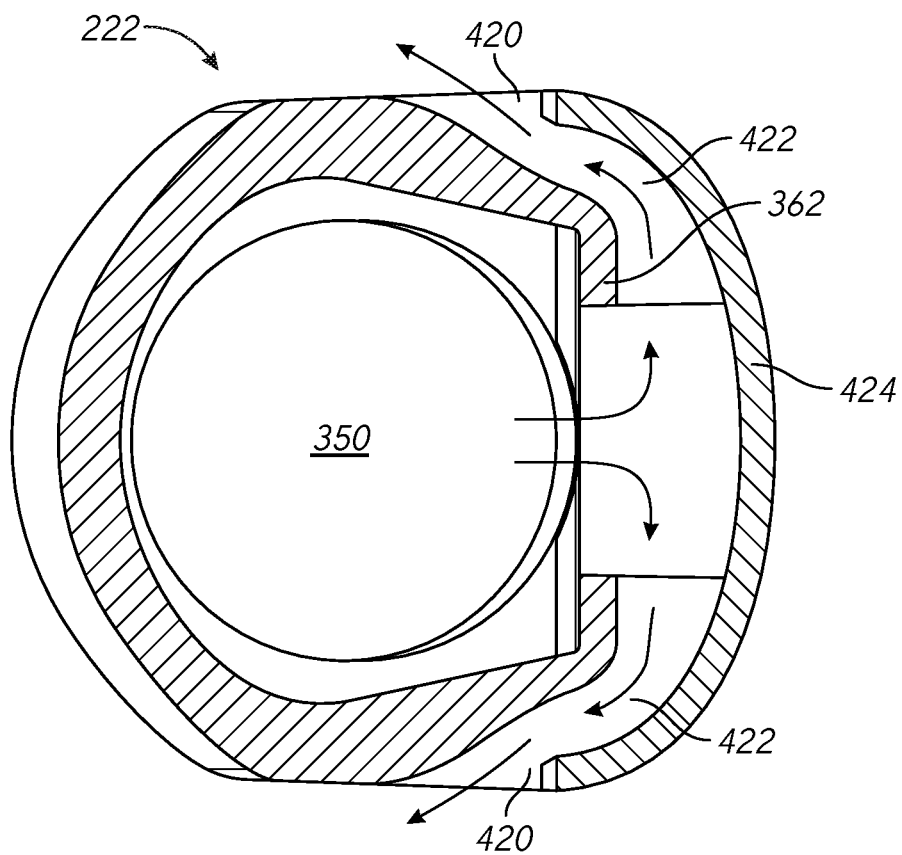
FIG. 13 is a cross-sectional view taken along line 13-13 of FIG. 10.

Another configuration of an elbow assembly 302 is illustrated in FIGS. 10-13. The elbow assembly 302 comprises an elbow 222, a sleeve, 310, and/or a swivel 330, as shown in FIG. 11. In some configurations, the elbow assembly 302 only includes the elbow 222 and sleeve and omits the swivel 330. The swivel may be permanently or removably attached to the sleeve 310 and elbow 222; in some configuration, the swivel 330 is integrally formed with the end of the delivery conduit. An anti-asphyxia valve flap 350 is positioned over the sleeve 310 such that it at least partially obstructs the sleeve's flow channel 352. The elbow assembly 302 functions similarly to the elbow assembly 302 of FIGS. 5-9; however, the elbow assembly 302 of FIGS. 10-13 provides the additional benefit of directing gases away from the patient when the flap 350 drops to its closed position (as shown in FIGS. 12 and 13).

With reference to FIG. 11, the sleeve 310 preferably comprises two or more cut out regions or recesses 356. The recesses 356 can have any suitable shape and, in the illustrated configuration, the recesses 356 comprise a semicircular configuration that extends upward into the sleeve 310. The sleeve 310 also comprises at least one bump 357, and preferably two or more bumps 357. Preferably, each of the bumps 357 extends around an arc of about 70 degrees. More preferably, each of the bumps 357 is generally centered between two recesses 356 and each of the bumps 357 extends about 70 degrees around an outer surface of the sleeve 310.

The swivel 330 preferably is generally cylindrical in configuration. As shown in FIG. 11, the swivel 330 has an inwardly extending ridge 358. The ridge 358 preferably encircles the entire inner surface. In some configurations, the ridge 358 can be interrupted. Preferably, however, the ridge 358 does not have any interruptions large enough to accommodate the entire bump 357 such that the ridge 358 and the bump 357 can cooperate to keep the swivel 330 mounted over the sleeve 310. When assembling the swivel 330 to the sleeve 310, the recesses 216 allow the bumps 220 to deflect inward such that the bumps 357 can slide over the ridge 358 and then snap back outward to secure the bumps 357 under the ridge 358.

The elbow 222 comprises openings 420 at its sides that are in fluid communication with an air venting channel 422. The air venting channel 422 is formed by the spacing between the elbow's inner and outer walls 362, 424, as shown in FIGS. 12 and 13.

When the flap 350 drops to its closed position, as shown in FIGS. 12 and 13, air exhaled from the user enters opening 370 of the elbow 222. The exhalation flows through the port 360 in the elbow's inner wall 362, and through the venting channel 422 until it exits the elbow 222 via the opening 420.

The configuration of FIGS. 10-13 provides a reduced overall length and improves product aesthetic by eliminating an unsightly hole positioned at the front of the elbow 222. In addition, the configuration of FIGS. 10-13 and improves patient comfort by preventing air from being directed towards the user. Instead, openings 420 direct air flow out of the sides of the elbow 222 and away from the patient.

Referring additionally to FIGS. 14 to 19, another configuration of an elbow assembly 702 comprises an elbow 722 and a sleeve 710. The swivel 330 as described above may also be provided but is not illustrated in FIGS. 14 to 19.

Figure 14:
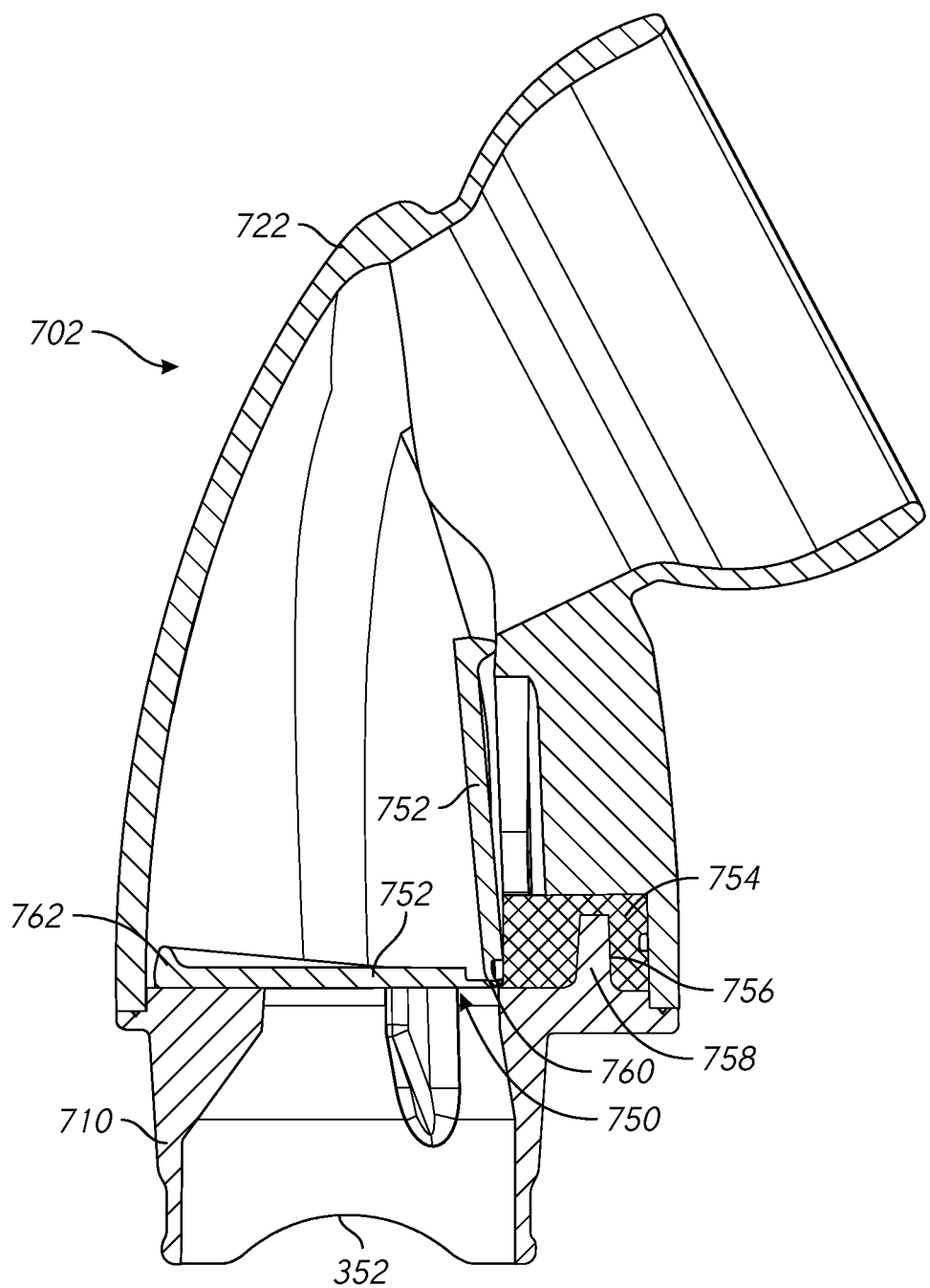
FIG. 14 is an enlarged cross-sectional side view of another elbow assembly, with an anti-asphyxia valve flap in an open and a closed condition.
Figure 15:
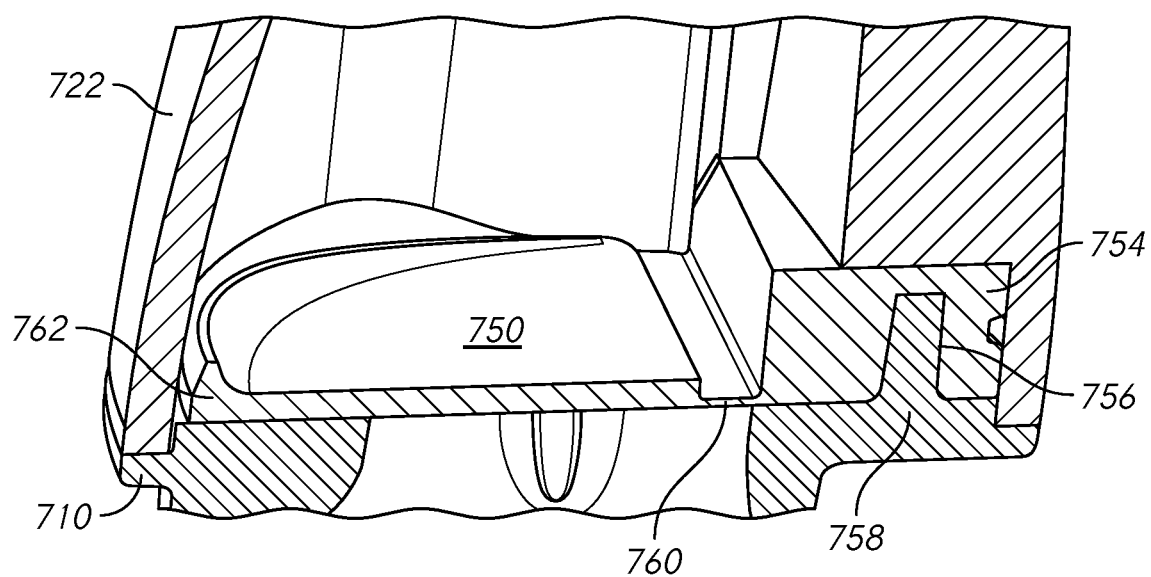
FIG. 15 is an enlarged cross-sectional side and perspective view of part of the elbow assembly of FIG. 14.
Figure 16:
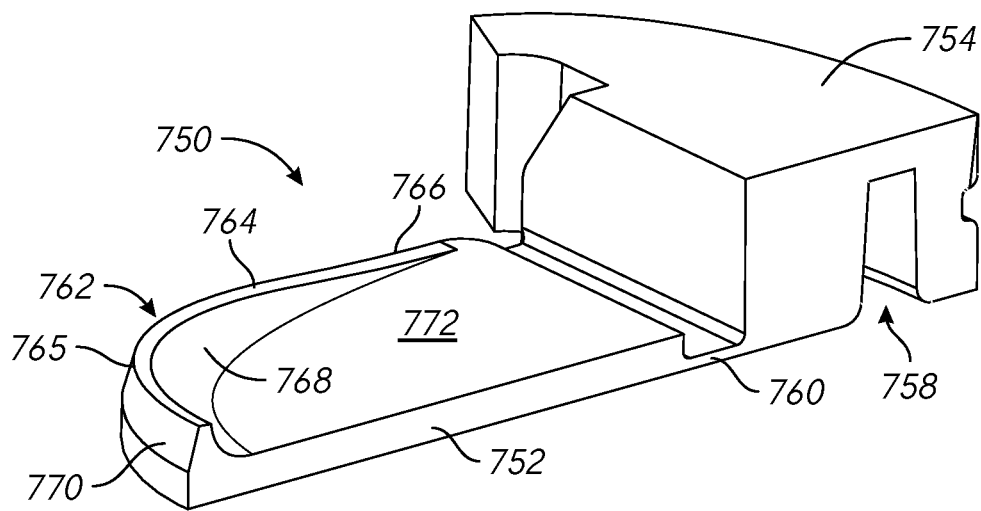
FIG. 16 is an enlarged perspective view of part of an anti-asphyxia valve of the elbow assembly of FIG. 14.
Figure 17:
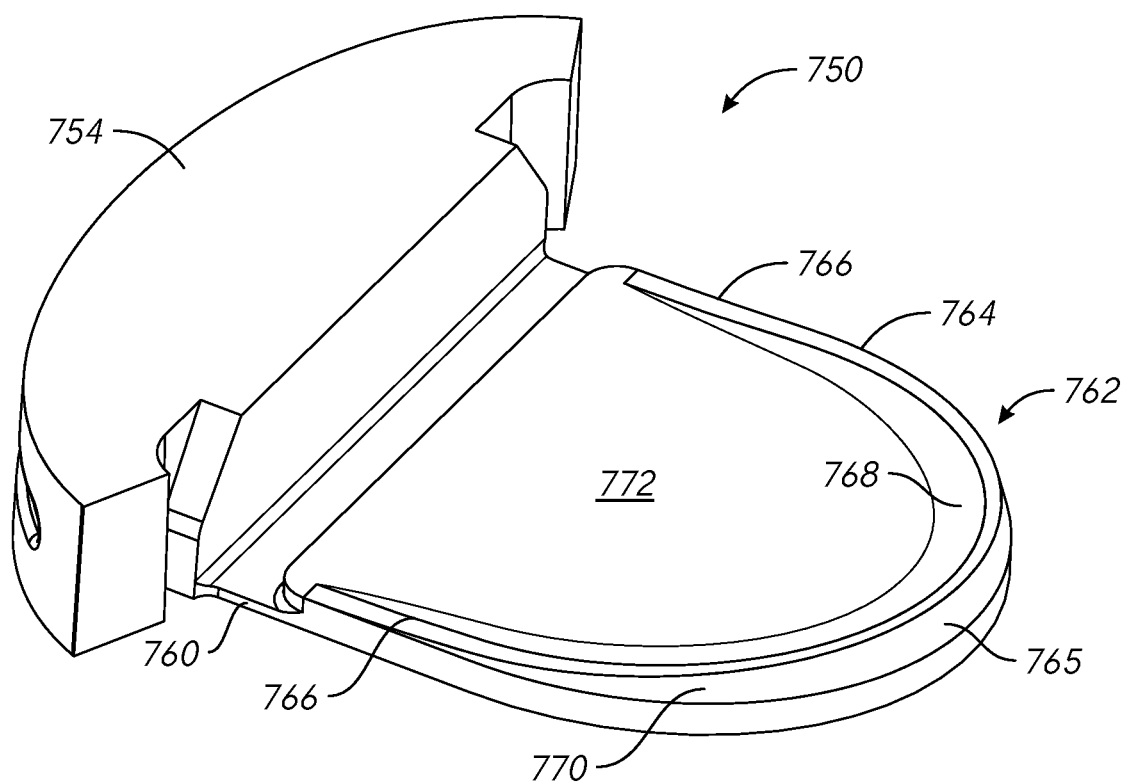
FIG. 17 is another enlarged perspective view of part of the anti-asphyxia valve of the elbow assembly of FIG. 14.
Figure 18:
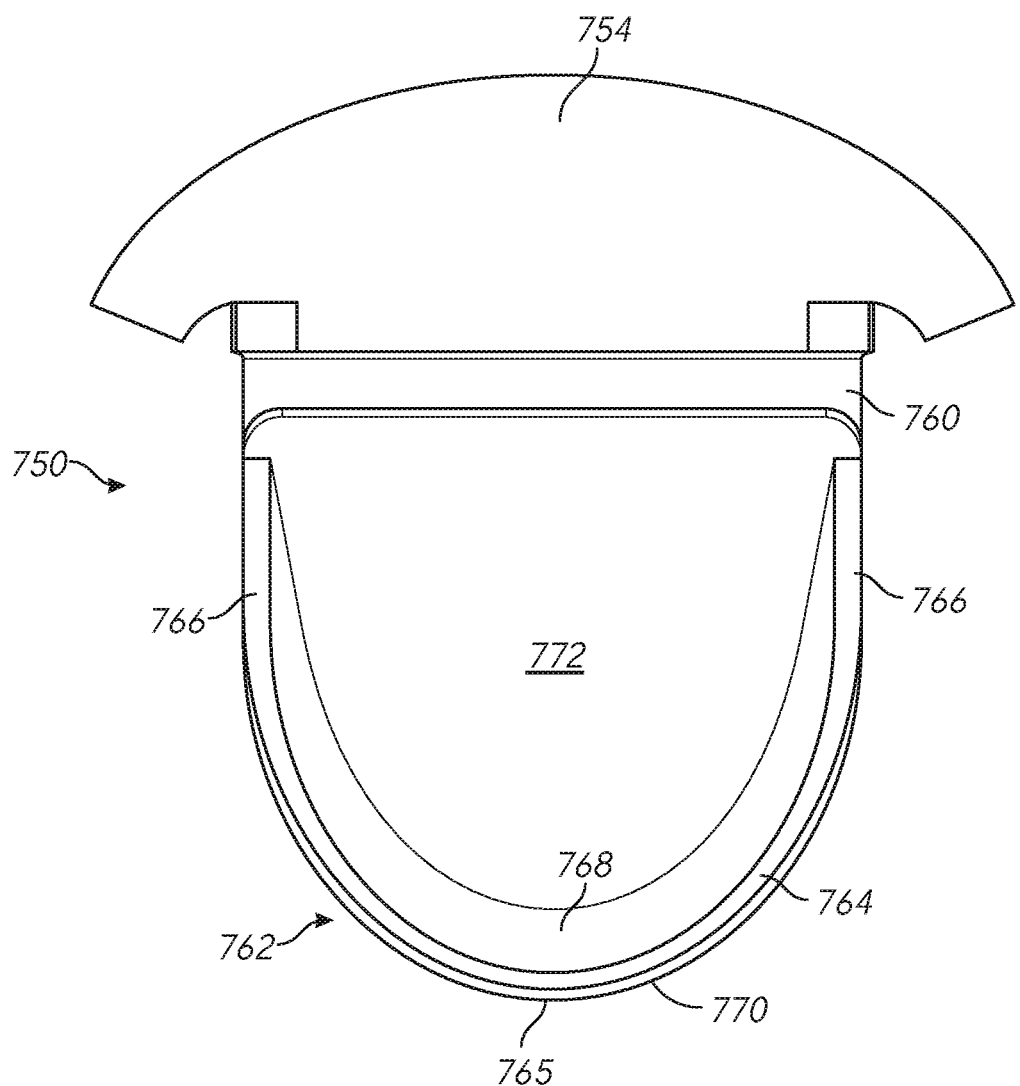
FIG. 18 is a plan view of part of the anti-asphyxia valve of the elbow assembly of FIG. 14.

An anti-asphyxia valve (AA valve) 750 is provided and positioned over the sleeve 710 such that it at least partially obstructs the sleeve's flow channel 352. The elbow assembly 702 functions similar to the elbow assembly 302 of FIGS. 10 to 13, and similarly directs gases away from the patient when the flap 752 of the AA valve 750 drops to its closed position, namely the generally horizontal position as shown in FIG. 14, closing the flow channel 352 through the sleeve 710.

The AA valve 750 comprises generally planar valve flap 752 which is hingedly mounted on a flap support 754. The flap support 754 may be integrally formed with the valve flap 752, and may comprise one or more orientation features which facilitate correct orientation and mounting of the valve 750 on the sleeve 710. In this example an orientation feature comprises a slot 756 formed in the underside of the flap support 754 which receives a corresponding protrusion 758 provided on an upper part of the sleeve 710. The engagement between the slot 756 and protrusion 758 helps retain the valve 750 on the sleeve 710 during assembly of the elbow assembly 702, and assists in correctly orientating the valve 750 relative to the sleeve 710 and elbow 722, and relative to the axis of the sleeve's flow channel 352. The slot 756 and protrusion 758 also prevent the valve 750 from being mounted on the sleeve 710 upside down, that is, with the flap 752 and flap support 754 rotated 180 degrees from the orientation illustrated in FIG. 14.

The AA valve 750 comprises a hinge 760, pivotally mounting the flap 752 on the support 754. The hinge 760 may be integrally formed with both the flap 752 and the support 754. The hinge 760 comprises a relatively thin strip of material which is of greater flexibility than the flap 752 and the support 754, enabling the thicker flap 752 to pivot about the support 754 from a generally horizontal position in which the flap 752 closes the flow channel 352 through the sleeve 710, to a generally vertical position in which the flap 752 opens the flow channel 352 in the sleeve 710 but closes the air venting channels 422 formed in the elbow 722.

The valve flap 752 comprises a bead or ridge or protrusion 762 which protrudes from a planar upper surface 764 of the flap 752. The bead 762 thus projects from the upper surface 764 of the flap 752. When the flap 752 is in the generally vertical position in which the flap 752 opens the flow channel 352 in the sleeve 710 but closes the air venting channels 422 formed in the elbow 722, the bead 762 contacts the part of the elbow 722 surrounding the venting channels 422, and forms a discrete sealing surface 764 which seals against the elbow 722 and closes the venting channels 422. The bead 762 thus forms a sealing surface 764 having a relatively small sealing area relative to the area of the valve flap 752 itself. That is, the area 764 of the bead 762 which seals against the elbow 722 when the flap 752 is in the generally vertical condition is relatively small, but still sufficient to seal the venting channels 422 closed.

When the elbow 722 has gone through multiple cleaning cycles, the plastic surfaces of the elbow 722 can become degraded, allowing water to more easily stick to those surfaces. Thus, the wetting angle of the water/plastic interface increases with the result that water droplets can sit on the contact surfaces of the elbow 722, rather than forming beads and rolling off the contact surfaces.

It can be a problem with prior art AA valves that the relatively large sealing surface of a planar valve flap can trap water between the contact surfaces of the elbow and the valve flap. The surface tension of the water can cause the water to act as an adhesive, sticking the valve flap against the elbow contact surfaces, such that the valve flap sticks in the generally vertical condition, closing the venting channels 422.

Providing bead 762 on the valve flap 752 creates a much smaller relative sealing surface in contact with the internal sealing surfaces of the elbow. This results in the amount of water between the flap and the elbow being lower, lowering the force that the water's surface tension can resist, and allowing the valve flap 752 to release from the elbow contact surfaces more easily. The provision of the bead 762 thus reduces or prevents the valve flap 752 sticking in the position where the venting channels 422 are closed.

In this example the bead 762 comprises an arcuate, curvilinear portion 765 which follows the curved periphery of the valve flap 752 distal from the hinge 760, and linear portions 766 which extend along the straight sides of the valve flap 752, towards the hinge 760. The bead 762 in this example therefore extends substantially around the entire periphery of the valve flap, to the hinge 760 and is substantially 'n' shaped when viewed in plan.

In this example, the bead 762 is tapered when viewed from the side. Thus, part of the bead 762 distal from the hinge 760 protrudes further from the planar upper surface of the flap 752 than the parts of the bead 762 nearer the hinge 760. In this example, the apex of the arcuate bead portion 764 projects further from the flap 752 than the linear bead portions 766. The bead tapers uniformly from the arcuate portion 764 to the linear portions 766, such that the bead 762 blends into the upper planar flap surface adjacent the hinge 760. This tapering along the longitudinal axis of the valve flap 752 allows the bead 762 to fully seal against the sealing surfaces of the elbow 722 around the entire periphery of the flap 752, to close the venting channels 422. The flap 752, when in the upright condition which closes the venting channels 422, is thus slightly inclined from the vertical when sealing against the elbow 722.

In this example, the profile of the bead 762 when viewed from the side, is rounded or chamfered. Thus, the sealing surface 764 of the bead 762, that is, the part of the bead 762 which protrudes the most from the valve flap 752 may be flat. However, the side walls of the bead which support the bead sealing surface 764 may be profiled, and may be rounded or chamfered for example. The profiled side walls 768, 770 of the bead 762 may extend all of the distance to the valve flap 752, or may be profiled only adjacent the sealing surface 764. As can be seen from FIG. 17 for example, the profile of one side wall 770 of the bead 762 may be different from the profile of the other side wall 772 of the bead 762. In this example, the inside side wall 768 of the bead 762 curves down from the sealing surface 764 and blends into the upper planar surface 772 of the valve flap 752 over a relatively large radius of curvature, that is, a relatively shallow curve from the bead sealing surface 764 to the valve flap 752. In contrast, the outside side wall 770 of the bead 762 is straight and has a relatively steep, straight angle of inclination from the bead sealing surface 764 to the valve flap 752.

Other profiles and shapes of bead are envisaged. For example, the bead may simply comprise a square, rectangular, oblong or triangular cross sectional profile. For example the cross section of the bead may vary along the length of the bead. Part or all of the bead 762 may comprise a semi-circular or arcuate cross sectional profile. The side walls of the bead 762 may not be rounded or chamfered, and may simply be straight sides extending between the bead sealing surface 764 and the valve flap 752. The straight sides may be inclined, or substantially perpendicular relative to the plane of the valve flap 752.

Figure 19:
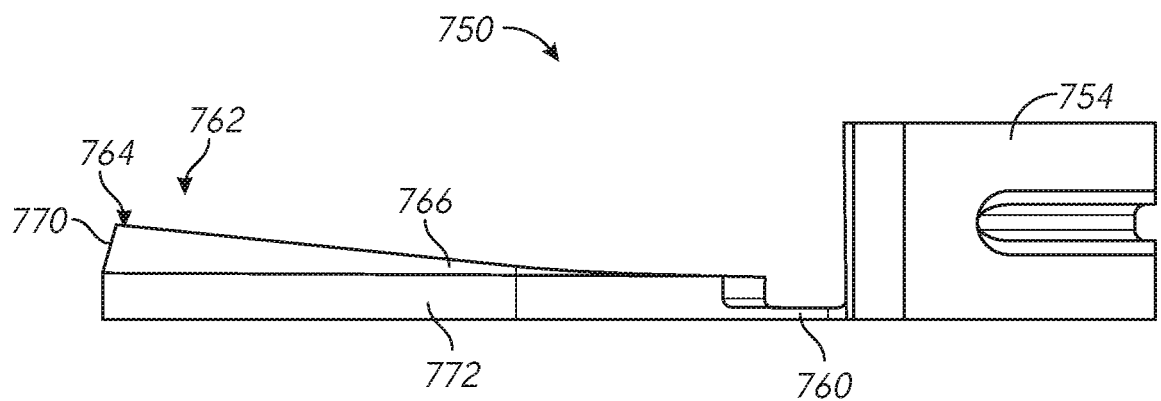
FIG. 19 is side view of part of the anti-asphyxia valve of the elbow assembly of FIG. 14.
Figure 20:
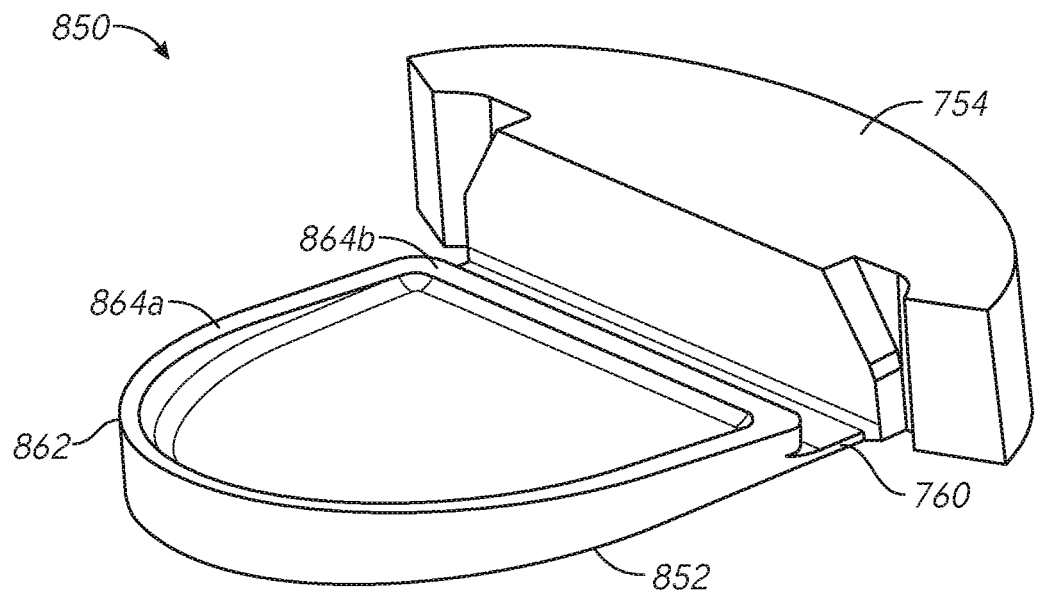
FIG. 20 is a perspective view of another embodiment of an anti-asphyxia valve.
Figure 21:
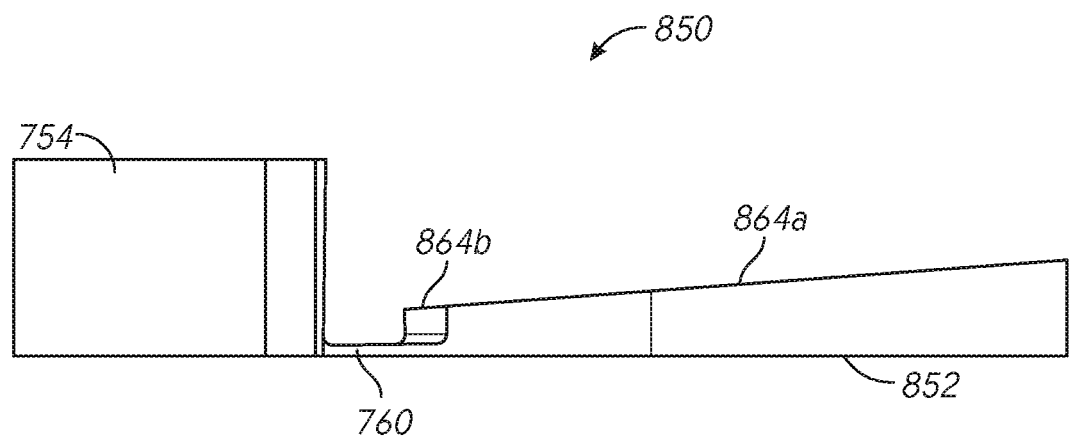
FIG. 21 is a side view of the valve of FIG. 20.

Referring to FIGS. 19 and 20, another embodiment of an anti-asphyxia valve 850 comprises many similar features to the valve 750 described above. However, in this example, the valve 850 comprises a bead 862 which extends around the entire periphery of the valve flap 852, with part of the bead 862 extending past the hinge 760. The bead 862 in this example is therefore substantially 'D' shaped when viewed in plan and comprises a sealing surface 864A extending away from the hinge 760, and a sealing surface 864B extending adjacent to and parallel with the hinge 760.

In this example, an alternative bead profile is provided. In this example, the side walls of the bead are substantially straight, and are not inclined with respect to the plane of the valve flap 852. Likewise, the sealing surface 864A in this example is straight when the bead 862 is viewed from the side, that is the sealing surface 864 is a planar surface with the plane inclining downwardly from the distal part of the flap 862 towards the hinge 760. Thus the bead 862 is tapered as with the bead 762, but the sealing surface 864A is straight with no curved or inclined regions when viewed from the side. This may enhance the seal provided between the sealing surface 864A and the elbow, and may reduce the likelihood of leak paths forming. The bead 862 in this example is also more rigid, which may help prevent the flap edges from lifting and leaking at lower pressures, due to the flap 852 bending.

Figure 22:
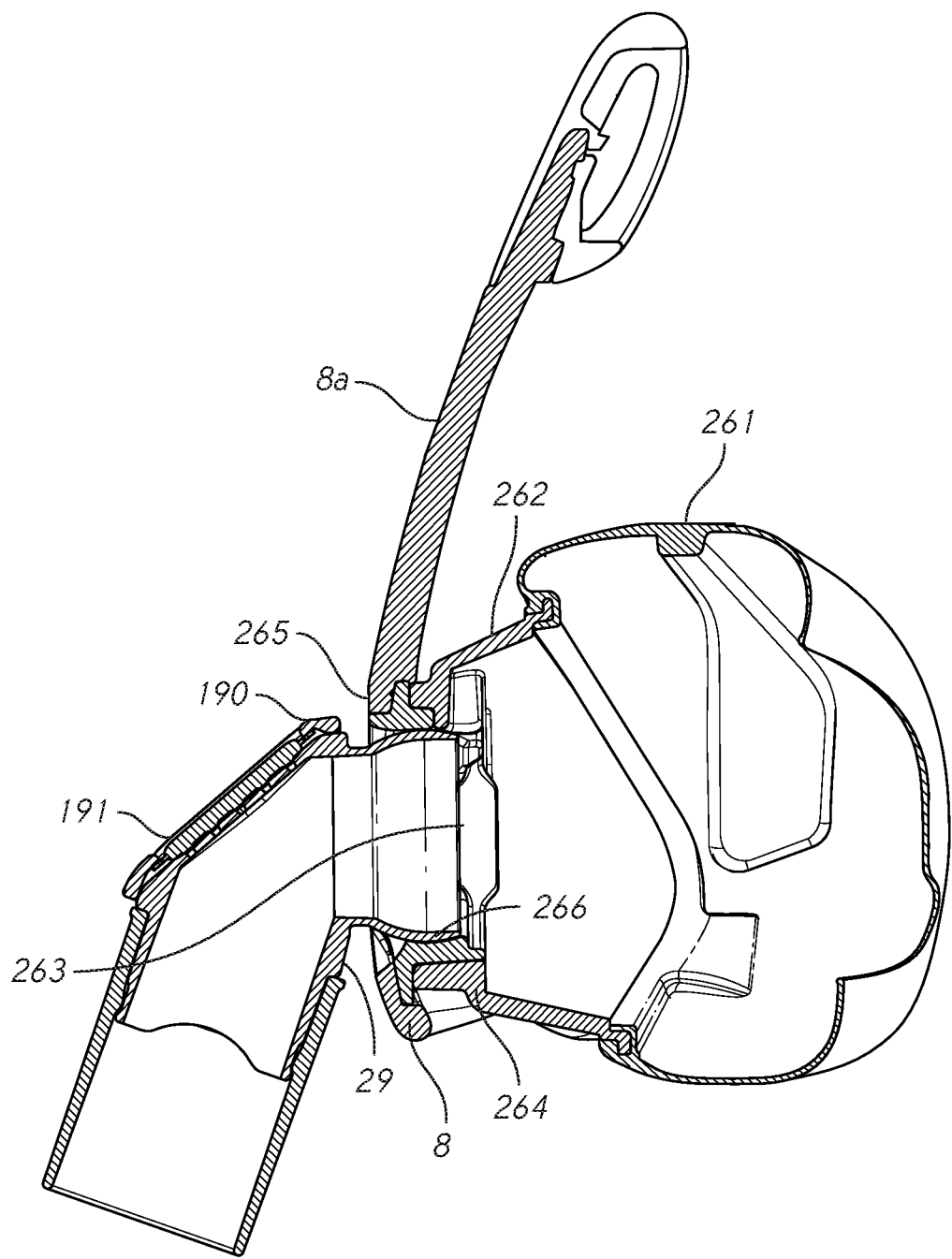
FIG. 22 is a cross-sectional view of a patient interface assembly.

FIG. 22 is a sectional view of a patient interface including a soft seal 261 which is fixed to a rigid or more rigid shell component 262. The shell 262 comprises a gases entry opening 263 with therearound an outwardly (or alternatively inwardly) projecting annular shell collar 264. Annular mounting collar 265 is mounted into frame 8 in a suitably shaped aperture in frame 8, which a click fit or snap fit, or is welded in place, and mounting collar 265 receives annular shell collar 264 preferably with a click fit or snap fit. The upper annular end 266 of the elbow 29 fixes into the internal diameter of mounting collar 265, for example in a click or snap fit, when the mask is assembled for use, so that the elbow is coupled to the annular mounting collar 265 (rather than to the frame or shell). Alternatively, the seal-shell component may comprise a single material seal component. Annular mounting collar 265 may be a different material and/or color to the material and/or color of frame 8. Further details of this patient interface are disclosed WO2015/057087, the entire contents of which are incorporated herein by reference.

The patient interface of FIG. 22 further comprises or is configured to connect to a connector 267, preferably via a snap fit, as shown. The outer surface 268 of connector 267 is configured to be received in a respiratory tube (not shown) or a collar connector provided at a patient end of a respiratory tube (also not shown). The connector 267 shown in FIG. 22 is configured to sealably engage the respiratory tube (or the collar terminating the respiratory tube) by a friction fit. To this end, one or more of the engaging walls may be tapered. For example, the outer surface 268 of connector 267 may have a narrower or smaller external dimension near first end 268, and a wider or larger external dimension at some point between said first end 268 and second end 269 of connector 267. Additionally or alternatively, the opening (internal dimension) of the respiratory tube may vary from a location near its mouth having a relatively large dimension to a smaller or narrower dimension at a location axially inward in the respiratory relative, the dimension and location of the narrower portion being relative to the wider portion. As will be appreciated, where the respiratory tube is provided with a collar termination, the tapering may be formed in said collar rather than the respiratory tube.

A problem with the arrangement in FIG. 22 is that it is possible for a user to push connector 267 onto elbow 29 in the reverse direction, for example with end 269 proximate the patient interface and end 268 distil therefrom. Due to the tapering of the wall(s) and the fact that the internal dimension of the connector is approximately the same as the outer dimension of the elbow 29, collar 267 may frictionally engage the elbow in this configuration. This is not ideal since the connection between the connector 267 and the elbow 29 may be compromised. Further, it can be difficult to remove the connector 267 from the elbow 29 or the respiratory tube (or terminating collar thereof) from the connector 267. More particularly, the provision or engagement of the respiratory tube with the connector 267 can exert pressure on the connector 267, tightening the fit between the connector 267 and the elbow 29. This can be exacerbated when the respiratory tube or collar therefor is pushed too far onto the connector 267 towards the patient interface.

To address these problems, a new connector 270 has been devised, as shown in FIGS. 23A-25F. FIGS. 23A-23D show the connector 270 coupled to an elbow similar to elbow 29 of FIG. 22. FIGS. 24A-24C show the elbow of FIGS. 23A-23D and FIGS. 25A-25F show the connector of FIGS. 23A-23D.

Connector 270 has first end 271 and second end 272. First end 271 is configured to couple to an elbow (such as elbow 29 shown in FIG. 22) or to a projecting collar otherwise forming a gases pathway with the interior of a patient interface or mask. For example, in a simpler arrangement, an elbow may be omitted and the connector may couple with a collar extending from the patient interface, that collar being integrally formed or coupled to the patient interface, such as via the shell.

At least the exterior surface of the wall forming the connector 270 preferably tapers along at least part of the length thereof such that at least a portion of the connector 270 nearer the first end 271 has a greater exterior dimension than an exterior dimension of a portion of the connector 27 nearer the second end 272. This tapering refers to the substantially cylindrical body forming the connector 270 and not the rib or projection 273 proximate the first end 271 of the connector 270. Tapering is commonly used for tube connectors and is configured to couple to a respiratory tube or a collar terminating such a tube as would be apparent to those skilled in the art. Additionally or alternatively, tapering may be provided in the inside of the respiratory tube (or collar terminating said tube), the inside of the tube (or collar) narrowing from its mouth. The tapering facilitates insertion of the second end 272 of the connector 270 into the respiratory tube, with a seal being formed on continued insertion thereof.

Figure 23D:
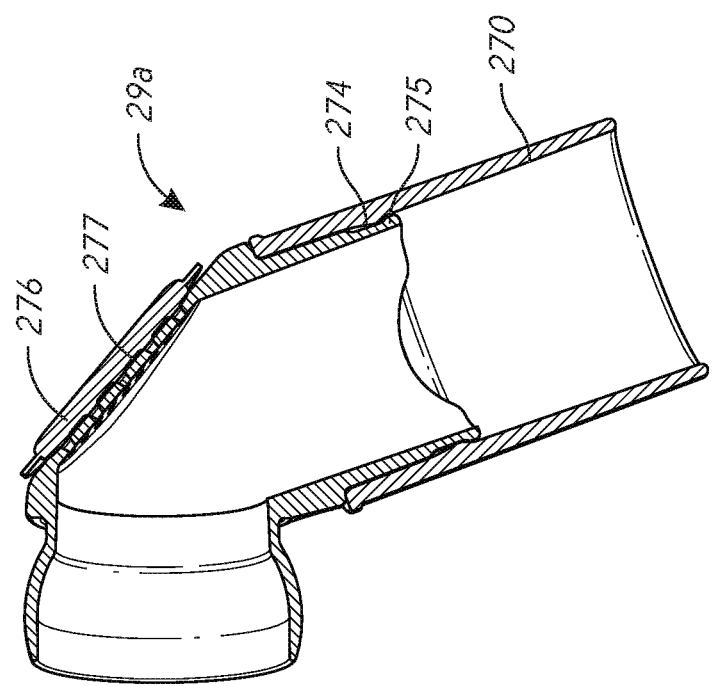
FIG. 23D is a cross-sectional view of the connector and elbow assembly of FIG. 23A
Figure 23C:
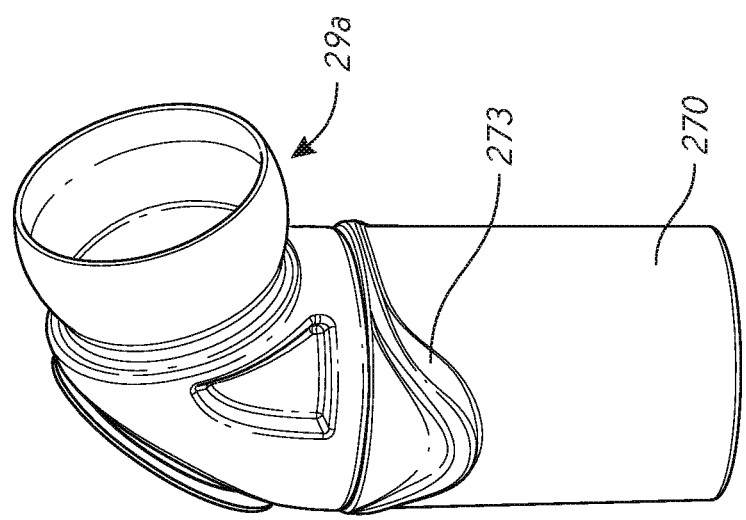
FIG. 23C is an alternative perspective view of the connector and elbow assembly of FIG. 23A.
Figure 24B:
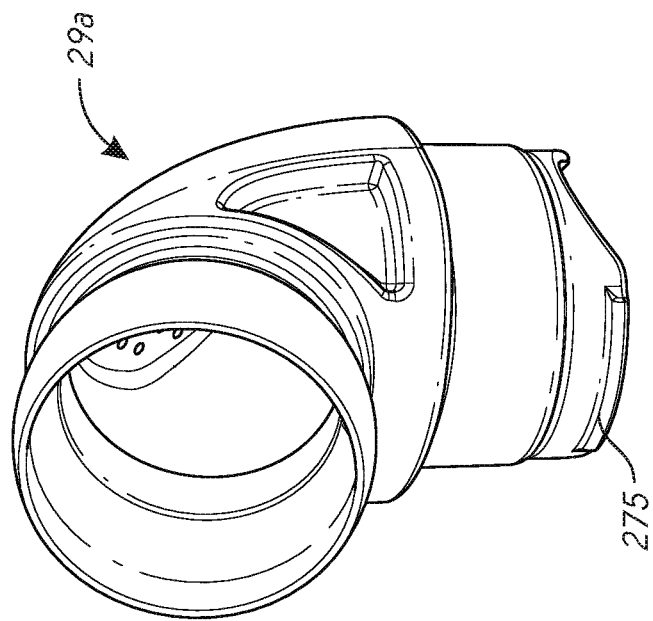
FIG. 24B is a perspective view of the connector and elbow assembly shown in FIGS. 23A-23D.
Figure 24A:
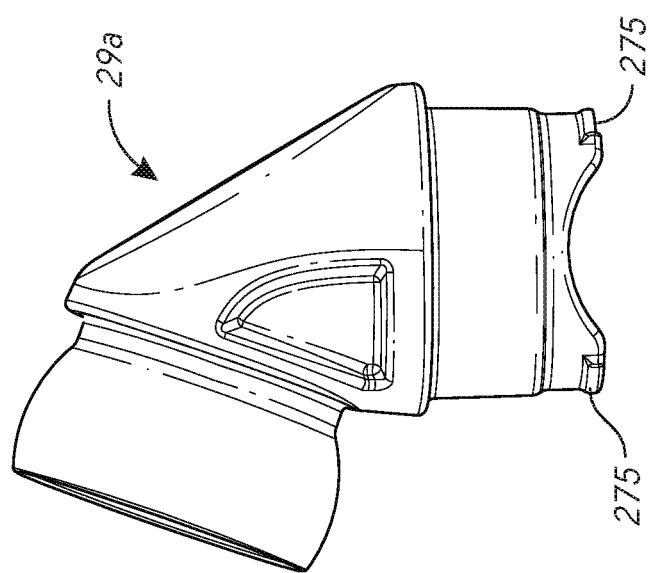
FIG. 24A is a side view of the connector and elbow assembly shown in FIGS. 23A-23D.
Figure 25A:
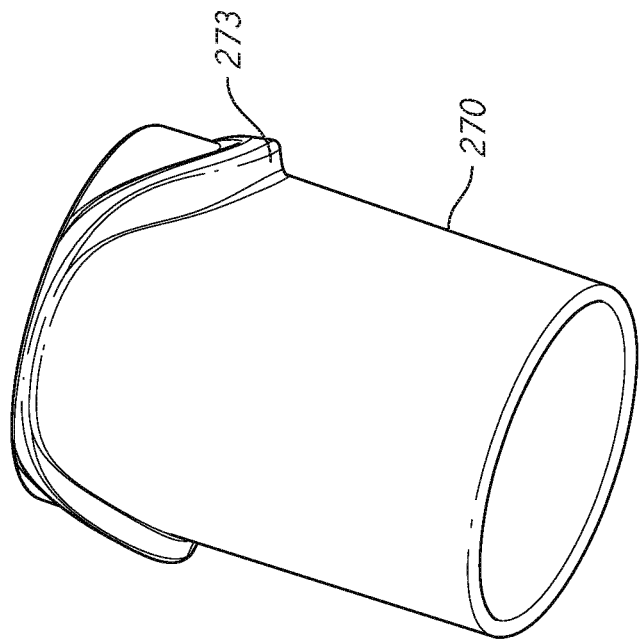
FIG. 25A is a perspective view of the elbow connector shown in FIGS. 23A-23D.
Figure 24C:
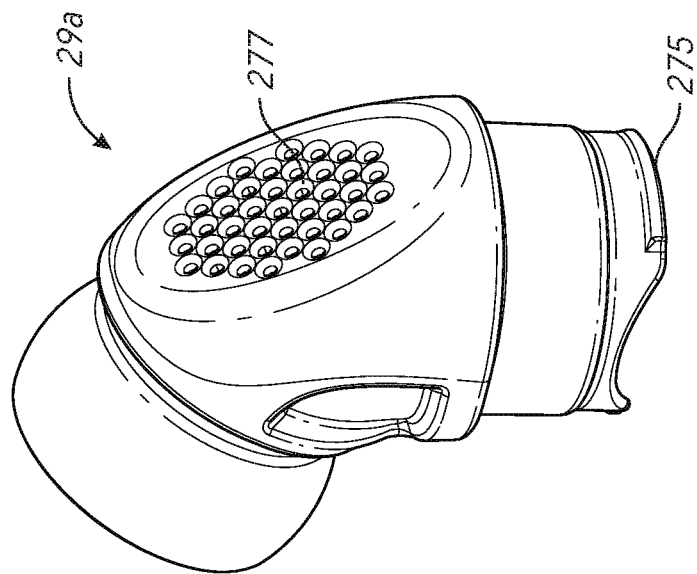
FIG. 24C is an alternative perspective view of the connector and elbow assembly shown in FIGS. 23A-23D.
Figure 25C:
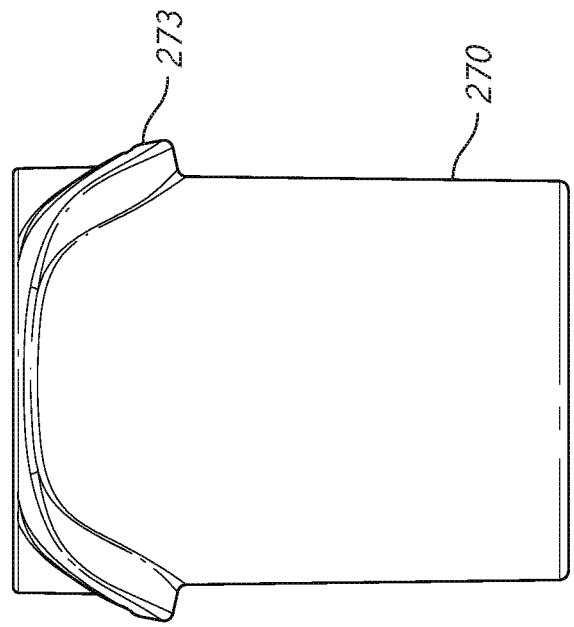
FIG. 25C is a side view of the elbow connector shown in FIGS. 23A-23D.
Figure 25B:
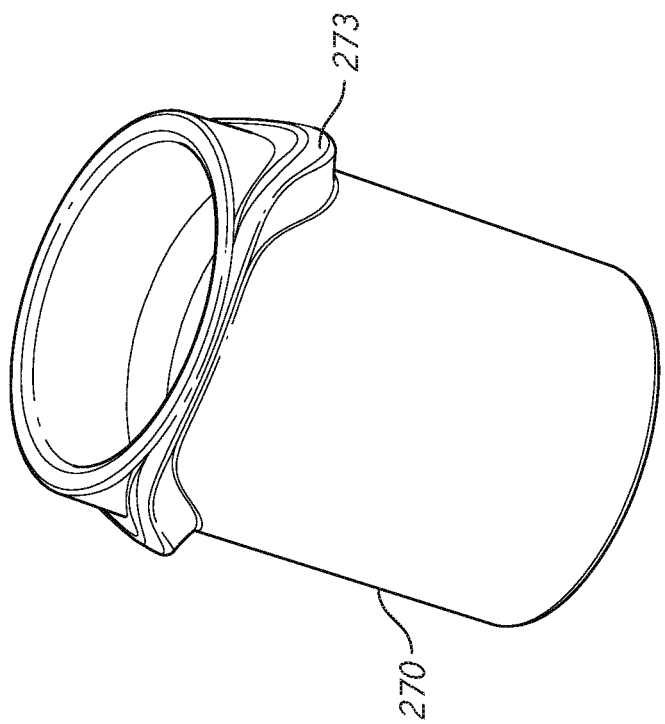
FIG. 25B is a perspective view of the elbow connector shown in FIGS. 23A-23D.
Figure 25D:
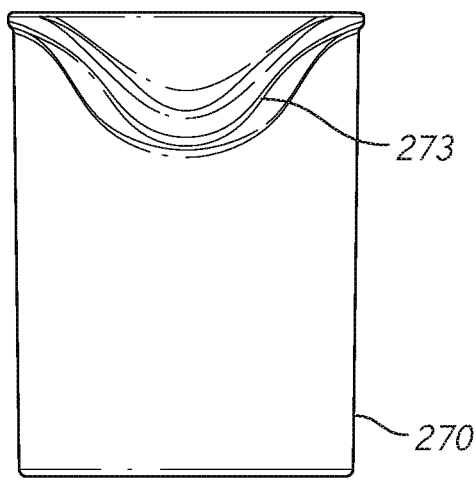
FIG. 25D is a front view of the elbow connector shown in FIGS. 23A-23D.
Figure 25E:
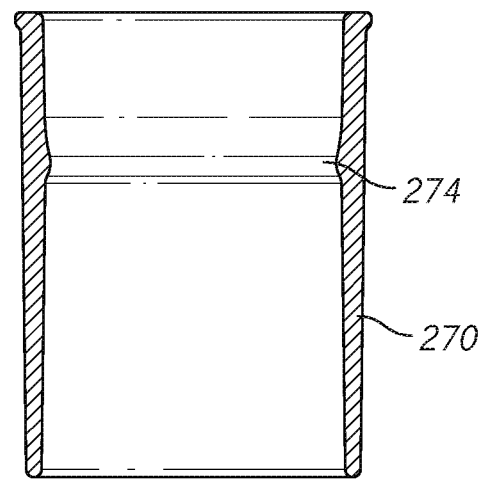
FIG. 25E is a cross-sectional view of the elbow connector shown in FIGS. 23A-23D.
Figure 25F:
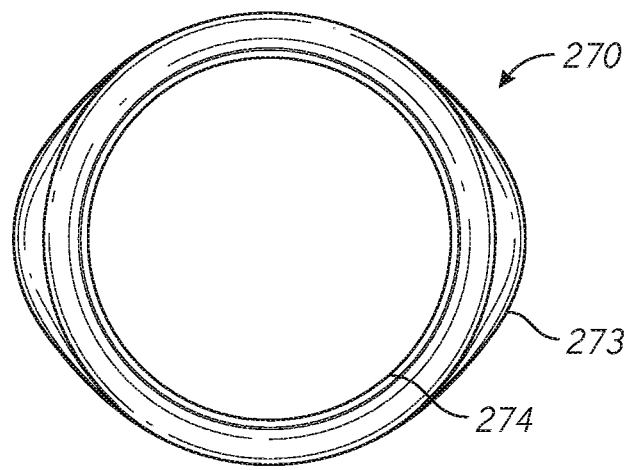
FIG. 25F is a top down perspective view of the elbow connector shown in FIGS. 23A-23D.
Figure 26:
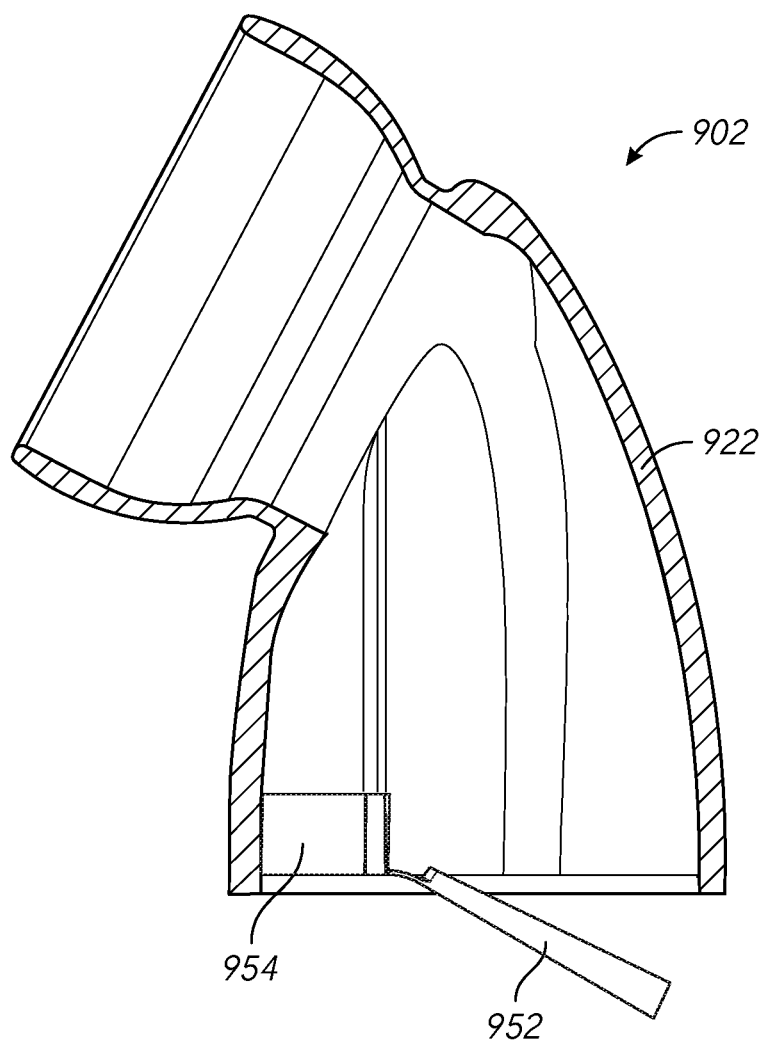
FIG. 26 is a cut-away side view of an elbow assembly in accordance with the present invention incorporating an anti-asphyxia valve.
Figure 27:
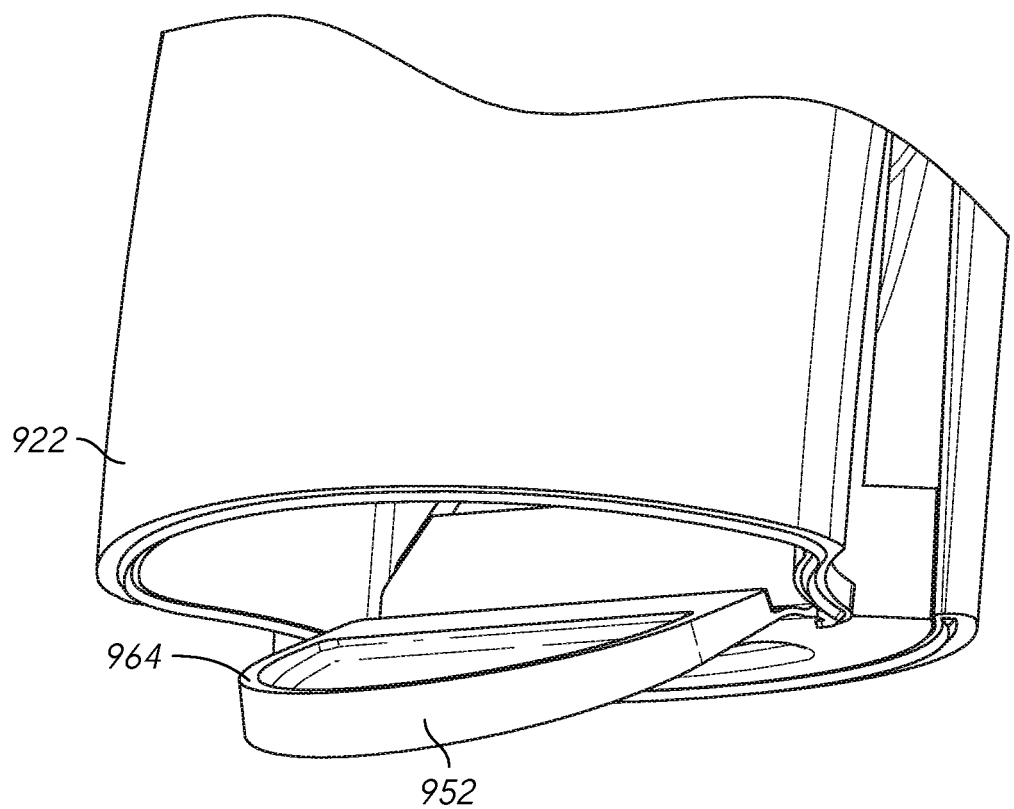
FIG. 27 is an enlarged perspective view from below of the elbow assembly of FIG. 26.

As best seen in FIGS. 23D and 25E, the interior of connector 270 includes a rib 274 which engages one or more projections 275 on elbow connector 29a, forming a click or snap fit. More generally, the elbow connector 29a is substantially the same or similar to the previous elbows connectors disclosed herein and only pertinent features of elbow connector 29a will be described. Note in FIG. 23A, elbow connector 29 is shown including cover 276 while this is omitted from FIG. 23D to expose a plurality of vent holes 277. Cover 276 could be a filter, allowing gases and/or moisture to pass therethrough or may solid and impermeable, so as to block the vent holes 277 when the cover 276 is in place.

The interior of the connector 270 extending from a point towards the second end 272 is preferably dimensioned to prevent engagement of the inside surface of the second end 272 of the connector 270 with the outer surface of the elbow connector 29a in the event a user attempts to incorrectly assemble the components together. In a preferred embodiment, this is realized by the inner dimension (generally diameter) of the connector 270 being greater than the external dimension of the elbow connector 29a that engages with the connector 270, such that it is readily apparent that the two are incorrectly assembled in view of the loose fit therebetween. Alternatively, the second end 272 of the connector 270 could have an inner dimension that prevents insertion of the elbow connector 29a therein i.e. it is too narrow or includes projections that act as stops.

Rib or projection 273 serves two functions. Firstly, it provides a grip for a user's fingers that may be used to remove the connector 270 from engagement with the elbow connector 29a. Secondly, it serves as a mechanical stop, limiting how far a respiratory tube may be pushed onto the second end 272 of the connector 270.

While the illustrated embodiment has the rib or projection 273 arcing in a sinusoidal pattern about the outer circumference of the connector 270 proximate the first end 271, the rib or projection 273 may be otherwise formed. For example, it may only extend part way around the circumference or comprise a number of discrete elements, each of which extends part way around the circumference. Further, the projection or rib may be substantially linear and/or comprise linear portions, in addition to or as an alternative to arcuate portions.

Referring additionally to FIGS. 26 to 31, another embodiment of an elbow assembly 902 comprises an elbow 922 and a sleeve (not shown), with similar features to elbow 722 and sleeve 710 of FIGS. 14 to 19. The swivel 330 as described above may also be provided but is not illustrated in FIGS. 26 to 31.

An anti-asphyxia valve (AA valve) 950 is provided and positioned over the sleeve such that it at least partially obstructs the sleeve's flow channel. AA valve 950 has similar features to valve 750 of FIGS. 14 to 19. The elbow assembly 902 functions similarly to the elbow assembly 302 of FIGS. 10 to 13 and to the elbow assembly of FIGS. 14 to 19, and similarly directs gases away from the patient when the flap 952 of the AA valve 950 drops to its closed position, namely a generally horizontal position, closing the flow channel through the sleeve.

The AA valve 950 comprises generally planar valve flap 952 which is hingedly mounted on a flap support 954 which may be integrally formed with the valve flap 952. In this example, in contrast to the valve flap 752 as shown in FIGS. 14 to 19, the valve flap 952 and the flap support 954 are configured so that at rest the flap 952 is biased downwardly so as to be inclined relative to a notional horizontal plane, that is, inclined downwardly relative to the planar underside of the flap support 954, before the sleeve is assembled on the elbow 922. When the valve 950 is in use, mounted in the elbow 922 with the sleeve in place, the flap 952 is horizontal, with the planar lower surface of the flap 952 flush with, and parallel to, the upper planar sealing surface of the sleeve, as shown in FIG. 14 for example.

During assembly, the sleeve moves the downwardly inclined valve flap 952 upwardly to the generally horizontal position when the sleeve is fully assembled on the elbow 922. When the valve flap 952 is at rest in the generally horizontal position, the flap 952 is trying to pivot downwardly against the sleeve, that is, the flap 952 is biased downwardly, away from the vertical orientation, helping the flap 952 remain in the horizontal orientation with the flow channel through the sleeve closed and the air venting channels in the elbow 922 open. This biased flap 952 helps to ensure that the user of the elbow can still breathe, through the air venting channels in the elbow 922, when breathing gas is not being delivered through the flow channel in the sleeve.

The degree of biasing created by the flap 952 being initially downwardly inclined can be configured by the thickness of the hinge 960 between the support 954 and the flap 952, and the size of the angle of the flap 952 relative to the notional horizontal plane (which is parallel with the planar undersurface of the support 954) when the flap 952 is in a rest condition, prior to assembly with the sleeve. If the hinge thickness is too great, the flap 952 will not flex sufficiently easily for the flap 952 to pivot about the hinge 960 in the above described manner. If the hinge thickness is too thin, the flap 952 can be unstable in that it flexes, deforms and vibrates too much to perform an effective seal when in the vertical and/or horizontal positions.

In this example, the valve 950 is provided with further features, which features may also be used with the other examples of the valve 350, 750 described herein. One such feature is that in this example, the sealing bead 964 extends around the top surface of the valve flap 952 to form a 'D' shaped seal, as per the bead 764 of valve flap 752. However, at a part of the bead 964 adjacent the support 954, the bead 964 comprises a linear bead portion 964a of increased surface area, which seals against the vertical front face 954a of the support 954, when the flap 952 is in a vertical orientation. The portion 964a comprises an oblong, planar sealing face which extends across the flap 952 from one side to the other, adjacent the hinge 960. The width and length of sealing face 964a closely corresponds to, or is preferably identical to, the height and width of front face 954a of support block 954 such that when the flap 952 is in the vertical position, sealing face 964a is substantially matched in size and shape with, and seals against, all of front face 954a. This generates an improved seal between the part of the flap 952 that contacts the support 954.

A margin of the oblong sealing face 964a comprises an inclined, transitional wall 964b where the face 964a meets the upper planar surface 972 of the valve flap 952. The upper planar surface 972 is defined as a recessed planar region bounded by the sealing bead 964. The thickness of the wall 964b can be configured to control the stiffness of the flap 952, that is, the wall 964b functions as a stiffening rib or reinforcement member. The wall 964b can help prevent the valve flap 952 from ballooning or otherwise flexing and distorting under pressure in use, where otherwise the flap 952, and particularly the upper planar surface 972, may be too thin to resist the pressures generated in use.

Figure 28A:
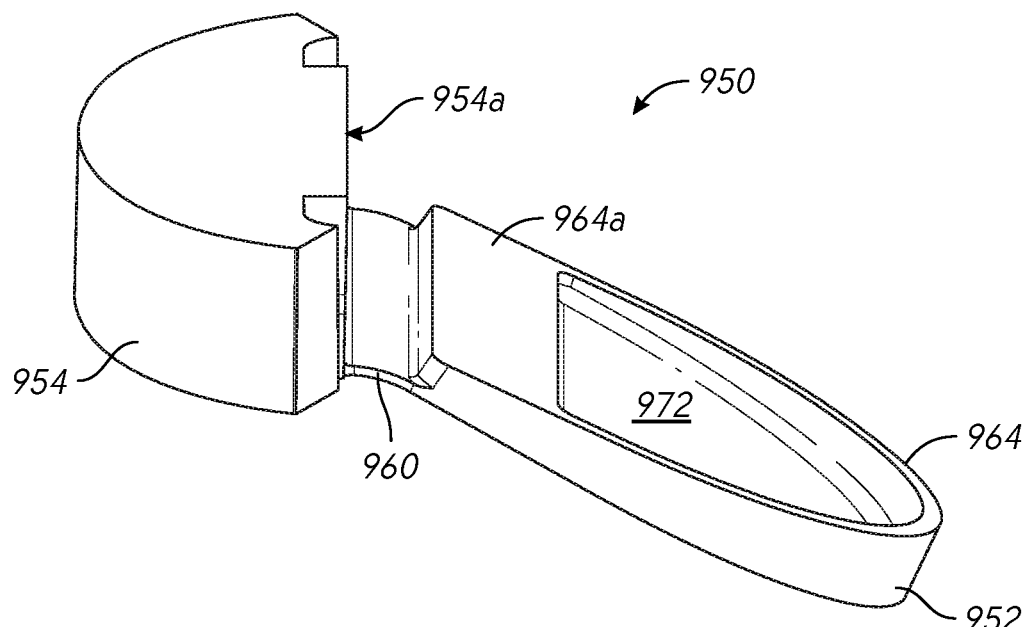
FIG. 28A shows a top perspective view of the anti-asphyxia valve of the elbow assembly of FIGS. 26 and 27.
Figure 28B:
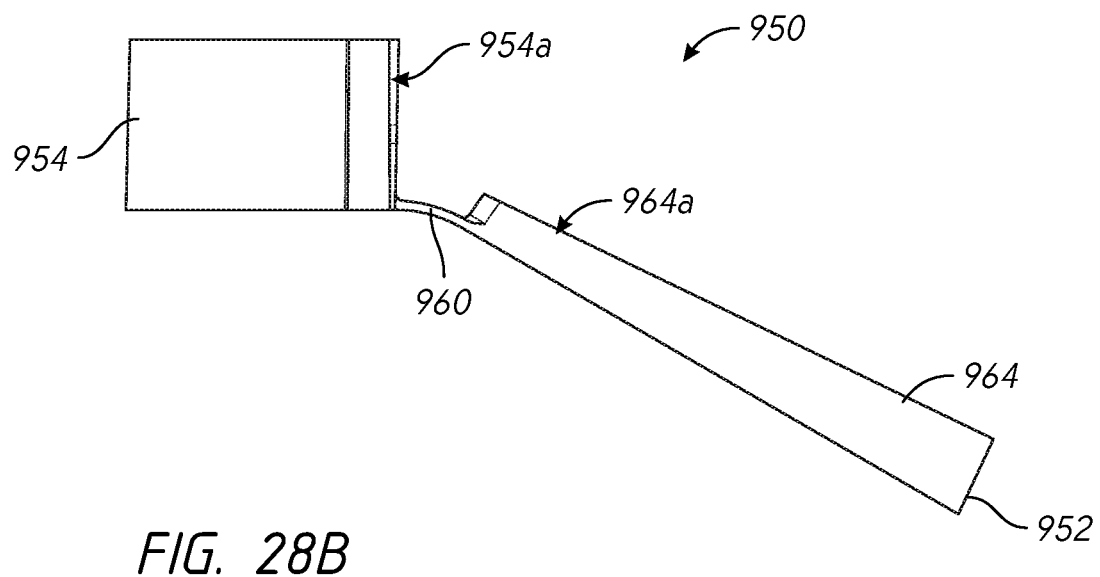
FIG. 28B shows a side perspective view of the anti-asphyxia valve of the elbow assembly of FIGS. 26 and 27.
Figure 28C:
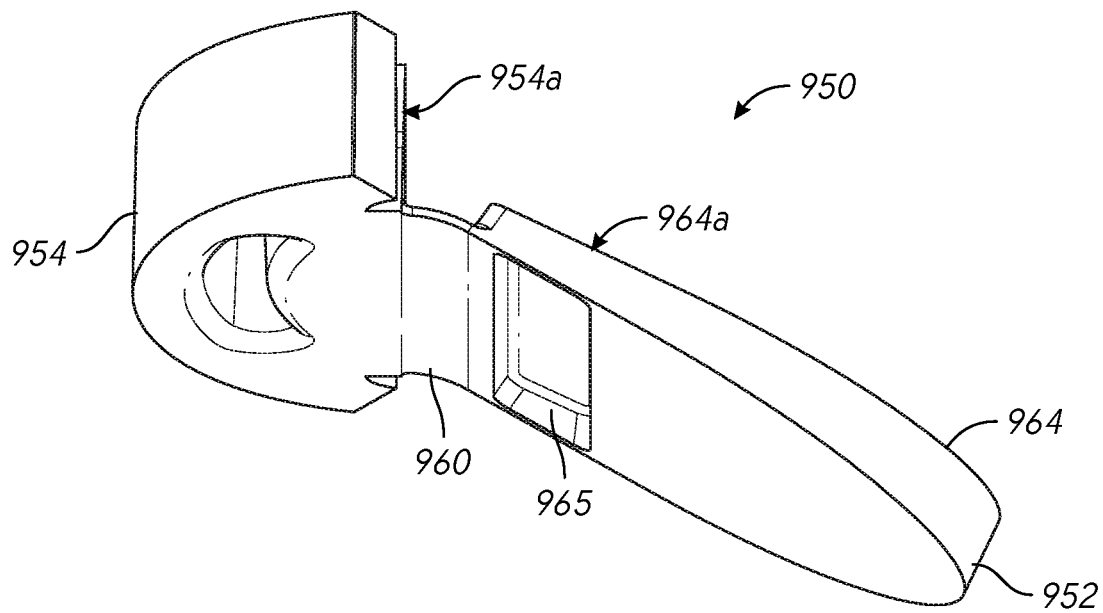
FIG. 28C shows a bottom perspective view of the anti-asphyxia valve of the elbow assembly of FIGS. 26 and 27.
Figure 29:
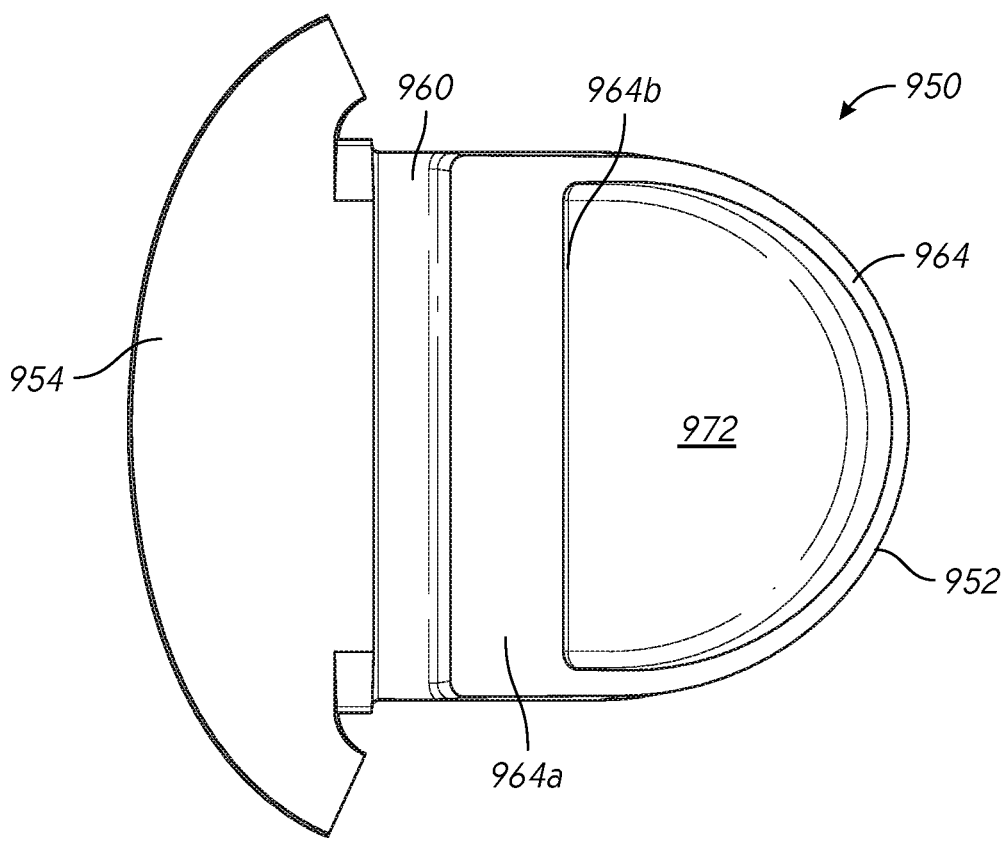
FIG. 29 is a plan view of the valve of FIGS. 26 to 28.
Figure 30:
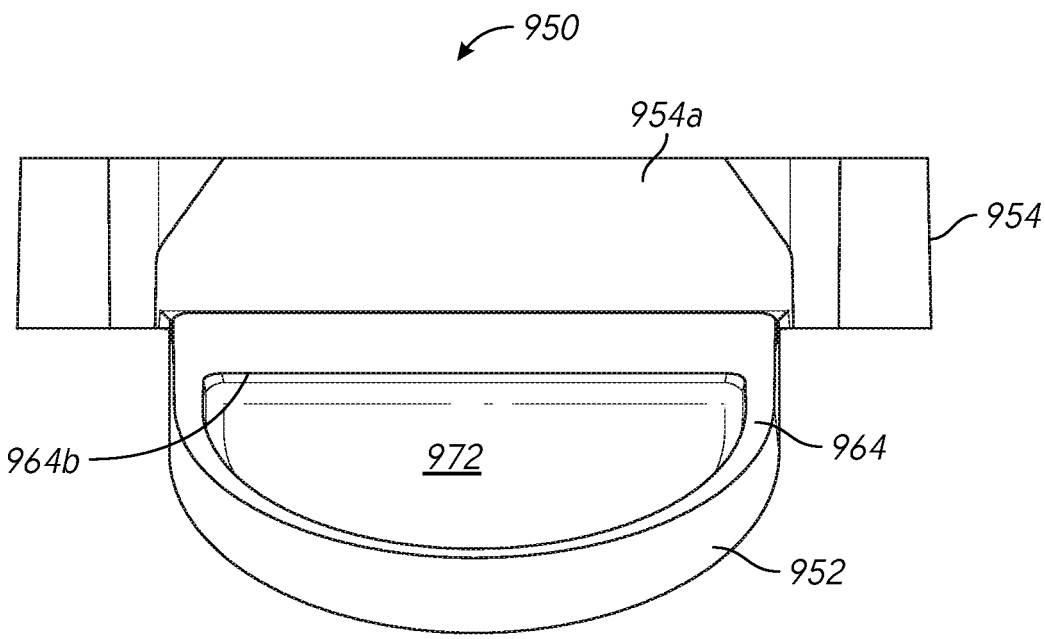
FIG. 30 is a front view of the valve of FIGS. 26 to 29

Likewise, and with particular reference to FIG. 28c, the underside of the valve flap 952, adjacent the hinge 960, may comprise a recess 965 configured to allow a desired amount of flex in the valve flap 952, adjacent the hinge 960. Some flex in the valve flap 952 is useful in allowing the flap 952 to deform sufficiently to achieve the best possible seal against the sealing faces of the elbow 922 and sleeve. In this example the recess 965 is oblong, defined directly underneath the upper sealing face 964a.

The dimensions and thicknesses of the features of the valve flap 952 and the support 954 may be configured as individual parameters, and/or relative to one another, to ensure that the valve flap 952 has the desired properties to achieve the best seal in both the horizontal and vertical positions, and also reacts appropriately to changes in pressure to move effectively from the horizontal to the vertical positions and vice versa. Additional reference is made to FIG. 31, which shows some example and non-limiting dimensions in one embodiment of the valve 950.

Figure 31:
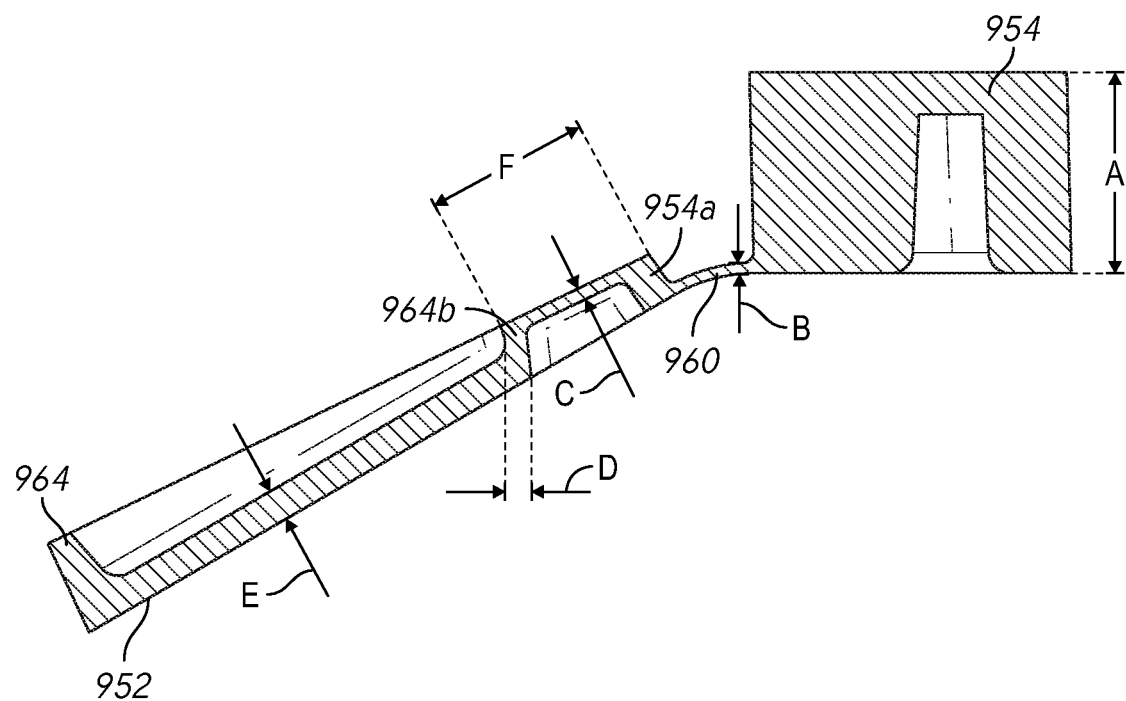
FIG. 31 is a sectional side view of the valve of FIGS. 28 to 30, showing non-limiting, optional example dimensions.

The valve 950 may have the following properties, each of which may be provided as an individual feature or in combination with a property of another feature or features:

a) The angle of the flap 952 prior to being assembled between the elbow and sleeve, in particular the angle of the planar undersurface of the flap 952, may be inclined between 0 and 90° from the notional horizontal plane, and is preferably between 0.5 and 75°, more preferably from 5 to 60°, more preferably 5 to 45°, and in one preferred embodiment between 10 and 40°.

b) The thickness B of the hinge 960, when viewed from the side as per FIG. 31 for example, may be between 0.05 and 1.0 mm, preferably between 0.1 and 0.75 mm, more preferably between 0.1 and 0.5 mm, more preferably between 0.15 and 0.4 mm, and in one preferred embodiment is 0.25 mm.

c) The thickness A of the support 954, when viewed from the side, may be between 1 and 10 mm, preferably between 1 and 7.5 mm, more preferably between 1 and 5 mm, and in one preferred embodiment is 4.75 mm.

d) The thickness E of the valve flap 952 in the region of the upper planar surface 972 between the sealing bead 964, may be between 0.1 and 2 mm, preferably between 0.5 and 1.5 mm, more preferably between 0.5 and 1 mm, and in one preferred embodiment is 0.75 mm.

e) The thickness D of the inclined wall 964b, when viewed in section from the side, may be between 0.1 and 1.5 mm, preferably between 0.2 and 1 mm, more preferably between 0.2 and 0.75 mm, more preferably between 0.3 and 0.6 mm, and in one preferred embodiment is 0.53 mm.

f) The thickness C of the bead region 964a above recess 965, when viewed in section from the side, may be between 0.1 and 1 mm, preferably 0.1 and 0.75 mm, more preferably between 0.1 and 0.5 mm, and in one preferred embodiment is 0.3 mm.

g) The width F of the bead region 964a, in a direction away from the hinge axis and away from the support 954 when viewed in plan, may be between 2 and 6 mm, preferably 2 and 5 mm, more preferably 3 and 4 mm, and in one preferred embodiment is 3.89 mm.

h) The length of the valve flap 952 in a direction extending perpendicularly from the hinge 960 to the apex of the valve flap 952 may be between 10 and 25 mm, preferably 10 and 20 mm, more preferably 12 and 18 mm, and in one preferred embodiment is about 15.5 mm.

i) The bead 964 preferably tapers towards the hinge 960 so as to be relatively thick distal from the hinge 960 and relatively thin adjacent the hinge 960, when the bead 964 is viewed from the side. The bead 964, and in particular the plane of the upper top surface of the bead 964 may be angled between 0 and 45° relative to the planar undersurface of the flap 952, preferably 0 and 30°, more preferably, 1 and 15°, and in one preferred embodiment is about 4°. The greater the angle, the greater the bead will project into the flow path of the elbow assembly. However, the smaller the angle, the more likely that the flap will undesirably stick in a vertical orientation.

j) The flap 964, when viewed from above, in the example of FIGS. 26 to 31 is substantially semi-circular or horse-shoe shaped. However, in other embodiments, the flap may be any other desired shape, and may, for example, be substantially square, oblong, triangular, circular or omega shaped, when viewed in plan.

In accordance with the invention, the following ratios of properties of features of the valve 950, may be varied as follows:

k) Support block 954 thickness to hinge 960 thickness: may be between 5:1 and 30:1, more preferably 10:1 to 25:1, more preferably 15:1 to 25:1, and in one preferred embodiment 19:1.

l) Valve flap 952 thickness in the region of upper planar surface 972 between the bead to hinge 960 thickness: may be between 1:1 and 10:1, more preferably 1:1 to 8:1, more preferably 2:1 to 5:1, and in one preferred embodiment 3:1.

m) Valve flap 952 thickness in the region of upper planar surface 972 between the bead to the thickness of the bead region 964a above recess 965: may be between 1:1 and 10:1, more preferably 1:1 to 8:1, more preferably 2:1 to 5:1, and in one preferred embodiment 2.5:1.

n) Valve flap 952 thickness in the region of upper planar surface 972 between the bead to thickness of the inclined wall 964b: may be between 1:1 and 10:1, more preferably 1:1 to 5:1, more preferably 1:1 to 2:1, and in one preferred embodiment 1.4:1.

o) Valve flap 952 thickness in the region of upper planar surface 972 between the bead to thickness of the bead region 964a above recess 965: may be between 1:1 and 10:1, more preferably 1:1 to 5:1, more preferably 2:1 to 3:1, and in one preferred embodiment 2.5:1.

p) Thickness of the inclined wall 964b to the thickness of the bead region 964a above recess 965: may be between 1:1 and 10:1, more preferably 1:1 to 5:1, more preferably 1:1 to 2:1, and in one preferred embodiment 1.75:1.

q) Support block 954 thickness to the width of bead region 964a: may be between 1:1 and 10:1, more preferably 1:1 to 5:1, more preferably 1:1 to 2:1, and in one preferred embodiment 1.2:1.

r) Width of bead region 964a to thickness of the bead region 964a above recess 965: may be between 1:1 and 30:1, more preferably 1:1 to 20:1, more preferably 1:1 to 15:1, and in one preferred embodiment 13:1.

Annular Bias-Flow Venting

Figure 32:
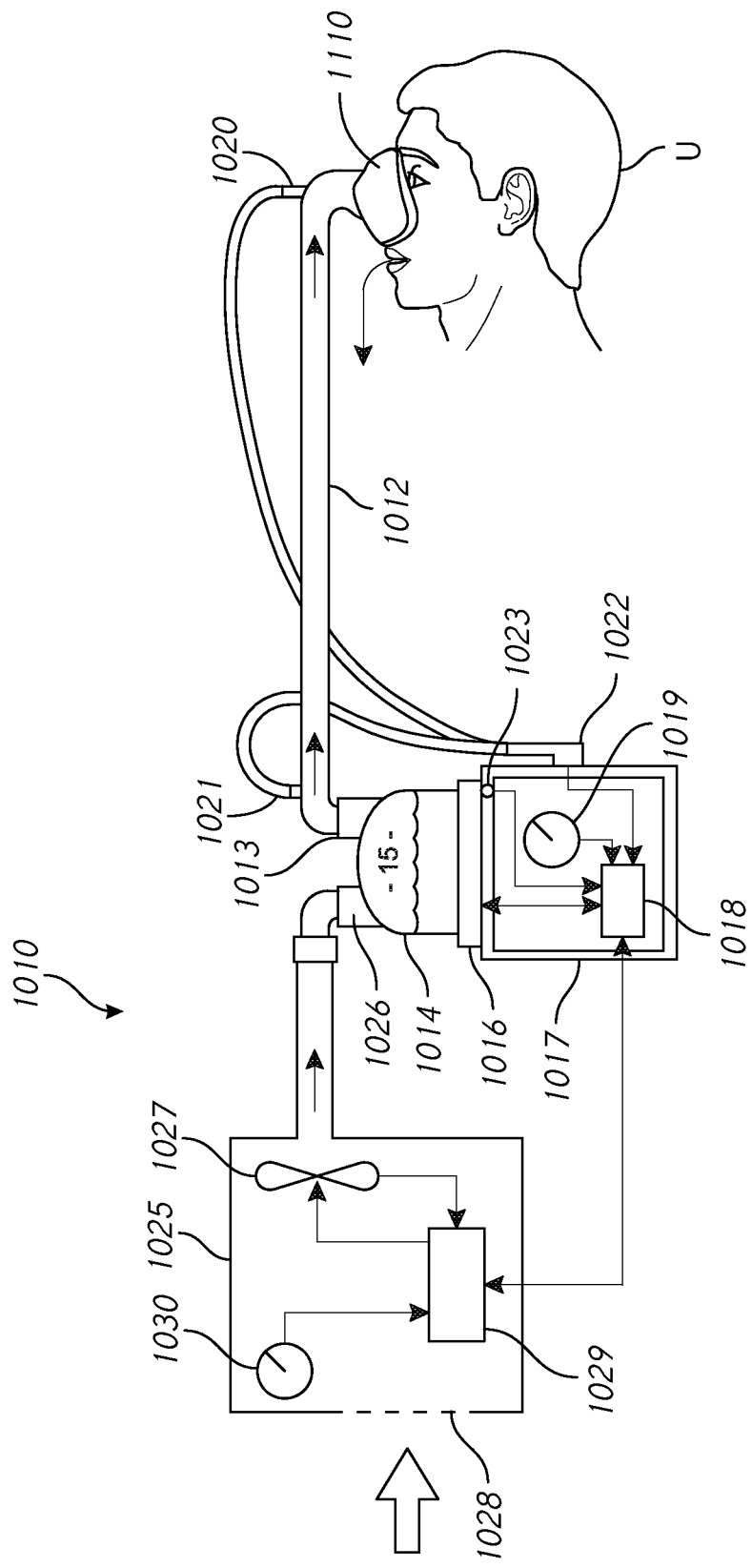
FIG. 32 is a view of a respiratory system comprising a flow generator, a humidifier and a user interface.

For a more detailed understanding of the disclosure, reference is first made to FIG. 32, which shows a breathing circuit according to at least one embodiment, which includes a respiratory mask.

FIG. 32 is a schematic diagram of a positive pressure respiratory therapy system in the form of a continuous positive airway pressure (CPAP) system 1010 for providing a heated and humidified air stream to a user U through an interface 1110 worn by the user, and which is connected to CPAP system 1010 by a conduit or tube 1012. A humidification chamber 1014 has a heat conductive base in contact with a heater plate 1016 of a humidifier 1017 to humidify the air stream. The conduit 1012 is connected to an outlet 1013 of the humidification chamber 1014 to convey humidified air to the user interface 1110. The humidifier 1017 comprises a controller 1018, such as a microprocessor-based controller that executes computer software commands stored in an associated memory, for example but without limitation. The controller 1018 receives input commands from multiple sources, including a user input interface 1019 such as a dial or touch screen, which enables the setting of a predetermined value of humidity, temperature, or other characteristic of the humidified air supplied to the user U. The controller 1018 also may receive input from one or more other sources, such as for example temperature and/or flow velocity sensors 1020 and 1021, which are connected through a connector 1022 to communicate with the controller 1018, and/or a heater plate temperature sensor 1023. In response to the selected humidity or temperature value, the controller 1019 determines when and/or to what level the heater plate 1016 should be energized to suitably heat the water contained in the humidification chamber 1014.

As the volume of water in the chamber is heated, water vapor begins to fill the volume of the chamber above a surface of the water. The water vapor passes out of the outlet 1013 of the humidification chamber with a flow of air that is provided from a supply 1025, such as a blower 1027, and which enters the humidification chamber 1030 through an inlet 1026. The blower 1027 can be a variable speed fan, or can include a variable pressure regulator. The blower 1027 draws air through an inlet 1028. The blower can be controlled by a controller 1029 or by the controller 1018, for example. The controller 1018 or 1029 may control blower speed, regulated pressure, or the like according to any suitable criteria. For example, the controller 1029 may respond to inputs from controller 1018 and a user set value (e.g., a preset value) of pressure and/or fan speed, which can be set with a user interface 1030 (e.g., a dial).

The conduit 1012 may comprise a heater such as a heater wire for example, to heat the walls of the conduit to reduce condensation of humidified gases within the conduit.

The respiratory masks and components of the disclosure can be used in such a CPAP system as described whether humidified or not, or alternatively in other forms of respiratory systems, such as for example VPAP (Variable Positive Airway Pressure) systems, BiPAP (Bi level Positive Airway Pressure) systems, or with a ventilator, and are described herein generally with reference to CPAP therapy by way of example only.

Bias-flow venting systems for use in expelling exhausted air from within a respiratory mask are described in even greater detail below. The venting systems generally provide paths through which gas, exhaled by a user, can be exhausted to atmosphere.

III. Bias Flow Venting in Two-Part Ball-Joint Socket and Connection Housing

In various embodiments, a bias-flow venting systems is incorporable in a connection housing engaging with a housing for a seal, such as a cushion. The connection housing directly engages a socket for a truncated ball-joint connector, forming a unitary (one-piece) structure. The unitary structure disassembles into at least two parts (for example, the separate socket and the connection housing) to facilitate cleaning the bias-flow venting system. When in use in a respiratory mask, the unitary structure is configured to pass inspiratory gas received from the truncated ball-joint connector to the respiratory mask's user. Because the unitary structure incorporates the bias-flow venting system, the unitary structure is not only capable of supplying inspiratory gas to the user but also removing expiratory gas from the user. The unitary structure's configuration improves overall compactness of the respiratory mask.

A. Assemblage through Slot in Socket

Figure 33A:
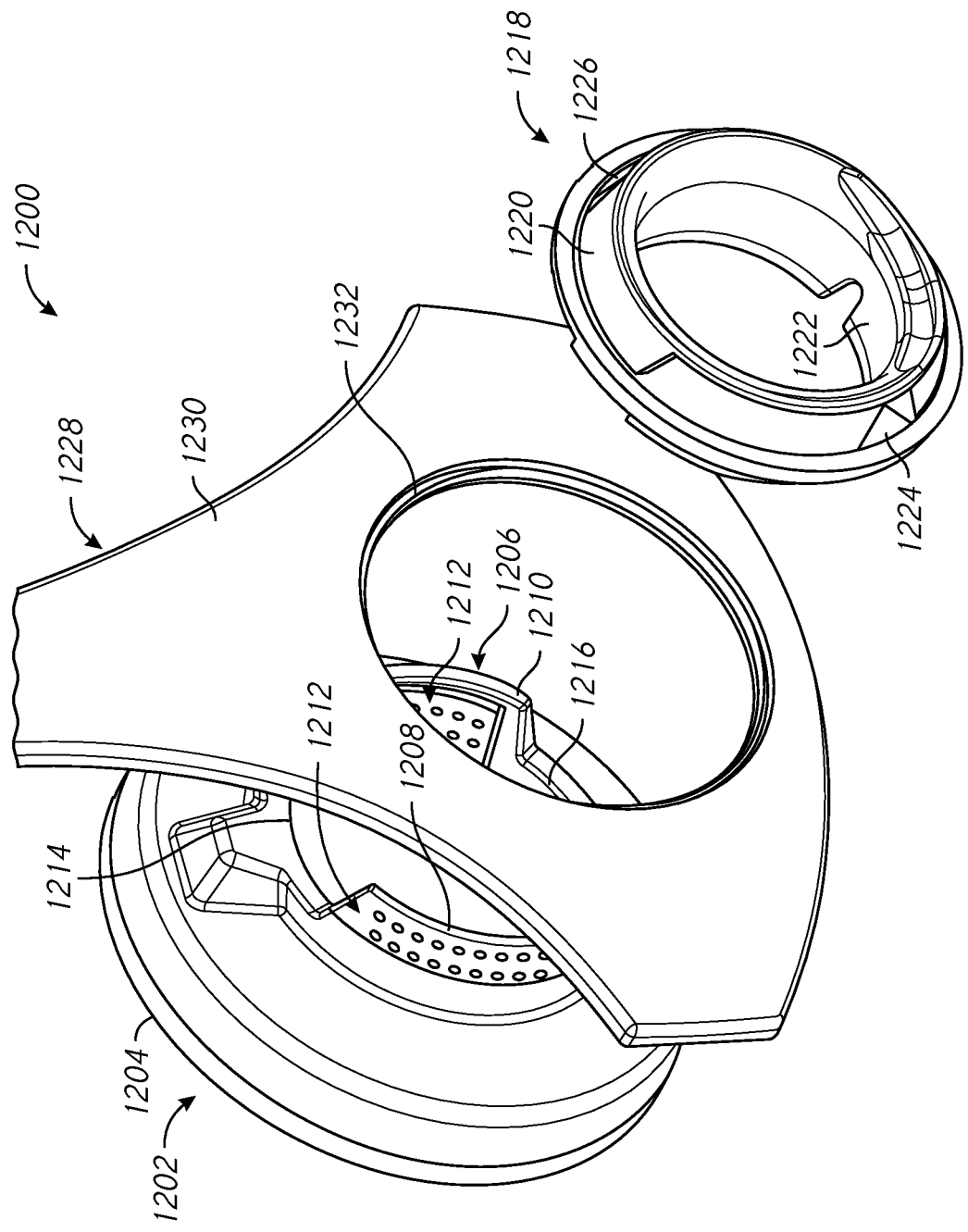
FIG. 33A shows components for bias flow venting in a two-part ball-joint socket and connection housing according to an embodiment.
Figure 33B:
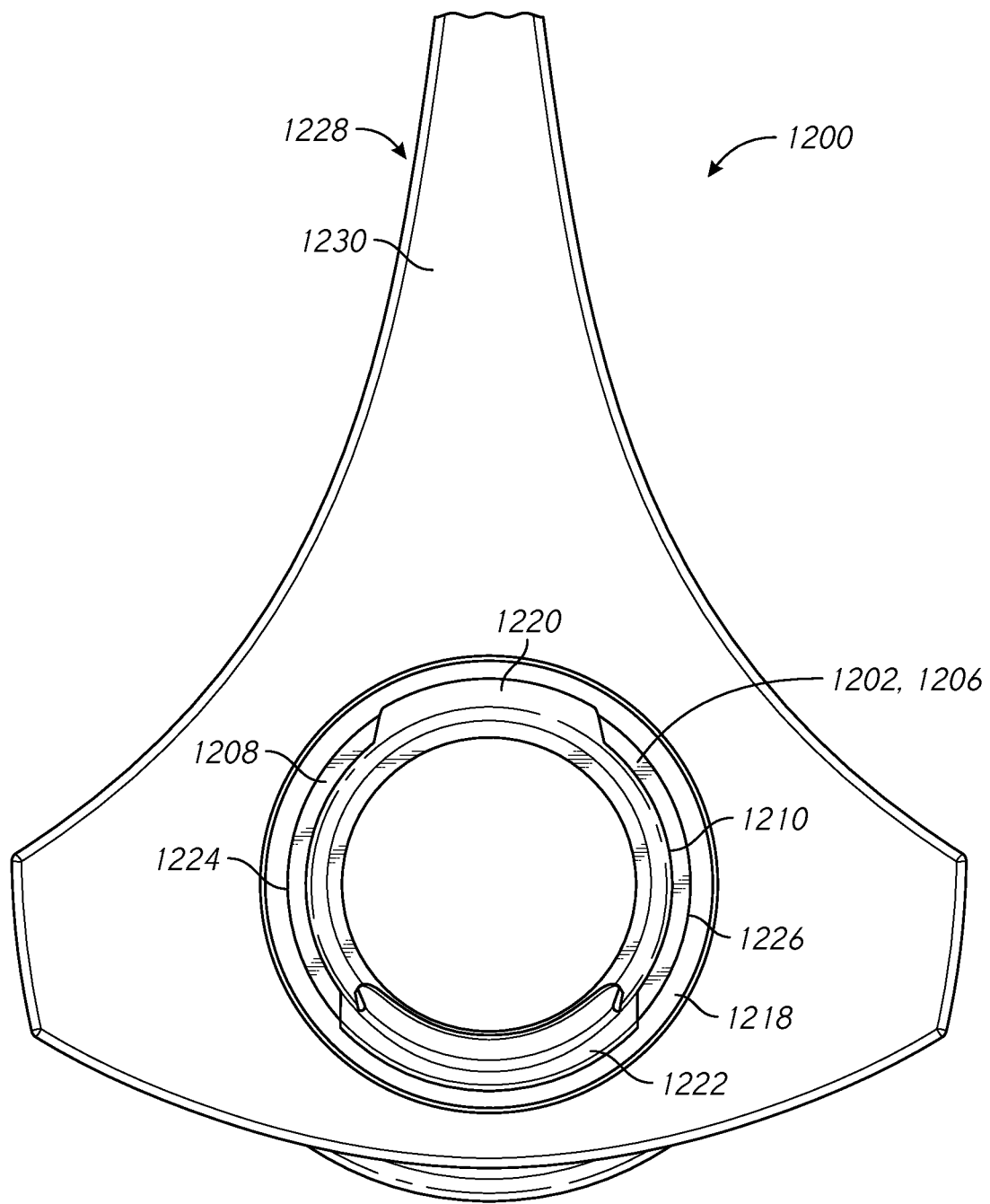
FIG. 33B shows a front view of the two-part ball-joint socket and connection housing of FIG. 33A.
Figure 33C:
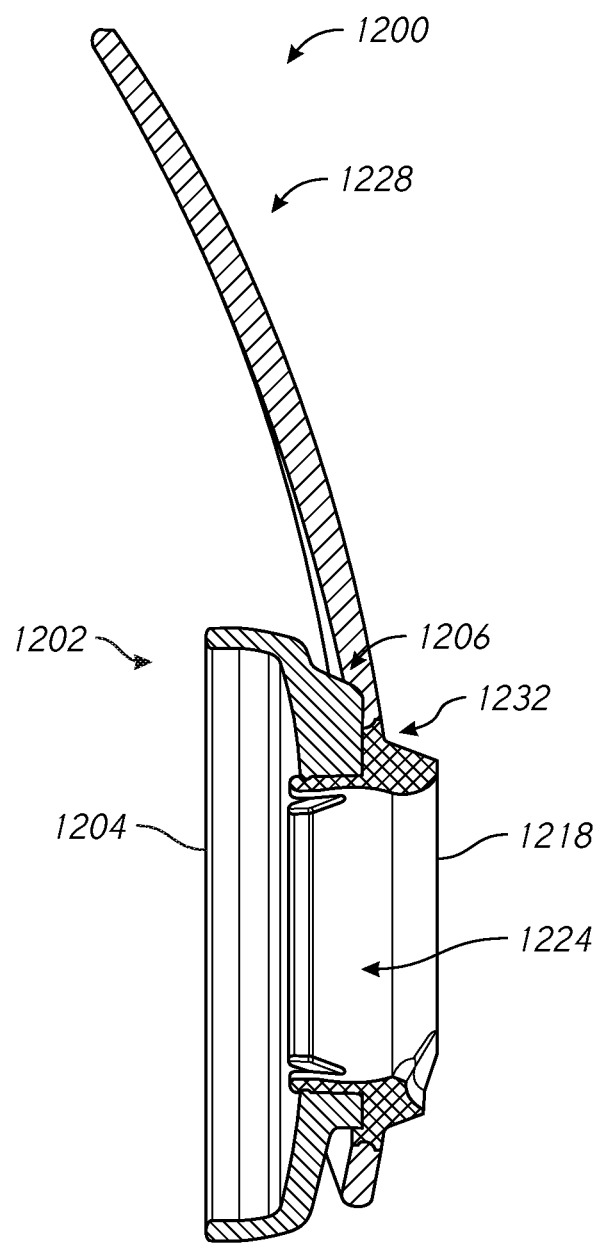
FIG. 33C shows a side cross-sectional view of the two-part ball-joint socket and connection housing of FIG. 33A.

With reference first to FIGS. 33A-33C, in at least one embodiment, a kit 1200 for a respiratory mask is disclosed. It should be understood that assemblages of one, some, or all of the kit 1200 components are within the scope of the disclosure and such assemblages and respiratory systems including such assemblages should be considered embodiments of the disclosure.

The kit 1200 includes a connection housing 1202 emplaced over the patient's face when in use. The connection housing 1202 includes a first end portion 1204 (FIGS. 33A and 33C) configured to engage a cushion housing for contacting the user's face. The connection housing is omitted from FIGS. 33A-33C to simplify the drawings. Suitable connection housings are shown and described, for example, in U.S. Patent Application No. 62/041,262 and U.S. Patent Application No. 62/096,481, previously incorporated herein by reference. It should be understood that, in certain embodiments, the connection housing can be included in the kit 1200, assemblages thereof, and respiratory systems including such assemblages.

The connection housing 1202 further includes a connection ring 1206 opposite the first end portion 1204. The connection ring 1206 includes a first connection-housing raised portion 1208 (FIGS. 33A and 33B) and a second connection-housing raised portion 1210 (FIGS. 33A and 33B). The first connection-housing raised portion 1208 and the second connection-housing raised portion 1210 are each generally arcuate and extend away from the first end portion 1204. In this example, the first connection-housing raised portion 1208 is opposite the second connection-housing raised portion 1210 around the connection ring 1206. Each includes at least one array of holes 1212 (FIG. 33A), extending along at least a part of the respective arc, configured to pass expiratory gas expired by the user to the ambient atmosphere when in use. Such holes 1212 can be formed during molding of the connection ring 1206 or could be drilled (for example, with a laser) after molding is complete. Many hole array configurations are contemplated and are within the scope of the disclosure. For example, single linear arrays and double linear arrays are contemplated. The holes 1212 can be circular or non-circular. Other examples of arrays are shown, for example, with reference to FIGS. 39A-39D. And while FIGS. 39A-39D relate to a different embodiment than the embodiment of FIGS. 33A-33C, it should be appreciated that the example hole arrays shown are incorporable in the present embodiment.

In the example embodiment of FIGS. 33A-33C, the connection housing 1202 includes two connection-housing raised portions 1208, 1210. But it should be understood that the first connection-housing raised portion 1208 and the second connection-housing raised portion 1210 can be elements of a larger plurality of connection-housing raised portions in other configurations. For example, the connection housing 1202 can include three, four, five or more connection-housing raised portions.

The first connection-housing raised portion 1208 and the second connection-housing raised portion 1210 define therebetween a generally arcuate first connection-housing recessed portion 1214 (FIG. 33A) and a generally arcuate second connection-housing recessed portion 1216 (FIG. 33A). In this example embodiment, the arc length of the first connection-housing recessed portion 1214 is less than the arc length of the second connection-housing recessed portion 1216. An advantage of this configuration is discussed below. In the example embodiment of FIGS. 33A-33C, the connection housing 1202 includes two connection-housing recessed portions 1214, 1216. But, again, it should be understood that the first connection-housing recessed portion 1214 and the second connection-housing recessed portion 1216 can be elements of a larger plurality of connection-housing recessed portions in other configurations. For example, the connection housing 1202 can include three, four, five or more connection-housing recessed portions.

The kit 1200 also includes a annular socket 1218 configured to pass inspiratory gas from a gas supply to the connection housing 1202 via a central bore in the socket 1218. The gas supply can be, for example, a swivel connector (not shown) configured to deliver inspiratory gas to a user. The swivel connector can include, for example, a generally tubular first end and a truncated ball joint at a second end opposite the first end, the truncation defining a ball joint opening configured to pass the inspiratory gas therethrough. Other configurations are contemplated, such as a swivel elbow configured to rotate on a single axis instead of a truncated ball joint. Other example swivel connectors are shown and described below and the depictions and descriptions are incorporated herein by reference. The socket 1218 is configured to receive the truncated ball joint, when in use. It should be understood that, in certain embodiments, the swivel connector can be included in the kit 1200, assemblages thereof, and respiratory systems including such assemblages.

The kit 1200 can optionally further include a frame 1228 emplaced over the connection housing 1202 when in use. In at least one embodiment, the frame 1228 includes a frame housing 1230 (FIGS. 33A and 33B), including a frame opening 1232 (FIGS. 33A and 33C) with a generally annular periphery, and the socket 1218, emplaced within the frame opening 1232. The frame housing 1230 optionally can be molded to the socket 1218 as a single piece. The socket 1218 optionally can be permanently installed in the frame housing 1230, for instance, by gluing, press fitting, welding, or soldering. In certain embodiments, the socket 1218 can be removably installed in the frame housing 1230, for instance, by click-together connection.

With reference again to the socket 1218, the socket 1218 includes a generally arcuate first socket raised portion 1220 (FIGS. 33A and 33B) and a generally arcuate second socket raised portion 1222 (FIGS. 33A and 33B). The arc length of the first socket raised portion 1220 can be less than the arc length of the second socket raised portion 1222.

The first socket raised portion 1220 and the second socket raised portion 1222 define therebetween a generally arcuate first socket slot 1224 (FIGS. 33A-33C) and a generally arcuate second socket slot 1226 (FIGS. 33A and 33B). In this example, the outer periphery of the socket 1218 completely and continuously engages the inner periphery of the frame opening 1232, and the socket 1218 includes socket slots 1224, 1226 within the outer periphery of the socket 1218 for uniting with the first connection-housing raised portion 1208 and the second connection-housing raised portion 1210. Further in this example, the first socket slot 1224 is opposite the second socket slot 1226. In the illustrated example, the socket raised portions 1220, 1222 are located at the top and bottom of the socket 1218. This configuration advantageously allows the socket slots to be located on the sides of the socket 1218, which is desirable for reasons discussed below.

The socket 1218 is configured to removably engage with the connection housing 1202 as a unitary structure, such that, when engaged, the first socket raised portion 1220 unites with the first connection-housing recessed portion 1214, the second socket raised portion 1222 unites with the second connection-housing recessed portion 1216, the first connection-housing raised portion 1208 passes through the frame opening 1232 and unites with the first socket slot 1224, and the second connection-housing raised portion 1210 passes through the frame opening 1232 and unites with the second socket slot 1226. Inspiratory gas flows from the swivel connector and passes through the central bore of the socket 1218 to the connection housing 1202. Expiratory gas flows from the connection housing 1202 and passes through a first space between the first connection-housing raised portion 1208 and a first region of the socket 1218 radially inward from the first socket slot 1224, and though a second space between the second connection-housing raised portion 1210 and a second region of the socket 1218 radially inward from the second socket slot 1226. From the first space and the second space, the expiratory gas passes to the ambient atmosphere via the at least one array of holes 1212 in each of the first connection-housing raised portion 1208 and the second connection-housing raised portion 1210. In this way, when in use, the inspiratory gas is passed to and the expiratory gas is passed from the respiratory mask via the unitary structure.

In the example embodiment of FIGS. 33A-33C, the socket 1218 includes two socket raised portions 1220, 1222 and two socket slots 1224, 1226. Again, it should be understood that the first socket raised portion 1220 and the second socket raised portion 1222 can be elements of a larger plurality of socket raised portions in other configurations. Likewise, the first socket slot 1224 and the second socket slot 1226 can be elements of a larger plurality of socket slots in other configurations. For example, the socket 1218 can include three, four, five or more socket raised portions. And the socket 1218 can include three, four, five or more socket slots. In general, the number of socket raised portions and socket slots can be selected to suitably engage the number of connection-housing raised portions and connection-housing recessed portions of the connection housing 1202.

As noted above, in the example of FIGS. 33A-33C, the arc length of the first connection-housing recessed portion 1214 is less than the arc length of the second connection-housing recessed portion 1216; and, similarly, the arc length of the first socket raised portion 1220 is less than the arc length of the second socket raised portion 1222. With this configuration, the first socket raised portion 1220 unites with the first connection-housing recessed portion 1214, and the second socket raised portion 1222 unites with the second connection-housing recessed portion 1216. But the first socket raised portion 1220 does not unite with the second connection-housing recessed portion 1216, and the second socket raised portion 1222 does not unite with the first connection-housing recessed portion 1214. In other words, the socket 1218 will only removably engage with the connection housing 1202 in one direction. This configuration can advantageously facilitate engagement by an unskilled user. It should be understood, however, that the arc lengths can be selected such that the socket 1218 with engage with the connection housing 1202 in any direction, or in multiple directions, if desired. For example, the arc lengths can be equal.

Figure 34A:
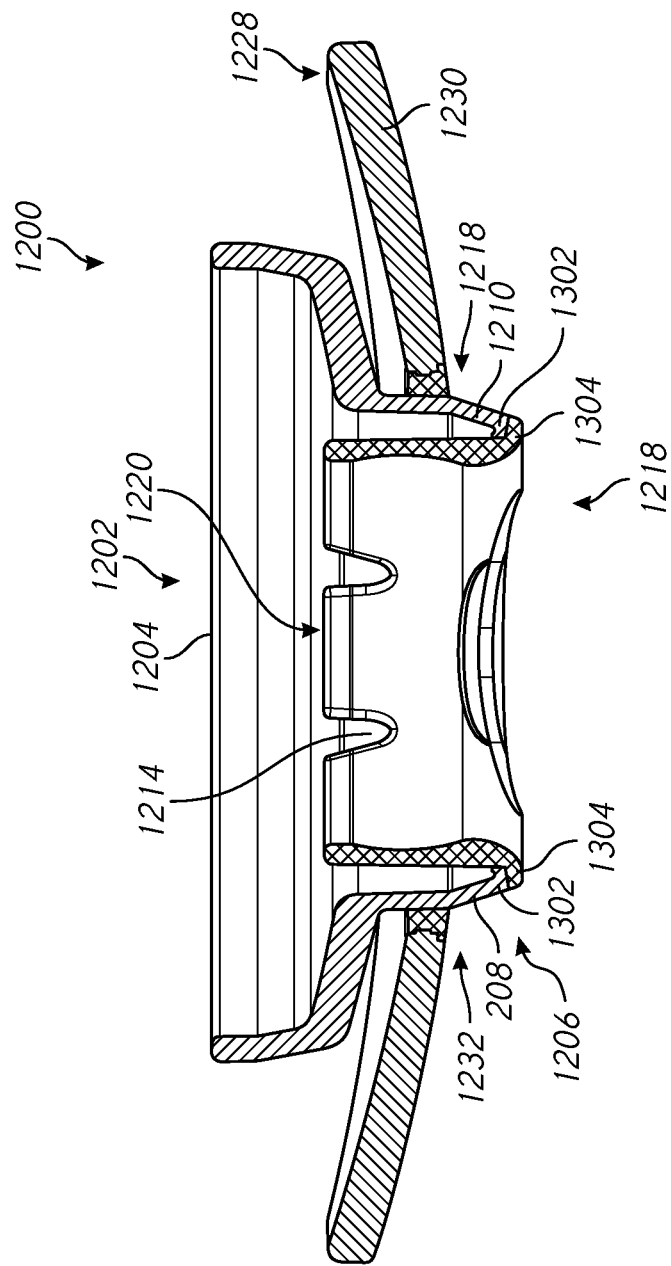
FIG. 34A shows a top cross-sectional view of a seal between the socket and connection housing in according to at least one embodiment.
Figure 34B:
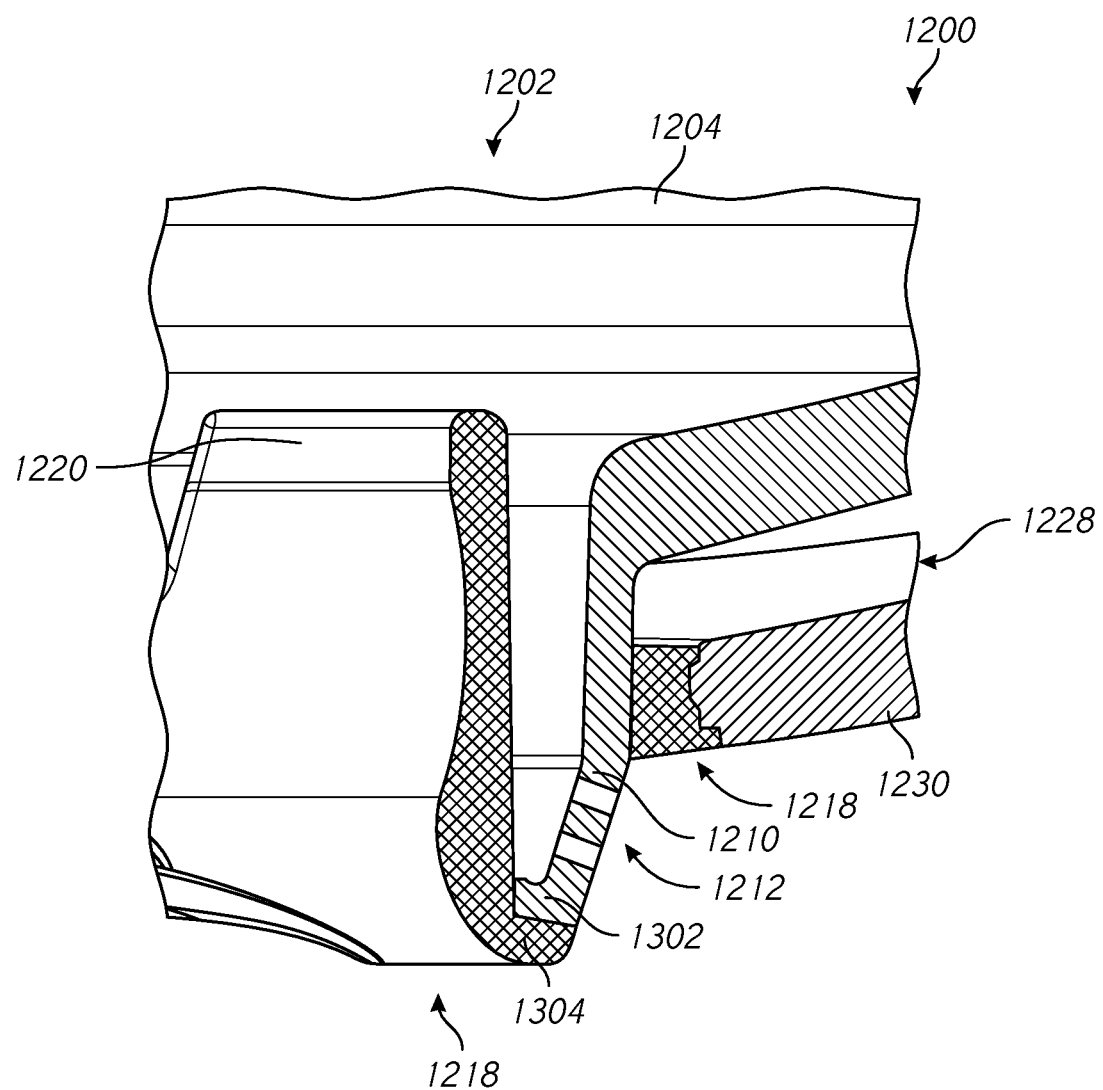
FIG. 34B shows a close-up cross-sectional view showing L-shaped side portions of a connection-housing raised portion between the socket and connection housing of FIG. 34A.

With reference next to FIGS. 34A and 34B, the first connection-housing raised portion 1208 (FIG. 34A) and the second connection-housing raised portion 1210 (FIGS. 34A and 34B) can each include generally L-shaped end portions 1302 at regions most distal from the first end portion 1204. The first socket raised portion 1220 (FIGS. 34A and 34B) and the second socket raised portion 1222 (not shown) each includes generally L-shaped side portions 1304 at regions adjacent the first socket slot (not shown in FIGS. 34A and 34B) and the second socket slot (also not shown in FIGS. 34A and 34B). The generally L-shaped end portions 1302 of the first connection-housing raised portion 1208 and the second connection-housing raised portion 1210 can be configured to seal with the generally L-shaped side portions 1304 of the first socket raised portion 1220 and the second socket raised portion 1222. This configuration can be advantageous because it effectively creates two sealing surfaces between the socket 1218 and the connection housing 1202, when the two components are engaged in the unitary structure. It was discovered that this configuration is less susceptible to leaks and tolerance issues than other sealing arrangements. An alternative engagement arrangement is shown and discussed below with reference to FIG. 36. The alternative engagement is equally applicable to the embodiments of FIGS. 33A and 33B, and the discussion and associated figures are incorporated in this paragraph by reference.

B. Assemblage through Gaps between Frame and Socket

Figure 35A:
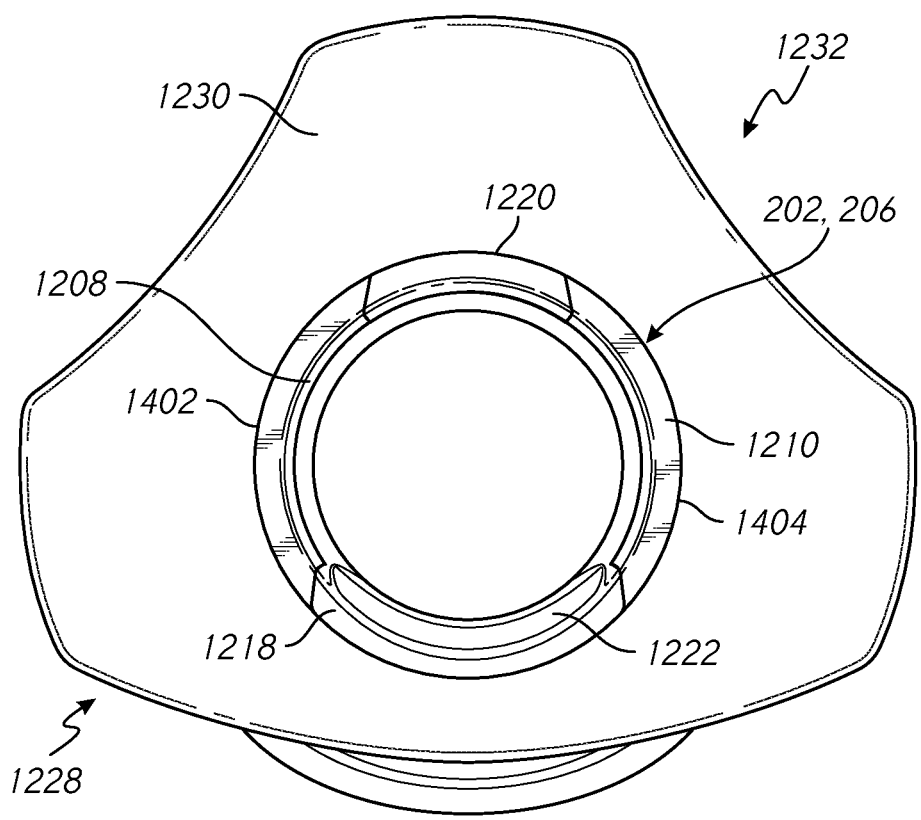
FIG. 35A shows a front view of bias flow venting in a two-part ball-joint socket and connection housing according to another embodiment.
Figure 35B:
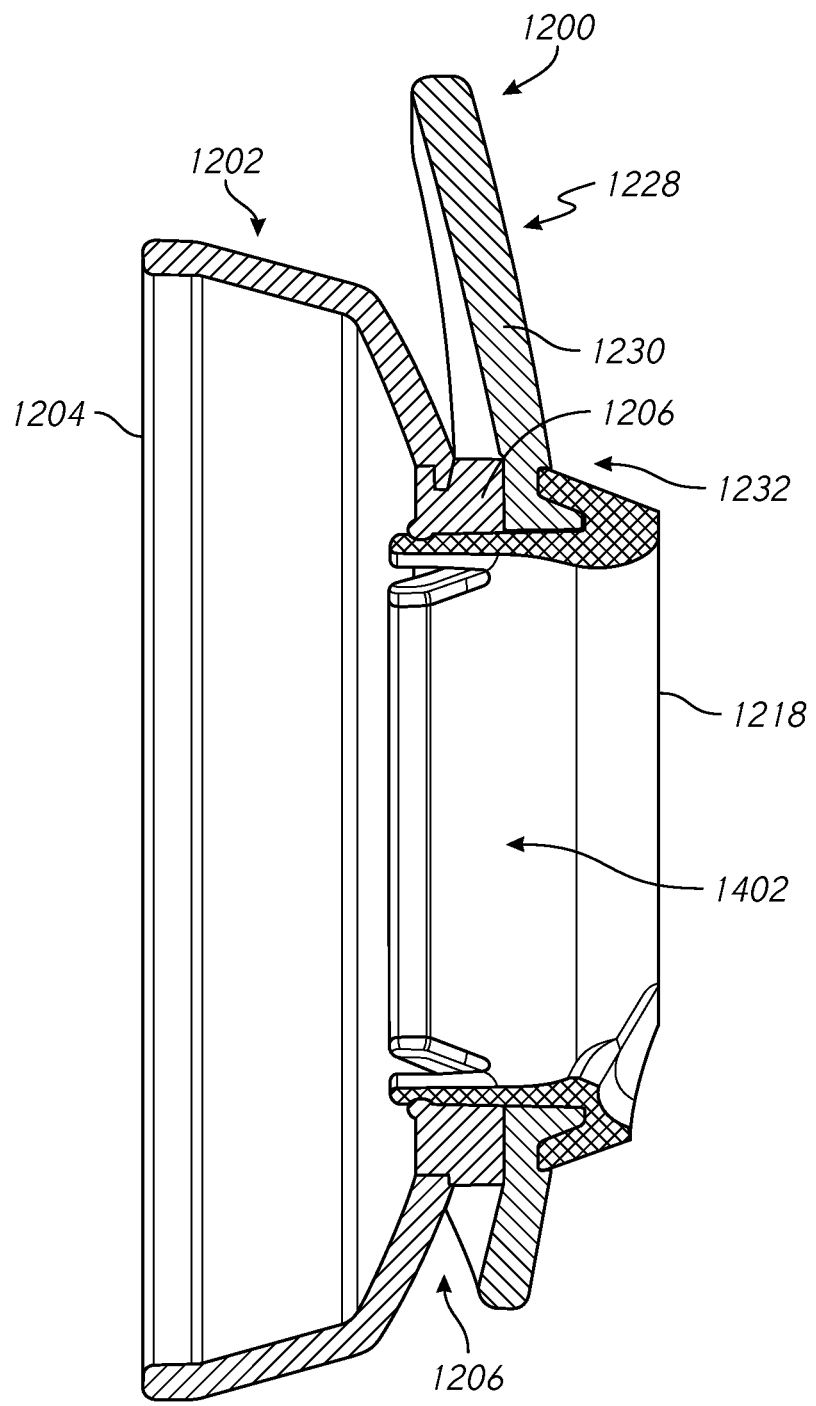
FIG. 35B shows a side cross-sectional view of the two-part ball-joint socket and connection housing of FIG. 35A.
Figure 35C:
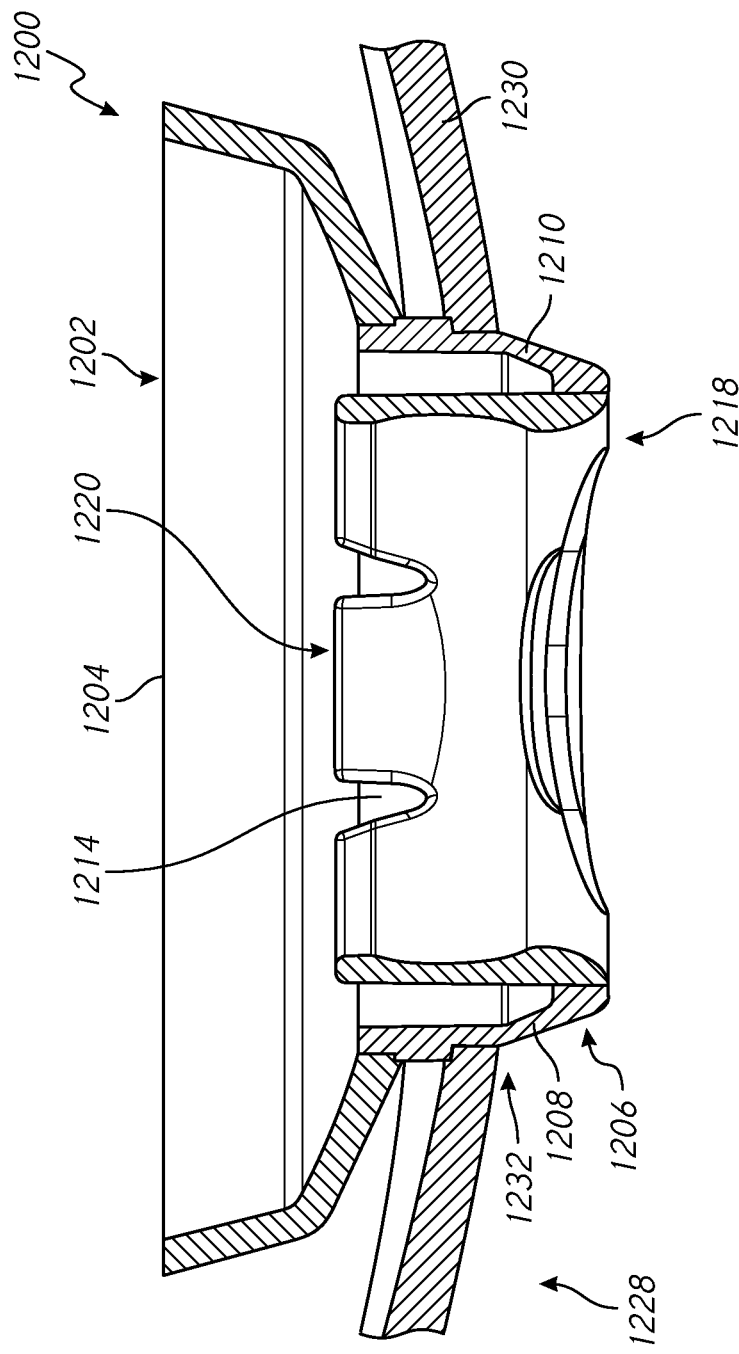
FIG. 35C shows a top cross-sectional view of the two-part ball-joint socket and connection housing of FIG. 35A.

With reference next to FIGS. 35A-35C, in at least one embodiment, another kit 1200 for a respiratory mask is disclosed. It should be understood that assemblages of one, some, or all of the kit 1200 components are within the scope of the disclosure and such assemblages and respiratory systems including such assemblages should be considered embodiments of the disclosure.

Like the kit 1200 described with reference to FIGS. 33A-33C, the kit 1200 for a respiratory mask of FIGS. 35A-35C includes a connection housing 1202 emplaced over the patient's face when in use. The kit 1200 also includes a socket 1218 and a frame 1228 (FIGS. 35A and 35B). The discussion of the connection housing 1202, frame 1228, and socket 1218 with reference to FIGS. 33A-33C is incorporated herein by reference. The kit 1200 can further include a swivel connector (not shown) configured to deliver inspiratory gas to a user, and the discussion of the swivel connection is also incorporated herein by reference.

A difference between the embodiment of FIGS. 33A-33C and the embodiment of FIGS. 35A-35C is the socket 1218 configuration. In the embodiment of FIGS. 33A-33C, the outer periphery of the socket 1218 completely and continuously engages the frame opening 1232, and the socket 1218 includes socket slots 1224, 1226 within the outer periphery of the socket 1218 for uniting with the first connection-housing raised portion 1208 and the second connection-housing raised portion 1210. In the embodiment of FIGS. 35A-35C, the outer periphery of the socket 1218 does not completely and continuously engage the frame opening 1232. Rather, the outer periphery is not annular like the frame opening 1232, such that there are spaces between the outer periphery of the socket 1218 and the frame opening 1232 including a first frame gap 1402 (FIGS. 35 and 35B) and a second frame gap 1404 (FIG. 35A).

Also like the kit 1200 described with reference to FIGS. 33A-33C (and with reference to those figures as well as FIGS. 35A-35C), the frame 1228 is configured to removably engage with the connection housing 1202 as a unitary structure, except that, when engaged, the first socket raised portion 1220 unites with the first connection-housing recessed portion 1214, the second socket raised portion 1222 unites with the second connection-housing recessed portion, the first connection-housing raised portion 1208 passes through the frame opening 1232 and unites with the first frame gap 1402, and the second connection-housing raised portion 1210 passes through the frame opening 1232 and unites with the second frame gap 1404.

Inspiratory gas flows from the swivel connector and passes through socket 1218 central bore to the connection housing 1202. Expiratory gas flows from the connection housing 1202 and passes through a first space between the first connection-housing raised portion 1208 and a first region of the socket 1218 radially inward from the first frame gap 1402, and though a second space between the second connection-housing raised portion 1210 and a second region of the socket 1218 radially inward from the second frame gap 1404. From the first space and the second space, the expiratory gas passes to the ambient atmosphere via the at least one array of holes (shown in FIG. 33A but not shown in FIGS. 35A-35C) in each of the first connection-housing raised portion 1208 and the second connection-housing raised portion 1210. Thus, in both embodiments, when in use, the inspiratory gas is passed to and the expiratory gas is passed from the respiratory mask via the unitary structure.

Figure 36:
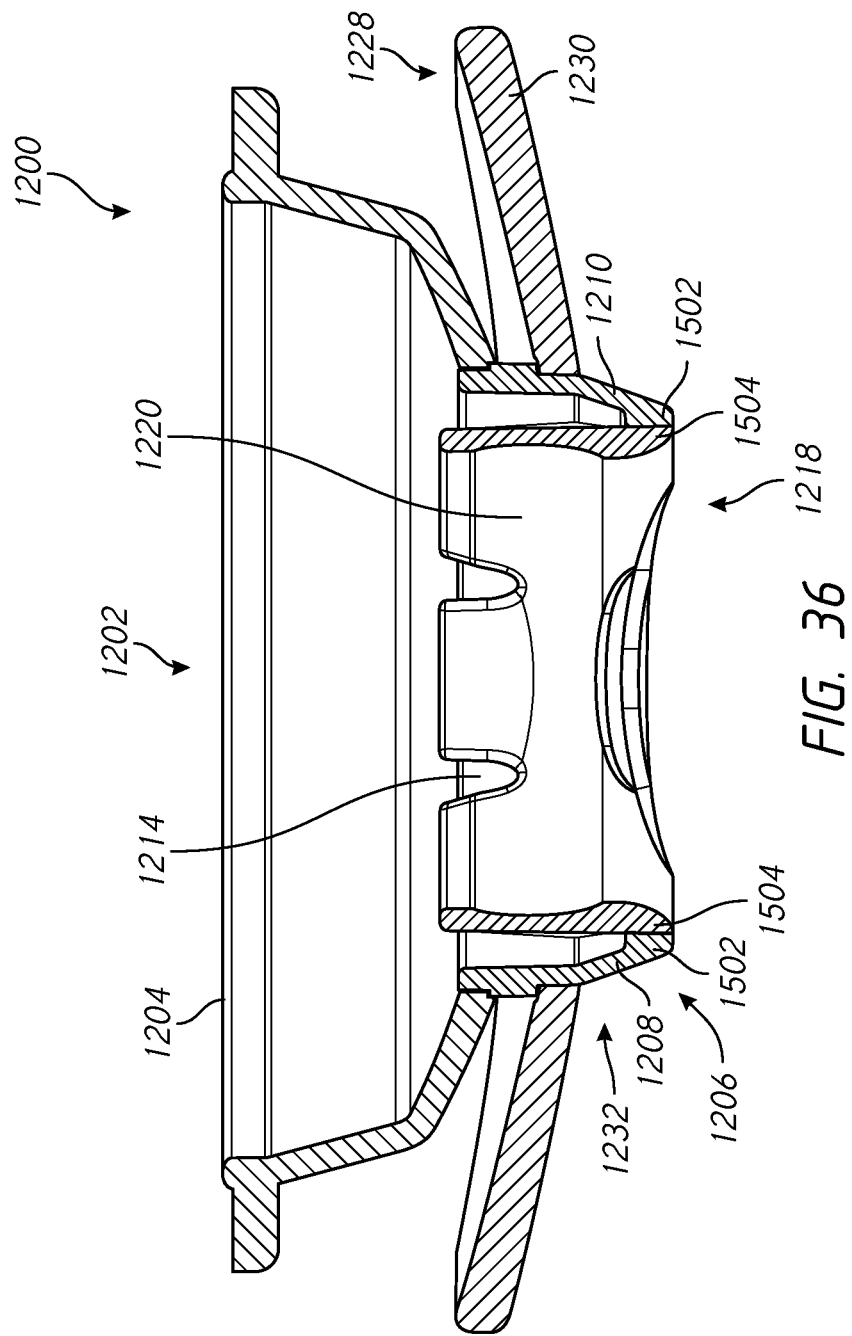
FIG. 36 shows a detail of a seal between the socket and connection housing according to at least one embodiment.

With reference next to FIG. 36, the first connection-housing raised portion 1208 and the second connection-housing raised portion 1210 can each include generally straight end portions 1502 at regions most distal from the first end portion 1204. The first socket raised portion 1220 and the second socket raised portion 1222 can each include generally straight side portions 1504 at regions adjacent the first socket slot 1224 and the second socket slot 1226 (not shown in FIG. 36). The generally straight end portions 1502 of the first connection-housing raised portion 1208 and the second connection-housing raised portion 1210 can be configured to seal with the generally straight side portions 1504 of the first socket raised portion 1220 (FIG. 36) and the second socket raised portion 1222 (not shown), for example, with a friction-fit seal. In alternative or modified configurations, a supplemental seal, such as a gasket, o-ring, or lip seal can be provided between the sealing surfaces.

Yet another alternative engagement arrangement (incorporating L-shaped fittings) is shown and discussed above with reference to FIGS. 34A and 34B. The alternative engagement is equally applicable to the embodiments of FIGS. 35A-35C, and the discussion and associated figures are incorporated in this paragraph by reference.

IV. Bias Flow Venting in Ball-Joint Socket with Recessed Flow Path

In various embodiments, a bias-flow venting system is incorporable in a socket for a truncated ball-joint connector. The socket includes regions facilitating cleaning the bias-flow venting system. When in use in a respiratory mask, the socket is configured to pass inspiratory gas received from the truncated ball-joint connector to the respiratory mask's user. Because the socket incorporates the bias-flow venting system, the socket is not only capable of supplying inspiratory gas to the user but also removing expiratory gas from the user. The socket's configuration improves overall compactness of the respiratory mask. Certain embodiments were also discovered to advantageously reduce noise produced by the respiratory mask, when in use.

With reference next to FIGS. 37A-37E and 38A-38E, in at least one embodiment, a kit 1600 for a respiratory mask is disclosed. It should be understood that assemblages of one, some, or all of the kit 1600 components are within the scope of the disclosure and such assemblages and respiratory systems comprising such assemblages should be considered embodiments of the disclosure.

In some embodiments, the kit 1600 comprises a swivel connector 1602 (FIGS. 37A, 37C, 37E, 38A, 38B, 38C, and 38E) configured to deliver inspiratory gas to a user. The swivel connector 1602 comprises a generally tubular first end 1604 (FIGS. 37A, 37C, 37E, 38A, and 38B) and a truncated ball joint 1606 (FIGS. 37A, 37C, 37E, 38A, 38B, 38E) at a second end opposite the first end 1604, the truncation defining a ball joint opening 1608 (FIGS. 37A, 37C, 37E, 38A, 38B, 38E) configured to pass the inspiratory gas therethrough.

The kit 1600 can further include a connection housing 1610 (FIGS. 37E and 38E) emplaced over the user's face when in use. The connection housing 1610 comprises a connection-housing opening 1612 (FIGS. 37E and 38E) configured, in use, to receive the inspiratory gas from the swivel connector 1602 and to receive an expiratory gas expired by the user. The connection housing 1610 also comprises a cushion end portion (not shown), opposite the connection-housing opening 1612, configured to engage a cushion housing for contacting the user's face.

The kit 1600 also includes a socket 1616. The socket 1616 includes a connection-housing engagement region 1620 (FIGS. 37A, 37B, 38A, and 38D). The connection-housing engagement region 1620 is generally circumferential around a first end 1622 (FIGS. 37A, 37B, 38A, and 38D) of the socket 1616. The connection-housing engagement region 1620 engages the connection-housing opening 1612 when in use and is configured to receive therefrom the expiratory gas.

The socket 1616 is hollow, such that the socket includes an enclosed interior region 1618 (FIGS. 37A-37E, 38A, 38B, 38D, and 38E) or bore. The enclosed interior region 1618 includes a ball-joint engagement region 1624 (FIGS. 37A, 37B, 37D, 37E, 38A, 38B, 38C, 38D, and 38E). The ball-joint engagement region 1624 is generally circumferential around a second end 1626 (FIGS. 37A, 37B, 38A, and 38D) of the socket 1616 opposite the first end 1622. The ball-joint engagement region 1624 engages the truncated ball joint 1606 of the swivel connector 1602 when in use and is configured to receive therefrom the inspiratory gas. In the example figures, the diameter of the ball-joint engagement region 1624 is less than the diameter of the connection-housing engagement region 1620.

The enclosed interior region 618 also has a generally arcuate first bearing region 1628 (FIGS. 37A, 37B, 37D, 37E, 38D) and a generally arcuate second bearing region 1630 (FIG. 37D, 38D), each extending from the ball-joint engagement region 1624 toward the connection-housing engagement region 1620, and each engaging the truncated ball joint 1606 of the swivel connector 1602 when in use. That is, the generally arcuate first and second bearing regions 1628, 1630 engaging opposite sides of the truncated ball joint 1606. Accordingly, the recessed regions are formed along an inner surface of the socket 1616 circumferentially between the generally arcuate first and second bearing regions 1628, 1630. The recessed regions provide a shallow gap or clearance between the ball-joint engagement region 1624 and the truncated ball joint 1606 that may be easily wiped and cleaned by the user. The bearing regions 1628, 1630 are sized and configured to prevent the truncated ball joint 1606 from falling into the socket 1616. In the example embodiments of FIGS. 37A-37E and 38A-38E, the socket 1616 includes two bearing regions 1628, 1630. It should be understood that the first bearing region 1628 and the second bearing region 1630 can be elements of a larger plurality of bearing regions in other configurations. For example, the socket 1616 can include three, four, five or more bearing regions. In an embodiment including three bearing regions, the first bearing region 1628, second bearing region 1630, and the one additional bearing region can be positioned at or around the 2-, 6-, and 10-o'clock positions, with the 6-o'clock position defining the bottom of the socket 1616.

The first bearing region 1628 and the second bearing region 1630 define therebetween a generally arcuate first expiratory region 1632 (FIGS. 37A, 37B, 37E, 38A, and 38E) and a generally arcuate second expiratory region 1634 (FIGS. 37A, 37B, 37E, 38A, and 38E). In some configurations, the generally arcuate first and second expiratory regions 1632, 1634 may be positioned in the recessed regions between the generally arcuate first and second bearing regions 1628, 1630. A flow path to the first and second expiratory regions 1632, 1634 may be defined by the generally arcuate first and second bearing regions 1628, 1630, an inner surface of the socket 1616, and an outer surface of the truncated ball joint 1606. Each of the first expiratory region 1632 and the second expiratory region 1634 includes at least one array of holes 1636 (FIGS. 39A-39D) configured to pass therethrough the expiratory gas to the ambient atmosphere outside the socket 1616. The first expiratory region 1632 and the second expiratory region 1634 are discontinuous, that is, separated by the bearing regions 1628, 1630. Nevertheless, in certain embodiments, the distance between the first expiratory region 1632 and the second expiratory region 1634 can be expressed in terms of a diameter, such as a straight line passing from a point on an arc length of the first expiratory region 1632 to a corresponding point on an arc length of the second expiratory region 1634 through a polar center of the enclosed interior region 1618 along that line. In the illustrated examples, the diameter between the first expiratory region 1632 and the second expiratory region 1634 is greater than the diameter of the ball-joint engagement region 1624 and less than or equal to the diameter of the connection-housing engagement region 1620. Also in the illustrated examples, the bearing regions 1628, 1630 are located at the top and bottom of the socket 1616, respectively. This configuration advantageously allows the expiratory regions 1632, 1634 to be located on the sides of the socket 1616, which can be desirable because it directs the expiratory flow away from a user's bed partner and from the user's face when a respiratory mask incorporating features of the kit 1600 is in use.

It should be understood that the first expiratory region 1632 and the second expiratory region 1634 can be elements of a larger plurality of expiratory regions in other configurations. For example, the enclosed interior region 1618 can include three, four, or more expiratory regions. For example, in an embodiment including three expiratory regions, the first expiratory region 1632, the second expiratory region 1634, and the one additional expiratory region can be positioned at or around the 12-, 4-5-, and 7-8-o'clock positions, with the 12-o'clock position defining the top of the socket 1616.

This configuration is advantageous for a number of reasons. The bearing regions 1628, 1630 provide structure and support to the socket 1616. And the expiratory regions 1632, 1634 are recessed from the bearing regions 1628, 1630, allowing for improved ease-of-cleaning.

Also in the illustrated examples, the arc length of the first expiratory region 1632 and the arc length of the second expiratory region 1634 are greater than the arc length of the first bearing region 1628 and the arc length of the second bearing region 1630.

Figure 39A:
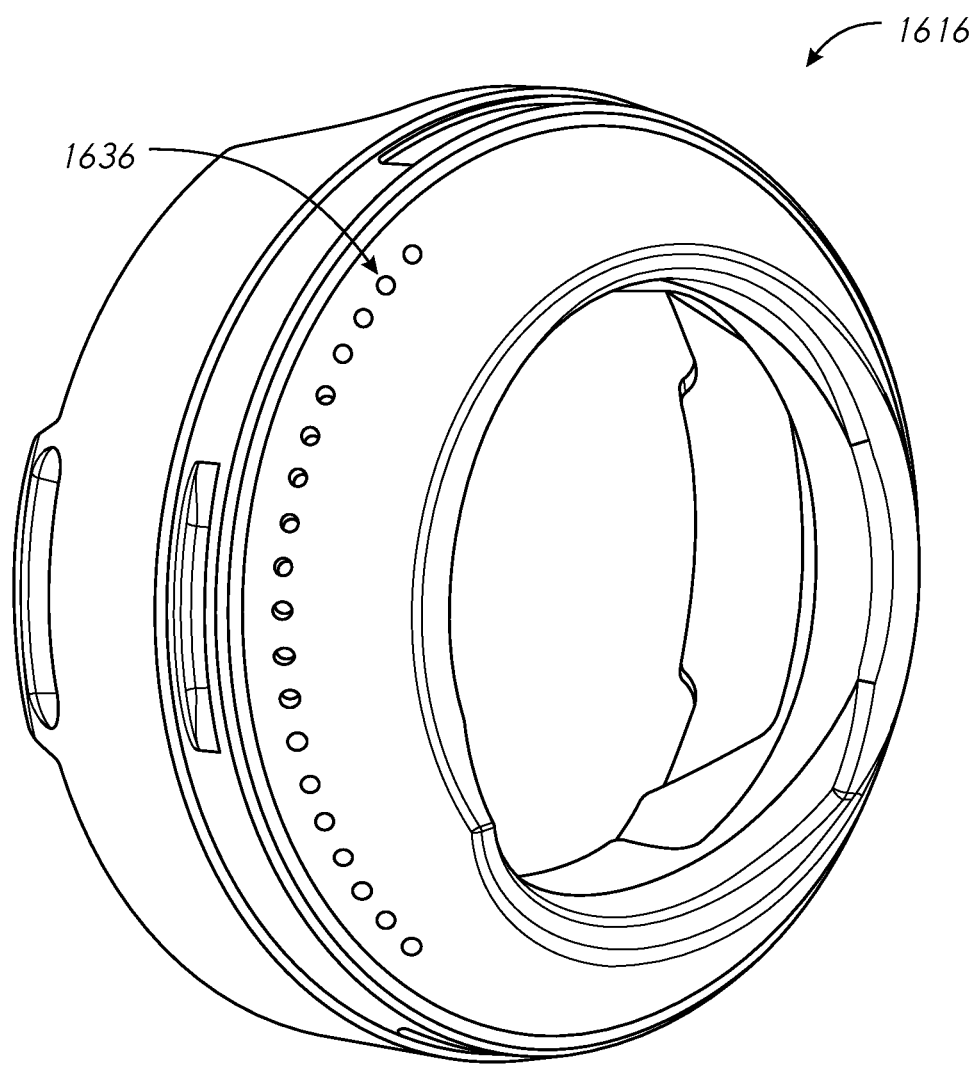
FIG. 39A shows a perspective view of a socket illustrating an arrangement of an array of holes.
Figure 39B:
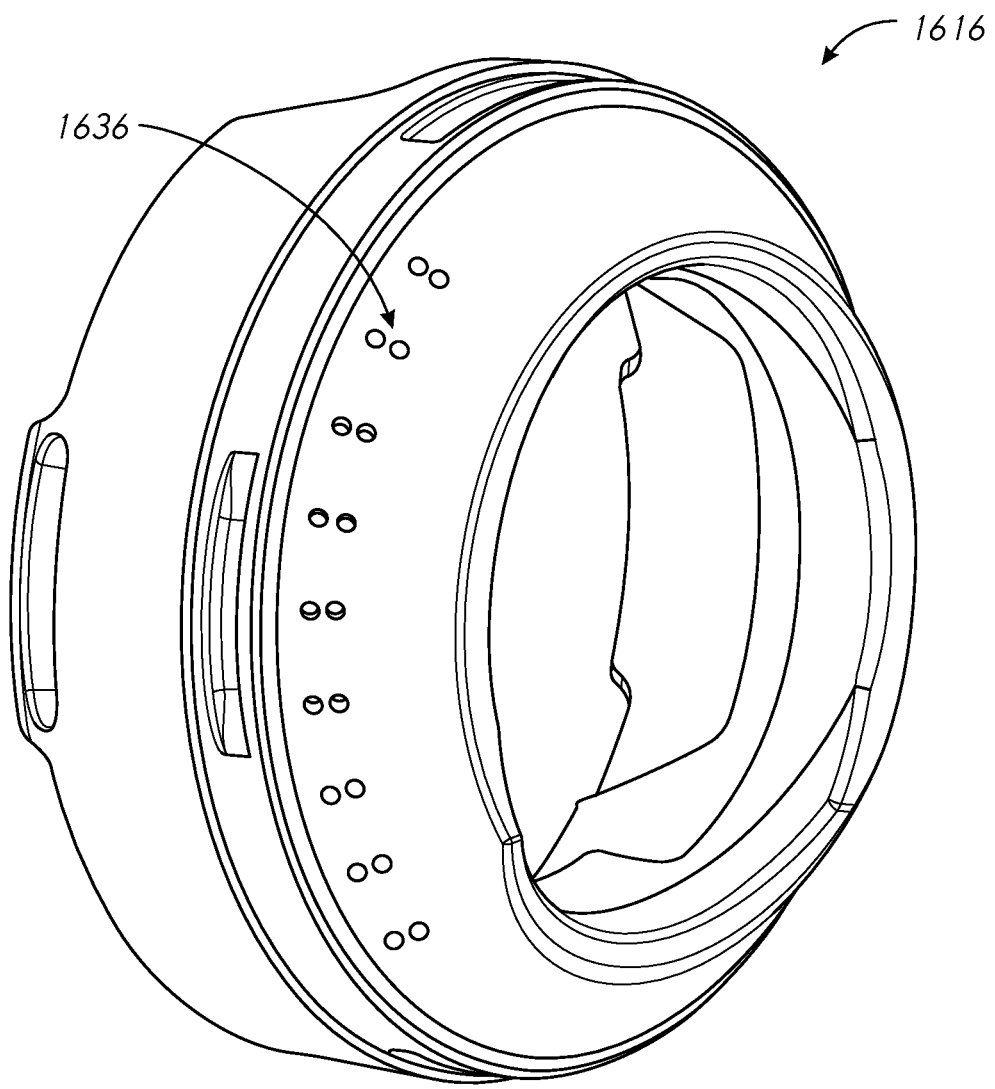
FIG. 39B shows a perspective view of a socket illustrating an alternative arrangement of an array of holes.
Figure 39C:
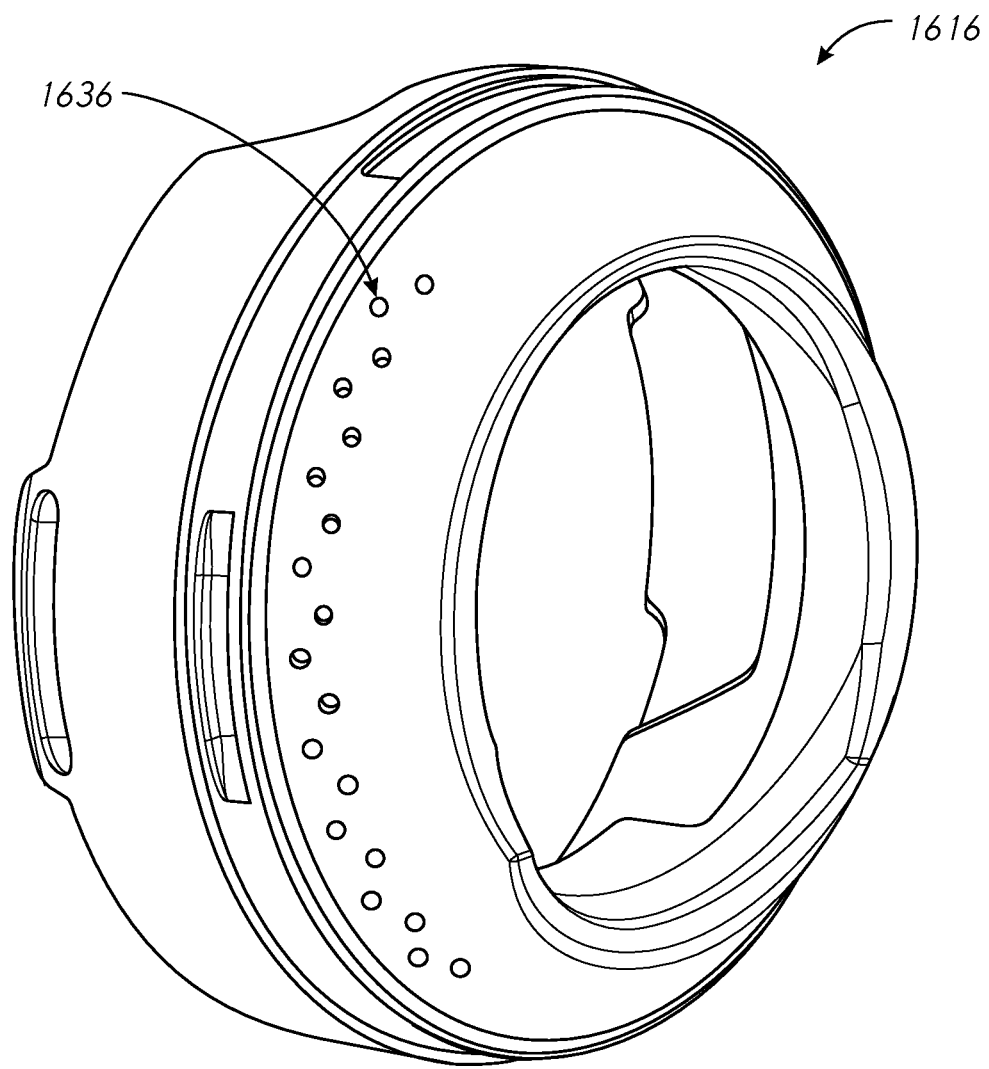
FIG. 39C shows a perspective view of a socket illustrating another alternative arrangement of an array of holes.
Figure 39D:
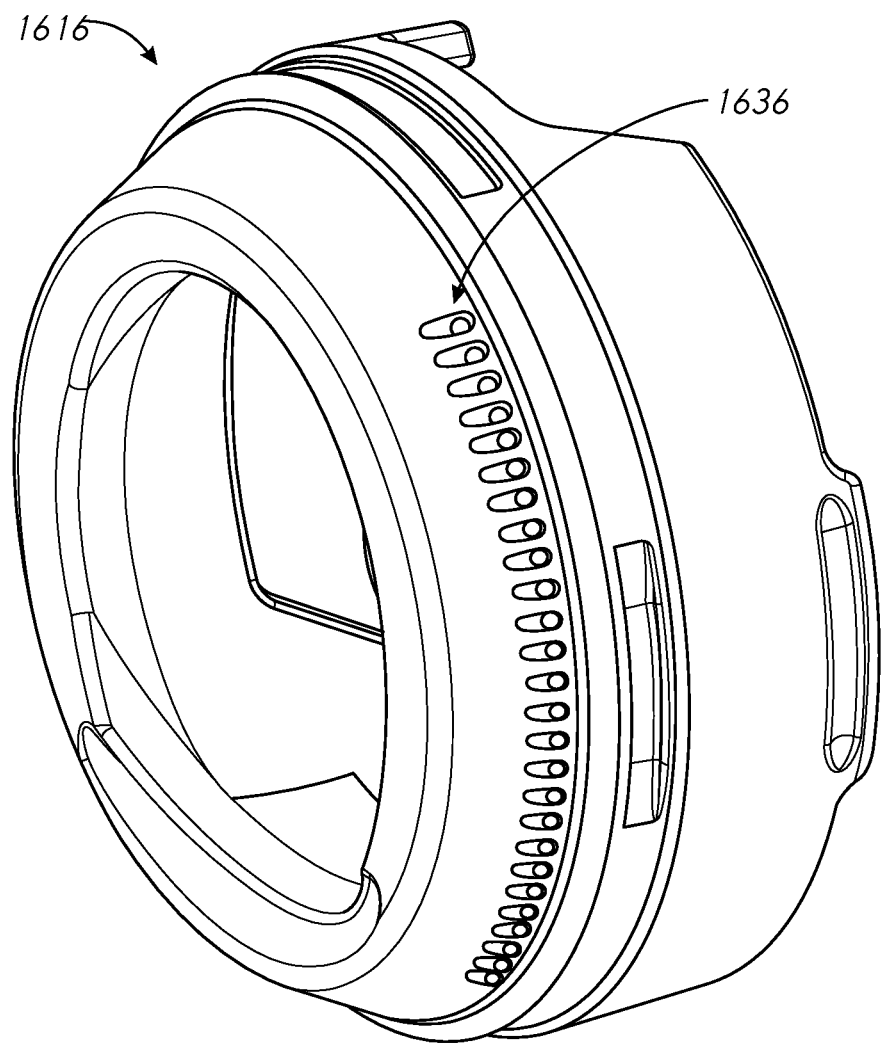
FIG. 39D shows a perspective view of a socket illustrating an arrangement of an array of elongated holes.

Example configurations for the at least one array of holes 1636 of the expiratory regions 1632, 1634 are shown in FIGS. 39A-39D. FIG. 39A shows a single array of holes 1636. This configuration can be advantageous because it provides the smallest axial arrangement of holes 1636. FIG. 39B shows two arrays of holes 1636. This configuration can be advantageous because it allows for more holes 1636 in a given arc length. FIG. 39C shows two arrays of holes 1636 in a staggered configuration. The staggering increases the distance between the holes 1636 in an array. This configuration can improve the jetting of air and improved noise, as it better separates flow. This configuration is also advantageous because it allows for more holes 1636 in a given arc length for a given distance between holes 1636. The elongated holes 1636 of FIG. 39D can be advantageous because they provide more vent area in a compact arrangement. The elongated holes 1636 can be spaced apart to avoid entrainment between vent holes 1636, while still providing sufficient exhaust capabilities. In other words, there can be fewer holes 1636 spaced farther apart because the increased area on the major (longitudinal) axis compensates for the reduced number of holes 1636.

The kit 1600 can optionally further include a frame 1638 (FIGS. 37C, 37E, 38B, 38E) emplaced over the connection housing 1610 when in use. The frame 1638 can include a frame housing with a frame opening with a generally annular periphery. The socket 1616 is emplaced within the frame opening. The frame housing optionally can be permanently engaged with the socket 1616, for instance, by molding, gluing, soldering, or the like. The socket 1616 also can be removably engaged with the socket 1616, for instance, by snap fitting.

A difference between the embodiment of FIGS. 37A-37E and 38A-38E is in the configuration of the interior profile of the truncated ball joint 1606. In the embodiment of FIGS. 37A-37E, the interior profile of the truncated ball joint 1606 generally tracks a corresponding exterior profile of the truncated ball joint 1606. As shown and discussed below in greater detail with reference to FIG. 37E, in this "expanding elbow" configuration, the inlet (inspiratory) gas can expand and/or separate at the truncated ball joint 1606 outlet, creating turbulence. In the embodiment of FIG. 38A-38E, in contrast, an interior of a length of the swivel connector 1602 including the second end, the entire truncated ball joint 1606, and a region directly adjacent the truncated ball joint 1606 extending toward the first end 1604 has a continuous cylindrical or continuous tapered cylindrical profile. A continuous tapered cylindrical profile can be advantageous because it can allow for simplified tooling during manufacture.

Figure 37A:
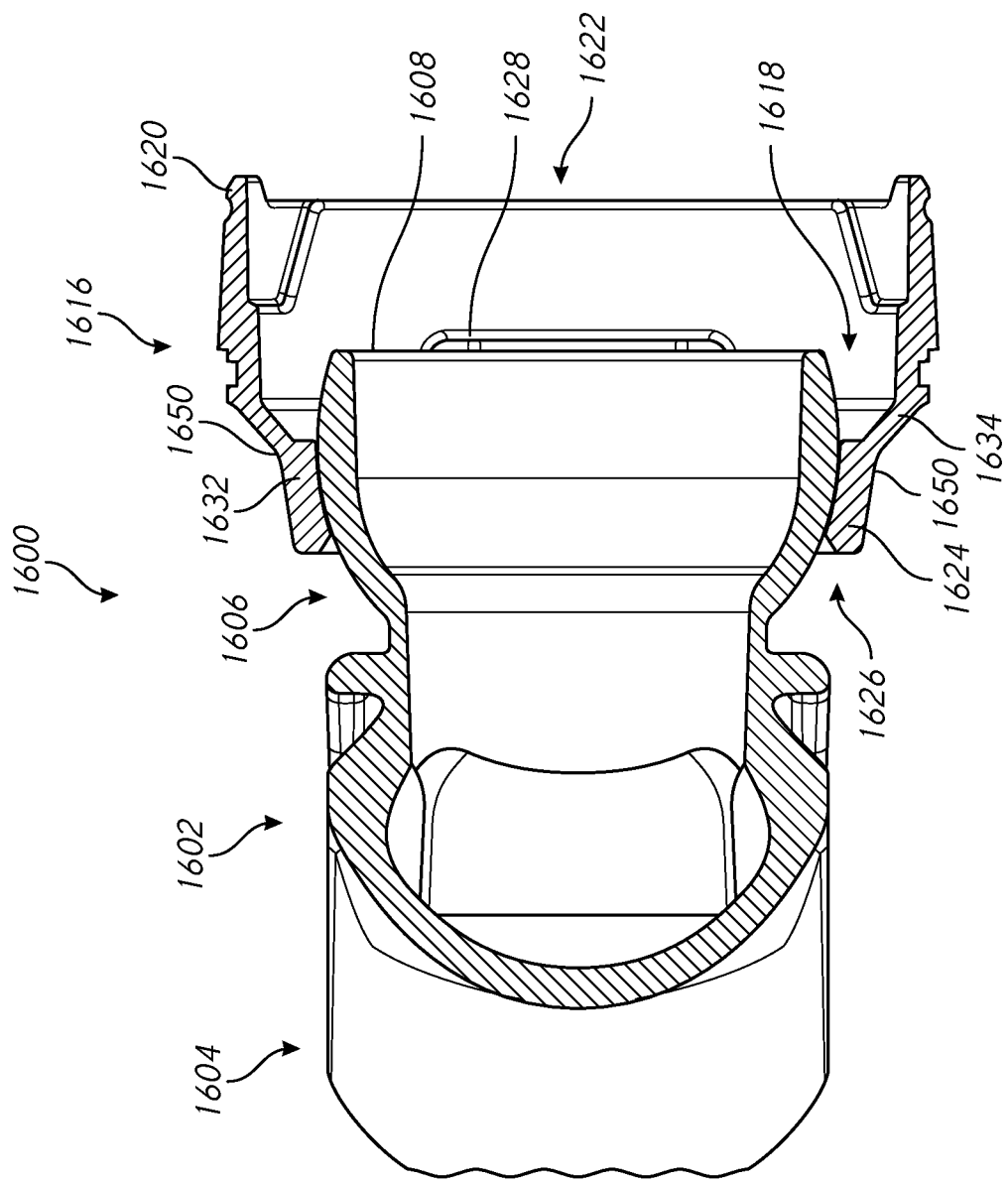
FIG. 37A shows a top cross-sectional view of bias flow venting in a ball-joint socket with a recessed flow path according to an embodiment.
Figure 37B:
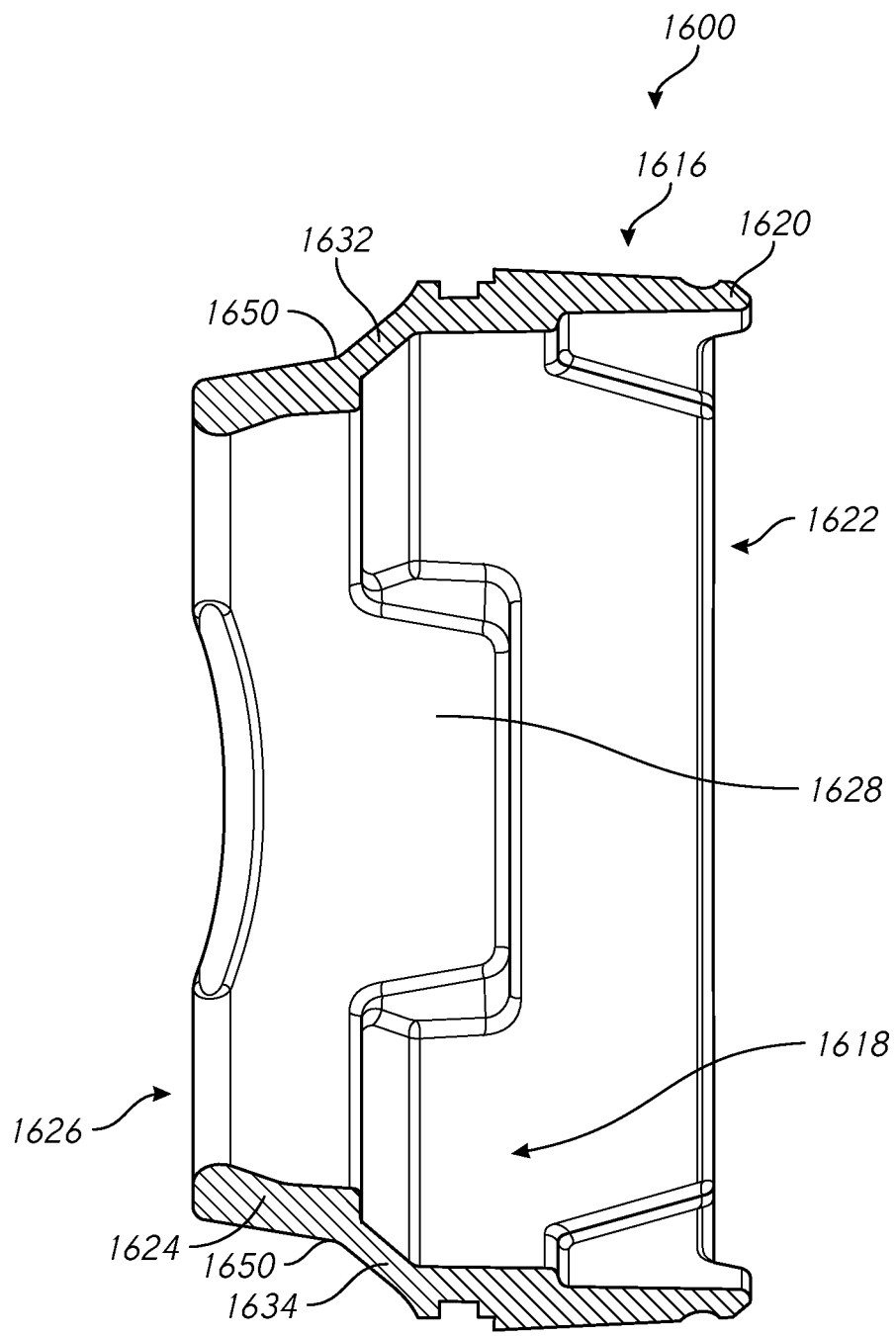
FIG. 37B shows a top cross-sectional view of the ball-joint socket of FIG. 37A without the truncated ball joint.
Figure 37C:
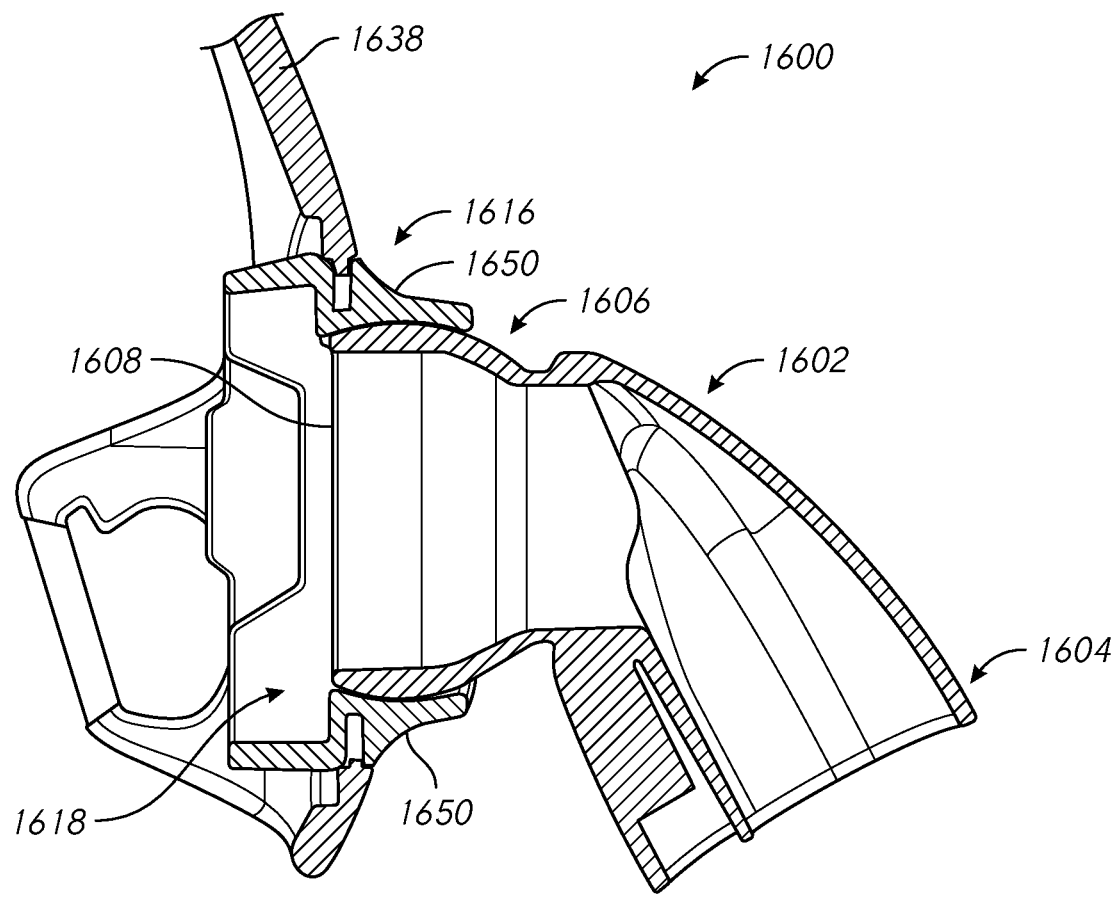
FIG. 37C shows a side cross-sectional view of bias flow venting in a ball-joint socket of FIG. 37A.
Figure 37D:
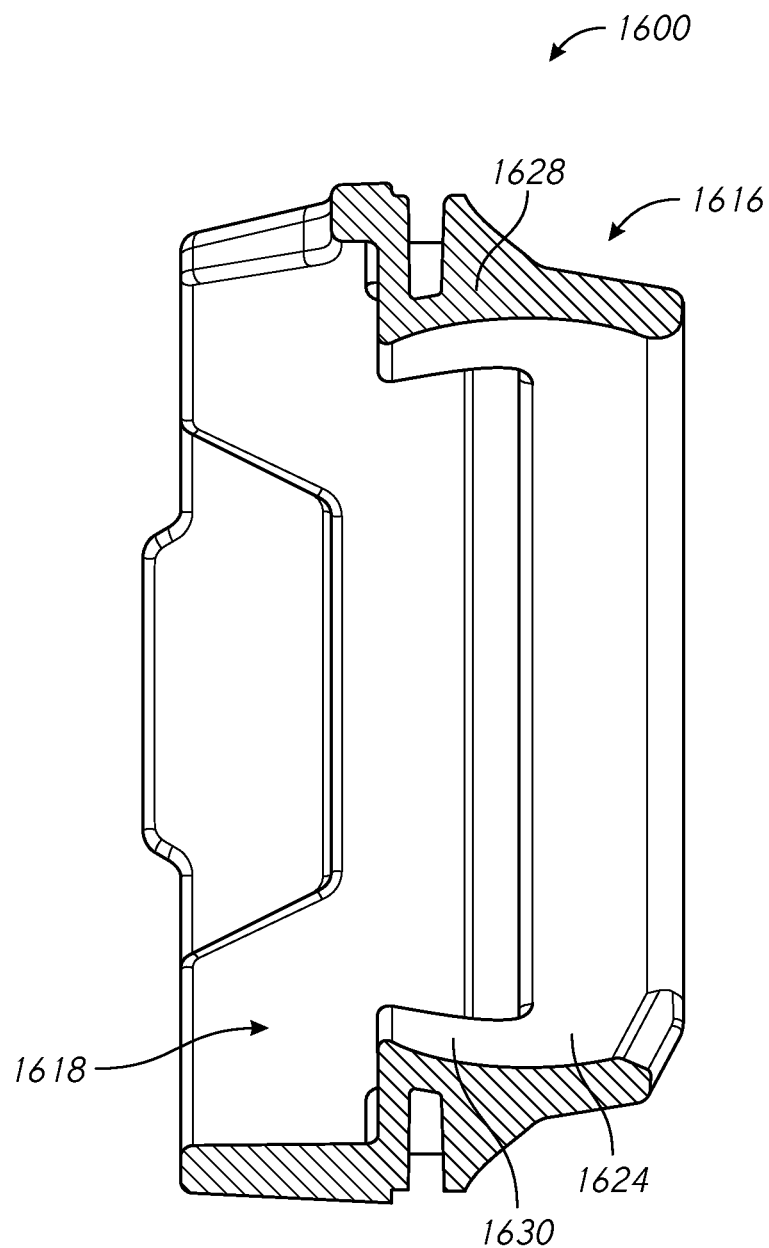
FIG. 37D shows a top cross-sectional view of the ball-joint socket of FIG. 37A showing a generally arcuate second bearing region.
Figure 37E:
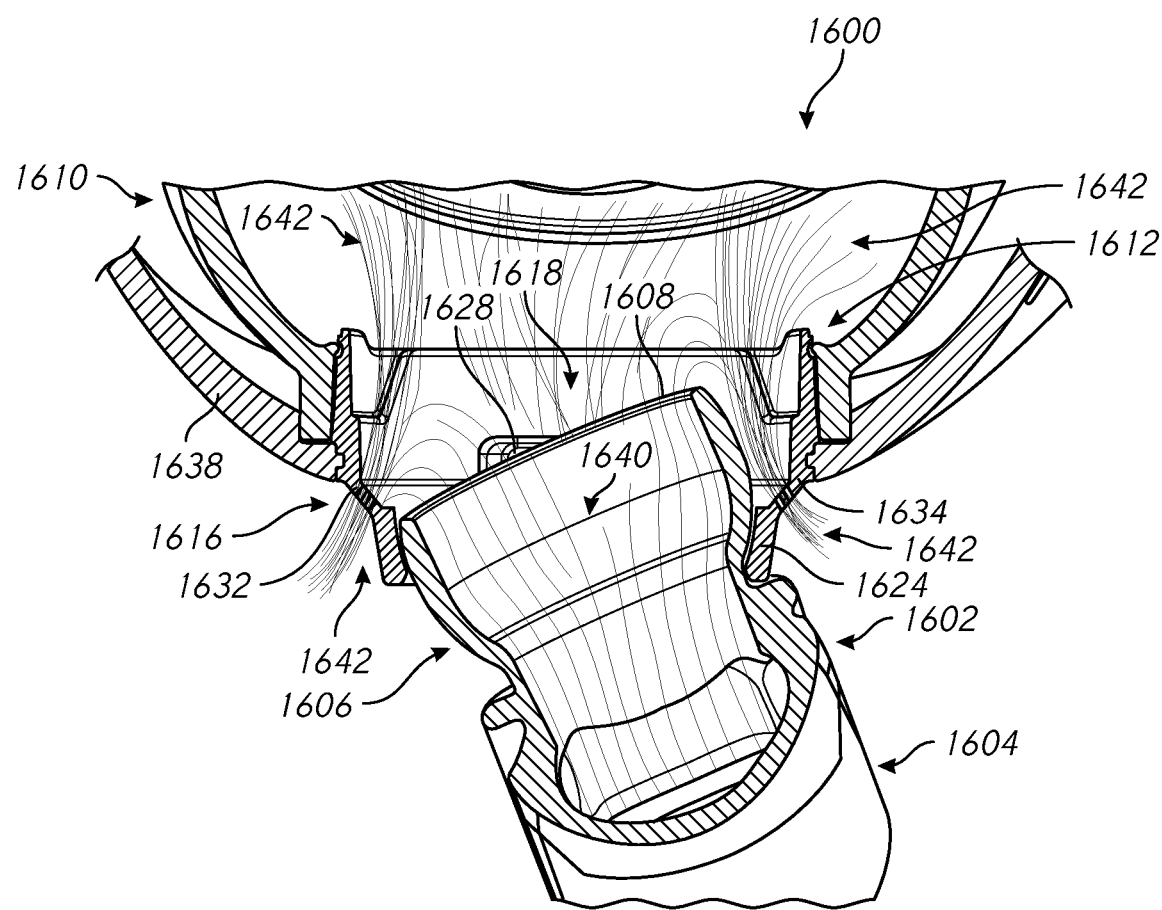
FIG. 37E shows a top cross-sectional view of the ball-joint socket of FIG. 37A in an "expanding elbow" configuration.

Another difference between the embodiment of FIGS. 37A-37E and 38A-38E is in the positioning of the swivel connector 1602 in the socket 1616. In the embodiment of FIGS. 37A-37E, the swivel connector 1602 and the socket 1616 are configured such that, when the truncated ball joint 1606 of the swivel connector 1602 is at a neutral position within the ball-joint engagement region 1628 of the socket 1616, the end of the truncated ball joint 1606 is approximately aligned with the end of the bearing region within the socket 1616, as shown in FIG. 37C. And the swivel connector 1602 and the socket 1616 are further configured such that, when the truncated ball joint 1606 of the swivel connector 1602 is maximally rotated within the ball-joint engagement region 1628 of the socket 1616 in any direction, the ball joint opening 1608 does not fully overhang the ball-joint engagement region 1624 within the socket 1616, as shown in FIG. 37E. At least some of the ball joint opening 1608 is approximately aligned with the end of the ball-joint engagement region 1628 within the socket 1616.

Figure 38A:
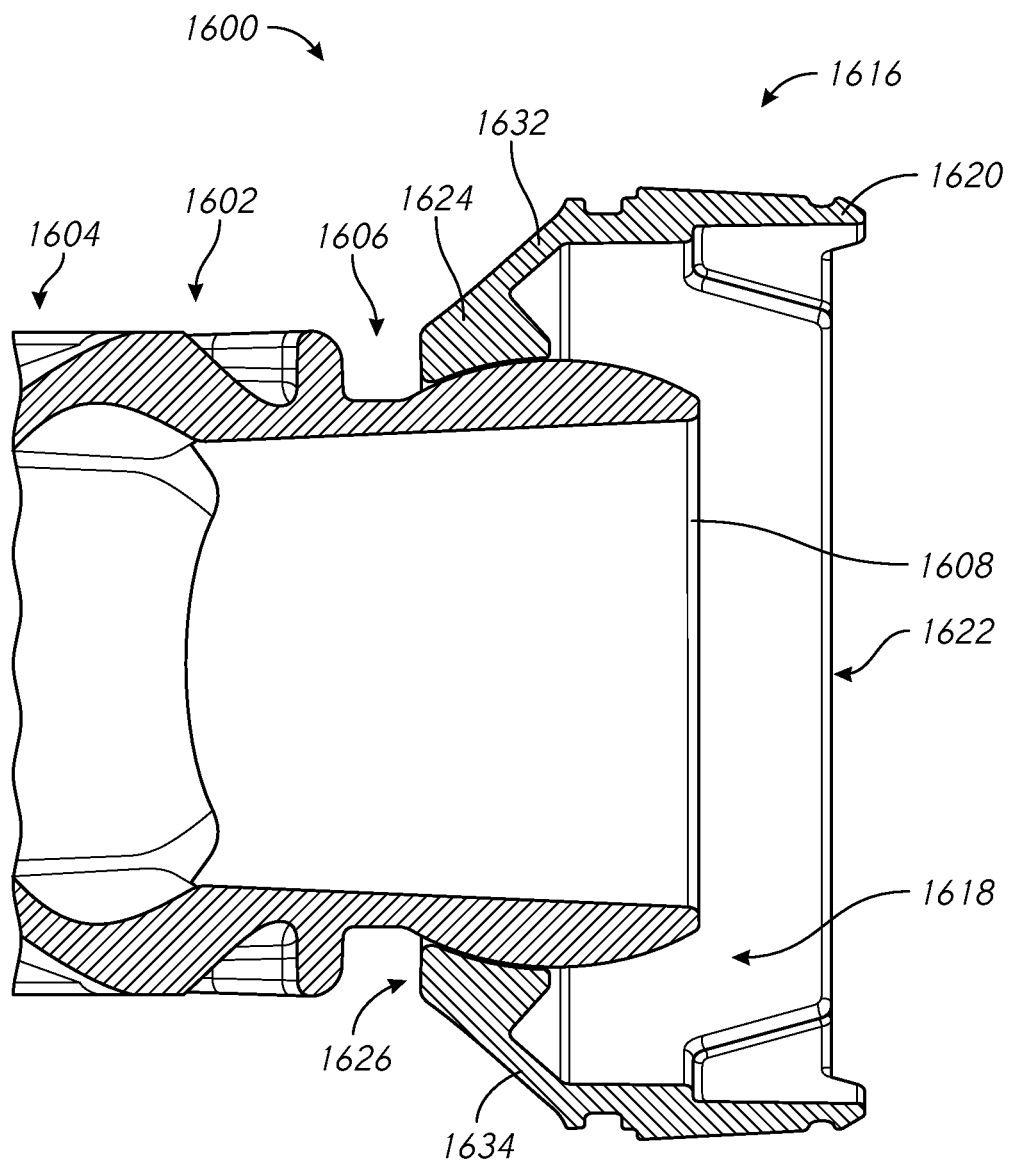
FIG. 38A shows a top cross-sectional view of bias flow venting in a ball-joint socket with a recessed flow path according to another embodiment.
Figure 38B:
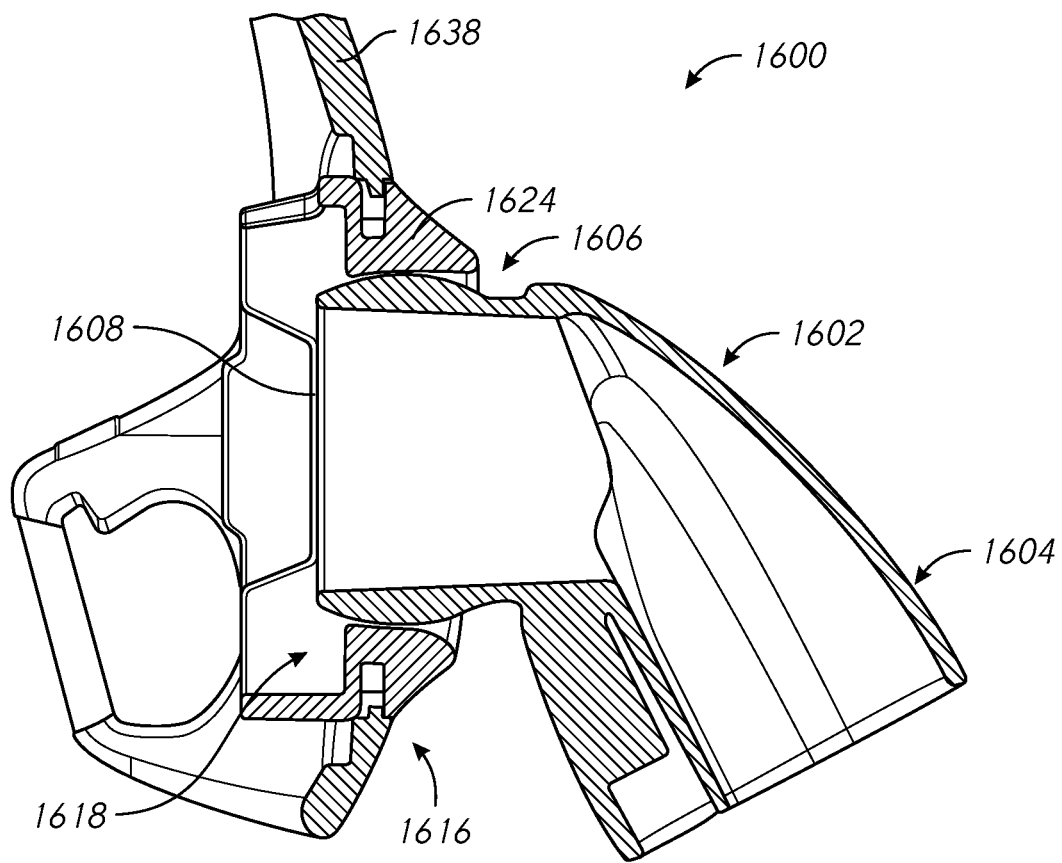
FIG. 38B shows a side cross-sectional view of bias flow venting in a ball-joint socket of FIG. 38A.
Figure 38C:
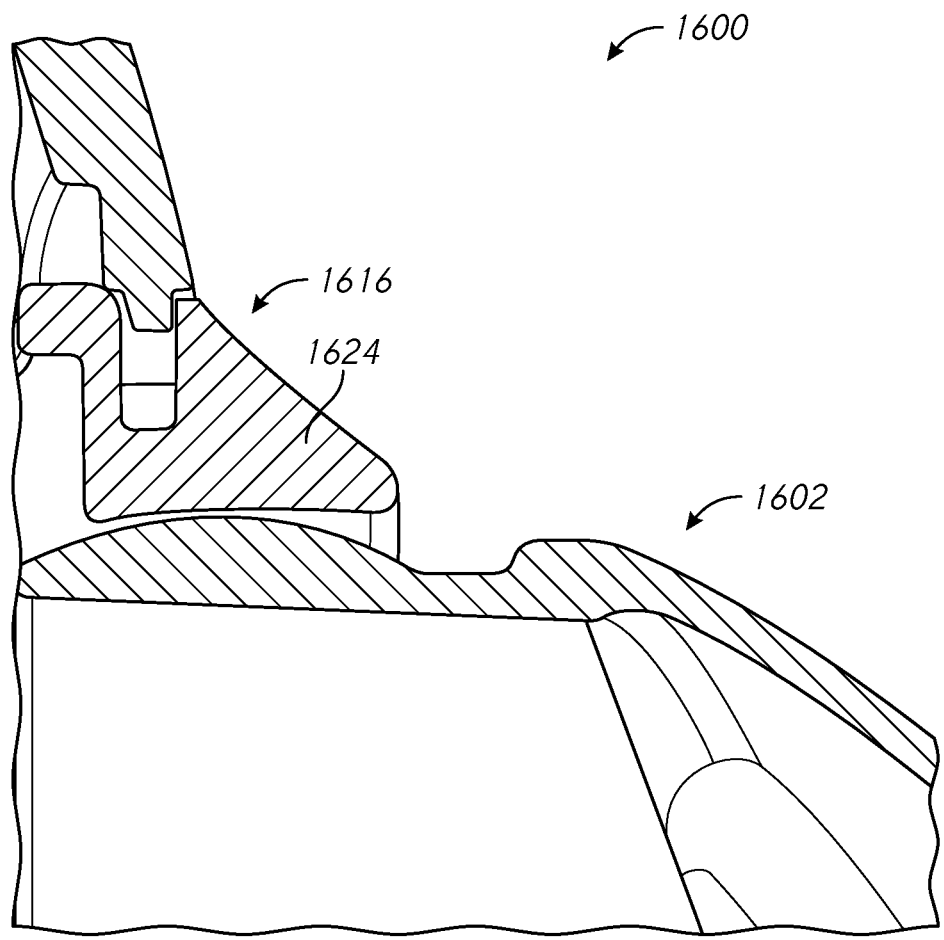
FIG. 38C shows a close-up side cross-sectional view of bias flow venting in a ball-joint socket of FIG. 38A.
Figure 38D:
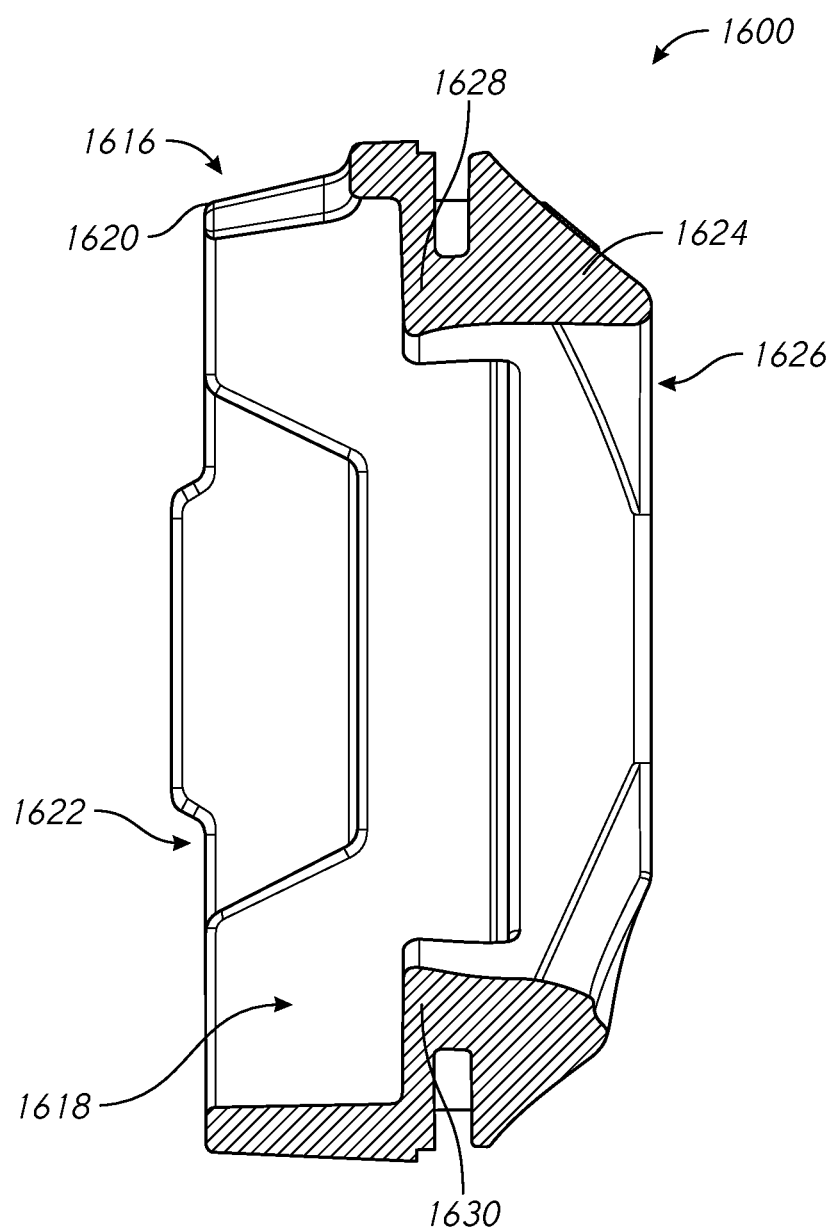
FIG. 38D shows a top cross-sectional view of the ball-joint socket of FIG. 32A showing a generally arcuate second bearing region.
Figure 38E:
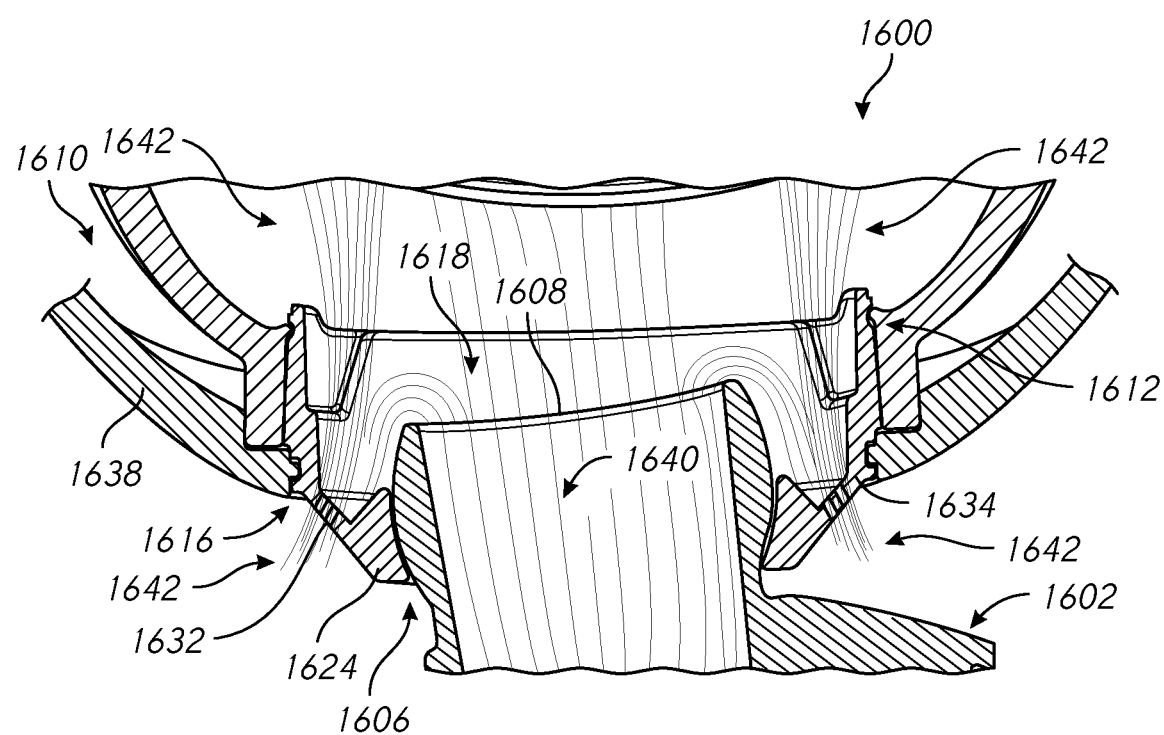
FIG. 38E shows a top cross-sectional view of the ball-joint socket of FIG. 38A having an end of the truncated ball joint fully overhanging the ball-joint engagement region within the socket.

In the embodiment of FIG. 38A-38E, however, the swivel connector 1602 and the socket 1616 are configured such that, when the truncated ball joint 1606 of the swivel connector 1602 is at a neutral position within the ball-joint engagement region 1628 of the socket 1616, the ball joint opening 1608 fully overhangs the bearing regions 1628, 1630 within the socket 1616, as shown in FIG. 38B. This overhang allows for a shorter overall socket 1616, improving compactness. This configuration can also allow for a smaller diameter truncated ball joint 1606. And the swivel connector 1602 and the socket 1616 are further configured such that, when the truncated ball joint 1606 of the swivel connector 1602 is maximally rotated within the ball-joint engagement region 1628 of the socket 1616 in any direction, the end of the truncated ball joint 1606 fully overhangs the ball-joint engagement region 1624 within the socket 1616, as shown in FIG. 38E.

Still another difference between the embodiment of FIGS. 37A-37E and 38A-38E is in the exterior profile of the ball-joint engagement region 1624. In the embodiment of FIGS. 37A-37E, the exterior profile of the ball-joint engagement region 1624, facing the ambient atmosphere, has a first slope for a distance from the second end 1622 to a point 1650 (FIGS. 37A-37C) and a second slope, different from the first slope, for the remaining length of the ball-joint engagement region 1624 from the point 1650 extending toward the first end 1622. In the embodiment of FIGS. 38A-38E, the exterior profile of the ball-joint engagement region 1624, facing the ambient atmosphere, has a continuous slope, as shown in FIG. 38B. The continuous sloped surface can be advantageous because it affords a cleaner appearance and requires less complicated tooling during manufacture. The continuous sloped surface can also be advantageous because it can allow for a longer exhaust flow channel (compare expiratory flow 1642 in FIG. 38E with expiratory flow 1642 in FIG. 37E). The longer exhaust flow channel can reduce static noise and particularly reduce dynamic noise. The exterior profile of the ball-joint engagement region 1628 in conjunction with the profile of the truncated ball joint 1606 also affects the rotational travel of the swivel connector 1602 in the socket 1616. The profile of FIG. 38B allows for less rotational travel than the profile of FIG. 37C; that limitation on rotation can reduce the chance of cross flow and thereby reduce noise.

Yet another difference between the embodiments of FIGS. 37A-37E and 38A-38E is in the flow path of the inspiratory gas and expiratory gas through the socket 1616. As shown in FIG. 37E, turbulence is low in the straight part of the swivel connector 1602. But the inspiratory flow 1640 expands and separates as it exits the truncated ball joint 1606, creating turbulent flow and eddies. When the swivel connector 1602 is in a maximally rotated position, some of the inspiratory flow 1640 will contact the wall of the socket 1616, which can impede the expiratory flow 1642. As a result, some of the expiratory flow 1642 is limited, while the expiratory flow 1642 on the opposite wall of the socket 1616 is increased. As noted above, the overhang in the embodiment of FIGS. 38A-38E allows for a smaller diameter truncated ball joint 1606. This configuration can help separate the inspiratory flow 1640 and expiratory flow 1642, as shown in FIG. 38E. In the configuration of FIG. 38E, due to the continuous tapered cylindrical profile of the truncated ball joint 1606 inner bore, the inspiratory flow 1640 does not significantly expand and separate as it exits the truncated ball joint 1606. Only minor eddying occurs as the inspiratory flow 1640 leaves the truncated ball joint 1606, which is attributable to the slight taper of the profile. And because rotation of the truncated ball joint 1606 in the socket 1616 is reduced, the bulk of the inspiratory flow 1640 is not directed toward the wall of the socket 1616, even at a maximally rotated position. As a result, the expiratory flow 1642 is not significantly impeded by the inspiratory flow 1640, other than minor interference from any eddying.

It should be understood that not all differences are confined to the referenced embodiments. Thus, the embodiment of FIGS. 38A-38E can be modified by incorporating one or more features of the embodiment of FIGS. 37A-37E, and vice versa. It also should be understood that the scope of this disclosure does not exclude the foregoing features of FIGS. 37A-37E, even if those features may include characteristics that can be considered less advantageous than the features of FIGS. 38A-38E under certain circumstances.

FIGS. 40A-40E highlight various example dimensional areas and inventive observations regarding the embodiments of FIGS. 38A-38E. Angle A and Angle F shown in FIG. 40A (that is, the arc length of the bearing regions 1628, 1630 of FIGS. 37A-37E and 38A-38E) each can be in the range of 40° and 80°, with the total arc length of the bearing regions (the sum of Angle A and Angle F) in the range of 80° and 160°. In this representation, the angles are the same. In other embodiments, however, the angles can be different. Angle B and Angle H shown in FIG. 34A (that is, the arc length of the expiratory regions 1632, 1634 of FIGS. 37A-37E and 38A-38E) can each be in the range of 80° and 160°, with the total arc length of the expiratory regions (the sum of Angle B and Angle H) in the range of 200° and 280°. Again, in this representation, the angles are the same. In other embodiments, however, the angles can be different. It should be understood that, because the sum of Angle A, Angle B, Angle F, and Angle H is constant (360°), as the total arc length of the expiratory length increases, the total arc length of the bearing region decreases accordingly.

Figure 40A:
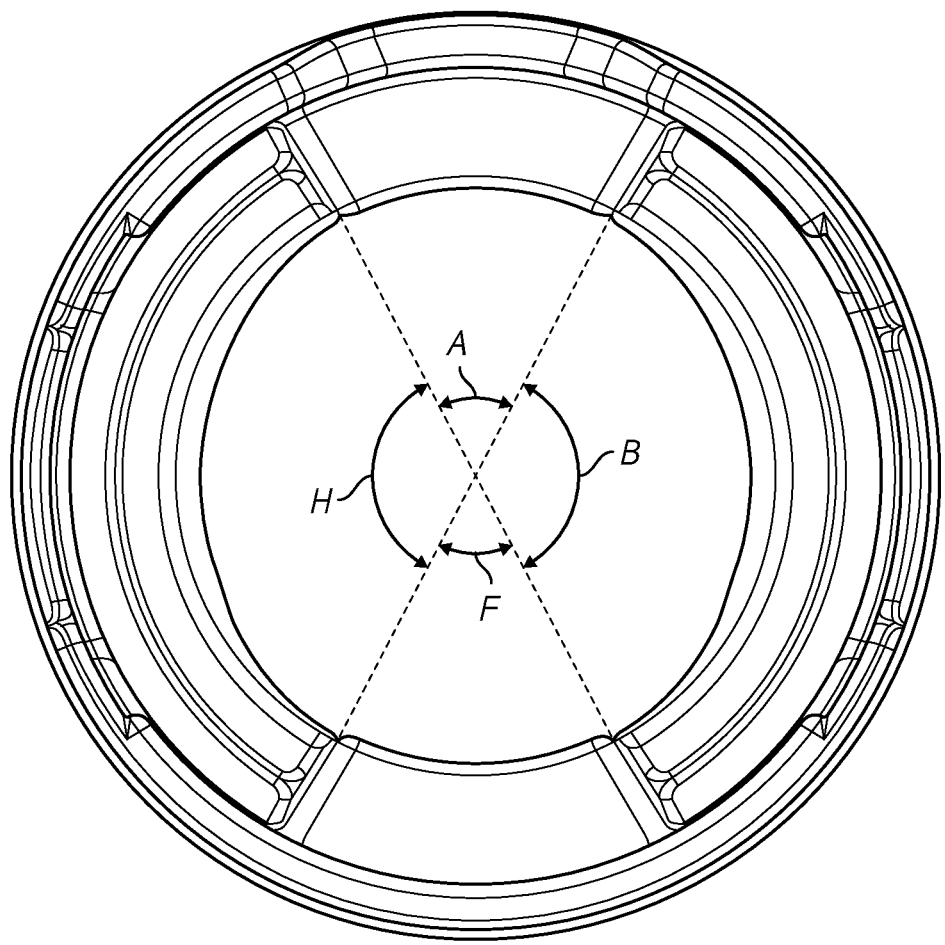
FIG. 40A shows the arc length of the bearing regions of the ball-joint socket with a recessed flow path of FIGS. 37A-37E and 38A-38E.
Figure 40B:
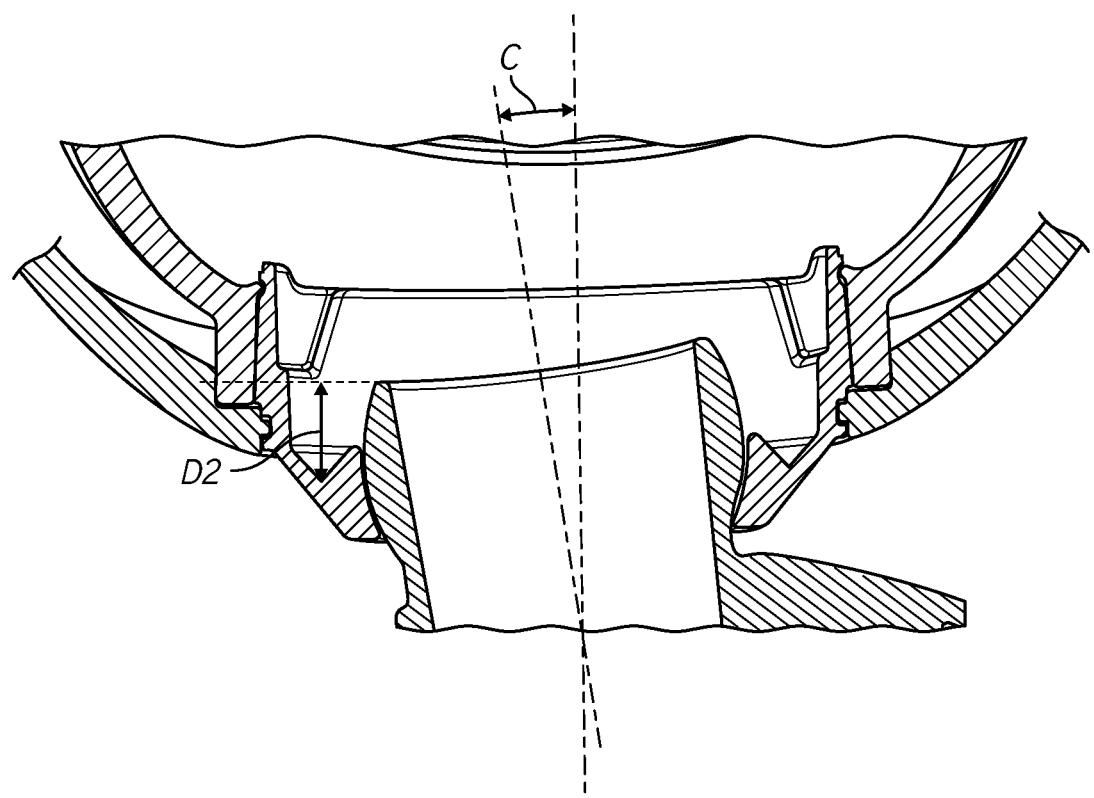
FIG. 40B shows channel depths of bias flow venting of the ball-joint socket with a recessed flow path of FIGS. 38A-38E.
Figure 40C:
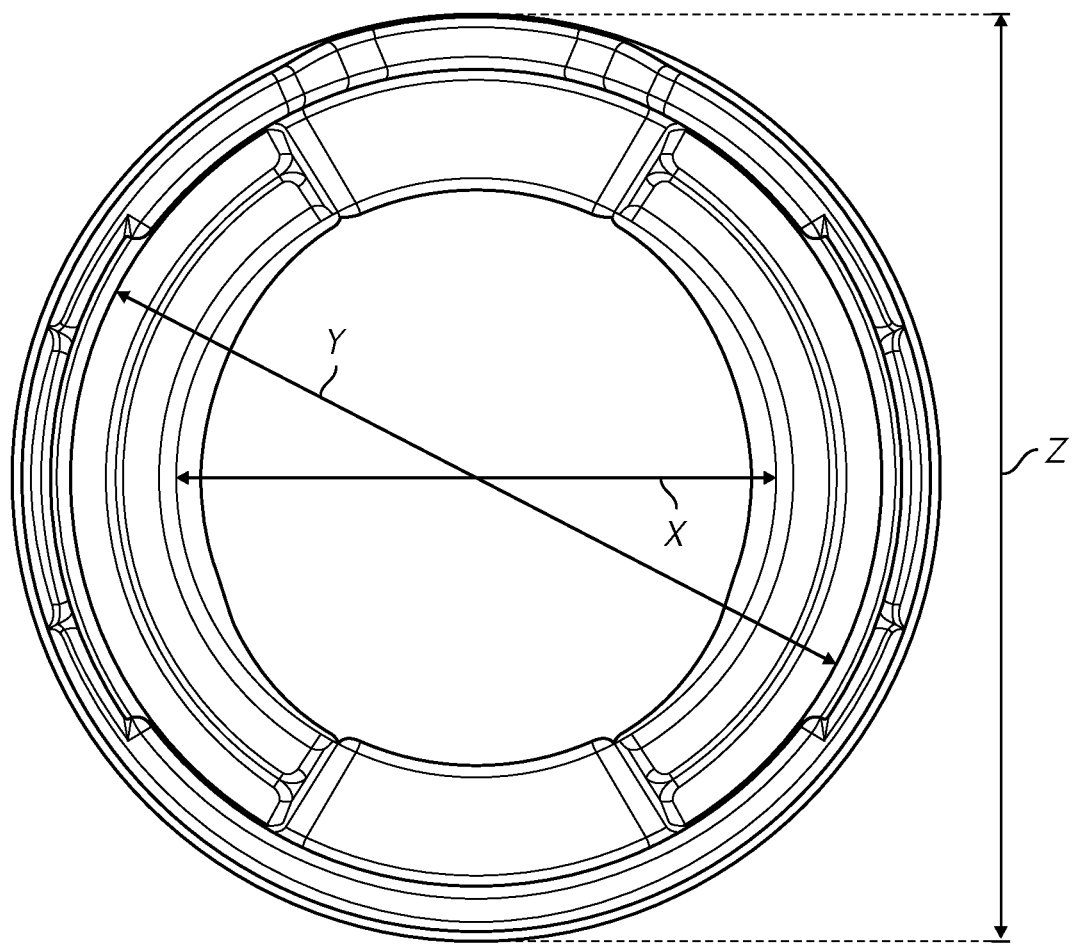
FIG. 40C shows the arc length of the bearing regions of the ball-joint socket with a recessed flow path of FIGS. 38A-38E.

With reference to FIG. 40C, Diameter Z (that is, the inner diameter of the connection housing 1610 of FIGS. 37A-37E and 38A-38E) can be in the range of 18 and 45 mm. Assuming a 1 mm wall thickness, Diameter Y is therefore in the range of 16 and 43 mm. Diameter X is smaller than Diameter Y. The slot width E (FIG. 40D) is related to Diameter X and Diameter Y according to the equation: $E=\frac{1}{2}(Y-X)$. The slot width E is desirably in the range of 1 and 12 mm. Thus, in this example, Diameter X is greater than 16 mm.

Figure 40D:
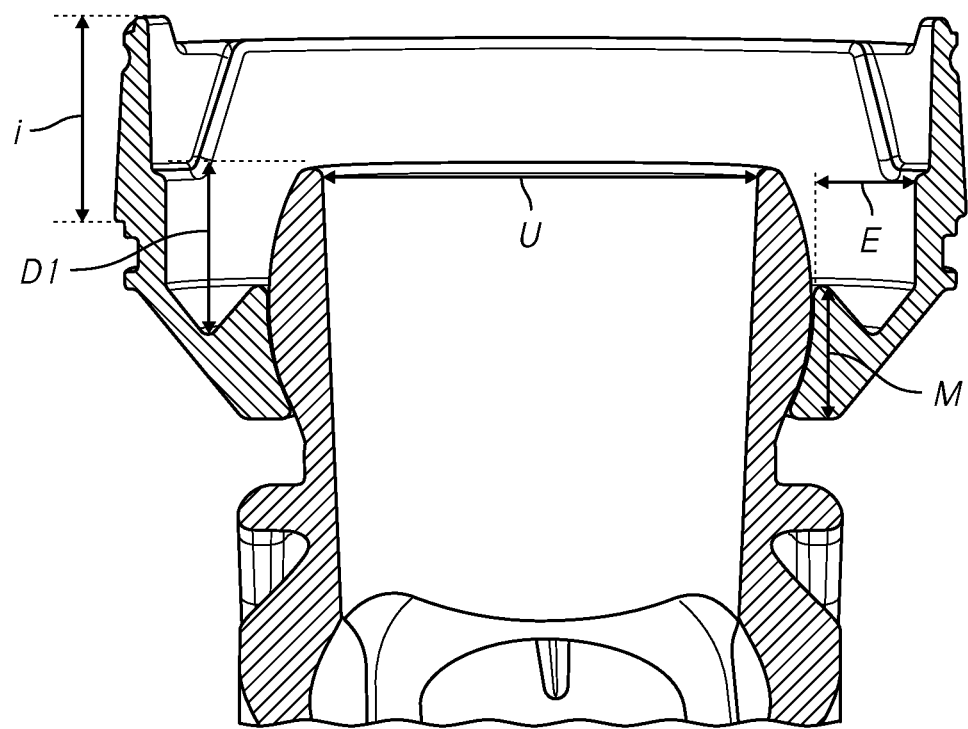
FIG. 40D shows the inner diameter of the connection housing of the ball-joint socket with a recessed flow path of FIGS. 38A-38E.
Figure 40E:
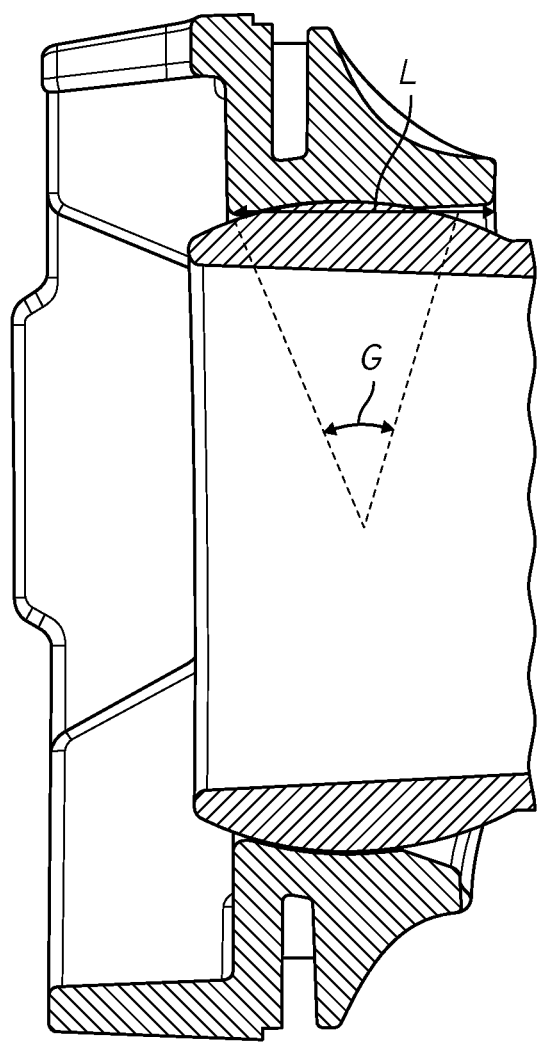
FIG. 40E shows the retention area of a bearing region of the ball-joint socket with a recessed flow path of FIGS. 38A-38E.

With reference to FIG. 40D, when the ball retention length M increases to the apex of the ball, leakage reduces. When the ball retention length M increases past the apex of the ball, leakage reduces and retention improves. It was also discovered that the channel depth D1 is related to the channel depth D2 (FIG. 39B), the inner diameter of the end of the truncated ball joint 1606 (Diameter U, FIG. 40D), and the angle of maximum rotation of the truncated ball joint 1606 in the ball-joint engagement region 1628 of the socket 1616 in any direction (Angle C, FIG. 40B) are related according to the equation: D1=D2+½(U tan C). It was also observed that dynamic noise improves as channel depth D2 increases. When channel depth D2 is equal to 7 mm and Diameter U is 20 mm, no dynamic noise was observed.

The retention area can be defined as the area required to keep the truncated ball joint 1606 in place. The retention area is a function of Angle A, Angle G, and the ball retention length L. For example, with reference to FIG. 40E, the angle (Angle G) subtended by the line representing the ball retention length L decreases as the total arc length of the bearing region (the sum of Angle A and Angle F) increases. The exhaust area can be defined as the area required for the bias vents. The exhaust area is a function of Angle B, the slot width E, and the ball retention length L. Minimizing the retention area maximizes the exhaust area of the expiratory region, improving noise and draft. The resistance to unwanted housing detachment can be defined as resistance to unintended housing detachment caused by a moment applied to the housing. The resistance to unwanted housing detachment is a function of Diameter Z and the housing taper length i (FIG. 40D). It was discovered that a maximum ratio of Z to i of 6 to 1 is preferred.

V. Respiratory Mask and Vent Arrangement

FIGS. 41A to 41E illustrate a respiratory mask assembly 1700 with a vented insert that includes an integrated elbow socket and is compact, easy to manufacture and easy to clean. The respiratory mask assembly 1700 comprises a frame 1710, a cushion 1712 attached to a cushion housing 1714, a swivel elbow 1716 having a ball-joint 1732, and a vent insert 1718. The vent insert 1718 is inserted, received and supported by the frame 1710. In operation, the vent insert 1718 connects the cushion housing 1714 to the elbow 716 such that inspiratory gas provided by a gas supply is supplied by the elbow 716 to the cushion 1712. The vent insert 1718 also receives the ball-joint 1732 to provide rotational adjustability of the swivel elbow 1716.

The frame 1710 has a frame opening 1720 that has a generally annular shape defined by an inner wall 1722. The frame opening 1720 has a symmetric tri-oval shape with a center that is aligned with a center of the frame 1710.

The vent insert 1718 is comprised of a cover portion 1740, an engagement region 1742, and an elbow socket 1744. The cover portion 1740 has a generally planar shape with an exterior surface that is substantially flush with the exterior surface of the frame 1710. The cover portion 1740 and its outer periphery have a shape that corresponds to the annular shape of the frame opening 1720.

The engagement region 1742 comprises a collar portion 1750 that extends substantially perpendicularly from the periphery of the cover portion 1740 in a direction towards the user. In some configurations, the collar portion 1750 extends a distance from the cover portion 1740 that is equal to or greater than the thickness of the frame 1710. The exterior surface of the collar portion 1750 has a shape that corresponds to the shape of the frame opening 1720 such that the collar portion 1750 engages the inner wall 1722 of the frame opening 1720.

The cover portion 1740 and the collar portion 1750 define an interior region 1752 of the vent insert 1718. The interior region 1752 provides a cavity within which inspiratory and expiratory gas are received from the swivel elbow 1716 and the cushion 1712, respectively. The interior region 1752 comprises vent regions 1754 positioned on left and right sides of the engagement region 1742. The vent regions 1754 have vent holes 1756 that extend through the cover portion 1740 such that the interior region 1752 is in fluid communication with atmosphere through the vent holes 1756. The vent holes 1756 extend through the cover portion 1740 to pass expiratory gas expired by the user to the ambient atmosphere when in use.

Each vent region 1754 vents expiratory gas in a different direction than the opposite vent region 1754 such that the expiratory gas from both vent regions 1754 do not combine and create a draft or noise which may disturb the user. The vent regions 1754 and/or the vent holes 1756 may be angled such that the expiratory gas is vented in different directions.

The vent holes 1756 are illustrated as cylindrical in shape. That is, the vent holes 1756 have a circular cross-section. In some configurations, the vent holes 1756 may have a planar shape. Vent holes 1756 having a planar shaped may improve the ease of which the vent holes 1756 may be cleaned. It should be understood to one of ordinary skill in the art that the vent holes 1756 are not limited to circular or planar shapes and may include a variety of shapes and geometries.

The vent insert 1718 is inserted into the frame opening 1720 during assembly of the respiratory mask assembly 1700. In some configurations, the collar portion 1750 and the inner wall 1722 of the frame opening 1720 may have a slight interference fit such that the cover portion 1740 of the vent insert 1718 is easily engaged with the exterior surface of the frame 1710 prior to welding. In other configurations, the collar portion 1750 may have a rim or beveled edge (not shown) that engages a corresponding chamfered region positioned on the inner wall 1722 such that the vent insert 1718 is seated in the correct position relative to the frame 1710.

The vent insert 1718 is welded to the frame 1710 to provide a permanent joint with the frame. A weld region 1726 of the vent insert 1718 is welded to a weld region 1724 of the frame 1710 along a join 1730 between the vent insert 1718 and the frame 1710. In some configurations, vent insert 1718 may be joined with the frame opening 1720, for instance, by gluing, press fitting, welding, or soldering. In other configurations, the vent insert 1718 can be removably installed in the frame opening 1720, for instance, by click-together connection. In still other configurations, the vent insert 1718 can be integrally molded with frame 1710 during a molding process.

The vent insert 1718 has an integrated elbow socket 1744 comprising a ball-joint hole 1746 and a ball-joint engagement region 1748. The ball-joint hole 1746 extends through the cover portion 1740 of the vent insert 1718. The ball-joint engagement region 1748 comprises bearing surfaces provided by upper and lower socket sidewalls 1760, 1762 and lateral socket sidewalls 1764 that surround the ball-joint hole 1746. The interior surfaces of the socket sidewalls 1760, 1762, 1764 support, retain, provide sealing engagement, and allow the ball-joint 1732 to rotate relative to the vent insert 1718. In some configurations, the upper and lower socket sidewalls 1760, 1762 may be integrally formed with an interior surface of the collar portion 750.

Figure 41D:
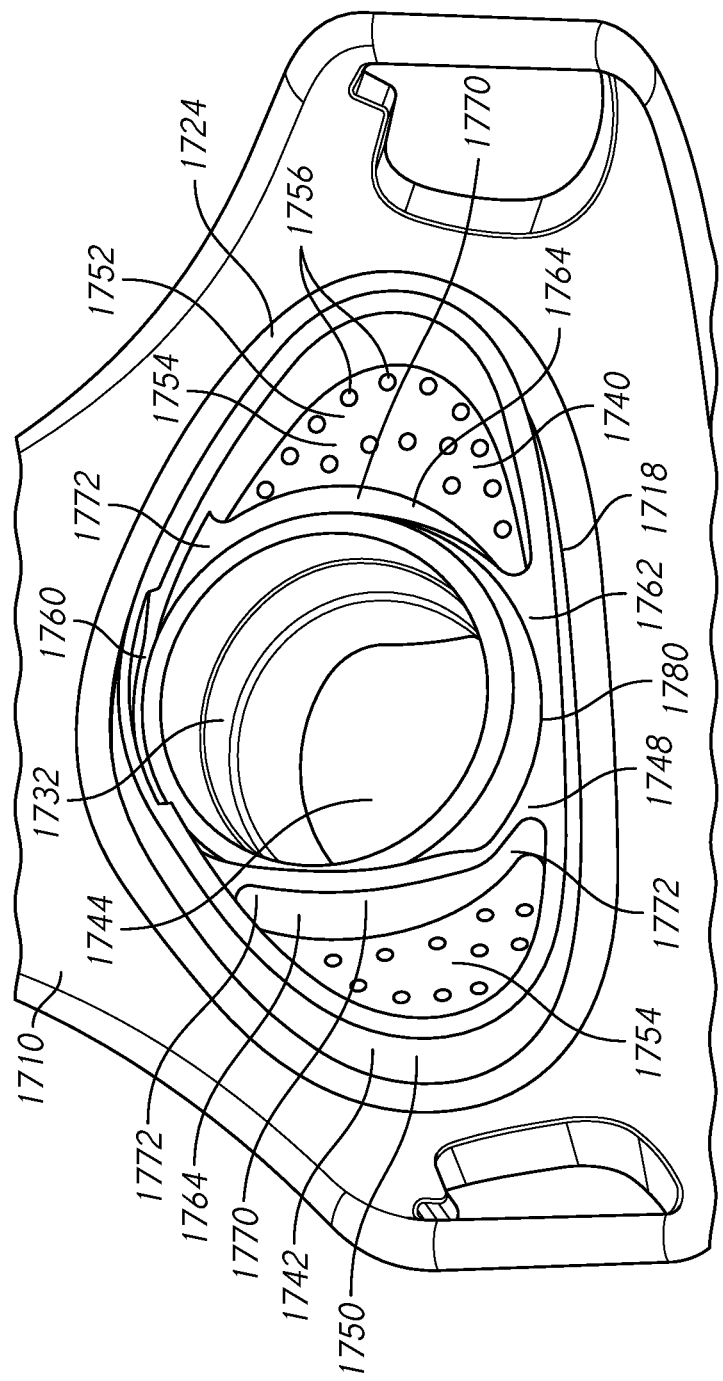
FIG. 41D shows a rear close-up perspective view of the respiratory mask assembly with a vented insert having an integrated elbow socket of FIG. 41A.
Figure 41E:
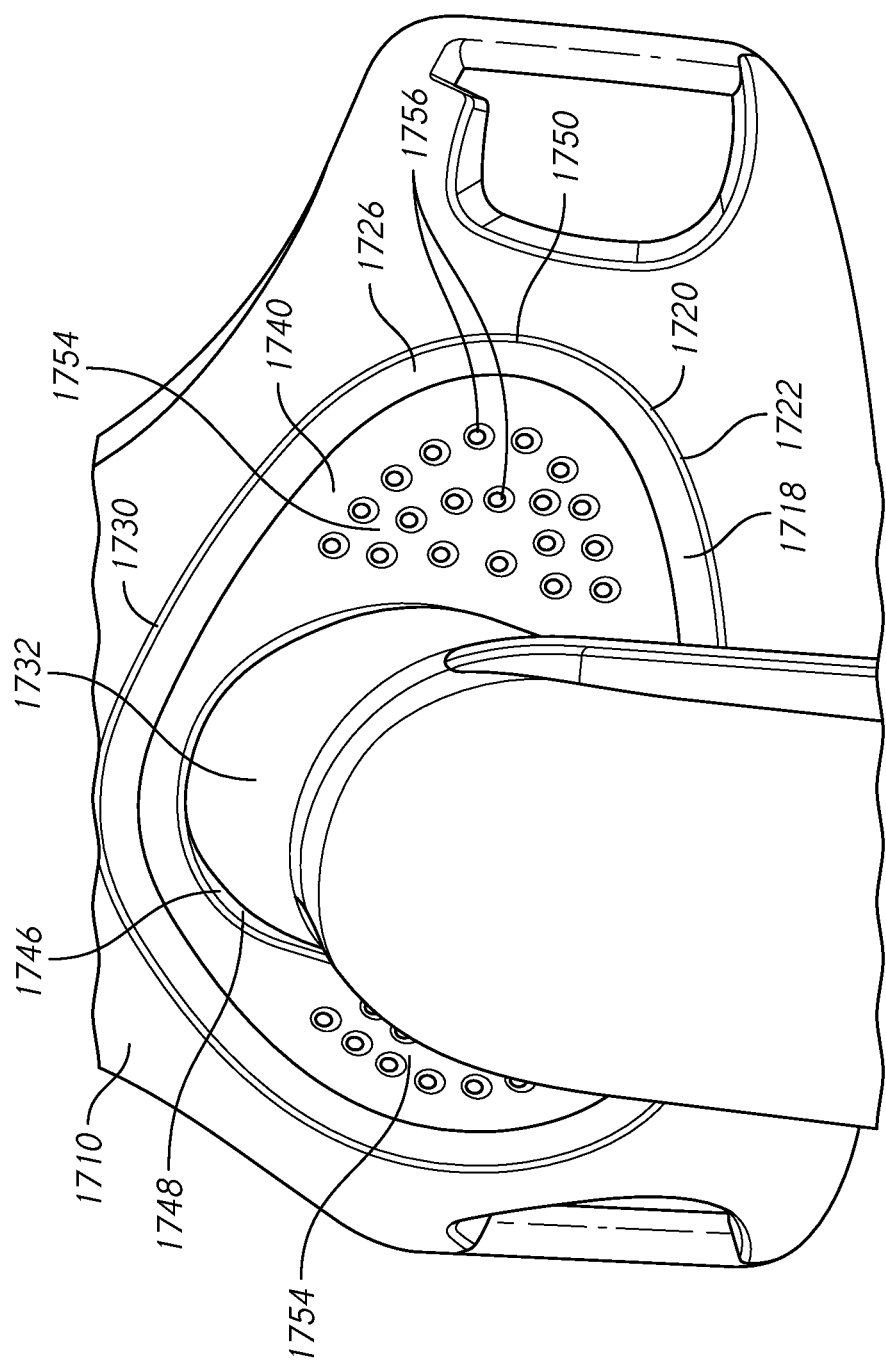
FIG. 41E shows a front close-up perspective view of the respiratory mask assembly with a vented insert having an integrated elbow socket of FIG. 41A.

The socket sidewalls 1760, 1762, 1764 extend substantially perpendicularly from the periphery of the cover portion 1740. As shown in FIG. 41D, the central portions 1770 of the lateral socket sidewalls 1764 extend a greater distance away from the cover portion 1740 than the end portions 1772 of the lateral socket sidewalls 1764. That is, the height (i.e., in a direction toward the user) of the lateral socket sidewalls 1764 at central portions 1770 is greater than a height of the lateral socket sidewalls 1764 at the end portions 1772. The height of the lateral socket sidewalls 1764 gradually decreases from a maximum height at the central portions 1770 to a minimum height at the end portions 1772.

As shown in FIG. 41D, the end portions 1772 of the lateral socket sidewall 1764 have a similar height as the lower socket sidewall 1762 such that the lower socket sidewall 1762 is flush with the end portions 1772 of the lateral socket sidewalls 1764. That is, a user-facing surface of the lower socket sidewall 1762 is flush with a user-facing surface of the end portions 1772 of the lateral socket sidewalls 1764. Accordingly, the central portions 1770 of the lateral socket sidewalls 1764 have a height that is a greater than the lower socket sidewall 1762. In some configurations, the upper socket sidewall 1760 may also have a similar height as the end portions 1772 of the lateral socket sidewall 1764.

The shorter heights of the end portions 1772 of the lower socket sidewall 1762 and the lateral socket sidewalls 1764 form a recessed region 1780. That is, the user-facing surfaces of the lower socket sidewall 1762 and the lateral socket sidewalls 1764 define a recessed region 1780 between the ball-joint 1732 and the collar portion 1750. The recessed region 1780 provides a shallow user accessible cavity at a location within the interior region 1752 where dirt may accumulate. The recessed region 1780 provides a shallow gap or clearance between the ball-joint 1732 and a bottom (i.e., the collar portion 1750) of the vent insert 1718 that may be easily wiped and cleaned by the user.

In some configurations, portions of the inner surface of the collar portion 1750 adjacent to the lower socket sidewall 1762 may have cut-away regions that further enlarge the recessed region 1780. That is, portions of the collar portion 1750 adjacent to the recessed region 1780 may be removed or recessed to enlarge the recessed region 1780. An interior surface of the collar portion 1750 may be recessed such that that the thickness of the collar portion 1750 is reduced while providing additional clearance between the collar portion 1750 and the ball-joint 1732.

In some configurations, the upper socket sidewall 1760 may also have a similar height as the end portions 1772 of the lateral socket sidewall 1764 such that a recessed region is formed above the ball-joint 1732 which provides ease of cleaning in an upper region of the vent insert 1718. Similarly, portions of the inner surface of the collar portion 1750 adjacent to the upper socket sidewall 1760 may have cut-away regions that further enlarge the recessed region.

In some configurations, the ball-joint 1732 may have a cut-away region (not shown) on a bottom portion of the ball-joint that engages interior region 1752. The cut-away region may be a removed or recessed portion of the ball-joint 1732 that aligns with the recessed region 1780 and provides additional clearance between the collar portion 1750 and the ball-joint 1732 to allow the user to remove dirt accumulation within the interior region 1752 of the vent insert 1718.

Figure 42A:
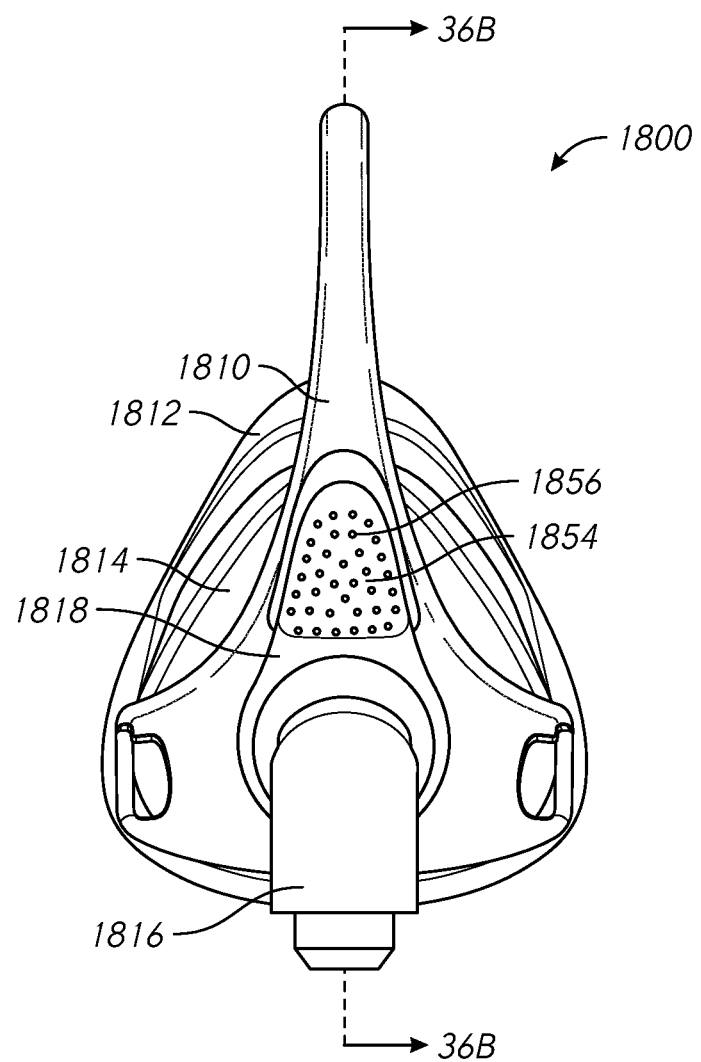
FIG. 42A shows a front view of an alternative respiratory mask assembly with a vented insert having an integrated elbow socket.
Figure 42B:
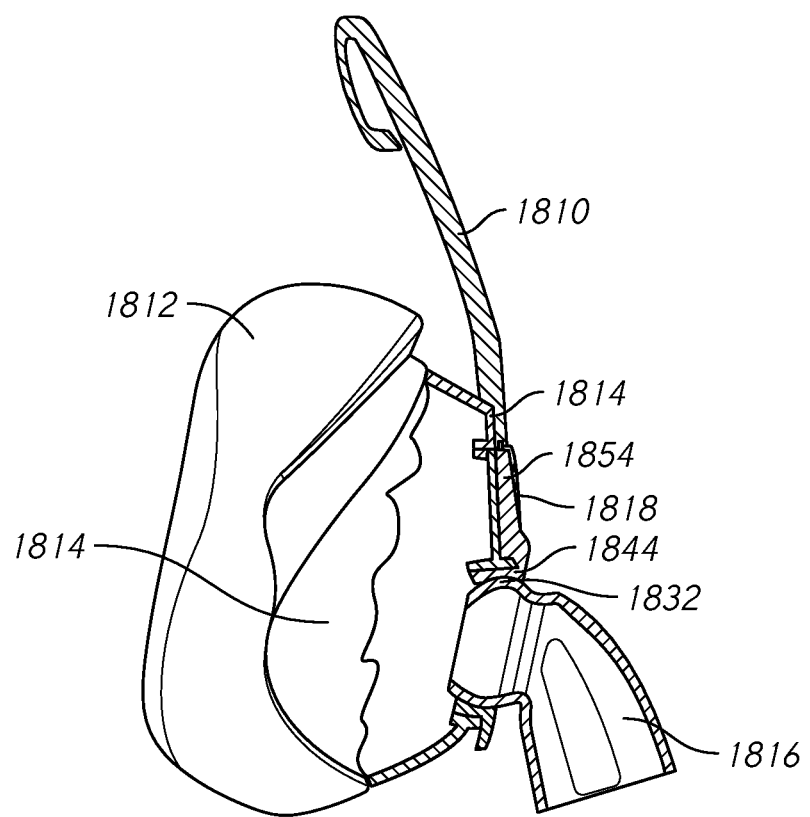
FIG. 42B shows a cross-sectional view along a line 36B-36B of the alternative respiratory mask assembly with a vented insert having an integrated elbow socket of FIG. 35A.

FIGS. 42A and 42B illustrate an alternative respiratory mask assembly 1800 for a bias vent in a full-face mask having a vented insert 1818 that includes an integrated elbow socket. The vented insert configuration is substantially similar to the side vent configuration of the respiratory mask assembly 1700 in FIGS. 41A-41E. However, the location of the bias vent 1854 is located above rather than to the sides of the swivel elbow 1816. Accordingly, the mask assembly 1800 is compact, easy to manufacture and easy to clean. For brevity, the redundant discussion of similar features between the respiratory mask assembly 1700 in FIGS. 41A-41E and the alternative respiratory mask assembly 1800 in FIGS. 42A-42B is omitted.

The bias vent 1854 has a plurality of vent holes 1856 that are provided in the vent insert 1818. The vent holes 1856 extend through the vent insert 1818 to pass expiratory gas expired by the user to the ambient atmosphere when in use.

The vent insert 1818 can protrude through an aperture in the frame 1810 and provide a connection means between the frame 1810 and the cushion housing 1814. The vent insert 1818 is permanently attached to the cushion housing 1814 of the mask. The vent insert 1818 may be friction/press fit or welded to provide a permanent joint with the frame 1810. In other configurations, the vent insert 1818 can be removably connected to the frame 1810, for instance, by a snap-fit or click-together connection. In still other configurations, the vent insert 1818 can be integrally molded with frame 1810 during a molding process.

The vent insert 1818 also includes an elbow socket 1844 that receives the ball-joint 1832 of the swivel elbow 1816. Similar to the elbow socket 1744 in FIGS. 41A-41E, the elbow socket 1844 supports, retains, provides sealing engagement, and allows the ball-joint 1832 to rotate relative to the vent insert 1818. The elbow socket 1844 includes a similar socket sidewall configuration and recessed regions as the elbow socket 1844 to allow the vent insert 1818 to be easily cleaned.

Headgear

Respiratory patient interfaces/masks can be used to treat a variety of conditions. One such condition is that of obstructive sleep apnoea (OSA). Certain features, aspects and advantages of the invention described herein are described with reference to use in the treatment of OSA through Continuous Positive Airway Pressure (CPAP), however this is not intended to be limiting and certain features, aspects and advantages of the present invention may be used in the treatment of other respiratory conditions.

The most common treatment for OSA is CPAP. This involves providing a constant supply of pressurized air to the patient's airway via a mask system. Most masks comprise a combination of a sealing interface, frame, air supply connection and a headgear structure. The headgear is attached to the frame and holds the seal against the patient's face. For treatment efficacy, it is desired that a generally leak free seal is achieved between the mask and the patient's face. Accordingly, the headgear structure is integral in securing the mask to the patient.

It is common for headgear to be made from breathable foam and fabric laminates, for example Breath-o-Prene®. Some common problems associated with current headgear designs include that they are bulky, heavy, hot and slow to dry when cleaned. Certain features, aspects and advantages of the current invention seek to provide improvements to these problems.

3D Fabric

Certain features, aspects and advantages of the present invention include headgear that is either completely or partially constructed from a 3 dimensional fabric. 2 dimensional fabrics are typically woven from two yarn sets as warp and weft yarns to form a woven surface or sheet material. The thickness of a 2 dimensional fabric is determined by the combined thickness of the yarns at a yarn crossing in the fabric. For example, in a fabric woven from warp and weft yarns the thickness of the fabric is equal to the thickness of a warp yarn and the weft yarn used in the construction of the fabric. The yarns in a 2D fabric generally extend in a single plane of the fabric. 2D fabrics lack fibres or yarns extending in a through-thickness direction of the fabric, and predominantly only have yarns extending in a general plane direction of the fabric. Two dimensional textiles or fabrics such as woven and knitted sheet fabrics tend to form a sharp edge when a fold in the 2D fabric is pressed flat or tension is applied along the folded edge. For example, when a fold in 2D fabric is placed under heat and/or pressure (e.g., ironing), a sharp creased edge is formed. A folded edge in a 2D fabric would be generally undesirable in a headgear application as the tension in the headgear components required to maintain a mask in a sealing position on a user's face would create a sharp edge. On soft tissue or sensitive areas of a user's head, such as around the ears or the back of the neck, this would not be desirable.

All fabrics have a 3D internal structure, however macroscopically most can be regarded as thin 2D fabrics. In 3D fabric structures, the thickness or Z-direction dimension is considerable relative to the X and Y dimensions. A 3D fabric may be generally defined as "a single-fabric system, the constituent yarns of which are supposedly disposed in a three mutually perpendicular plane relationship" (Behera B. K., Mishra R. (2008), 3-Dimensional Weaving, *Indian Journal of Fibre & Textile Research*, Vol. 33, pp. 274-287). Khokar provided a similar definition for 3D woven fabrics as "a fabric, the constituent yarns of which are supposed to be disposed in a three-mutually-perpendicular-planes relationship" (Khokar, N. (2001), 3D-Weaving: Theory and Practice, *Journal of the Textile Institute*, Vol. 92 No. 2, pp. 193-207).

A basis common definition for 3D fabric is that these types of fabrics have a third dimension in the thickness layer. For example, a 3D fabric has yarns in the warp, weft and through-thickness directions of the fabric. Khokar classified 3D fabrics into different types of 3D fabrics including interlaced 3D fabrics, non-interlaced 3D fabrics and fully interlaced 3D fabrics.

In this specification and claims, unless the context suggests otherwise, the term 'yarn' is intended to mean yarn, filament, fibre, thread or any other constituent element for forming a fabric by weaving, knitting, braiding or other construction.

As stated above, a 3D fabric has a thickness that is greater than a stack up of the constituent yarns used in the construction of the fabric. In other words a 3D fabric has a density of constituent material thickness to overall fabric thickness that is relatively low compared to traditional 2D textiles. A 3D fabric construction provides for thicker fabrics which are lightweight and breathable for a given fabric thickness as they are less dense than traditional 2D fabrics for a given thickness. Further, the structure of 3D fabrics is less prone to creasing when folded, and the increased thickness compared to 2D fabrics provides for additional cushioning.

Figure 43:
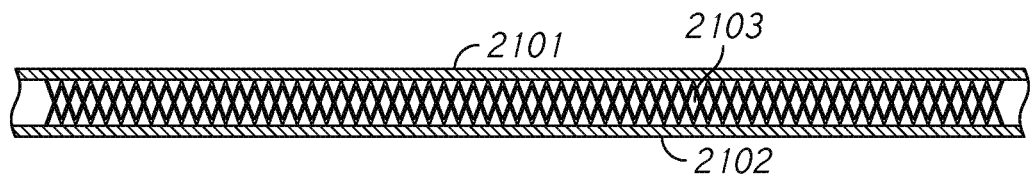
FIG. 43 is a sectioned view of 3D spacer fabric, showing two outer sheets of fabric and internal spacing fibres or filaments between the sheets.

One form of 3D fabric is 3D spacer fabric or textile (herein a 'spacer fabric'), which is a fabric that has two sheets formed from yarns connected by a series of yarns (e.g. filaments or fibres) running between the sheets, for example as shown in FIG. 43. With reference to FIG. 43, a spacer fabric may comprise a first sheet 2101 formed from a yarn or yarns (e.g. warp and weft yarns) in a first plane, a second sheet 2102 formed from a yarn or yarns (e.g. warp and weft yarns) in a second plane parallel to the first plane, and a yarn or yarns 2103 running between and connecting the two sheets together extend in a through-thickness direction of the fabric. The distance between the sheets and the physical properties of the fabric sheets and the filaments running or connecting between the sheets can be specified to provide a variety of physical properties. In some embodiments the distance between the sheets may fall within the range of 1 mm to 5 mm.

Spacer fabrics generally are breathable, provide compressible cushioning, are light weight, can be anti-allergenic and anti-bacterial and can be stretch or non-stretch. Spacer fabrics are commonly made from thermoplastics, such as polyester, but can be made from a variety of other fibrous materials. A combination of different materials may be used to provide specific physical characteristics.

Embodiments of the present disclosure comprise 3D spacer fabric by way of example only. The disclosed embodiments may utilise other types of 3D fabrics as alternatives to or in combination with 3D spacer fabrics as described.

Figure 44:
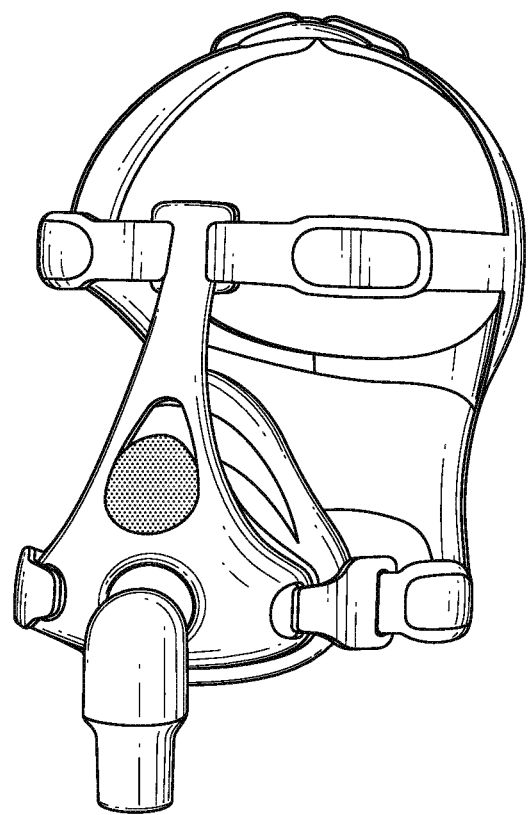
FIG. 44 is a perspective view of a full-face patient interface and headgear assembly.
Figure 45:
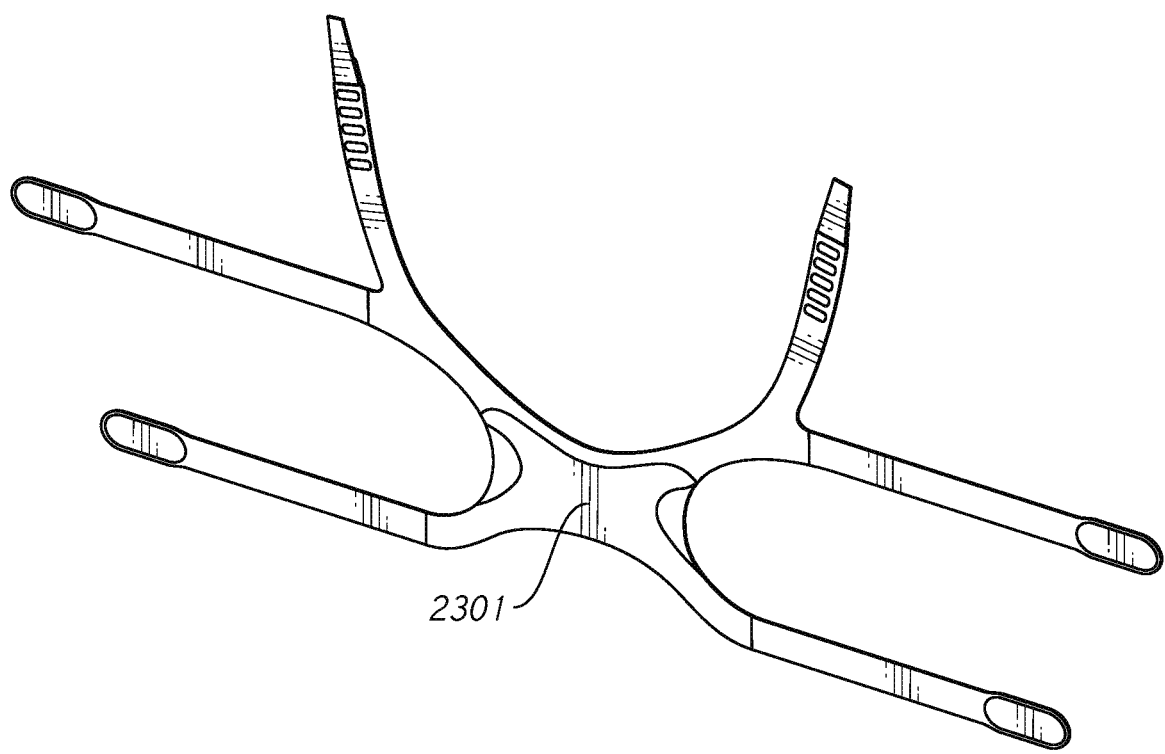
FIG. 45 is an isometric view of a full face headgear configuration when it is laid flat.

A typical headgear design for a full-face mask is shown in FIG. 44. It includes four mask attachment points in the form of adjustable upper and lower side straps, an adjustable top strap and a back portion. FIG. 45 shows the same headgear in a flattened out position. Similar four-point headgear configurations can be used in combination with nasal masks. For some direct nasal masks, two-point headgear configurations are used. These tend to have a more centrally located attachment strap on each side of the headgear. Additionally, four-point headgear may attach to a mask with or without a T-piece.

In some configurations, a headgear configuration can be generally shaped as shown in FIG. 45 but may be made at least in part from spacer fabric. For example, the back section or back panel portion 2301 can be made from spacer fabric and the remainder of the headgear can be made from traditional materials, such as breathable foam and fabric laminate. The back panel of the headgear provides a section of the headgear from which straps of the headgear extend at the required positions and orientations to fit to the head of a range of different user's. The back panel is often larger and more bulky than other parts of the headgear such as the headgear straps.

The back panel is sufficiently large to provide stability to the headgear on the user's head. The panel contacts a sufficient area of the user's head to assist with maintaining the correct positioning of the headgear on the user's head. However, as the panel covers a larger area of the user's head the headgear can be hot and uncomfortable to users. The use of spacer fabric in the back portion 2301 of the headgear may be beneficial in reducing the overall weight and improving the breathability of the headgear thus improving user comfort and reducing sweating and/or a temperature at which the user's scalp covered by the headgear may reach. Spacer fabric can be more compressible than traditional headgear materials, such as breathable foam and fabric laminate. This is advantageous in that it may make the headgear less noticeable on the patient's head when they are lying down. The thickness of traditional materials can mean that patients can feel the headgear between their head and a pillow and or the edges of the headgear can dig into the head. Since spacer fabric can compress down to a minimal thickness, it is less likely to be felt on the patient's head.

The use of spacer fabric as a component of the headgear is not restricted to this location. Any component of the headgear can be made from spacer fabric where the physical properties of the fabric are chosen to meet the requirements of the specific location. Alternatively, the entire headgear can be made entirely from one or more grades of spacer fabric. A combination of spacer fabrics with differing physical properties may be incorporated into a single headgear. For example, the straps that connect to the mask may be non-stretch and the back panel may be a thicker material to provide additional cushioning.

There are several physical characteristics that are beneficial in headgear fabrics. These include having a soft surface finish for contact with the patient, being stretch or non-stretch dependent on the location within the headgear and having a certain amount of rigidity in order to maintain the shape of the headgear.

Spacer fabric is typically manufactured in large sheets and, as such, the headgear components are cut from these sheets and assembled. The cut edges of the fabric preferably are finished in some manner so as to reduce the likelihood of fraying, an untidy appearance and a rough edge against the patient's skin. There are many techniques and methods that can be used to assemble headgear components and finish edges. Several embodiments of these are detailed as follows.

Edge Finishing Techniques

Figure 46A:
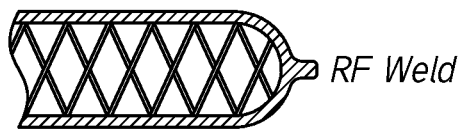
FIG. 46A is a cross-sectional view of a spacer fabric edge that is finished by a welding and die cutting technique.

FIGS. 46A, B, C and D illustrate several edge finishing methods that can utilize welding and/or sewing techniques. Welding and die cutting can be used to create a sealed and tidy edge, as shown in FIG. 46A. The heat generated by welding techniques, such as radio frequency (RF) welding, can be used to melt the fabric joining the outer fabric sheets of the spacer fabric together thus creating a closed edge and sealing off the filament region between the sheets. Once the edges are sealed, they can be trimmed and tidied by a die cutting process. In some configurations, individual headgear components can be joined together to form a complete headgear using RF welding. This would enable combinations of different grades or types of fabric to be used within a single headgear, e.g. multiple grades of spacer fabric can be joined together or spacer fabric components can be joined to breathable foam and fabric laminate components.

Figure 46B:
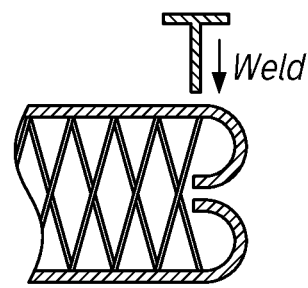
FIG. 46B is a cross-sectional view of a spacer fabric edge that is finished by welding together upper and lower surfaces at a centre of the fabric.
Figure 46C:
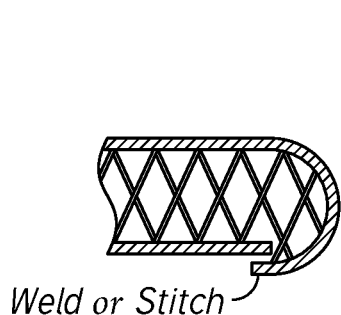
FIG. 46C is a cross-sectional view of a spacer fabric edge that is finished by folding and welding an upper surface to a lower surface.

FIGS. 46B and 46C show embodiments of edge finishes where the exterior surface of the spacer fabric extends further than the internal filaments and is folded over the exposed edge of the spacer fabric. In FIG. 46B, both the upper and lower surfaces are extended and are then folded towards the centre of the fabric. The folded in edges are secured in place by a weld joint that goes through the outer surfaces of the spacer fabric. As an alternative to welding or in addition to welding, a line of stitches may be sewn into the edge of the spacer fabric that catches the folded in raw edges. In FIG. 46C, one external surface is extended further than the other and is folded over the entire edge of the spacer fabric. The folded over raw edge is then welded and/or sewn in place as per the previous embodiment.

Figure 46D:
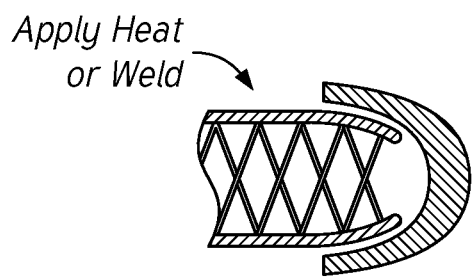
FIG. 46D is a cross-sectional view of a spacer fabric edge that is finished by welding a separate finishing component to the edge of the spacer fabric.

A further embodiment that can utilize welding techniques is shown in FIG. 46D. A separate finishing component can be applied to the edge of the spacer fabric, where the finishing component can be made of a textile or a plastic. A textile, such as bias binding, for example, can be folded over the spacer fabric edge and fixed in place either by sewing through the fabric outer sheets and inner spacer elements or by welding the fabric outer sheets and inner spacer elements together. In some configurations, a moulded plastic bead or casing can be applied to the spacer fabric edge using welding and/or sewing techniques, or any other appropriate method. The moulded bead or casing can have a circular or rounded cross-section, for example but without limitation.

Figure 46E:
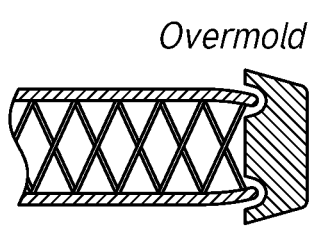
FIG. 46E is a cross-sectional view of a spacer fabric edge that is finished by overmoulding a bead onto the edge of the spacer fabric.

Over-moulding is another technique that can be used to provide a finished edge on spacer fabric. FIG. 46E shows a cross-section of a bead that can be moulded onto the edge of the spacer fabric headgear. The cross-section of the bead may be substantially trapezoidal in shape as shown in FIG. 46E, or of any other suitable cross-sectional shape. The over-moulded bead can be made from a soft material, such as a thermoplastic elastomer, for example, to provide a comfortable contact between the headgear and the patient. This finishing technique may also provide a source of structural reinforcement to the headgear, providing non-stretch or semi-rigid portions within the headgear. The over mould material may over-moulded onto the external surface of the edge of the spacer fabric using any suitable moulding techniques. The over moulding material may be over-moulded to the spacer fabric in a three dimensional shape so that the headgear maintains its structure when not on a patient's head. This will help reduce the likelihood of the headgear straps tangling and also makes the headgear easier to fit. Due to the open structure of spacer fabrics, over-moulding may result in plastic material being positioned on the external surfaces of the spacer fabric and/or through the spacer fabric layers. FIG. 46E shows the over-moulded edge material moulded to the external surfaces of the fabric. FIG. 46F shows one possible configuration where the plastic edge material has permeated all layers of the spacer fabric.

Figure 46G:
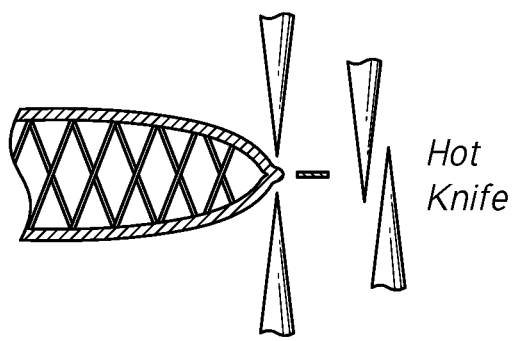
FIG. 46G is a cross-sectional view of a spacer fabric edge that is finished by a hot knife technique to both seal and trim the spacer fabric.
Figure 46F:
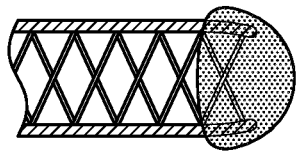
FIG. 46F is a cross-sectional view of a spacer fabric edge that is finished by permeating a plastic material through the spacer fabric.

Another embodiment, shown in FIG. 46G, utilizes a hot knife technique to both seal and trim the spacer fabric. A hot knife can be used to die cut the headgear components from a larger sheet of spacer fabric. The hot knife will compress and melt the two outer sheets and the filament region together before cutting through the fabric. This method will leave a tidy edge on the spacer fabric because the shape of the sealed edges will exactly match the shape of the cut pieces.

Sewing techniques, such as over-locking (serging), and the use of bias binding may be used to tidy edges.

A number of embodiments of headgear incorporating spacer fabric are illustrated in FIGS. 47A to 57. The headgear in these figures each comprises a back panel 2301 from which straps of the headgear extend, as described earlier. As illustrated, the headgear may comprise lower straps 2156, upper straps 2152, and top straps 2154. In the illustrated embodiments the headgear comprises a left and right lower strap, a left and right upper strap, and a left and right top strap. The left and right straps (e.g. the left and right lower straps) are connected together in use. However, in some embodiments one or more of the lower, upper and top straps may be provided as a single strap connected to each side of the back panel of the headgear. The left and right straps, for example the top straps 2154, may be connectable by a buckle or clip or other component, and/or may comprise features to allow the straps to be connected together, for example as described in U.S. application 62/187,010 the contents of which are incorporated herein by reference.

Figure 47A:
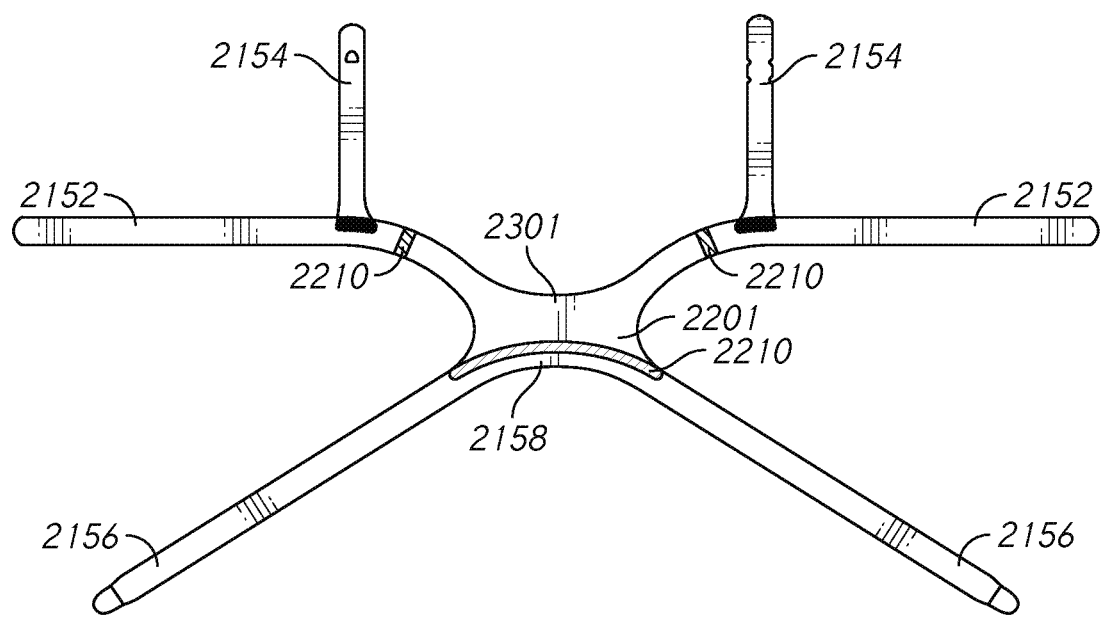
FIG. 47A shows a headgear comprising spacer fabric laid flat.
Figure 47B:
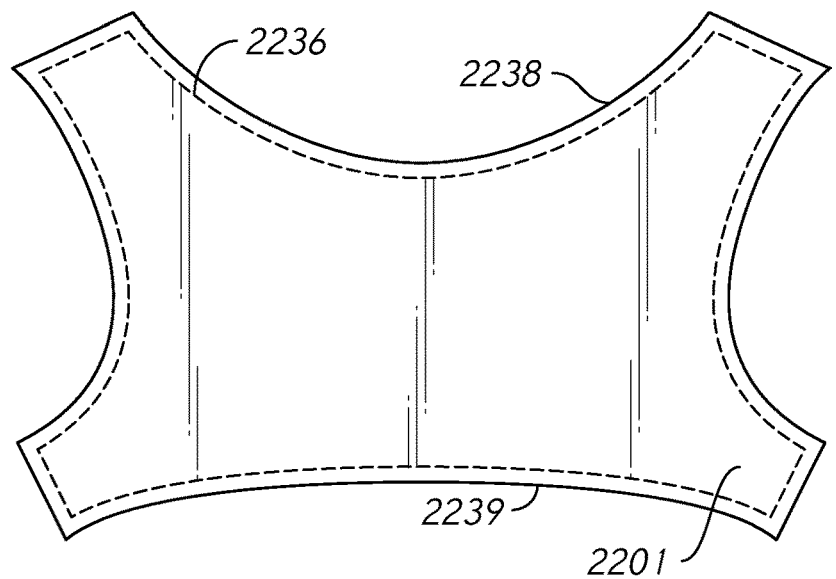
FIG. 47B-47D shows details of a spacer fabric panel incorporated in the headgear of FIG. 47A.
Figure 47C:
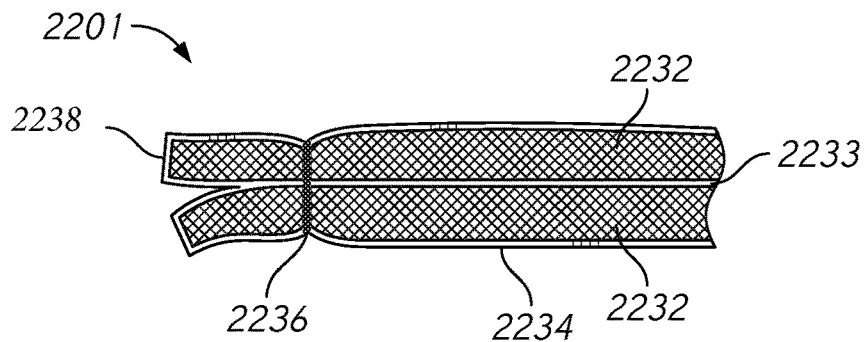
Figure 47D:
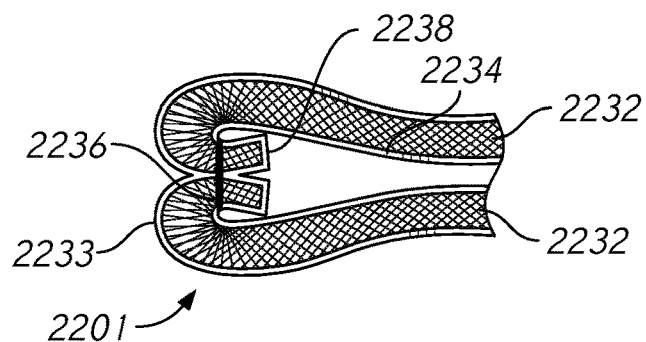

In some embodiments, at least a portion of the back panel 2301 comprises spacer fabric. In some embodiments, at least a portion of the back panel comprises two layers of spacer fabric. For example, as shown in FIGS. 47A and 47B, in some embodiments the back panel 2301 comprises a spacer fabric pad or panel 2201 comprising two layers of spacer fabric, and a lower back strap 2158. The spacer fabric panel 2201 comprises a substantially rectangular portion with scalloped edges with the corners cut off. The cut off corners are configured to attach to the upper straps 2152 and the lower straps 2156. The spacer fabric panel 2201 comprises two spacer fabric layers 2232 layered one on top of the other. The spacer fabric layers have a right side 2233 and a wrong side 2234. The two layers may be sewn together, inside out (i.e., with the wrong sides of the fabric facing out) to form a seam 2236 near the raw edges 2238 of the spacer fabric layers. Once sewn together the layers 2232 are then turned right-side out, such that the right sides 2233 are on the outside and the raw edges 2238 are on the inside. The seam 2236 extends around the perimeter of the spacer fabric pad 2201 leaving the bottom edge 2239 open. The open bottom edge 2239 allows the spacer fabric pad 2201 to be turned right-side out. Once turned right-side out, the upper straps 2152 and lower back strap 2158 are attached to the spacer fabric pad 2201. The lower straps and upper straps may be sewn to the spacer fabric; however, other attachment methods, such as but not limited to welding or bonding may be appropriate. In the illustrated embodiment of FIG. 47A the straps and fabric are welded to form welded joints 2210 between the straps and the two layers of spacer fabric. The open bottom edge 2239 may be sealed (closed) at the same time as being attached to the lower back strap 2158. The lower back strap may be integrally formed with the lower straps.

The lower back strap 2158 extends along the bottom edge 2239 of the spacer fabric pad. The lower back strap 2158 may be made of a material that is less stretchy than the spacer fabric pad 2201. The lower back strap provides structural reinforcement to the spacer fabric pad 2201 to reduce or eliminate the likelihood of excessive stretching that may cause the mask to become displaced from a user's face during use.

Figure 48:
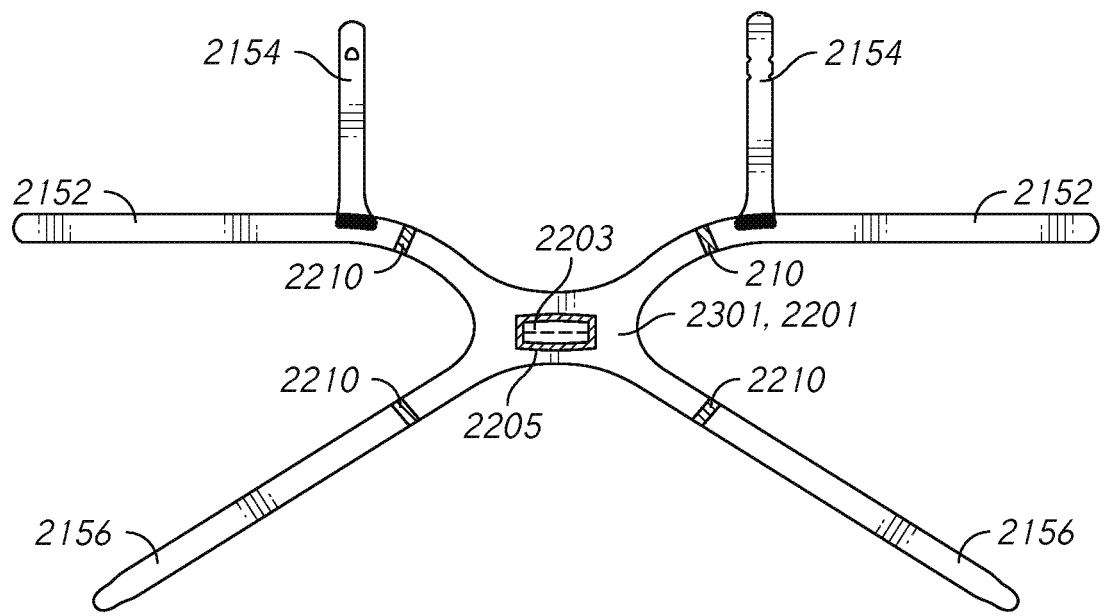
FIG. 48 shows a headgear arrangement where, in use, the bottom edge of the spacer fabric panel sits above or across the user's neck.

FIG. 48 illustrates an embodiment, where, in use, the bottom edge of the spacer fabric panel sits above or across the user's neck. The two layered spacer fabric may be stitched together with the right side of the fabric inwards and then turned right-side out so that the raw edges of the fabric are on the inside of the back panel as described above. However, in some embodiments as illustrated in FIG. 48, one layer of the spacer fabric may comprise an opening such as a hole or a slit (illustrated by dashed line 2203) through which the layers may be turned right side out. In this way, all four edges of the back panel may be provided with the raw edges of the fabric turned inside the back panel. In such an embodiment the opening 2203 may be covered by a patch 2205, for example a label bearing a maker's mark or brand. Alternatively in some embodiments the two layers of fabric may be turned right side out through one of the cut off corners of the back panel.

Figure 49:
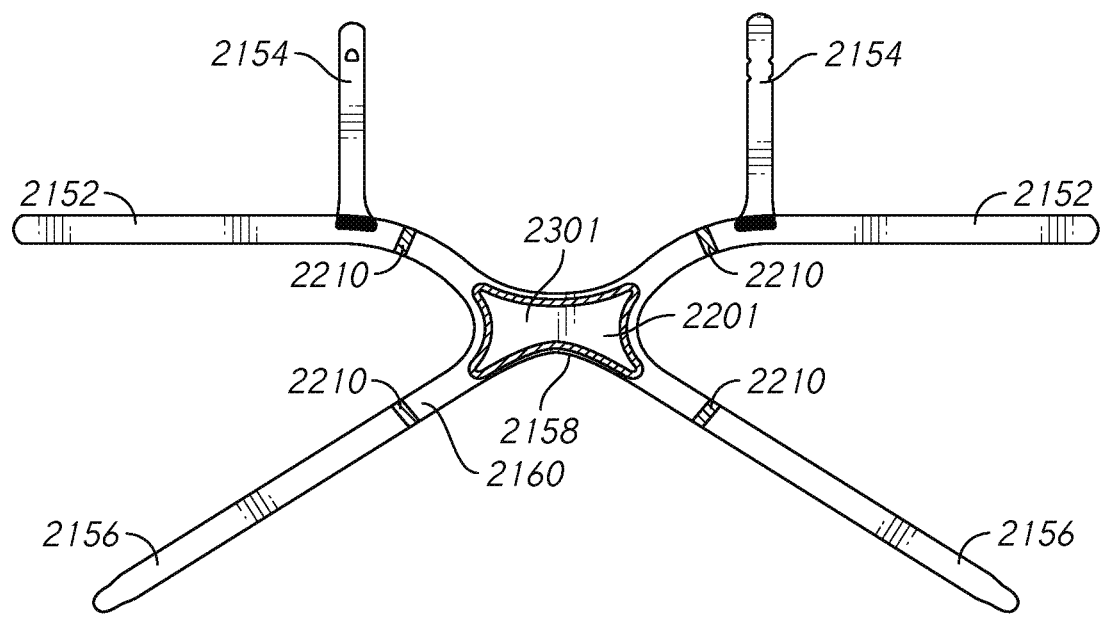
FIG. 49 shows a headgear arrangement having a back panel formed from two layers of spacer fabric and a perimeter portion formed from another headgear material extending around the full perimeter of the spacer fabric.

In some embodiments the back panel may comprise a two layered spacer fabric panel and a perimeter portion extending around the spacer fabric formed from another material suitable for use in a headgear, for example a typical headgear material such as breathable foam and fabric laminate. In the embodiment of FIG. 49 the back panel 2301 comprises two layers of spacer fabric 2201 and a perimeter portion 2160 formed from another headgear material extending around the full perimeter of the spacer fabric. In some embodiments the back panel may comprise two layers of spacer fabric and a perimeter portion formed from another headgear material extending around a portion of the perimeter of the spacer fabric. The other headgear material such as breathable foam and fabric laminate may extend into and/or form the headgear straps such as the lower straps 2156 and upper straps 2152. In some embodiments the lower straps and or headgear straps may be integrally formed via a perimeter portion of the back panel wherein the perimeter portion and the straps are formed from the same material. The two layered spacer fabric panel 2201 may be attached to the material of the perimeter portion 2160 by bonding, stitching or welding or other joining method. In such an embodiment the edges of the spacer fabric layers may be sealed/closed and attached to the material of the perimeter portion by the joining method, for example by welding. The perimeter portion extending along a bottom edge of the back panel may be described as a back strap, e.g. like back strap 2158 in FIG. 47A.

In the embodiment of FIG. 49 the back strap 2158 or perimeter portion extending along the bottom edge of the back panel has a 'higher lift' or comprises a pronounced inverted (up-side-down) V shape, compared to the back strap in other embodiments such as the embodiments of FIGS. 47A and 48. The higher lift or pronounced V shape is provided by shortening the radius of curvature in the bottom edge of the back panel and/or reducing the angle between the lower straps at which they extend from the back panel. In some embodiments, lower straps 2156 are at an angle or approximately 45 degrees to 70 degrees, measured from a vertical centre line of the headgear. If the angle of lower straps is less than 45 degrees (i.e., the strap is oriented 'too horizontally' in use) when laid flat, the lower straps 2156 may contact the user's ears in use. If the angle of lower straps 2156 is greater than 70 degrees (i.e. the strap is oriented 'too vertically' in use) the straps may twist and dig into the user as the lower straps 2156 are aligned to extend forward and upward from an untwisted position to attach to the patient interface.

Figure 50:
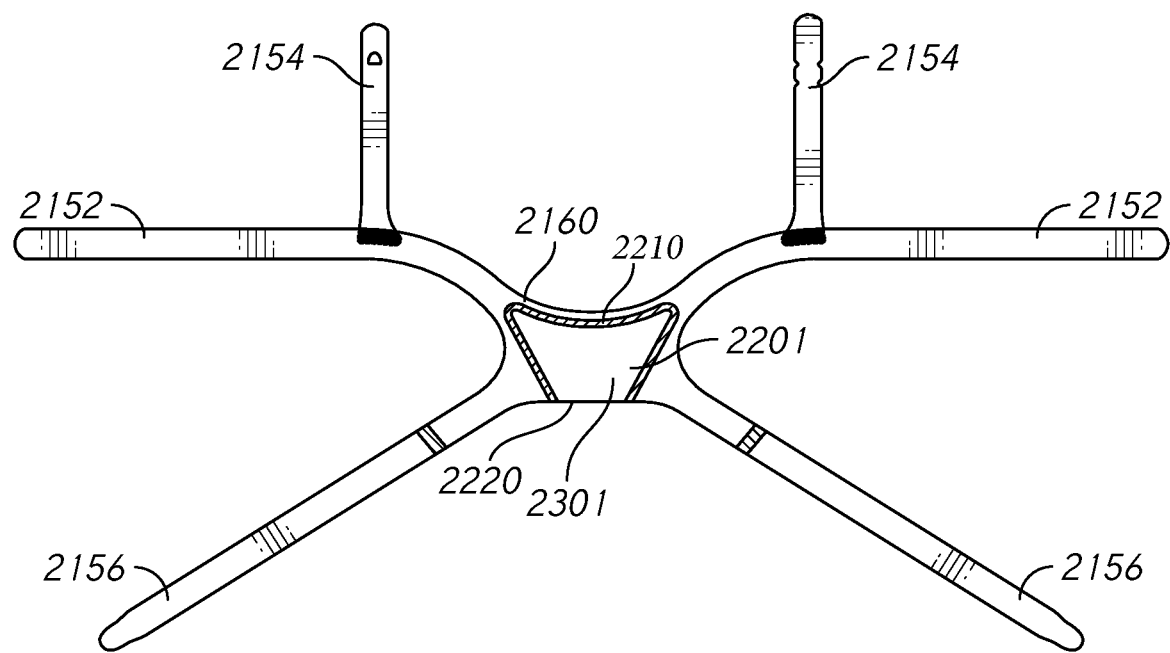
FIG. 50 shows a headgear arrangement having a back panel formed from two layers of spacer fabric folded from a sheet or blank of spacer fabric.

In some embodiments, the back panel or the portion of the back panel comprising two layers of spacer fabric is folded from a sheet or blank of spacer fabric. The sheet or blank of spacer fabric is folded to provide two layers of spacer fabric to form at least a portion of the back panel 2301. The spacer fabric may have a right side and a wrong side, and is folded so that the wrong side of the fabric is on the inside of the panel, with the right side of the fabric on the outside of the panel. Folding the spacer fabric provides a back panel with a folded edge of spacer fabric. For example, with reference to FIGS. 50-52, in some embodiments the folded edge 2220 is provided at a bottom edge of the back panel. The bottom edge of the back panel sits above or on the neck of the user. In some applications, the bottom edge of the headgear extending across the user's neck is preferably soft. Positioning the folded edge at the bottom edge of the back panel provides a soft edge at this location which can improve comfort for a user. As the folded edge does not include any joining structure such as stitching, welding or bonding, the folded edge is particular soft and also may provide additional flexibility which may be preferred in some applications. In some embodiments, other edges of the two layers are joined together by bonding, stitching or welding. For example, in the embodiments of FIGS. 51 and 52, all edges of the two layers other than the folded edge are welded together. In the embodiment of FIG. 50, the back panel has a perimeter portion extending around the two layers of spacer fabric from one end of the folded edge to the other end of the folded edge. The perimeter portion of the back panel is formed from a material suitable for use in headgear such as a foam material or other fabric material, such as breathable foam and fabric laminate, or a single layer of spacer fabric. In some embodiments, the edges of the two layers of spacer fabric other than the folded edge are attached to the perimeter portion by bonding, stitching or welding or other joining method. In the embodiment of FIG. 50, the edges of the two layers of spacer fabric other than the folded edge are welded to the perimeter portion of the back panel. In some embodiments, the material of the perimeter portion may extend into and form at least part of a strap of the headgear, such as the lower and/or upper straps.

Figure 51:
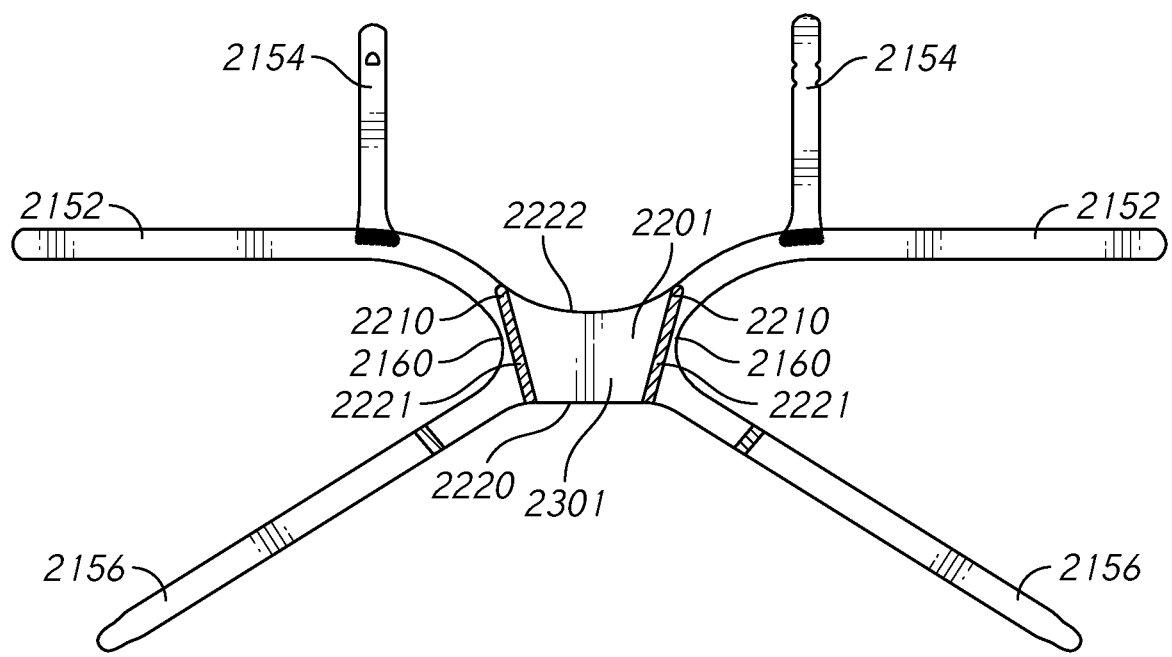
FIG. 51 shows a headgear arrangement formed from two layers of spacer fabric welded together along each lateral edge and stitched together along an edge opposite to the folded edge.
Figures 55, 56:
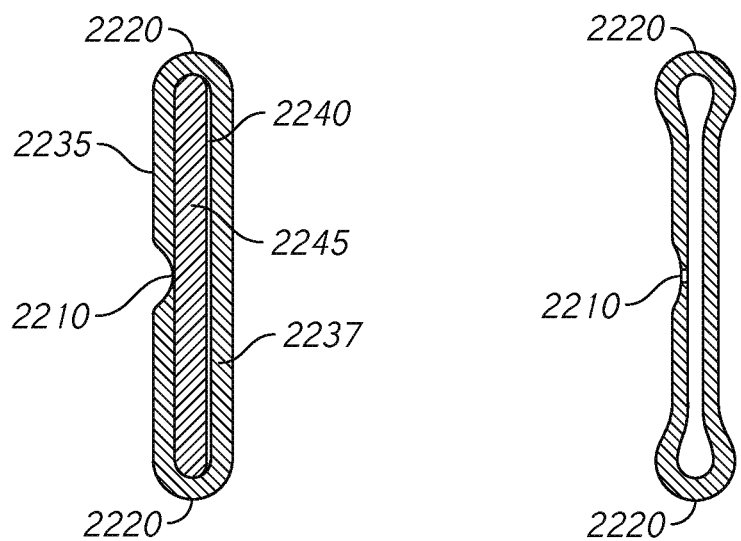
FIG. 55 is a cross section of a back panel of the headgear of FIG. 54.
FIG. 56 is a cross section of a back panel of the headgear described with reference to the embodiment of FIG. 51.

In some embodiments, edges other than the folded edge of the two layers of spacer fabric may be joined together using one or more joining methods to achieve desired properties. For example, in some embodiments one or more edges may be stitched and one or more edges may be welded or bonded. In some embodiments, the two layers of spacer fabric are welded or bonded together along each lateral edge of the two layers of spacer fabric. In some embodiments, the two layers of spacer fabric are stitched together along an edge of the two layers of spacer fabric opposite to the folded edge of the two layers of spacer fabric. For example, as shown in FIG. 51, in some embodiments the two layers of spacer fabric are welded together along each lateral edge 2221 of the two layers of spacer fabric and are stitched together along an edge 2222 opposite to the folded edge 2220 of the two layers of spacer fabric. In such an embodiment the bottom folded edge 2220 provides a particularly soft edge. The upper stitched edge may also be particular soft, for example if stitched together using a soft yarn or thread, or an elastic yarn or thread. In an alternative configuration the spacer fabric may include a folded edge at one edge 2220 of the back panel and a second folded edge at an opposite edge 2222 of the back panel, with a join in one of the two layers of spacer fabric. For example, the spacer fabric of the back panel may have a folded edge 2220 at an upper edge (edge 2222 in FIG. 51) of the back panel and a folded edge 2220 at the bottom edge (edge 2220 in FIG. 51) of the back panel. The outer layer of the two layers of spacer fabric may have a join 2210, the outer layer facing away from a user's head during use. An example cross section is provided in FIG. 56. In some embodiments the join may be covered by a patch, for example a label bearing a maker's mark or brand. The join 2210 may be a welded joint. A non-welding material (not shown in FIG. 56) may be provided between the two layers of spacer fabric so that when welding the joint 2210 the two layers are not welded together. A non-welding material may be a material that is not weldable, for example at a welding temperature of the spacer fabric and the underlying material. The non-bonding or non-welding film or material prevents the layers of the spacer fabric from being joined together. In a further alternative embodiment a 3D fabric may be formed in a continuous tube, for example in a knitted tube. To achieve two layers of 3D fabric the tube of 3D fabric is flattened, to provide two layers of 3D fabric with a folded edge at each of two opposed edges. A cross section of the two layers of 3D fabric may be as represented in FIG. 56, but as the two layers are formed from a flattened tube no join 2210 exists.

Welded or bonded joins have a higher hardness than the spacer fabric due to a change in the structure of the fabric caused by the bonded or welded joint, or resulting from the bonding material. The welded or bonded joints have less stretch than a folded edge. For example, an embodiment such as that shown in FIG. 51 may provide a back panel with a higher level of stretch in a lateral (the user's side to side direction) compared to a longitudinal direction (the user's top to bottom direction). The approximately vertical welded edges of the two layers of spacer fabric are less flexible than the stitched and/or folded lateral edges. In the embodiment of FIG. 51 the back panel 2301 comprises the panel of two layers of spacer fabric 2201 and a perimeter portion 2160 at each lateral edge formed from another material suitable for use in a headgear, for example a typical headgear material such as breathable foam and fabric laminate. In the illustrated embodiment the lateral edges 2221 of the two layers of spacer fabric are welded to the corresponding lateral perimeter portion 2160. Each perimeter portion 2160 may extend into and form at least part of a strap of the headgear, such as the lower and/or upper straps 2156, 2152. The welding of the spacer fabric to the perimeter portions may also close or join the edges of the two layers of spacer fabric together.

Figure 52:
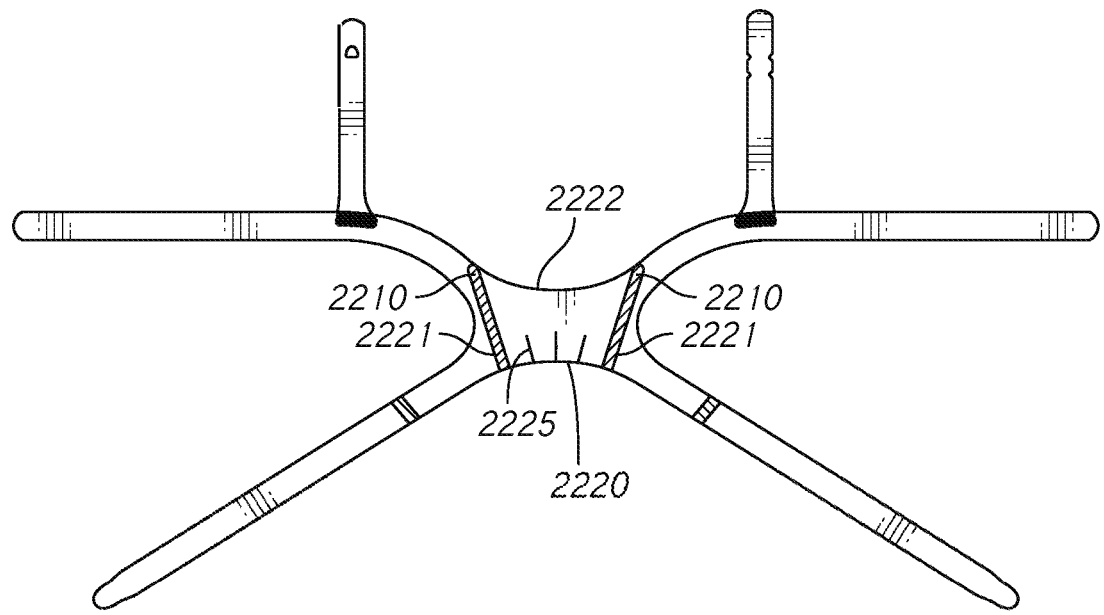
FIG. 52 shows a headgear arrangement having a curved folded edge and pleated layers.

In the embodiments of FIGS. 50 and 51 the folded edge 2220 of the two layers of spacer fabric is a straight edge as the spacer fabric is folded on a straight fold line. In some embodiments, as illustrated in FIG. 52 the folded edge 2220 may be curved, for example by gathering each layer of the spacer fabric adjacent to the folded edge, for example by pleating the layers on pleat lines 2225.

Figure 53:
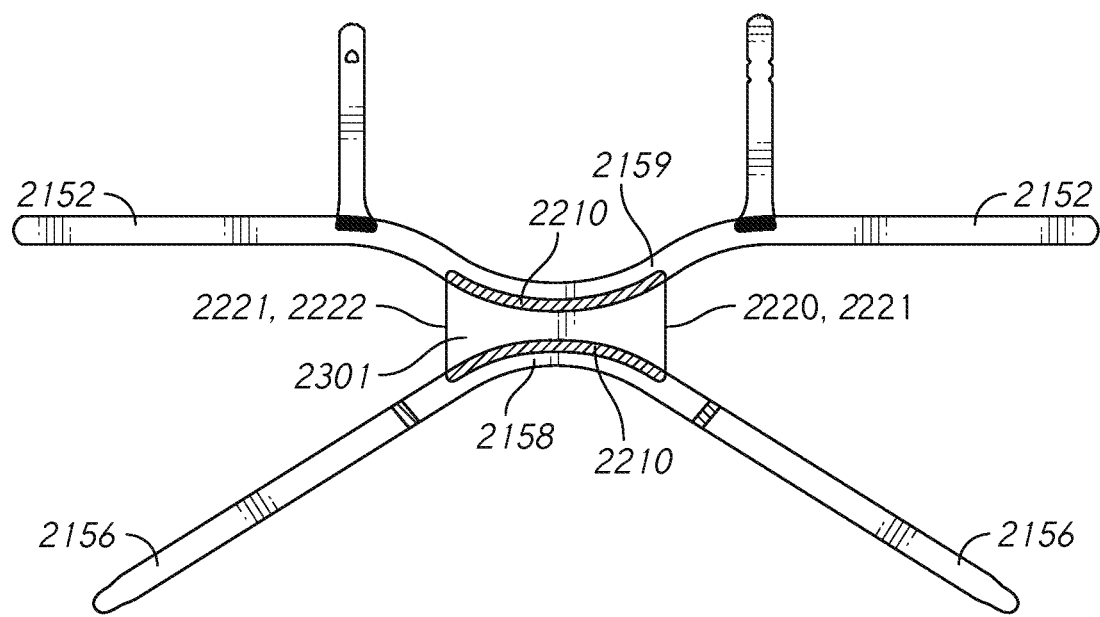
FIG. 53 shows a headgear arrangement formed from two layers of spacer fabric welded along the upper and lower edges to an upper strap and lower strap, respectively.

In some embodiments as illustrated by the embodiment of FIG. 53, the folded edge 2220 may be positioned at a lateral edge 2221 of the back panel 301. The two layers of spacer fabric may be stitched together along a lateral edge 2222 of the two layers of spacer fabric opposite to the folded edge 2220. Alternatively the spacer fabric may comprise two folded edges, for example as described with reference to FIG. 51 but with the folded edges at the lateral edges of the two layers of spacer fabric. An upper and a lower edge of the two layers of spacer fabric may be bonded, welded or stitched to an upper and lower strap of the headgear. In the embodiment of FIG. 53 the two layers of spacer fabric are welded 2210 along the upper and lower edges to an upper strap 2159 and lower strap 2158 respectively.

Figure 54:
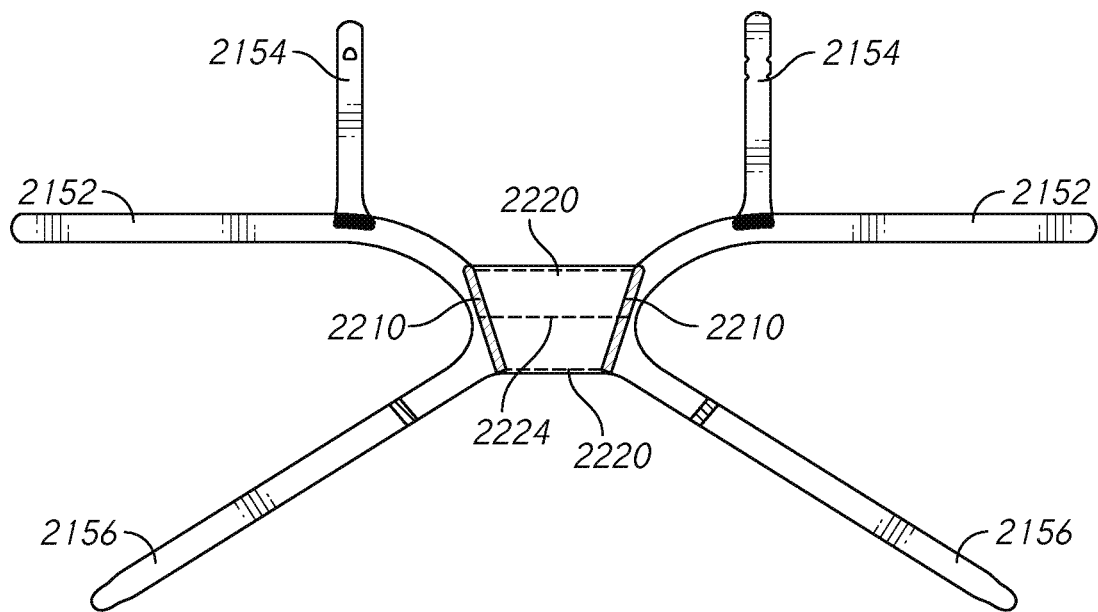
FIG. 54 shows a headgear arrangement formed from spacer fabric wrapped around other headgear material to have a folded edge at an upper and at a lower edge of the back panel.

In some embodiments spacer fabric may be applied to a headgear by being wrapped around another component of the headgear. For example, as shown in FIGS. 54 and 49, the headgear may comprise a back panel formed from a headgear material such as breathable foam and fabric laminate or other suitable material with a covering of spacer fabric. In the embodiment of FIGS. 54 and 55, the spacer fabric is wrapped around the other headgear material of the back panel. In some embodiments the two layers of spacer fabric may be joined, for example by stitch, bonding or welding, at an edge of the two layers of spacer fabric. As illustrated in FIGS. 54 and 55, in some embodiments, the spacer fabric is wrapped around the other headgear material to have a folded edge 2220 at an upper and at a lower edge of the back panel. One layer of the two layers of spacer fabric may have a join, for example a stitched, boned or welded joint, represented by the dashed line 2224 in FIG. 54. The join may be in an outer layer of the two layers of spacer fabric, the outer layer being the layer that does not contact the user's head during use. In the cross sectional view of FIG. 55 the join 2224 is illustrated as a welded joint 2210. In some embodiments the join 2224 in the spacer fabric may be made prior to wrapping the spacer fabric around the other headgear material. In such an embodiment, the fabric is joined to form a continuous piece of fabric with an open end to be slipped over the other headgear material. Alternatively in some embodiments the fabric may be wrapped around the other headgear material and subsequently joined. In some embodiments the joint in a layer of spacer fabric may also join the spacer fabric to the underlying material of the headgear. In some embodiments, a non-bonding or welding material or film may be provided between the underlying material of the headgear and either one or both layers of spacer fabric. A non-bonding or non-welding material may be a material that is incompatible with a bonding material such that no bond is formed with the non-bonding material. A non-welding material may be a material that is not weldable, for example at a welding temperature of the spacer fabric and the underlying material. The nonbonding or non-welding film or material prevents the layer or layers of the spacer fabric from attaching to the underlying material of the headgear. For example, a non welding film 2240 may be provided between the underlying material 2245 of the headgear and a layer 2237 of the spacer material that contacts the user's head in use (an inner layer of the two layers of spacer fabric). The non-welding material or film 2240 prevents the welded joint 2210 in the outer layer 2235 of spacer fabric from penetrating the underlying material 2245 and the inner layer 2237 of spacer fabric so that the inner layer of spacer fabric is not welded to the underlying material. However, the weld in the outer layer 2235 of spacer fabric may weld the outer layer of spacer fabric to the underlying material 2245. Bonding or welding the outer layer of spacer fabric to the underlying material helps to maintain the covering of spacer fabric in a correct position over the underlying material. The inner layer 2237 of spacer fabric spaces the underlying material of the headgear off the head of the user which can improve comfort by providing a cushioning effect and also reduce sweating and/or a temperature at which the user's scalp covered by the headgear may reach.

Figure 57:
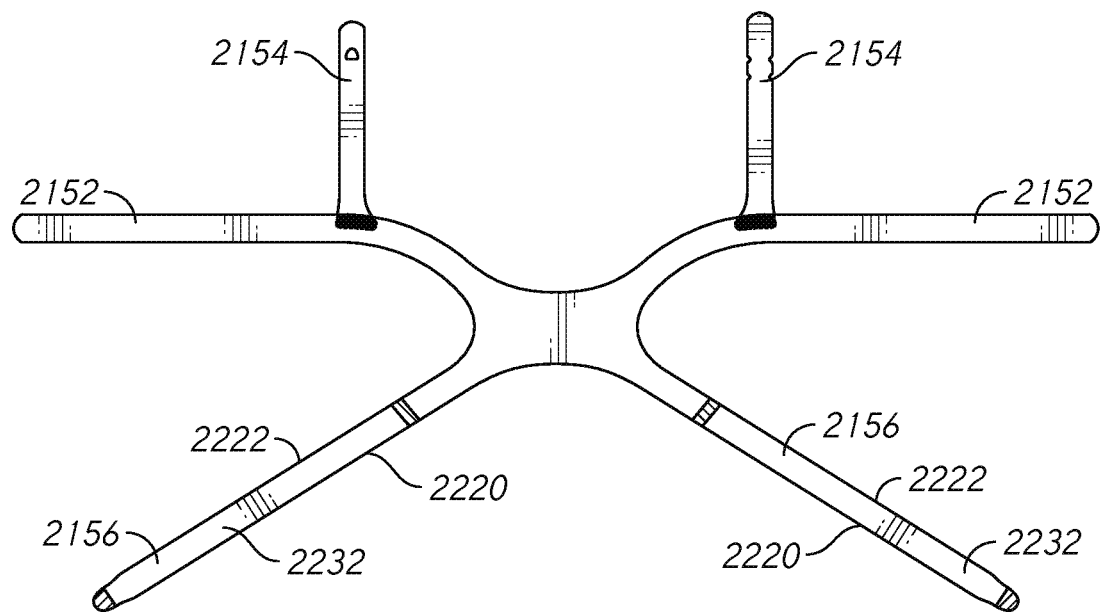
FIG. 57 shows another headgear embodiment laid flat.

The headgear embodiments of FIGS. 47A to 54 comprise two layers of spacer fabric in at least a portion of the back panel of the headgear. However, in some embodiments two layers of spacer fabric may be used in or to form other components of headgear. For example, as shown in FIG. 57, in some embodiments a headgear strap 2156 may comprise two layers 2232 of spacer fabric. The spacer fabric 2232 may be formed to have a folded edge 2220 at an edge of the strap with a join at an opposite edge 2222 of the strap, or a folded edge 2220 at one edge of the strap and a folded edge at an opposite edge 2222 of the strap with a join in one of the two layers 2232 of spacer fabric. For example the join could be in an outer layer of spacer fabric as explained in relation to the embodiment of FIG. 54.

In the manufacture of embodiments described above with reference to FIGS. 51 to 57, in some embodiments a join between layers or within a layer of the two layers of spacer fabric may be made with the fabric turned wrong side out. Once the join has been made, the spacer fabric is then turned right side out so that the join is located inside the two layers of spacer fabric, for example as described with reference to the embodiment of FIG. 47A.

Weld Detail

In some embodiments, for example as described with reference to FIG. 50, an edge or edges of the panel of two layers of spacer fabric is welded to another portion of the headgear, for example a perimeter portion of the back panel. For example, in FIG. 50 edges of the two layers of spacer fabric are welded to the perimeter portion 2160 of the back panel extending from one end of the folded edge 2220 to the other end of the folded edge. And in FIG. 51, lateral edges 2221 of the two layers of spacer fabric 2201 are welded to lateral perimeter portions 2160. In some embodiments, the portion of the headgear is formed from another material suitable for use in headgear, such as breathable foam and fabric laminate.

In some embodiments an edge region of the two layers of spacer fabric is overlapped with an edge region of the portion of the headgear to form a weld region comprising two layers of spacer fabric and the portion of the headgear. In the weld region, one layer (an internal layer) of the spacer fabric is located between the portion of the headgear and the other layer (an external layer) of the spacer fabric. The overlapping materials comprising the two layers of spacer fabric and the portion of the headgear are preferably welded together by radio frequency welding, with the materials pressed together between two welding heads, for example between a table/platen and a die/horn, as known in the art. However, any other suitable welding technique may be employed, for example ultra-sonic welding or thermo compression welding.

Figure 59A:
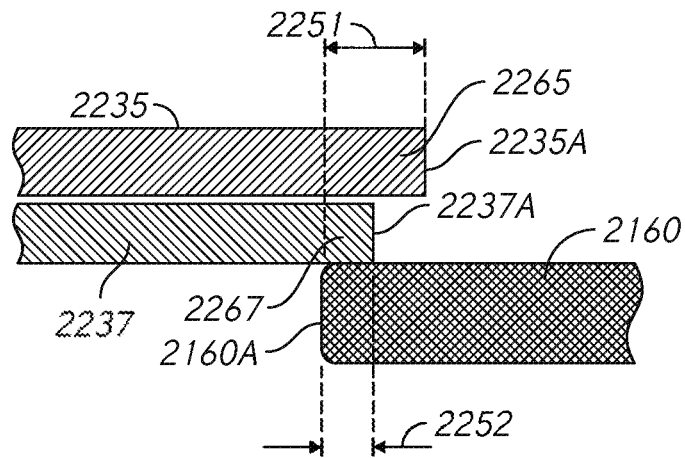
FIG. 59A shows a stack up of materials prior to welding.
Figure 59B:
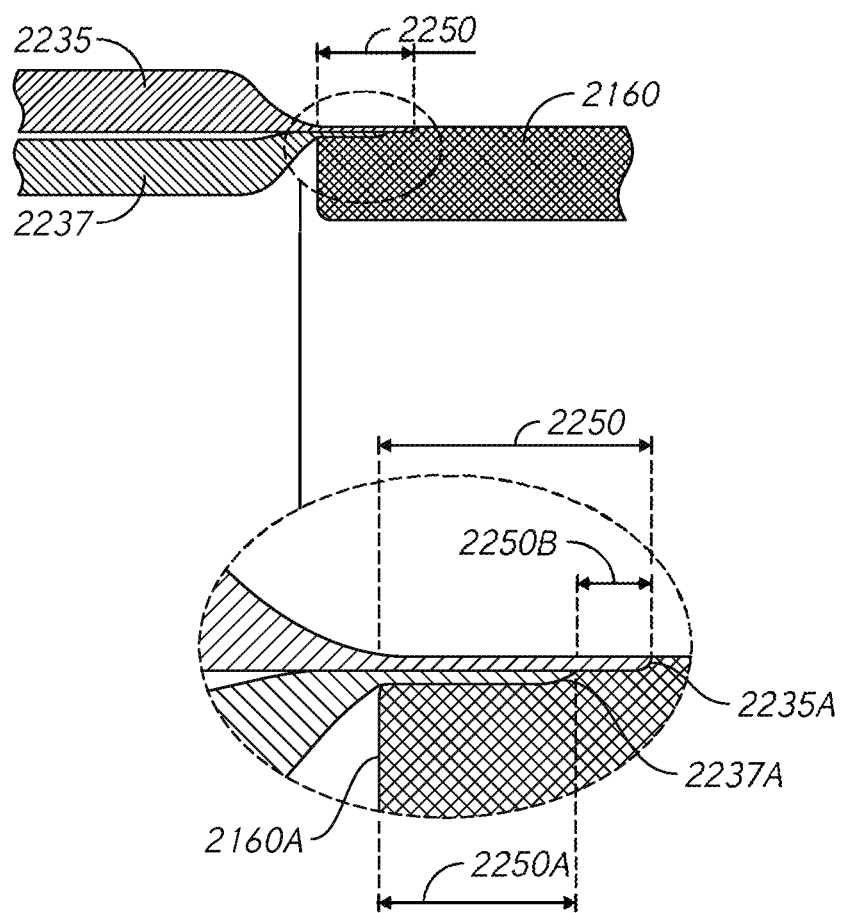
FIG. 59B shows an enlarged view of the materials in FIG. 59A that are welded together in a welded joint.

In some embodiments, as shown in FIG. 59B, in the weld region 2250, one layer 2235 of the two layers of spacer fabric (an overlapping layer) overlaps the edge of the other layer 2237 of the two layers of spacer fabric so that the weld comprises a first region 2250A formed from two layers of spacer fabric and the portion 2160 of the headgear and a second region 2250B formed from one layer of spacer fabric and the portion of the headgear. In some embodiments the weld comprises a first region 2250A formed from two layers of spacer fabric and the portion 2160 of the headgear and a second remaining region 2250B formed from one layer of spacer fabric and the portion of the headgear. This arrangement creates a weld with a 'stepped thickness' of welded spacer fabric. The thickness of the welded spacer fabric is greater at the edge 2160A of the portion of headgear than at the edge 2235A of the overlapping layer 2235 of spacer fabric.

Each of the two layers of spacer fabric has an overlapping region that overlaps a portion of the headgear to be welded to the two layers of spacer fabric. The width of the overlapping region of a first one of the two layers is greater than the width of the overlapping region of a second one of the two layers of spacer fabric. For example, with reference to FIGS. 58A to 59C, the two layers of spacer fabric may be folded from a single blank 2300 cut from a sheet of spacer fabric. The blank is folded to form two layers of spacer fabric as shown in FIGS. 58B and 58C. The fabric is folded along a fold region 2310 shown in FIG. 58A. One section 2315 of the blank that forms one layer 2237 of the two layers of spacer fabric is sized smaller than a corresponding section 2320 of the blank that forms the second layer 2235 of the two layers of spacer fabric, so that once the fabric is folded along the fold region 2310 to form the two layers of spacer fabric, one layer 2235 overlaps the edge of the other layer 2237, as shown in FIGS. 58B and 58C. With one layer 2235 overlapping the edge of the other layer 2237 the two layers of spacer fabric comprises a 'stepped edge'. In the illustrated embodiment the two layers of spacer fabric has a stepped edge at each lateral edge 2221 of the two layers of spacer fabric. At an edge 2222 opposite to the folded edge 2220 the edges of the layers are aligned, to for example provide for a stitched edge. Thus the two layers of spacer fabric illustrated in FIG. 58B may be suitable for use in the construction of the headgear illustrated in FIG. 51. As shown in FIG. 58B, a fold in the spacer fabric results in a rounded edge. Unlike a fold in a 2D fabric which can result in a sharp creased edge, a fold in a 3D fabric results in a rounded soft edge. Due to the thickness and/or structure of a 3D fabric, the folded edge 2220 results in a gap between the two layers of fabric at the folded edge, so that the edge is particularly soft and suitable for use in headgear.

Figure 58A:
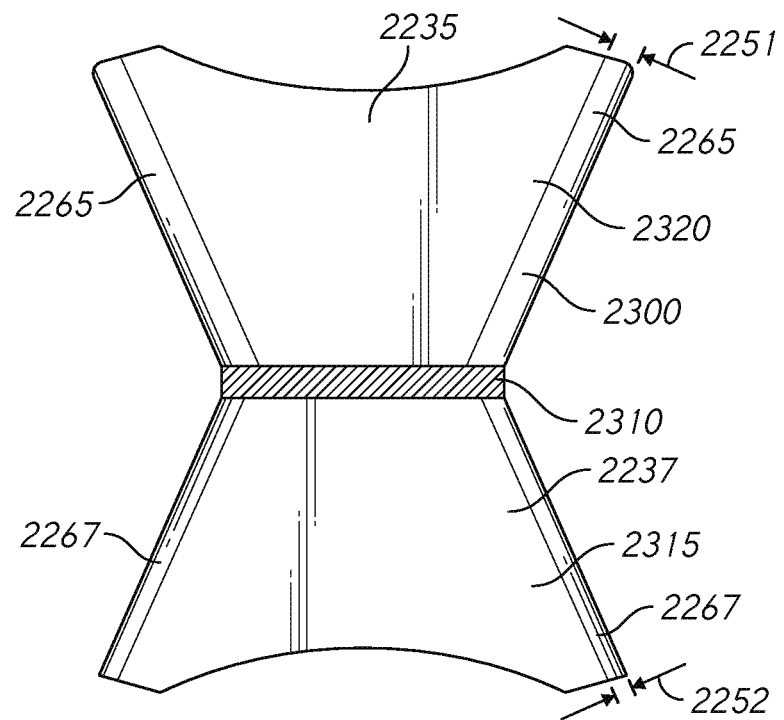
FIG. 58A shows a blank of spacer fabric.
Figure 58B:
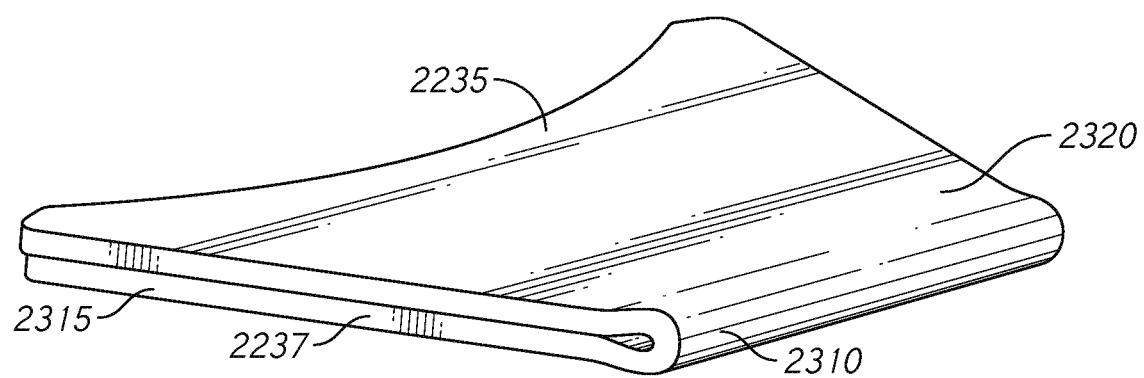
FIG. 58B shows a perspective profile view of the blank of spacer fabric in FIG. 58A folded to form two layers of spacer fabric.
Figure 58C:
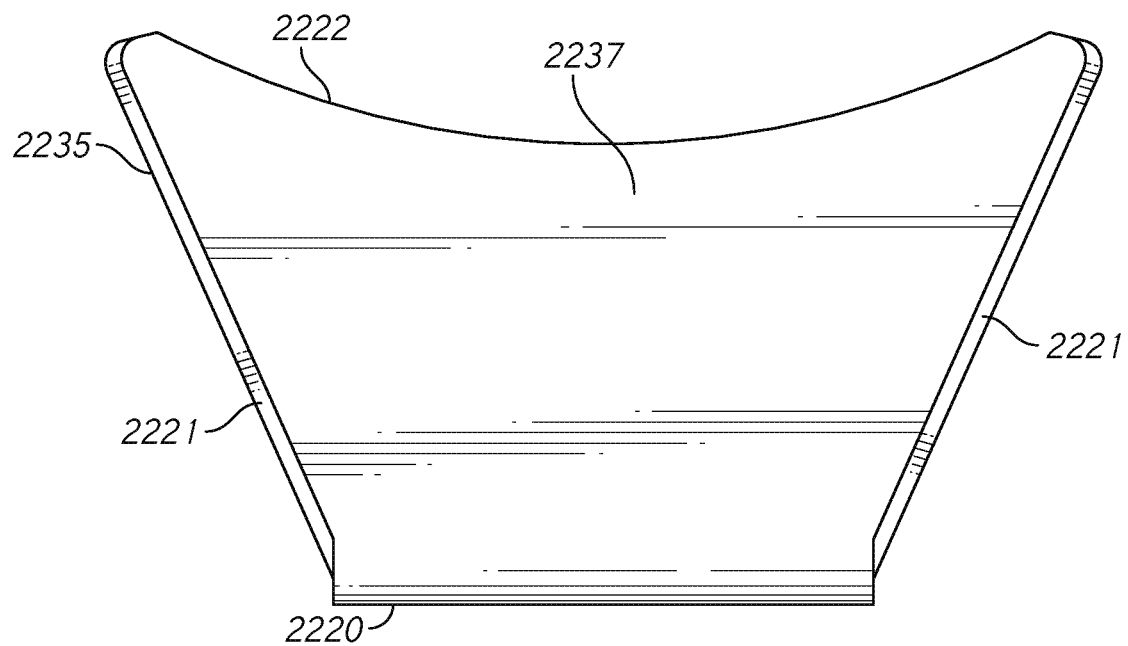
FIG. 58C shows a side view of the blank of spacer fabric of FIG. 58A folded to form two layers of spacer fabric.
Figure 58D:
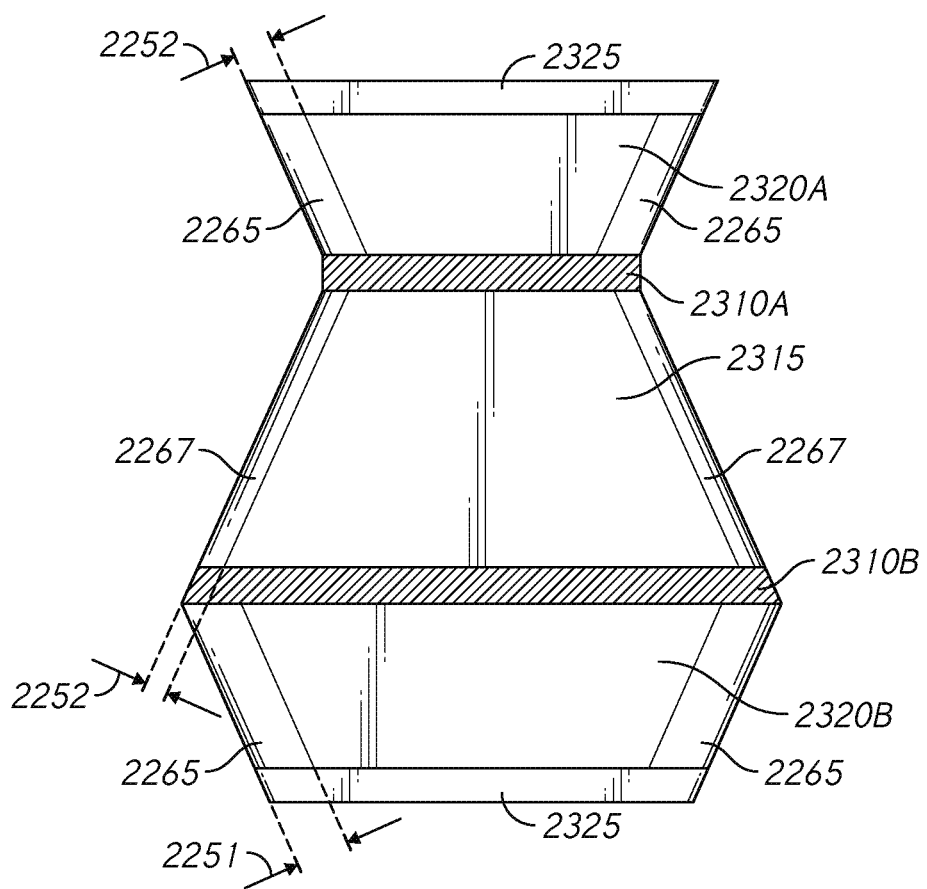
FIG. 58D shows another blank of spacer fabric for forming a back panel comprising two layers of spacer fabric.

An alternative blank of material for forming two layers of spacer fabric is illustrated in FIG. 58D. In this embodiment the blank comprises two fold regions 2310A and 2310B. Once folded on the two fold regions to form two layers of spacer fabric, one of the two layers comprises a join, formed in a join region 2325 of the blank. One section (or sections) of the blank that forms one layer of the two layers of spacer fabric is sized slightly smaller than a corresponding section (or sections) of the blank that forms the second layer of the two layers of spacer fabric, so that once the fabric is folded along the fold regions 2310A and 2310B to form two layers, one layer 2235 overlaps the edge of the other layer 2237. In the illustrated embodiment, the section of the blank that forms the overlapping layer comprises two sections 2320A and 2320B that together form the overlapping layer of the two layers of spacer fabric, so that the join (e.g. join 2210 of FIG. 56) formed in the join region 2325 of the blank is formed in the overlapping layer 2235 of spacer fabric. The blank of FIG. 58D forms two layers of spacer fabric having two folded edges as shown in FIG. 56.

As described earlier, in some embodiments a 3D fabric may be formed in a continuous tube, for example in a knitted tube. To achieve two layers of 3D fabric the tube of 3D fabric is flattened, to provide two layers of 3D fabric with a folded edge at each of two opposed edges. In such an embodiment, a 'stepped edge' may be achieved by cutting or otherwise forming a tube with a first tube length extending for a first half of the circumference of the tube and a second tube length extending for the other half of the circumference of the tube, wherein the first and second lengths are different to give a stepped edge when the tube is flattened to bring the first and second halves of the circumference of the tube together.

In some embodiments, in the weld region the external layer of spacer fabric overlaps the edge of the internal layer of spacer fabric. For example, FIG. 59A illustrates the material stack-up prior to welding. The stack-up shows the portion of headgear 2160 overlapped by the internal layer 2237 of spacer fabric and the external layer 2235 of spacer fabric. The external layer 2235 of spacer fabric overlaps the edge 2237A of the internal layer 2237 of spacer fabric. In an alternative embodiment the internal layer may overlap the edge of the external layer. In such an embodiment both edges of the two layers may be visible in the surface of the welded joint.

As shown in FIGS. 58A and 59A, the overlapping layer 2235 of spacer fabric has an overlapping region 2265 that overlaps a portion 2160 of the headgear to be welded to the two layers of spacer fabric. The under-lapping layer 2237 of spacer fabric has an overlapping region 2267 that overlaps the portion of the headgear to be welded to the two layers of spacer fabric. The width 2251 of the overlapping region 2265 of the overlapping layer 2235 is greater than the width 2252 of the overlapping region 2267 of the under-lapping layer 2237 of the two layers of spacer fabric. Therefore, the weld comprises a first region 2250A formed from two layers 2235, 2237 of spacer fabric and the portion 2160 of the headgear and a second region 2250B formed from one layer 2235 of spacer fabric and the portion 2160 of the headgear, as described above.

A weld formed from a single layer of spacer fabric may have less welded (melted and solidified) material and therefore may be more flexible and less brittle than a weld formed from two layers of spacer fabric. It follows therefore that a weld comprising two layers of spacer fabric in a portion 2250A of the weld width 2250 and one layer of spacer fabric in a remaining portion 2250B of the weld width may be more flexible and/or less brittle than a weld having two layers of spacer fabric for the full width 2250 of the weld. Thus the weld comprising one layer 2235 of spacer fabric overlapping the edge 2237A of the other layer 2237 of spacer fabric may provide an improved strength weld compared to a weld comprising two layers of spacer fabric for the full width of the weld. FIG. 59B illustrates the weld once the welding process (for example RF welding) has been completed. The width 2250 of the weld is determined by the width 2251 of the overlapping region 2265 of the external layer 2235 of spacer fabric that overlaps the portion 2160 of headgear. The width 2251 of the overlapping region of the external layer that overlaps the portion of headgear can be chosen to ensure a weld is made with adequate peel strength. However, the underlying or internal layer 2237 of spacer fabric need not overlap the portion of headgear by as much, as the peel strength of the weld is determined by the width 2251 that the external layer overlaps the portion of headgear. Thus the width 2252 (FIG. 59A) that the internal layer of spacer fabric overlaps the portion of headgear can be less than the width that the external layer overlaps the portion of headgear to achieve a more flexible and/or less brittle weld without a reduction in peel strength. Also, a further benefit is that with the external layer the two layers of spacer fabric overlapping the edge of the internal layer of the two layers of spacer fabric the manufacturing process for the headgear is simplified, as the edges of each layer of the two layers of fabric need not be aligned. The overlapping external layer hides the edge of the internal layer, presenting a tidy edge in the welded joint between the two layers of spacer fabric and the portion of the head gear. In some embodiments, the external layer of the two layers of spacer fabric faces away from the user's face when the headgear is in place on the user's head in use (in other words, the external layer is the outer layer of spacer fabric described earlier). This presents the weld to the outside of the headgear in use. In some embodiments the welded material of the joint (the melted and solidified material) does not fully penetrate the portion of the headgear material and so the weld material is placed away from the inner side of the headgear in contact with the user's head or face. However, in an alternative embodiment the external layer of spacer fabric may contact the user's head in use.

Figure 60:
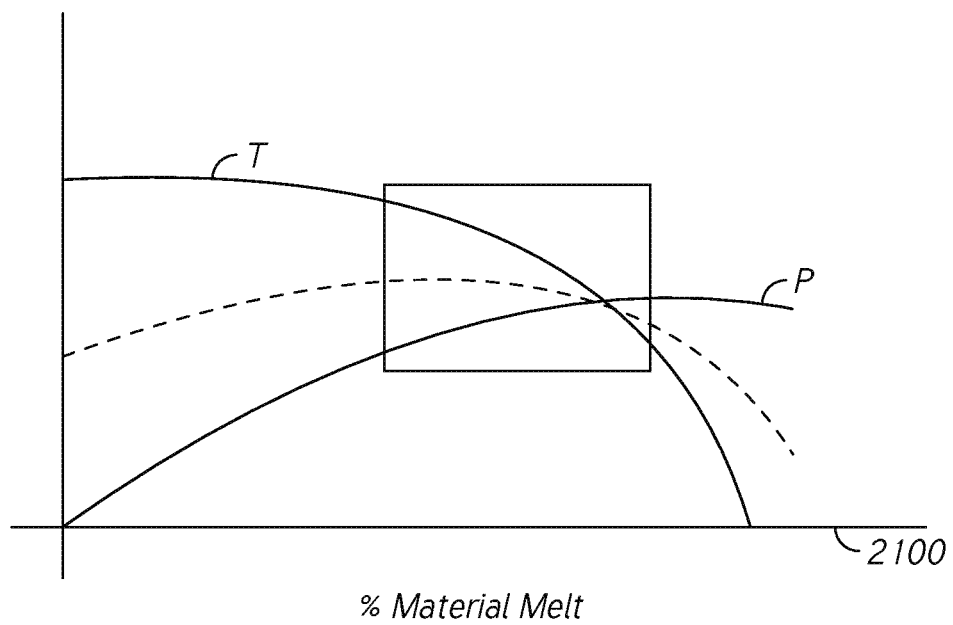
FIG. 60 shows a schematic graph to describe an optimum weld thickness.

In order to provide an aesthetic appearance and improved comfort to a user, it is preferable to keep the width 2250 of the weld in a 3D fabric as narrow as possible. However, a very narrow weld may tend to crack during use, especially when the weld is joining the spacer fabric to a portion of the headgear formed from another material such as a foam material. The melted foam material is very brittle, such that a very narrow weld is prone to cracking. For welding 3D spacer fabric to a foam material such as polyurethane foam a preferred weld has a width of greater than 3 mm, and preferably around 3 to 6 mm in width, and most preferably 5 mm to 6 mm in width. The strength of the weld is also determined by the thickness of the weld, which may be defined in terms of a percentage of the thickness of the material to which the spacer fabric is being welded (e.g. the foam material). The foam material in the weld region is very brittle. The greater the weld thickness the more brittle and less flexible the weld region can become, and thus the more susceptible the weld is to cracking. However, the peel strength of the weld increases as the weld thickness increases. Therefore an optimum depth of weld exists to achieve a weld with a combination of sufficient peel strength and resistance to cracking. The optimum depth of weld is considered to be 50% to 80% of the thickness of the foam material to which the 3D fabric is being welded. The trade-off of weld tensile strength to peel strength is represented in FIG. 60. In FIG. 60 the chart illustrates weld strength versus weld thickness as a percentage of material thickness on the x-axis, with P representing the peel strength and T representing the weld tensile strength (resistance to cracking). An optimum weld thickness is represented by a window that encompasses the cross-over point between the peel and tensile strength of the weld.

Some exemplary dimensions for providing an improved weld for headgear are provided below. In some embodiments, the spacer fabric may have a thickness of about 3 mm (two layers having a combined thickness of about 6 mm) and the portion (for example the perimeter portion of the back panel) may be formed from breathable foam and fabric laminate having a thickness of about 4 mm. The external layer of spacer fabric may overlap the breathable foam and fabric laminate by about 4 mm to 6 mm. The internal layer of spacer fabric may overlap the breathable foam and fabric laminate by about 3 to 4.5 mm. The external layer of spacer fabric may overlap the internal layer of spacer fabric by about 1 mm to about 2.5 mm. The total weld width defined by the extent the external layer overlaps the breathable foam and fabric laminate is about 4 mm to 6 mm.

Figure 61:
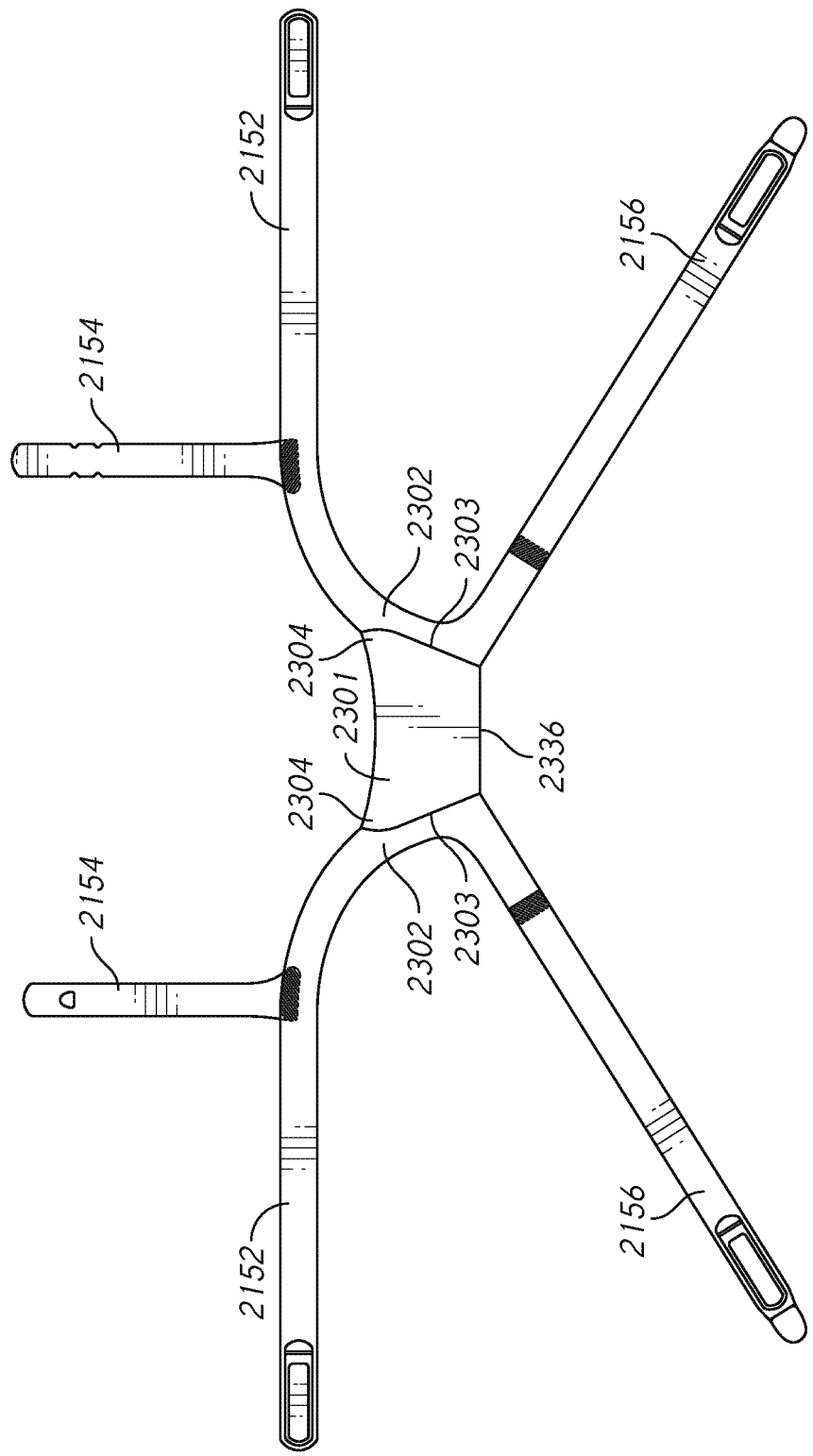
FIG. 61 shows a headgear arrangement having a back panel formed from 3D fabric that is stitched to perimeter portions formed from a foam and fabric laminate material.
Figure 62:
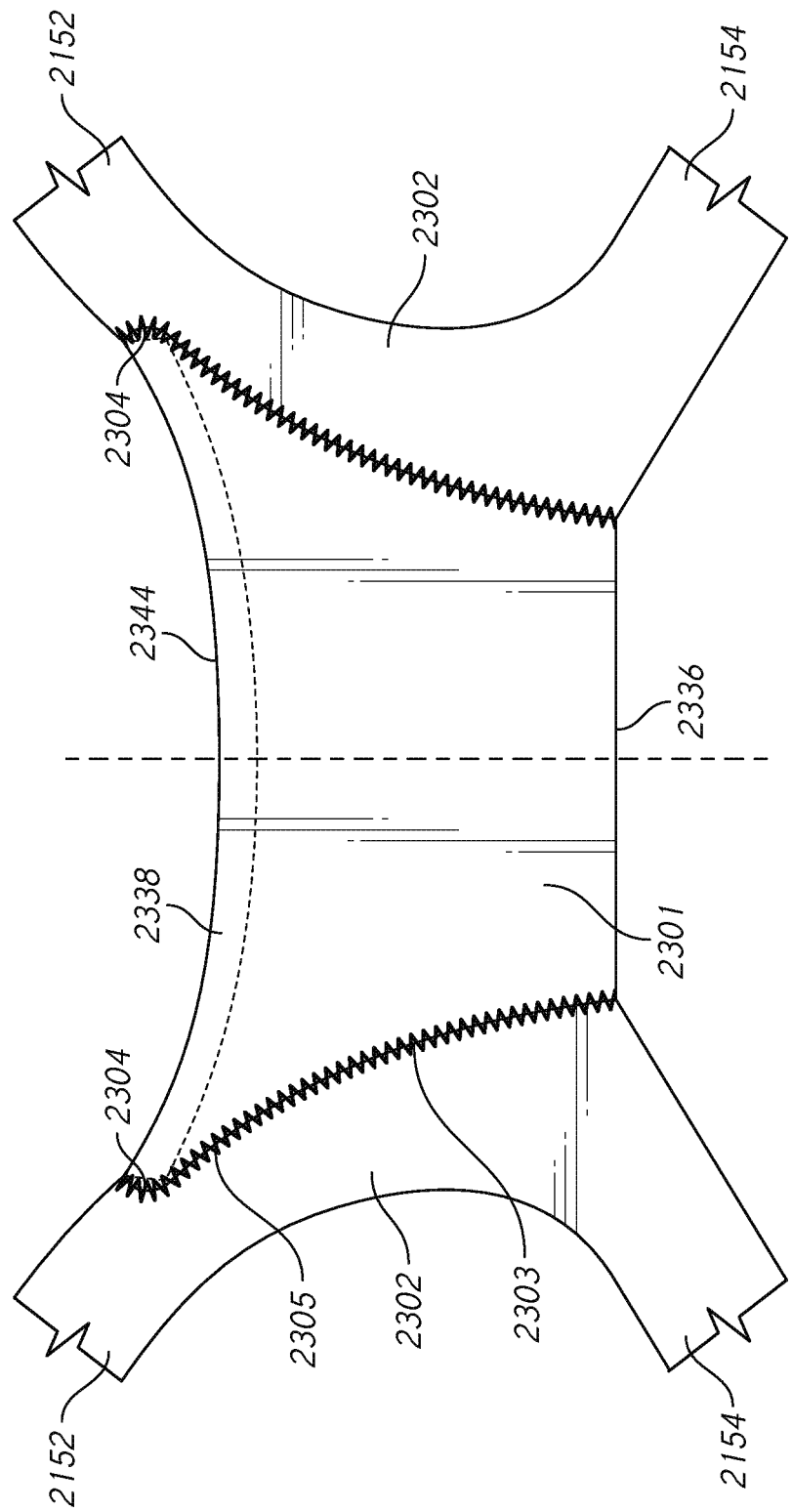
FIG. 62 shows an alternative headgear arrangement having a back panel formed from 3D fabric that is stitched to perimeter portions formed from a foam and fabric laminate material.

FIGS. 61-67 illustrates a headgear arrangement having a back panel formed from 3D fabric that is stitched to perimeter portions formed from a foam and fabric laminate material. The headgear arrangement reduces or inhibits both bunching of the stitching and bunching of the 3D fabric along a join. Preventing bunching of the stitching and the 3D fabric ensures that the join has a tidy aesthetic appearance and that the headgear arrangement is comfortable when worn by the user. As shown in FIGS. 61 and 62, the headgear arrangement comprises a back panel 2301 and perimeter portions 2302. The perimeter portions include upper straps 2152, top straps 2154 and lower straps 2156. The back panel 2301 and the perimeter portions 2302 are stitched together by a back-and-forth stitching 2305 along a join 2303. In some configurations, other variants of back-and-forth stitching may also be used.

Generally, it is difficult to stitch together materials that have different and/or mechanical properties. As a non-limiting example, the stitching together of two materials having different material constructions, such as, a 3D fabric and a more rigid foam and fabric laminate, can present the bunching issues described above because of the different properties (i.e., flexibility, compressibility, hardness, etc.) caused by the differences in material construction.

Similarly, as another non-limiting example, the stitching together of 3D fabric to plastic-based or intramoulded headgear straps (which is more rigid than 3D fabric) can also present the bunching issues described above. That is, in some configurations, bunching may occur when 3D fabric is joined with plastic-based portions of a headgear because of the different properties (i.e., flexibility, compressibility, hardness, etc.) caused by the differences in material construction.

Alternatively, as a non-limiting example, the stitching together of two materials having similar material constructions but different mechanical properties, such as, a foam and fabric laminate having a 7 pound density and foam and fabric laminate having a 10 pound density (which is more rigid than a 7 pound density), can also present the bunching issues described above because of the different properties (i.e., flexibility, compressibility, hardness, etc.) caused by the differences in mechanical properties despite having similar material construction.

Typically, between a rigid material and a non-rigid material, the more rigid material retains its shape under the tension of stitching, whereas the less rigid material is prone to deformation and distortion under the tension applied by the stitching. Accordingly, sewing together a back panel formed from 3D fabric and a perimeter portion formed from a foam and fabric laminate material may cause the stitching and the 3D fabric to bunch. Bunching of the stitching and the 3D fabric (i.e., back panel) results in an untidy appearance that is neither aesthetically pleasing nor appealing to the user. Further, bunching of the stitching and the fabric may also cause looseness in the join such that the back panel and the perimeter portions are not tightly fastened together. For illustration, FIGS. 68-71 depict stitching 2305 that is bunched along a join 2303 between the back panel 2301 and the perimeter portions 2302.

Figure 68:
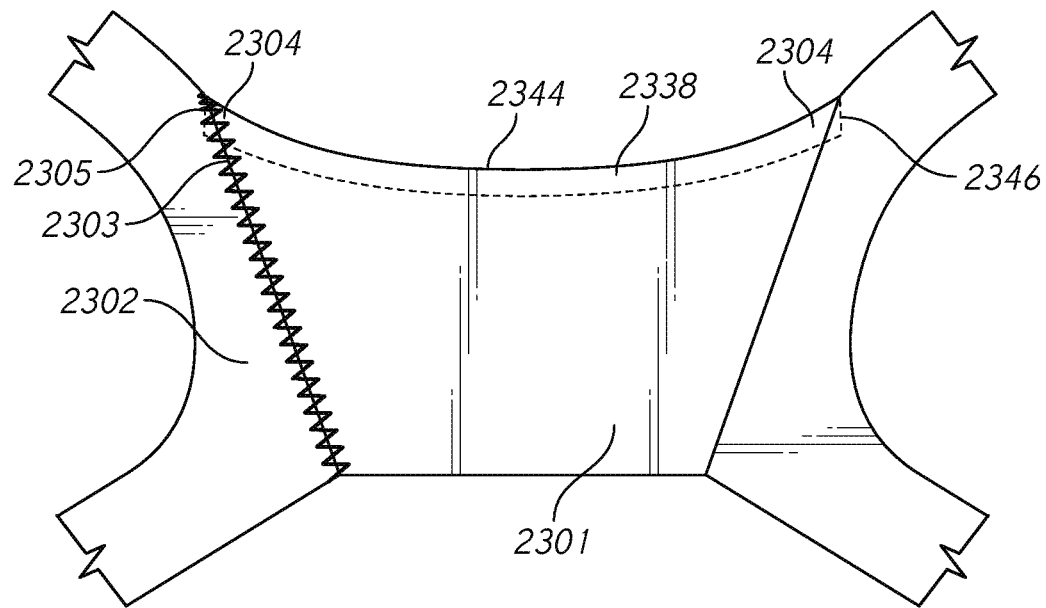
FIG. 68 shows a headgear arrangement having bunched stitching.
Figure 69:
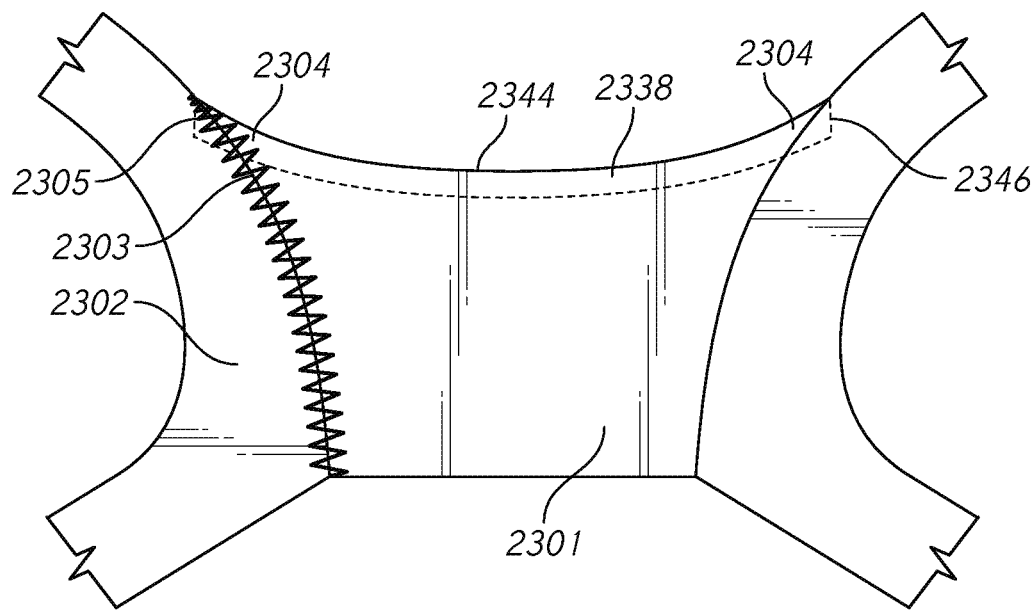
FIG. 69 shows another headgear arrangement having bunched stitching.
Figure 70:
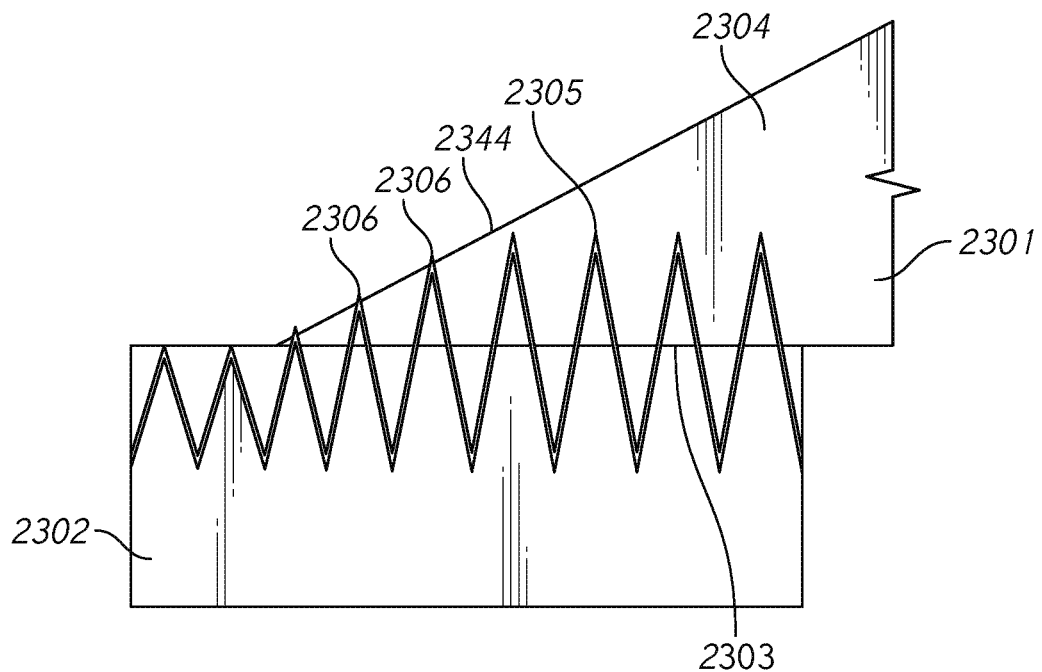
FIG. 70 is a close-up view of bunched stitching along a join between a back panel and a perimeter portion.

In addition to the differences in material construction and/or mechanical properties of the back panel and perimeter portions, the shape of the back panel may also affect bunching of the stitching and the fabric. More specifically, a back panel having corners that form sharp acute angles may cause bunching of the stitching at the corners. For illustration, FIGS. 68 and 69 illustrate the back panels 2301 with upper corners 2304 formed at angles less than 45 degrees and 30 degrees, respectively. As shown, the upper corners 2304 quickly narrow such that little material is available for the stitching 2305 to be sewn and passed through the back panel 2301. FIG. 70 is a close-up view illustrating the decrease in the width of the stitching 2305 at the end of the join 2303. As shown, the sharp upper corners 2304 of the back panel 2301 provide less available material for the stitching 2305 to be sewn and passed through. Accordingly, the width of the stitching 2305 also decreases which causes bunching of the stitching 2305. As a result, the width of the stitching 2305 decreases at the end of the join 2303. That is, the narrowing width of the upper corner 2304 of the back panel 2301 causes the width of the stitching 2305 to also narrow. As such, the decreasing width of the stitching 2305 causes bunching of the stitching 2305 at the end of the join 2303.

Figure 71:
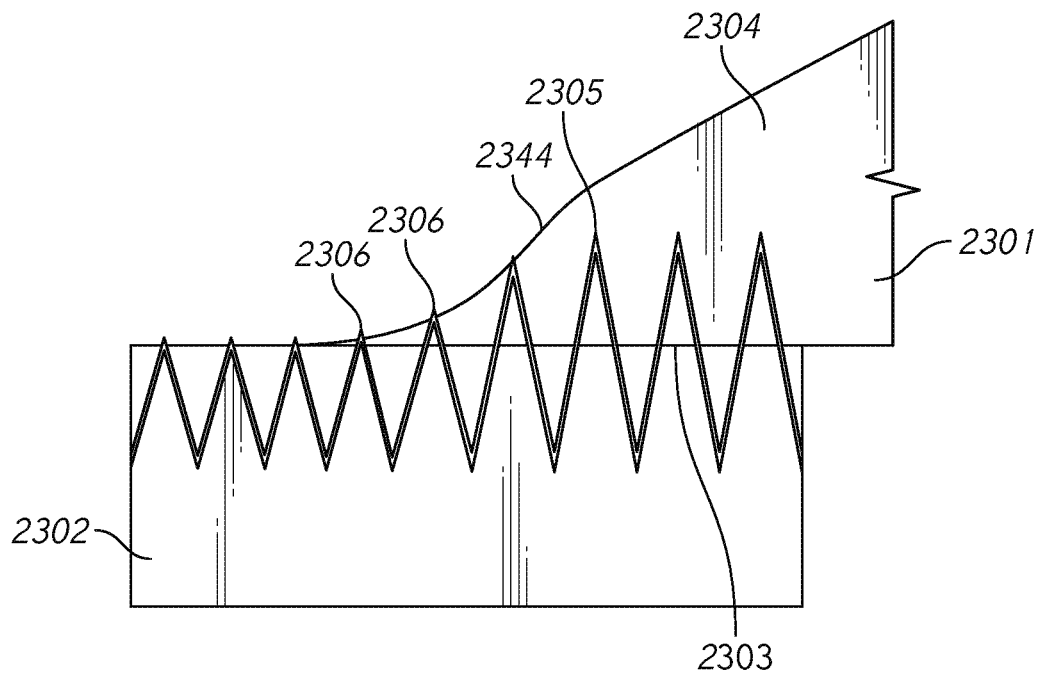
FIG. 71 is a close-up view of bunched stitching along a join between a back panel and a perimeter portion with deformed upper corners of the back panel.

FIG. 71 illustrates the bunching of the 3D fabric of the back panel 2301 that is caused by a combination of sharp acute angles at the upper corners 2304 of the back panel 2301 and the greater compressibility of the 3D fabric back panel 2301 relative to the foam and fabric laminate perimeter portion 2302. As shown, the stitches indicated at 2306 are sewn over the edge 2344 of the sharp upper corner 2304 of the back panel 2301, which is similar to FIG. 70. However, due to the greater compressibility of the 3D fabric back panel 2301 relative to the foam and fabric laminate perimeter portion 2302, the upper corners 2304 of the back panel 2301 is compressed and deformed under the tension of the stitching 2305 while the foam and fabric laminate material of the perimeter portion 2302 remains undeformed. It should be noted that for the purpose of illustration in FIG. 70, the back panel 2301 and the perimeter portion 2302 are illustrated as if they are formed from identical materials or materials having similar mechanical properties. The compressing causes the 3D fabric at the upper corners 2304 of the back panel 2301 to bunch up and create a hard lump or pressure points, in combination with the bunched stitches, that dig into a user's head and cause discomfort. The compressing of the 3D fabric also further decreases the width of the stitching 2305 which further increases the amount of bunching of the stitching 2305.

In contrast, FIGS. 61-67 illustrates a back panel 301 formed from 3D fabric that is stitched to perimeter portions 2302 formed from a foam and fabric laminate material by stitching 2305 without bunching of the stitching and bunching of the 3D fabric along the join 2303. More specifically, the stitching 2305 has a generally consistent width throughout the length of the join 2303 such that the stitching is substantially evenly spaced on both sides of the join 2303 between the back panel 2301 and the perimeter portion 2302. A stitching having a generally consistent width reduces bunching of the stitching and bunching of the 3D fabric along the join 2303. A generally consistent stitch width may be generally defined as having a repeatable in pattern along a straight length that is within standard manufacturing tolerances. It should be understood to one of ordinary skill in the art that the stitching along a curve may have a stitch width that is smaller on the inside of the curve than the outside of the curve.

As shown in a non-limiting embodiment, FIGS. 61 and 62 show the back panel 2301 having a generally inverted isosceles trapezoidal shape comprising a top edge, a bottom edge and lateral edges that connect the top edge to the bottom edge. That is, the back panel 2301 has four sides each of which can be linear or curved, one set of opposing sides having a relatively longer length side and a relatively shorter length side, and a second set of opposing sides that are approximately equal in length. The back panel 2301 is symmetrical across a vertical centreline, as shown in FIG. 62. In some configurations, the back panel 2301 has a generally inverted isosceles trapezoidal shape. The trapezoidal shape is configured to follow the contours of the user's upper neck and lower skull region. That is, the top edge is positioned slightly below the user's occipital lobe and the bottom edge is positioned on the user's neck. Accordingly, the top edge of the back panel 2301 is wider than the bottom edge and the lateral edges extend laterally outward (relative to the vertical centreline) from the bottom edge toward the top edge to accommodate the increasing width to the user's occipital bone relative to the user's neck. The top edge of the back panel may be curved to accommodate the shape of the user's occipital lobe.

It should be understood to one of ordinary skill in the art that the back panel 301 is not limited to having four sides and a generally inverted isosceles trapezoidal shape. In some configurations, the geometry of the back panel 2301 may include other quadrilateral or polygonal shapes. In addition, the lengths, shape and curvature of the top, bottom and lateral edges of the back panel 2301 may vary according to the size, shape and geometry of the user's head.

Figure 63:
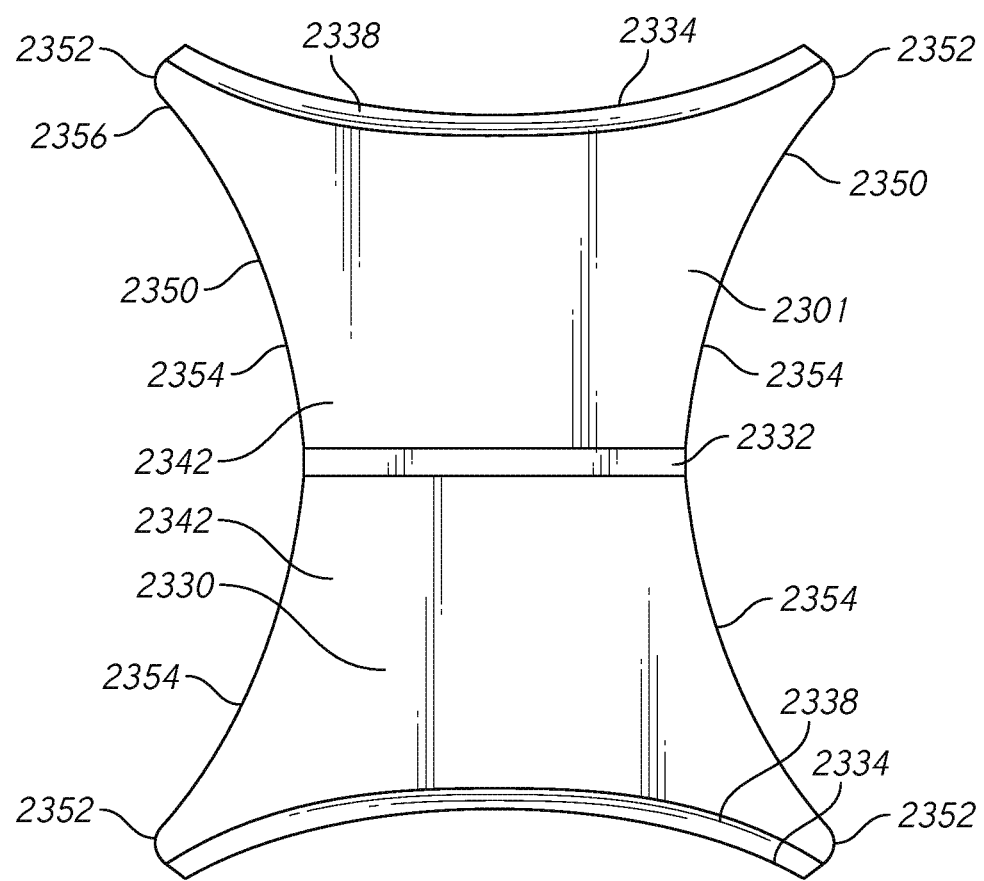
FIG. 63 shows the back panel of the headgear arrangement in FIG. 62 that is laid flat.

FIG. 63 shows the back panel 2301 in its unfolded and unsewn state. The back panel 2301 comprises a single layer of 3D fabric 2330 that is folded over upon itself along a fold region 2332. When folded, the fold region 2332 provides a folded edge 2336 that provides a natural and soft edge to the back panel 2301 that is comfortable against the user's neck. Similar to the back panel 2201 in FIG. 47B, the 3D fabric 2330 has a right side 2340 and a wrong side 2342. The free ends 2334 of the 3D fabric 2330 are joined together to form a hollow tubular shape when the 3D fabric 2330 is inside out (i.e., with the wrong sides 2342 of the fabric facing out). Sewing the free ends 2334 together forms a seam allowance 2338 that is opposite the fold region 2332. The seam allowance extends radially outward from a center of the tubular shaped 3D fabric 2330 when the 3D fabric 2330 is inside out.

Figure 64:
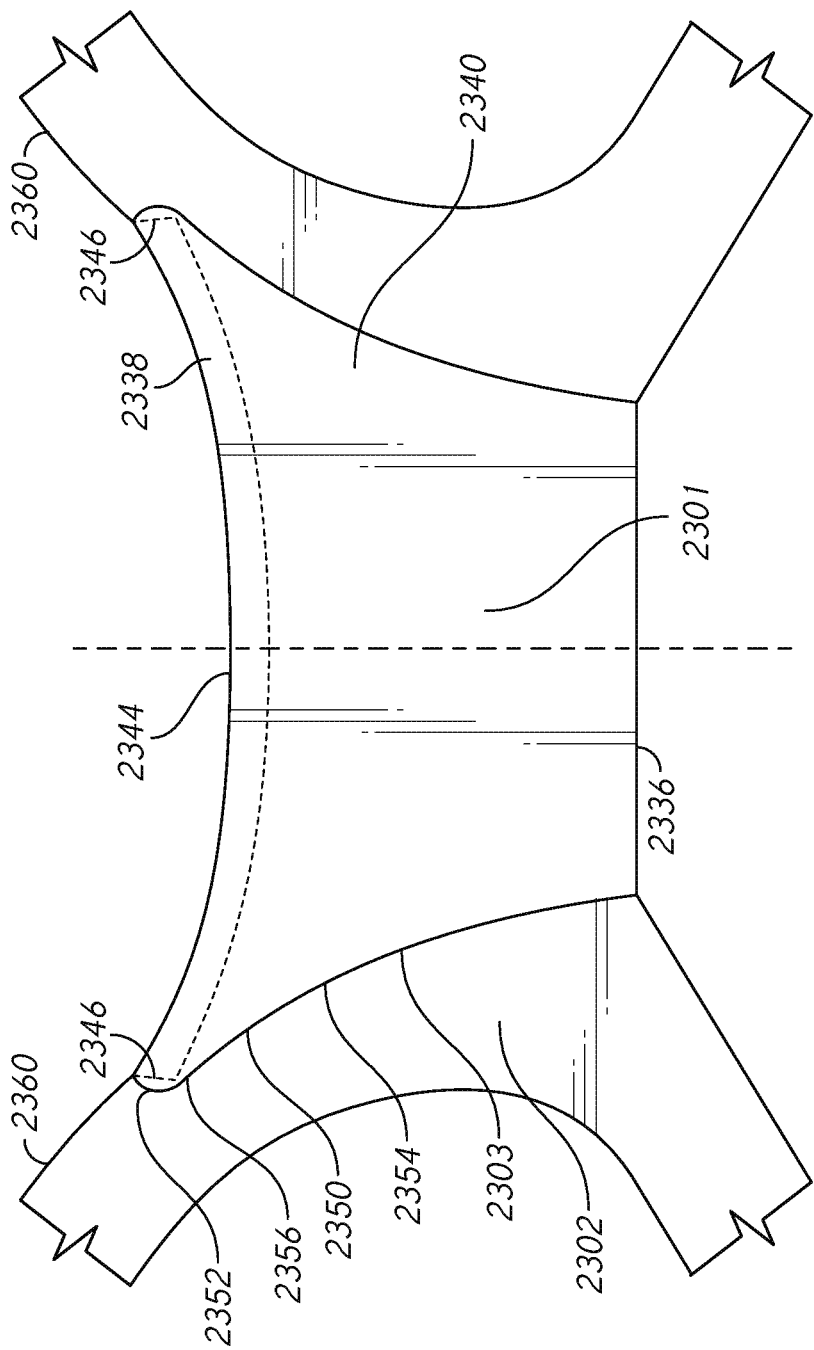
FIG. 64 shows the back panel and the perimeter portions of the headgear arrangement in FIG. 62.

During assembly, the 3D fabric 2330 is then turned right-side out, such that the right sides 2340 are facing outward and the wrong sides 2342 are facing inward, as shown in FIG. 64. Accordingly, the seam allowance 2338 extends radially inward toward a center of the tubular shaped 3D fabric 2330. That is, the seam allowance 2338 is positioned within a hollow interior cavity of the back panel 2301.

The free ends 2334 of the 3D fabric 2330 may be sewn together by a seam (not shown) to form a tube. In some configurations, the seam may be formed by sewing a straight, zigzag or overlocking stitch. The seam forms a sewn edge 2344 of the back panel 2301 when the 3D fabric 2330 is turned right-side out. Similarly, the fold region 2332 forms a folded edge 2336 when the 3D fabric 2330 is turned right-side out, similar to the fold region 2310 in FIG. 58B. Accordingly, the sewn edge 2344 forms the top edge of the back panel 2301 and the folded edge 2336 forms the bottom edge of the back panel 2301. In other configurations, the seam may be formed by bonding, adhesives, welding, etc. instead of stitching.

Figures 65, 66:
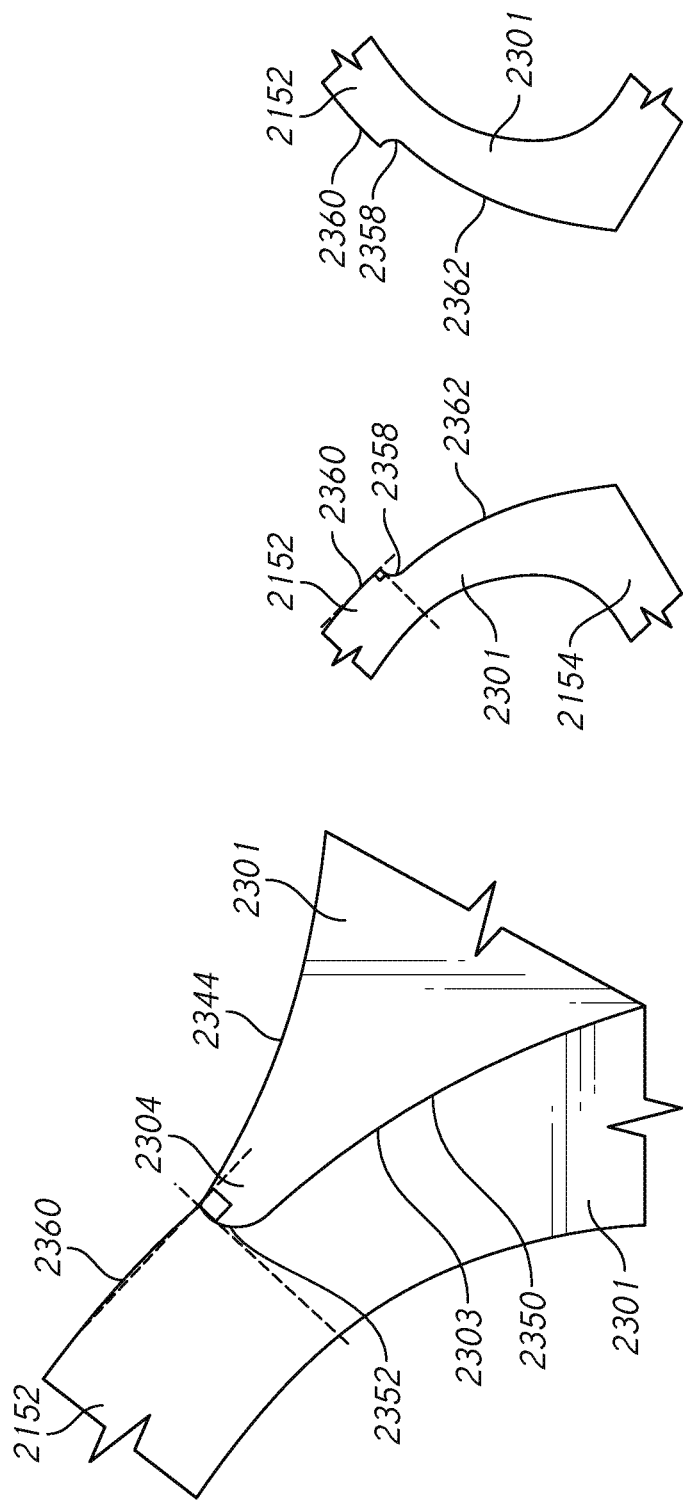
FIG. 65 is a close-up view of the join between the back panel and the perimeter portion of the headgear arrangement in FIG. 62.
FIG. 66 shows the perimeter portions of the headgear arrangement in FIG. 62.

As shown in FIGS. 63-65, the back panel 2301 has lateral edges 2350 extending between the folded edge 2336 and the sewn edge 2344. The lateral edges 2350 have a curving contoured shape with a convex region 2352 and a concave region 2354. The convex region 2352 (i.e., curving in a direction outward relative to a centreline of the back panel 2301) is connected to and/or extends towards the sewn edge 2344. The concave region 2354 (i.e., curving in a direction inward relative to a centreline of the back panel 2301) is connected to and/or extends towards the folded edge 2336. The convex region 2352 transitions into the concave region 2354 at an inflection point 2356. The inflection point 2356 is positioned below the seam allowance.

The lateral edges 2350 at the convex region 2352 have a curved shape such that the lateral edges 2350 substantially intersect the sewn edge 2344 at a perpendicular angle. The sewn edge 2344 is curved upward toward the upper edge 2360 of the perimeter portion 2302 and extends away from the center of the back panel 2301. Therefore, to form a perpendicular angle with the sewn edge 2344, the lateral edges 2350 transition from extending away from a center of the back panel 2301 (indicated by the centerline shown in FIG. 64) within the concave region 2354 to extending towards a center of the back panel 2301 in the convex region 2352. That is, the lateral edges 2350 in the convex region 2352 extend towards the center of the back panel 2301 to form a perpendicular angle with the upward and outwardly extending sewn edge 2344.

Figure 67:
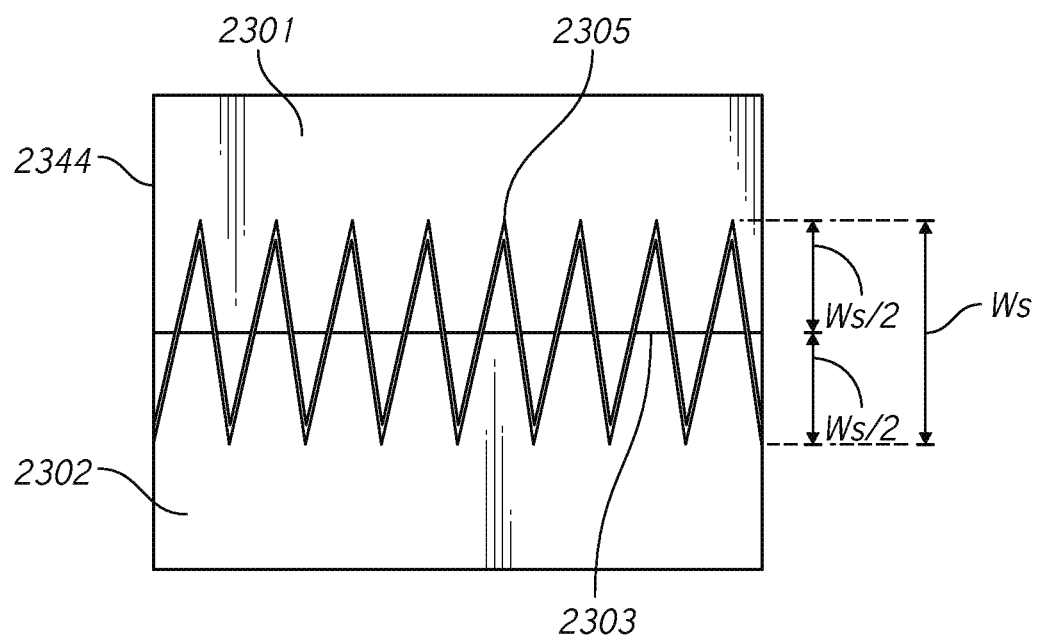
FIG. 67 is a close-up view of the stitching along the join of the headgear arrangement in FIG. 62.

As shown in FIG. 65, the intersection of the lateral edges 2350 and the sewn edge 2344 forms a substantially 90 degree angle. In contrast to the sharp acute angles of the upper corners 2304 in FIGS. 68-71, the intersection of the sewn edge 2344 and the lateral edges 2350 provides more material and space on both sides of the join 2303 for the stitching 2305 to pass through the 3D fabric. As shown in FIG. 62, the width of the stitching 2305 remains generally consistent and the stitching 2305 straddles the join 2303 throughout the entire length of the join 2303. FIG. 67 is a close-up view of the stitching 2305 at the upper corner 2304. As shown, the stitching 2305 has a stitch width Ws that is generally evenly distributed across the join 2303 such that roughly half of the stitch width Ws/2 on each side of the join 2303 and into each of the back panel 2301 and the perimeter portion 2302.

As a result, the substantially 90 degree angle between the convex region 2352 of the lateral edge 2350 and the sewn edge 2344 allows the stitching 2305 to finish substantially evenly between both the back panel 2301 and the perimeter portion 2302. The width of the stitching 2305 does not decrease at the end of the join 2303 and does not cause bunching of the stitching 2305 at the end of the join 2303. Accordingly, compression and deformation of the back panel 2301 at the upper corners 2304 is prevented or inhibited. Similarly, a decreasing of the width of the stitching 2305 at the end of the join 2303 is also prevented or inhibited.

The substantially 90 degree angle between the lateral edges 2350 and the sewn edge 2344 causes the upper portion of the back panel 2301 to be wider between the lateral edges 2350 at the convex regions 2352 compared to the back panel 2301 in FIG. 68, which has straight lateral edges. Due to the increased width of the convex region 2352, the concave region 2354 allows the lateral edge 2350 to accommodate the width of the convex region 2352 while also narrowing towards the folded edge 2336 such that the back panel 2301 may accommodate the narrower width of the user's neck.

As shown in FIG. 66, the perimeter portion 2302 may have a corresponding notched region 2358 defined by a receiving edge 2362 having an inward or concave shape that corresponds with the convex region 2352 of the lateral edge 2350. That is, the receiving edge 2362 has a shape that matches the convex and concave regions 2352, 2354 of the lateral edge 2350 of the back panel 2301. Accordingly, the notched region 2358 receives the upper corners 2304 of the back panel to provide a tidy aesthetic appearance.

In addition, as shown in FIGS. 64 and 65, the upper edge 2360 of the perimeter portion 2302 forms a substantially continuous curve with the sewn edge 2344 of the back panel 2301. Accordingly, as a result of the notched region 2358 of the perimeter portion 2302 having a corresponding shape as the upper corner 2304 of the back panel 2301, the receiving edge 2362 of the perimeter portion 2302 also forms a substantially perpendicular angle with the upper edge 2360, as shown in FIG. 66. Similar to the back panel 2301, the substantially 90 degree angle (as opposed to a sharp acute angle) between the upper edge 2360 and the receiving edge 2362 of the perimeter portion 2302 provides material and space on the perimeter portion 2302 for the stitching 2305 to be formed completely within the fabric and to finish substantially evenly between both the back panel 2301 and the perimeter portion 2302. In other configurations, the upper edge 2360 and the receiving edge 2362 of the perimeter portion 2302 may form an angle less than 90 degrees. This is because the perimeter portion 2302 is formed from a more rigid foam and fabric laminate material (e.g., neoprene or Breath-O-Prene) than the back panel 2301 (i.e., 3D fabric) and the perimeter portion 2302 is compressed less by the stitches 2305 than the back panel 2301.

The lateral edge 2350 of the back panel 2301 extends a distance away from the sewn edge 2344 of the back panel 2301 in a direction perpendicular to the sewn edge 2344 such that the inflection point 2356 is located below the seam allowance 2338, as shown in FIG. 64. In some configurations, the convex region 2352 of the lateral edge 2350 has a radius of curvature that is larger than the stitch width Ws which further avoids bunching of stitches along the convex region 2352. In other configurations, the convex region 2352 may have a radius that is greater than a length of the seam allowance 2338 (i.e., a distance between the sewn edge 2344 and the free end 2334). In addition, the widest distance between the lateral edges 2346 of the seam allowance 2338 is less than the widest distance between the lateral edges 2350 of the back panel 2301 within the convex region 2352. As a result, the lateral edges 2346 of the seam allowance 2338 do not extend beyond the lateral edges 2350 of the back panel 2301 such that the convex region 2352 entirely covers the seam allowance 2338 and the seam allowance 2338 is entirely contained and enclosed within the extents of the back panel 2301. That is, the lateral edges 2346 of the seam allowance 2338 are positioned laterally inward of the lateral edges 2350 of the back panel 2301. Accordingly, when the back panel 2301 and the perimeter portions 2302 are stitched together by stitching 2305 the seam allowance 2338 does not extend over the join 2303 such that the stitching 2305 is stitched over the seam allowance 2338. Stitching over the seam allowance 2338, as shown in the back panels 2301 in FIGS. 68 and 69, causes a hard lump or pressure points to be created in the upper corners 2304 of the back panel 2301 which dig into a user's head and cause discomfort. In some configurations, the lateral edges 2346 of the seam allowance 2338 are positioned laterally inward of the stitching 2305 such that no portion of the seam allowance 2338 is stitched over. Accordingly, the stitching 2305 would have a more uniform thickness, flexibility, hardness, etc. throughout the length of the stitching 2305. Further, having the edges 2346 of the seam allowance 2338 contained within the cavity of the back panel 2301 and not overhanging the join 2303 prevents or inhibits the raw edges 2346 of the seam allowance 2338 from being exposed, which results in an untidy appearance and may also cause the ends of the fabric to unravel.

It should be understood to one of ordinary skill in the art that the angle between the sewn edge 2344 and the lateral edge 2350 is not limited to 90 degrees and may include angles less than or greater than 90 degrees so long as sufficient material is provided for the stitching to finish substantially evenly between the back panel and perimeter portions such that bunching of the stitching and/or material does not occur. The minimum or maximum angle between the sewn edge 2344 and the lateral edge 2350 may depend on the width, length and type of stitching, the type of materials to be joined, the shapes of the back panel and perimeter portions, etc.

Figure 72:
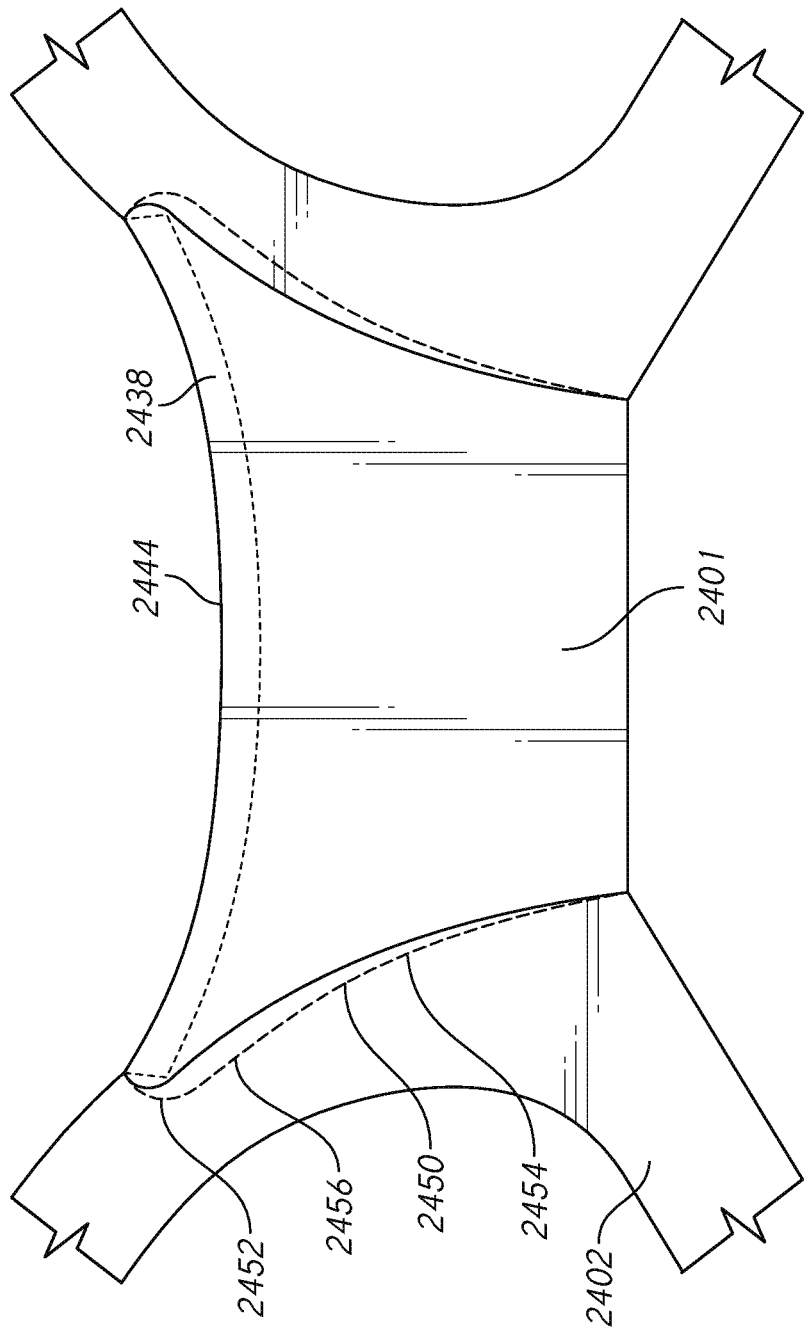

FIG. 72 shows an alternative configuration (shown in longer dashed lines) of a back panel 2401 having a convex region 2452 of a lateral edge 2450 extending a greater distance outwardly from the end of the sewn edge 2444 of the back panel 2401 than the back panel 2301 in FIG. 62 (shown in solid lines). Relative to the back panel 2301 in FIG. 62, the radius of curvature of the convex region 2452 is greater and the inflection point 2456 is lower. The alternative configuration of the back panel 2401 provides addition distance between the lateral edges 2450 of the back panel 2401 from the seam allowance 2438 (shown in shorter dashed lines) such that the stitching (not shown) overlaps less or none of the seam allowance 2438.

Figure 73:
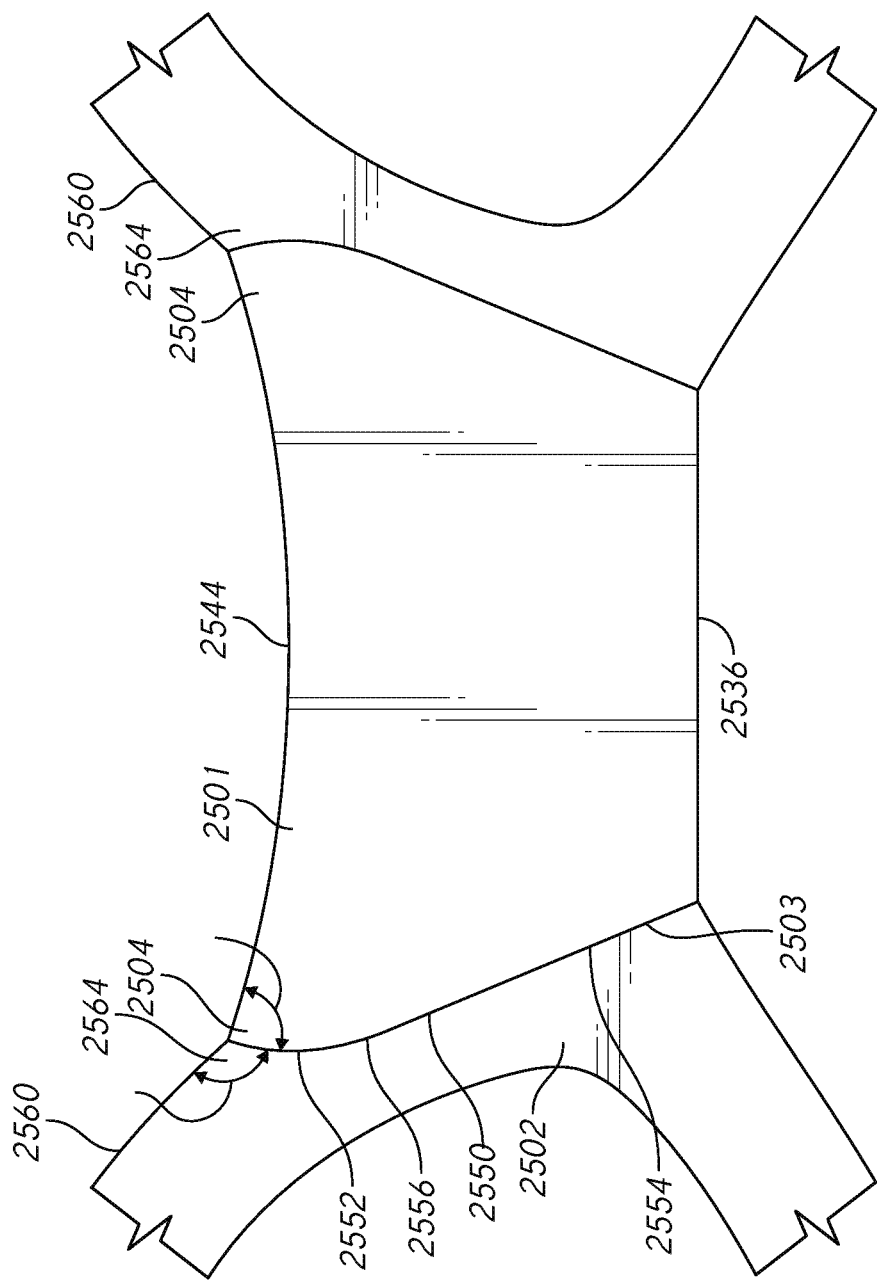

FIGS. 73 and 74 illustrate an alternative back panel and perimeter portion arrangement that provides a different aesthetic whilst maintaining a tidy join finish. In the alternative arrangement, the lateral edges of the back panel 2501 are linear towards the folded edge 2536 and convex towards the sewn edge 2544. The linear region 2554 transitions into the convex region 2552 at a tangent point 2556. The tangent point 2556 is below the seam allowance 2538. The linear regions 2554 are convergent towards the folded edge 2536.

In contrast to the back panel and perimeter portion arrangement in FIGS. 63-67, the back panel 2501 has a sewn edge 2544 that does not form a continuous curve with the upper edge 2560 of the perimeter portion 2502. That is, the intersection of the sewn edge 2544 and the upper edge 2560 forms a corner. Accordingly, back panel upper corners 2504 and the perimeter portion upper corners 2564 also form corners. The back panel upper corners 2504 have an angle θ that is close to 90 degrees, which prevents compression of the upper corners 2504 by the stitching and bunching of the stitches. The perimeter portions upper corners 2564 have an angle β that is greater than 90 degrees. In some configurations, the angle θ can be between 70 and 120 degrees. Preferably, the angle β is greater than 70 degrees. The angle β may be less than 90 degrees since the material of the perimeter portions 2502 (i.e., foam and fabric laminate) is less likely to compress and distort under tension and pressure of the stitching.

The back panel 2501 has a trapezoidal shape that is symmetrical across a vertical centreline, as shown in FIG. 74. The folded edge 2536 and sewn edge 2544 define top and bottom edges of the back panel 2501. The folded edge 2536 and sewn edge 2544 define a first width $W_1$ and a second width $W_2$, respectively. As shown, the first width $W_1$ is less than the second width $W_2$. That is, the back panel 2501 has a top edge that is wider than a bottom edge.

The distance between the lateral edges 2550 of the convex region 2552 defines a third width $W_3$, which is the widest point of the back panel 2501. The corners of the free ends 2534 of the seam allowance 2538 define a fourth width $W_4$. The fourth width $W_4$ is less than the third width $W_3$ such that the seam allowance 2538 does not extend beyond the lateral edges 2550 of the back panel 2501. In addition, the convex region 2552 of the lateral edge 2550 extends a distance outwardly from the end of the sewn edge 2544 of the back panel 2501 such that the tangent point 2556 is below the seam allowance 2538 and the convex region 2552 entirely covers the seam allowance 2538 when the back panel 2501 is right-side out. Accordingly, when the back panel 2501 and the perimeter portions 2502 are stitched together (stitching not shown) the seam allowance 2538 does not extend over the join 2503 such that the seam allowance 2538 is stitched over. As such, the stitched join 2503 will have substantially uniform hardness, flexibility, etc. along the entire length of the join 2503.

It should be understood to one of ordinary skill in the art that the above described techniques to avoid bunching of the stitching and/or fabric is not limited to the joining of 3D fabrics and foam/fabric laminates. The above described techniques may be utilized to join any material or combination of materials having different material constructions and/or mechanical properties. Similarly, the above described techniques may also be used to join components formed from the same material in which the material has low rigidity, density, hardness, etc. and is susceptible to bunching.

VI. Additional Terminology

Unless the context clearly requires otherwise, throughout the description and the claims, the words "comprise," "comprising," and the like, are to be construed in an inclusive sense as opposed to an exclusive or exhaustive sense, that is to say, in the sense of "including, but not limited to." Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Reference to any prior art in this specification is not, and should not be taken as, an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of said parts, elements or features. The various features described above may be used independently of one another, or may be combined in various ways. All possible combinations and subcombinations are intended to fall within the scope of this disclosure. In addition, certain features may be omitted in some implementations. Any methods and processes described herein are not limited to any particular sequence, and the acts or steps relating thereto can be performed in other sequences that are appropriate. For example, described acts or steps may be performed in an order other than that specifically disclosed, or multiple acts or steps may be combined in a single act or step. The example acts or steps may be performed in serial, in parallel, or in some other manner. Features may be added to or removed from the disclosed example embodiments. The example systems and components described herein may be configured differently than described. For example, elements may be added to, removed from, or rearranged compared to the disclosed example embodiments. In addition, the inventions illustratively disclosed herein suitably may be practiced in the absence of any element which is not specifically disclosed herein.

Where, in the foregoing description reference has been made to integers or components having known equivalents thereof, those integers are herein incorporated as if individually set forth.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A headgear for use with a respiratory mask, comprising:
    a component formed from a single piece of 3D fabric folded onto itself along a continuous fold line to form a continuous folded edge and a first layer and a second layer of the single piece of 3D fabric extending from the folded edge, the folded edge configured to be aligned with a top of a user's neck in use and forming an edge of the headgear,
    wherein the component is a back panel having a substantially trapezoidal shape, the folded edge forming a bottom edge of the back panel,
    wherein the two layers of 3D fabric are joined together to form a top edge of the back panel, the top edge positioned opposite of the bottom edge, the top edge having a greater length than a length of the bottom edge, and
    wherein the two layers of 3D fabric are joined together at lateral edges, the lateral edges each extending from the bottom edge to the top edge,
    wherein, with the back panel in a laid flat orientation, the bottom edge of the back panel is straight in a length direction and the top edge of the back panel is continuously curved in the length direction; and
    a perimeter portion formed from a material suitable for use in headgear, the perimeter portion being attached to and extending along an entirety of at least one of the lateral edges of the back panel, wherein the material of the perimeter portion extends into and forms at least part of a strap of the headgear.

2. The headgear as claimed in claim 1, wherein the headgear comprises a lower strap and an upper strap extending from the back panel to connect to the respiratory mask.

3. The headgear as claimed in claim 1, wherein the bottom edge of the back panel extends across a back of a user's neck in use.

4. The headgear as claimed in claim 1, wherein the two layers of 3D fabric are joined together by bonding, stitching or welding at the lateral edges of the component.

5. The headgear as claimed in claim 4, wherein the two layers of 3D fabric are joined together by bonding, stitching or welding at the top edge of the component.

6. The headgear as claimed in claim 1, wherein the two layers of 3D fabric are stitched together at the top edge to have a seamed edge.

7. The headgear as claimed in claim 1, wherein the two layers of 3D fabric have a join in an outer layer of the 3D fabric.

8. The headgear as claimed in claim 7, wherein the join is a welded joint.

9. The headgear as claimed in claim 1, wherein the 3D fabric has a right side and a wrong side, and is folded so that the wrong side of the 3D fabric is on an inside of the component and the right side of the 3D fabric on an outside of the component.

10. The headgear as claimed in claim 1, wherein the perimeter portion extends around the two layers of 3D fabric from one end of the folded edge to another end of the folded edge.

11. The headgear as claimed in claim 10, wherein the back panel comprises said perimeter portion along each of the lateral edges of the back panel.

12. The headgear as claimed in claim 10, wherein one or more edges of the two layers of 3D fabric other than the folded edge are attached to the perimeter portion by bonding, stitching or welding.

13. The headgear as claimed in claim 1, wherein each of the two layers of 3D fabric comprises a wrong side and a right side, wherein a join between layers of the 3D fabric or within a layer of the 3D fabric is made with the 3D fabric turned wrong side out, the 3D fabric then turned right side out so that the join is located inside the two layers of 3D fabric.

14. The headgear as claimed in claim 1, wherein one or more edges of the two layers of 3D fabric other than the folded edge are welded to a portion of the headgear, wherein one of the two layers of 3D fabric overlaps an edge of another one of the two layers of 3D fabric so that the weld comprises:

a first region formed from both of the two layers of 3D fabric and the portion of the headgear, and a second region formed from one of the two layers of 3D fabric and the portion of the headgear.

15. The headgear as claimed in claim 1, wherein the 3D fabric is a 3D spacer fabric.

16. The headgear as claimed in claim 1, wherein the 3D fabric folded from the single piece of 3D fabric is folded approximately in half, such that each of the two layers of the single piece of 3D fabric folded are approximately equal in size.

17. The headgear as claimed in claim 1, wherein the top edge is a peripheral edge of the headgear.

18. The headgear as claimed in claim 1, wherein the top edge is concave.

19. A headgear for use with a respiratory mask, comprising:

a component formed from a single piece of 3D fabric folded onto itself along a continuous fold line to form a continuous folded edge and a first layer and a second layer of the single piece of 3D fabric extending from the folded edge, the folded edge configured to be aligned with a top of a user's neck in use and forming an edge of the headgear, wherein the component is a back panel having a substantially trapezoidal shape, the back panel having a top edge, a bottom edge, and lateral edges connecting the top edge to the bottom edge, the top edge having a greater length than a length of the bottom edge, the folded edge forming the bottom edge of the back panel, wherein the two layers of 3D fabric are adjacent to one another and define a hollow interior cavity of the back panel, in use, and wherein, with the back panel in a laid flat orientation, the bottom edge of the back panel is straight in a length direction and the top edge of the back panel is continuously curved in the length direction; and a perimeter portion formed from a material suitable for use in headgear, the perimeter portion being attached to an entirety of at least one of the lateral edges of the back panel, wherein the material of the perimeter portion extends into and forms at least part of a strap of the headgear.

20. The headgear as claimed in claim 19, wherein the single piece of 3D fabric comprises two sheets formed from yarns connected by a series of yarns running between the two sheets, wherein the single piece of 3D fabric comprises a thickness within a range of 1 mm to 5 mm.

21. The headgear as claimed in claim 19, wherein the top edge is a peripheral edge of the headgear.

22. The headgear as claimed in claim 19, wherein the top edge is concave.

23. A headgear for use with a respiratory mask, comprising:

a back panel formed from a single piece of 3D fabric folded onto itself along a continuous fold line to form a continuous folded edge and a first layer and a second layer of the single piece of 3D fabric extending from the folded edge;

wherein the back panel comprises a top edge, a bottom edge, and lateral edges, each of the lateral edges extending from the bottom edge to the top edge, wherein the top edge of the back panel is positioned opposite of the bottom edge of the back panel, wherein a length direction extends from one of the lateral edges to another one of the lateral edges, a length of the top edge being greater than a length of the bottom edge, wherein the folded edge forms the bottom edge of the back panel, the bottom edge of the back panel configured to be aligned with a top of a user's neck in use, wherein, with the back panel in a laid flat orientation, the bottom edge of the back panel is straight in the length direction and the top edge of the back panel is continuously curved in the length direction; and a perimeter portion formed from a material suitable for use in headgear, an entirety of at least one of the lateral edges of the back panel being attached to the perimeter portion, wherein the material of the perimeter portion extends into and forms at least part of one or more straps of the headgear, the one or more straps extending from the back panel to connect to a respiratory mask.

24. The headgear as claimed in claim 23, wherein the top edge is a peripheral edge of the headgear.

25. The headgear as claimed in claim 23, wherein the top edge is concave.

26. A back panel for use with a headgear assembly, the back panel consisting essentially of:
- a single piece of 3D fabric folded onto itself along a continuous fold line to form a continuous folded edge, a first layer and a second layer of the single piece of 3D fabric extending from the folded edge,
- wherein the folded edge is configured to be aligned with a top of a user's neck in use;
- wherein the first layer and the second layer are joined together to form a top edge of the back panel, the top edge positioned opposite of the folded edge, the top edge having a greater length than a length of the folded edge, the top edge being continuously curved in a length direction;
- wherein the first layer and the second layer are joined together to form a first lateral edge and a second lateral edge of the back panel, each of the first lateral edge and the second lateral edge extending between the folded edge and the top edge, the first layer and the second layer being joined together along an entire length of each of the first lateral edge and the second lateral edge.

27. A headgear for use with a respiratory mask, comprising:
- a back panel, the back panel consisting essentially of:
    - a single piece of 3D fabric folded onto itself along a continuous fold line to form a continuous folded edge, a first layer and a second layer of the single piece of 3D fabric extending from the folded edge,
    - wherein the folded edge is configured to be aligned with a top of a user's neck in use;
    - wherein the first layer and the second layer are joined together to form a top edge of the back panel, the top edge positioned opposite of the folded edge, the top edge having a greater length than a length of the folded edge, the top edge being continuously curved in a length direction;
    - wherein the first layer and the second layer are joined together to form lateral edges of the back panel, the lateral edges extending between the folded edge and the top edge;
- a perimeter portion formed from a material suitable for use in headgear, the perimeter portion being attached to and extending along an entirety of the lateral edges of the back panel,
- two lateral side straps, wherein the material of the perimeter portion extends into and forms at least part of each of the two lateral side straps of the headgear.

* * * * *